US008524722B2

(12) United States Patent
Schirok et al.

(10) Patent No.: US 8,524,722 B2
(45) Date of Patent: Sep. 3, 2013

(54) SUBSTITUTED TRICYCLIC COMPOUNDS AND METHODS OF USE THEREOF

(75) Inventors: Hartmut Schirok, Langenfeld (DE); Ying Li-Sommer, Düsseldorf (DE); Michael Brands, Berlin (DE); Mario Lobell, Wuppertal (DE); Adrian Tersteegen, Wuppertal (DE); Herbert Himmel, Essen (DE); Karl-Heinz Schlemmer, Wuppertal (DE); Dieter Lang, Velbert (DE); Kirstin Petersen, Berlin (DE); Matthias Renz, Berlin (DE); Dominik Mumberg, Glienicke (DE); Jens Hoffmann, Mühlenbeck (DE); Gerhard Siemeister, Berlin (DE); Ulf Bömer, Glienicke/Nordbahn (DE)

(73) Assignee: Bayer Intellectual Property GmbH, Monheim (DE)

( * ) Notice: Subject to any disclaimer, the term of this patent is extended or adjusted under 35 U.S.C. 154(b) by 456 days.

(21) Appl. No.: 12/678,288

(22) PCT Filed: Sep. 2, 2008

(86) PCT No.: PCT/EP2008/007137
§ 371 (c)(1),
(2), (4) Date: Sep. 2, 2010

(87) PCT Pub. No.: WO2009/033581
PCT Pub. Date: Mar. 19, 2009

(65) Prior Publication Data
US 2011/0021493 A1 Jan. 27, 2011

(30) Foreign Application Priority Data

Sep. 14, 2007 (EP) .................... 07018082

(51) Int. Cl.
*A01N 43/54* (2006.01)
*A01N 43/40* (2006.01)
*A61K 31/505* (2006.01)
*A61K 31/445* (2006.01)
*C07D 239/00* (2006.01)
*C07D 471/00* (2006.01)
*C07D 491/00* (2006.01)
*C07D 401/00* (2006.01)
*C07D 405/00* (2006.01)
*C07D 409/00* (2006.01)

(52) U.S. Cl.
USPC ........... 514/267; 514/322; 544/250; 544/251; 546/256

(58) Field of Classification Search
USPC .......... 514/267, 322; 544/250, 251; 546/256
See application file for complete search history.

(56) References Cited

FOREIGN PATENT DOCUMENTS

| CA | 2365578 A1 | 10/2000 |
| WO | 9313104 A1 | 7/1993 |
| WO | 02088138 A1 | 11/2002 |
| WO | 03035653 A1 | 1/2003 |
| WO | 2005010008 A1 | 2/2005 |
| WO | 2007092879 A2 | 8/2007 |
| WO | 2007097470 A2 | 8/2007 |
| WO | 2007109279 A2 | 9/2007 |
| WO | WO 2007/109279 * | 9/2007 |

OTHER PUBLICATIONS

Janne Pasi A, et al., Phase I dose-escalation study of the pan-HER inhibitor, Clinical cancer research : an official journal of the American Association for Cancer Research, vol. 17, No. 5, pp. 1131-1139 (Mar. 1, 2011).*
West, Anthony R., Solid State Chemistry and Its Applications, Wiley, New York, 1988, 358.*
T. Holbro et al., The ErbB receptors and their role in cancer progression, Exp. Cell Res. 2003, 284 (1), 99-110.
R. I. Nicholson, et al., EGFR and cancer prognosis, Eur. J. Cancer 2001, 37, Suppl. 4, S9-S15.
Y. Yarden et al., Untangling the ErbB Signalling Network, Nat. Rev. Mol. Cell Biol. 2001, 2(2), 127-137.
S. M. Berge et al., Pharmaceutical Salts J. Pharm. Sci. 1977, 66, 1-19.
Sabnis et al., 2-Aminothiophenes by the Gewald Reaction, J. Heterocyclic Chem. 1999, 36, 333-345.
D. S. Yoon et al., Efficient Synthesis of 4-Aminoquinazoline and Thieno[3,2-d]pyrimidin-4-ylamine Derivatives by Microwave Irradation, Org. Lett. 2004, 6, 4775-4778.
M. J. Zacuto and D. Cai, alpha-Hydroxylation of Carbonyls using iodine, Tetrahedron Lett. 2005, 46, 447-450.
DeShong, et al., A General Method for the Synthesis of Tetramic Acid Derivatives, J. Org. Chem. 1988, 53, 1356-1364.
Silvestri et al. Invitro cytotoxic activity of taxol and taxotere on primary cultures and established cell lines of human ovarian cancer, Stem Cells 1993, 11(6), 528-35.
Bissery et al., Docetaxel (Taxotere(R) a review of preclinical and clinical experience. Part 1: Preclinical experience, Anti Cancer Drugs 1995, 6(3), 339.
Edelman et al., Promising new agents in the treatment of non-small cell lung cancer, Cancer Chemother. Pharmacol. 1996, 37(5), 385-393.
S. P. Crouch, et al., The Use of ATP Bioluminescence as a Measure of Cell Proliferation and Cytotoxicidy, J. Immum. Methods, 1993, 160, 81-88.
American Cancer Society, Cancer Facts and Figures 2005.
The Scientist 2001, 15(13), 26.
JP 01-313480 [Chem. Abstr. 112:216955 (1990)].

* cited by examiner

*Primary Examiner* — Erich A Leeser

(57) ABSTRACT

This invention relates to novel compounds and processes for their preparation, methods of treating diseases, particularly cancer, comprising administering said compounds, and methods of making pharmaceutical compositions for the treatment or prevention of disorders, particularly cancer.

20 Claims, No Drawings

SUBSTITUTED TRICYCLIC COMPOUNDS AND METHODS OF USE THEREOF

This invention relates to novel compounds and processes for their preparation, methods of treating diseases, particularly cancer, comprising administering said compounds, and methods of making pharmaceutical compositions for the treatment or prevention of disorders, particularly cancer.

Cancer is a disease resulting from an abnormal growth of tissue. Certain cancers have the potential to invade into local tissues and also metastasize to distant organs. This disease can develop in a wide variety of different organs, tissues and cell types. Therefore, the term "cancer" refers to a collection of over a thousand different diseases.

Over 4.4 million people worldwide were diagnosed with breast, colon, ovarian, lung, or prostate cancer in 2002 and over 2.5 million people died of these devastating diseases (Globocan 2002 Report; http://www-dep.iarc.fr/globocan/downloads.htm). In the United States alone, over 1.25 million new cases and over 500,000 deaths from cancer were expected in 2005. The majority of these new cases will be cancers of the colon (~100,000), lung (~170,000), breast (~210,000) and prostate (~230,000). Both the incidence and prevalence of cancer is predicted to increase by approximately 15% over the next ten years, reflecting an average growth rate of 1.4% (American Cancer Society, Cancer Facts and Figures 2005; http://www.cancer.org/docroot/STT/content/STT_1x_Cancer_Facts_Figures_2007.asp).

Cancer treatments are of two major types, either curative or palliative. The main curative therapies for cancer are surgery and radiation. These options are generally successful only if the cancer is found at an early localized stage. Once the disease has progressed to locally advanced cancer or metastatic cancer, these therapies are less effective and the goal of therapy aims at symptom palliation and maintaining good quality of life. The most prevalent treatment protocols in either treatment mode involve a combination of surgery, radiation therapy and/or chemotherapy.

Cytotoxic drugs (also known as cytoreductive agents) are used in the treatment of cancer, either as a curative treatment or with the aim of prolonging life or palliating symptoms. Cytotoxics may be combined with radiotherapy and/or surgery, as neo-adjuvant treatment (initial chemotherapy aimed at shrinking the tumor, thereby rendering local therapy such as surgery and radiation more effective) or as adjuvant chemotherapy (used in conjunction or after surgery and/or localized therapy). Combinations of different drugs are frequently more effective than single drugs: they may provide an advantage in certain tumors of enhanced response, reduced development of drug resistance and/or increased survival. It is for these reasons that the use of combined cytotoxic regimens in the treatment of many cancers is very common.

Cytotoxic agents in current use employ different mechanisms to block proliferation and induce cell death. They can be generally categorized into the following groups based on their mechanism of action: the microtubule modulators that interfere with the polymerization or depolymerization of microtubules (e.g. docetaxel, paclitaxel, vinblastine, vinorelbine); anti-metabolites including nucleoside analogs and other inhibitors of key cellular metabolic pathways (e.g. capecitabine, gemcitabine, methotrexate); agents that interact directly with DNA (e.g. carboplatin, cyclophosphamide); anthracycline DNA intercalators that interfere with DNA polymerase and Topoisomerase II (e.g. doxorubicin, epirubicin); and the non-anthracycline inhibitors of Topoisomerase II and I enzymatic activity (e.g. topotecan, irinotecan, and etoposide). Even though different cytotoxic drugs act via different mechanisms of action, each generally leads to at least transient shrinkage of tumors.

Cytotoxic agents continue to represent an important component in an oncologist's arsenal of weapons for use in fighting cancer. The majority of drugs currently undergoing late Phase II and Phase III clinical trials are focusing on known mechanisms of action (tubulin binding agents, anti-metabolites, DNA processing), and on incremental improvements in known drug classes (for example the taxanes or the camptothecins). A small number of cytotoxic drugs based on novel mechanisms have recently emerged. Modes of action for these cytotoxics include inhibition of enzymes involved in DNA modification (e.g. histone deacetylase (HDAC)), inhibition of proteins involved in microtubule movement and cell cycle progression (e.g. kinesins, aurora kinase), and novel inducers of the apoptotic pathway (e.g. bcl-2 inhibitors).

Even though cytotoxic agents remain in the forefront of approaches to treat patients with advanced solid tumors, their limited efficacy and narrow therapeutic indices result in significant side effects. Moreover, basic research into cancer has led to the investigation of less toxic therapies based on the specific mechanisms central to tumor progression. Such studies could lead to effective therapy with improvement of the quality of life for cancer patients. Thus, a new class of therapeutic agents has emerged, referred to as cytostatics. Cytostatics direct their action on tumor stabilization and are generally associated with a more limited and less aggravating side effect profile. Their development has resulted from the identification of specific genetic changes involved in cancer progression and an understanding of the proteins activated in cancer such as tyrosine kinases and serine/threonine kinases.

In addition to direct inhibition of tumor cell targets, cytostatic drugs are being developed to block the process of tumor angiogenesis. This process supplies the tumor with existing and new blood vessels to support continued nourishment and therefore help promote tumor growth. Key tyrosine kinase receptors including Vascular Endothelial Growth Factor Receptor 2 (VEGFR2), Fibroblast Growth Factor 1 (FGFR1) and Tie2 have been shown to regulate angiogenesis and have emerged as highly attractive drug targets.

Several new drugs that are directed at various molecular targets have been approved over the past five years for the treatment of cancer. Imatinib is an inhibitor of the Abl tyrosine kinase and was the first small molecule tyrosine kinase inhibitor to be approved for the treatment of chronic myeloid leukemia (CML). Based on additional activity of imatinib against the receptor tyrosine kinase activated in gastrointestinal stromal tumors (GIST), c-KIT, it was subsequently approved for the treatment of advanced GIST. Erlotinib, a small molecule inhibitor of EGFR, was approved in late 2004 for the treatment of non-small-cell lung carcinoma (NSCLC). Sorafenib, an inhibitor of multiple kinases including c-Raf and VEGFR2, was approved for the treatment of advanced renal cell carcinoma (RCC) in December, 2005. Recently in January of 2006, Sunitinib, a multikinase inhibitor, was approved for the treatment of refractory- or resistant-GIST and advanced RCC. These small molecule inhibitors demonstrate that targeted approaches are successful for the treatment of different types of cancers.

Epidermal growth factor receptors (EGFRs) comprise a family consisting of four known tyrosine kinase receptors, HER1 (EGFR, ErbB1), HER2 (neu, ErbB2), HER3 (ErbB3) and HER4 (ErbB4). These receptors are activated by a number of ligands including EGF, TGFα, epiregulin, amphiregulin and heregulins (neuregulins). The HER family receptors generate cell signaling cascades that transduce extracellular stimulation into intracellular events that control various cellular functions including proliferation, differentiation and apoptosis [T. Holbro, G. Civenni, N. E. Hynes, *Exp. Cell Res.* 284 (1), 99-110 (2003)]. These receptors are elevated and abnormally activated in a large number of epithelial tumors, and this increase has been associated with the disruption of normal cellular control resulting in more aggressive tumors and a poor disease prognosis [R. I. Nicholson, J. M. Gee, M. E. Harper, *Eur. J. Cancer* 37, Suppl. 4, S9-S15 (2001); Y. Yarden, M. X. Sliwkowski, *Nat. Rev. Mol. Cell. Biol.* 2 (2), 127-137 (2001)]. Recently, HER1 mutations conferring increased sensitivity and resistance to HER1 small molecule inhibitors have been identified in clinical samples. The emergence of mutations in this receptor family, especially the mutations conferring resistance to approved HER inhibitors, creates an unmet medical need for inhibitors having an irreversible, dual HER based mechanism.

The technical problem to be solved according to the present invention may therefore be seen in providing alternative compounds having an inhibitory activity on HER kinases, thus offering new therapeutic options for the treatment of diseases, in particular cancer and other proliferative disorders.

WO 00/59912 and WO 03/035653 disclose 2-substituted 5,6,7,8-tetrahydropyrido[4',3':4,5]thieno[2,3-d]pyrimidine derivatives as cGMP phosphodiesterase inhibitors for the treatment of cardiovascular diseases and impotence. Fused 4-amino-thieno[2,3-d]pyrimidines and their use for the treatment of PDE 7B mediated diseases, such as osteoporosis and asthma, have been described in WO 02/088138. JP 01-313480 [*Chem. Abstr.* 112:216955 (1990)] relates to tetrahydropyridothieno- and -furopyrimidine derivatives as agrochemical fungicides. In WO 93/13104, fused 4-amino-thieno[2,3-b]pyridines for the treatment of CNS disorders have been disclosed. Recently, thiatriaza-acenaphthylene-6-carbonitriles as inhibitors of protein kinases were disclosed in WO 2007/092879, and various fused pyrimidine derivatives were described in WO 2007/097470 to possess EGFR and/or HER2 kinase inhibitory activity. In the interim, certain tetrahydropyridothienopyrimidine compounds for treating cancer have been disclosed in WO 2007/109279.

In one aspect, the present invention relates to substituted tricyclic compounds of the general formula (I)

wherein
A is N or C—CN,
D is absent or is —CH$_2$— or —CH(CH$_3$)—,
E is O, S or N—R$^{12}$, wherein
  R$^{12}$ is hydrogen or (C$_1$-C$_4$)-alkyl,
L represents —C(=O)—, —S(=O)$_q$— or —S(=O)(=N—R$^{13}$)—, wherein
  q is 1 or 2,
  and
  R$^{13}$ is hydrogen or (C$_1$-C$_4$)-alkyl,
m is 1 or 2,
n is 1, 2 or 3,
p is 0, 1 or 2,
R$^1$ represents hydrogen or halogen,
R$^2$ represents hydrogen, halogen or (C$_1$-C$_4$)-alkyl,
R$^3$ is selected from the group consisting of hydrogen, halogen, cyano, (C$_1$-C$_4$)-alkyl, (C$_1$-C$_4$)-alkoxy, (C$_2$-C$_4$)-alkenyl and (C$_2$-C$_4$)-alkinyl,
R$^4$ is selected from the group consisting of hydrogen, halogen, cyano, (C$_1$-C$_4$)-alkyl, hydroxy, (C$_1$-C$_4$)-alkoxy, (C$_2$-C$_4$)-alkenyl and (C$_2$-C$_4$)-alkinyl,
R$^5$ is selected from the group consisting of hydrogen, halogen, cyano, (C$_1$-C$_4$)-alkyl, (C$_2$-C$_4$)-alkenyl and (C$_2$-C$_4$)-alkinyl,
or
R$^5$ is a group of the formula ♦-O—(CH$_2$)$_r$—R$^{14}$, wherein
  ♦ denotes the point of attachment,
  r is 0, 1 or 2,
  and
  R$^{14}$ represents phenyl or 5- or 6-membered heteroaryl which are optionally substituted with one to three substituents independently selected from the group consisting of halogen, (C$_1$-C$_4$)-alkyl and (C$_1$-C$_4$)-alkoxy,
or
R$^4$ and R$^5$ are linked together and form a fused heterocyclic moiety of the formula

* indicates the point of attachment to the phenyl ring in R$^4$ position,
** indicates the point of attachment to the phenyl ring in R$^5$ position,
and
R$^{15}$ represents phenyl or 5- or 6-membered heteroaryl which are optionally substituted with one to three substituents independently selected from the group consisting of halogen, (C$_1$-C$_4$)-alkyl and (C$_1$-C$_4$)-alkoxy,
R$^6$ represents a substituent independently selected from the group consisting of (C$_1$-C$_4$)-alkyl, hydroxy and (C$_1$-C$_4$)-alkoxy,
R$^7$ and R$^8$ both represent hydrogen or are taken together to form a bond, resulting in an acetylenic linkage,
and either
R$^9$ and R$^{10}$ are joined, and taken together with the atoms to which they are attached, form a 5- to 7-membered heterocycloalkyl ring which is optionally substituted with one or two substituents independently selected from the group consisting of (C$_1$-C$_4$)-alkyl, hydroxy and (C$_1$-C$_4$)-alkoxy, and
R$^{11}$ represents hydrogen or (C$_1$-C$_4$)-alkyl,
or
R$^9$ is hydrogen,
and then
R$^{10}$ and R$^{11}$ are independently selected from the group consisting of hydrogen, (C$_1$-C$_6$)-alkyl, (C$_3$-C$_{10}$)-cycloalkyl and 4- to 7-membered heterocycloalkyl, wherein
  (i) said (C$_1$-C$_6$)-alkyl is optionally substituted with one to three substituents independently selected from the group consisting of fluoro, cyano, hydroxy, $(C_1-C_4)$-alkoxy, oxo, amino, mono-$(C_1-C_4)$-alkylamino, di-$(C_1-C_4)$-alkylamino, $(C_1-C_4)$-alkylcarbonylamino, $(C_1-C_4)$-alkoxycarbonylamino, hydroxycarbonyl, $(C_1-C_4)$-alkoxycarbonyl, aminocarbonyl, mono-$(C_1-C_4)$-alkylaminocarbonyl, di-$(C_1-C_4)$-alkylaminocarbonyl, $(C_1-C_4)$-alkylsulfonyl, S—$(C_1-C_4)$-alkylsulfonimidoyl, $(C_3-C_7)$-cycloalkyl, phenyl, 5- or 6-membered heteroaryl and 4- to 7-membered heterocycloalkyl, wherein said $(C_3-C_7)$-cycloalkyl, phenyl, 5- or 6-membered heteroaryl and 4- to 7-membered heterocycloalkyl substituents in turn are optionally substituted with one or two residues independently selected from the group consisting of fluoro, chloro, trifluoromethyl, $(C_1-C_4)$-alkyl, hydroxy, $(C_1-C_4)$-alkoxy, amino, mono$(C_1-C_4)$-alkylamino and di-$(C_1-C_4)$-alkylamino, and (ii) said $(C_3-C_{10})$-cycloalkyl and 4- to 7-membered heterocycloalkyl are optionally substituted with one to three substituents independently selected from the group consisting of $(C_1-C_4)$-alkyl, oxo, hydroxy, $(C_1-C_4)$-alkoxy, amino, mono-$(C_1-C_4)$-alkylamino and di-$(C_1-C_4)$-alkylamino, or $R^{10}$ and $R^{11}$ are joined, and taken together with the nitrogen atom to which they are attached, form a 3- to 10-membered heterocycloalkyl ring which is optionally substituted with one or two substituents independently selected from the group consisting of $(C_1-C_6)$-alkyl, hydroxy, $(C_1-C_4)$-alkoxy, amino, mono-$(C_1-C_4)$-alkylamino, di-$(C_1-C_4)$-alkylamino, $(C_1-C_4)$-alkylcarbonylamino, $(C_1-C_4)$-alkylcarbonyl, $(C_1-C_4)$-alkylsulfonyl, hydroxycarbonyl, $(C_1-C_4)$-alkoxycarbonyl, aminocarbonyl, mono-$(C_1-C_4)$-alkylaminocarbonyl, di-$(C_1-C_4)$-alkylaminocarbonyl, $(C_3-C_7)$-cycloalkyl, phenyl, phenoxy, 5- or 6-membered heteroaryl and 4- to 7-membered heterocycloalkyl, wherein (i) said $(C_1-C_6)$-alkyl substituent in turn is optionally substituted with one or two residues independently selected from the group consisting of hydroxy, $(C_1-C_4)$-alkoxy, oxo, amino, mono-$(C_1-C_4)$-alkylamino, di-$(C_1-C_4)$-alkylamino, $(C_1-C_4)$-alkylcarbonylamino, $(C_1-C_4)$-alkoxycarbonylamino, hydroxycarbonyl, $(C_1-C_4)$-alkoxycarbonyl, aminocarbonyl, mono-$(C_1-C_4)$-alkylaminocarbonyl, di-$(C_1-C_4)$-alkylaminocarbonyl and 4- to 7-membered heterocycloalkyl, wherein said $(C_1-C_4)$-alkoxy residue is optionally substituted with hydroxy or $(C_1-C_4)$-alkoxy, and (ii) said $(C_3-C_7)$-cycloalkyl, phenyl, phenoxy, 5- or 6-membered heteroaryl and 4- to 7-membered heterocycloalkyl substituents in turn are optionally substituted with one or two residues independently selected from the group consisting of fluoro, chloro, trifluoromethyl, $(C_1-C_4)$-alkyl, hydroxy, $(C_1-C_4)$-alkoxy, amino, mono-$(C_1-C_4)$-alkylamino and di-$(C_1-C_4)$-alkylamino, or $R^{10}$ and $R^{11}$ are joined, and taken together with the nitrogen atom to which they are attached, form a heterocyclic group of the formula

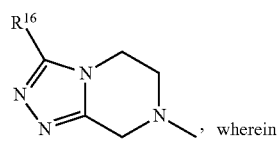, wherein # denotes the point of attachment to the $CHR^9$ group, and $R^{16}$ represents hydrogen, trifluoromethyl or $(C_1-C_4)$-alkyl.

The compounds according to this invention can also be present in the form of their salts, hydrates and/or solvates.

Salts for the purposes of the present invention are preferably pharmaceutically acceptable salts of the compounds according to the invention (for example, see S. M. Berge et al., "Pharmaceutical Salts", *J. Pharm. Sci.* 1977, 66, 1-19).

Pharmaceutically acceptable salts include acid addition salts of mineral acids, carboxylic acids and sulfonic acids, for example salts of hydrochloric acid, hydrobromic acid, sulfuric acid, phosphoric acid, methanesulfonic acid, ethanesulfonic acid, toluenesulfonic acid, benzenesulfonic acid, naphthalenedisulfonic acid, acetic acid, propionic acid, lactic acid, tartaric acid, malic acid, citric acid, fumaric acid, maleic acid and benzoic acid.

Pharmaceutically acceptable salts also include salts of customary bases, such as for example and preferably alkali metal salts (for example sodium and potassium salts), alkaline earth metal salts (for example calcium and magnesium salts), and ammonium salts derived from ammonia or organic amines, such as illustratively and preferably ethylamine, diethylamine, triethylamine, ethyldiisopropylamine, monoethanolamine, diethanolamine, triethanolamine, dicyclohexylamine, dimethylaminoethanol, dibenzylamine, N-methylmorpholine, N-methylpiperidine, dihydroabietylamine, arginine, lysine, and ethylenediamine.

Hydrates of the compounds of the invention or their salts are stoichiometric compositions of the compounds with water, such as, for example, hemi-, mono-, or dihydrates.

Solvates of the compounds of the invention or their salts are stoichiometric compositions of the compounds with solvents.

The compounds of this invention may, either by nature of asymmetric centers or by restricted rotation, be present in the form of isomers (enantiomers, diastereomers). Any isomer may be present in which the asymmetric center is in the (R)-, (S)-, or (R,S) configuration.

It will also be appreciated that when two or more asymmetric centers are present in the compounds of the invention, several diastereomers and enantiomers of the exemplified structures will often be possible, and that pure diastereomers and pure enantiomers represent preferred embodiments. It is intended that pure stereoisomers, pure diastereomers, pure enantiomers, and mixtures thereof, are within the scope of the invention.

Geometric isomers by nature of substituents about a double bond or a ring may be present in cis (=Z-) or trans (=E-) form, and both isomeric forms are encompassed within the scope of this invention.

All isomers, whether separated, pure, partially pure, or in racemic mixture, of the compounds of this invention are encompassed within the scope of this invention. The purification of said isomers and the separation of said isomeric mixtures may be accomplished by standard techniques known in the art. For example, diastereomeric mixtures can be separated into the individual isomers by chromatographic processes or crystallization, and racemates can be separated into the respective enantiomers either by chromatographic processes on chiral phases or by resolution.

In addition, all possible tautomeric forms of the compounds described above are included according to the present invention.

Unless otherwise stated, the following definitions apply for the substituents and residues used throughout this specification and claims:

Alkyl in general represents a straight-chain or branched saturated hydrocarbon radical having 1 to 6, preferably 1 to 4 carbon atoms. Non-limiting examples include methyl, ethyl, n-propyl, isopropyl, n-butyl, isobutyl, sec.-butyl, tert.-butyl, pentyl, isopentyl, neopentyl, hexyl, isohexyl. The same applies to radicals such as alkoxy, alkylamino, alkylcarbonyl, alkylsulfonyl, and the like.

Alkenyl in general represents a straight-chain or branched unsaturated hydrocarbon radical having 2 to 4 carbon atoms and one carbon-carbon double bond. Non-limiting examples include vinyl, allyl, isopropenyl, 2-methylprop-1-en-1-yl, 2-methylprop-2-en-1-yl, n-but-1-en-1-yl, n-but-2-en-1-yl, n-but-3-en-1-yl.

Alkinyl in general represents a straight-chain or branched unsaturated hydrocarbon radical having 2 to 4 carbon atoms and one carbon-carbon triple bond. Non-limiting examples include ethinyl, n-prop-1-in-1-yl, n-prop-2-in-1-yl, 1-methylprop-2-in-1-yl, n-but-1-in-1-yl, n-but-2-in-1-yl, n-but-3-in-1-yl.

Alkoxy illustratively and preferably represents methoxy, ethoxy, n-propoxy, isopropoxy, n-butoxy and tert.-butoxy.

Alkylcarbonyl in general represents a straight-chain or branched alkyl radical having 1 to 4 carbon atoms which is bonded via a carbonyl group to the rest of the molecule. Non-limiting examples include acetyl, n-propionyl, n-butyryl, isobutyryl, pivaloyl.

Alkoxycarbonyl illustratively and preferably represents methoxycarbonyl, ethoxycarbonyl, n-propoxycarbonyl, isopropoxycarbonyl, n-butoxycarbonyl and tert.-butoxycarbonyl.

Alkylsulfonyl in general represents a straight-chain or branched alkyl radical having 1 to 4 carbon atoms which is bonded via a sulfonyl (—SO$_2$—) group to the rest of the molecule. Non-limiting examples include methylsulfonyl, ethylsulfonyl, n-propylsulfonyl, isopropylsulfonyl, n-butylsulfonyl, tert.-butylsulfonyl.

S-Alkylsulfonimidoyl in general represents a straight-chain or branched alkyl radical having 1 to 4 carbon atoms which is bonded via a sulfonimidoyl [—S(=O)(=NH)—] group to the rest of the molecule and which is attached to the sulfur atom of that group. Non-limiting examples include S-methylsulfonimidoyl, S-ethylsulfonimidoyl, S-n-propylsulfonimidoyl, S-isopropylsulfonimidoyl, S-n-butylsulfonimidoyl, S-tert.-butylsulfonimidoyl.

Monoalkylamino in general represents an amino radical having one alkyl residue attached to the nitrogen atom. Non-limiting examples include methylamino, ethylamino, n-propylamino, isopropylamino, n-butylamino, tert.-butylamino. The same applies to radicals such as monoalkylaminocarbonyl.

Dialkylamino in general represents an amino radical having two independently selected alkyl residues attached to the nitrogen atom. Non-limiting examples include N,N-dimethylamino, N,N-diethylamino, N,N-diisopropylamino, N-ethyl-N-methylamino, N-methyl-N-n-propylamino, N-isopropyl-N-n-propylamino, N-tert.-butyl-N-methylamino. The same applies to radicals such as dialkylaminocarbonyl.

Monoalkylaminocarbonyl illustratively and preferably represents methylaminocarbonyl, ethylaminocarbonyl, n-propylaminocarbonyl, isopropylaminocarbonyl, n-butylaminocarbonyl and tert.-butylaminocarbonyl.

Dialkylaminocarbonyl illustratively and preferably represents N,N-dimethylaminocarbonyl, N,N-diethylaminocarbonyl, N,N-diisopropylaminocarbonyl, N-ethyl-N-methylaminocarbonyl, N-methyl-N-n-propylaminocarbonyl, N-isopropyl-N-n-propylaminocarbonyl and N-tert.-butyl-N-methylaminocarbonyl.

Alkylcarbonylamino in general represents a straight-chain or branched alkyl radical having 1 to 4 carbon atoms which is bonded via a carbonylamino (—CO—NH—) group to the rest of the molecule and which is attached to the carbon atom of that group. Non-limiting examples include acetylamino, n-propionylamino, n-butyrylamino, isobutyrylamino, pivaloylamino.

Alkoxycarbonylamino illustratively and preferably represents methoxycarbonylamino, ethoxycarbonylamino, n-propoxycarbonylamino, isopropoxycarbonylamino, n-butoxycarbonylamino and tert.-butoxycarbonylamino.

Cycloalkyl in general represents a mono-, bi- or tricyclic saturated hydrocarbon radical having 3 to 10, preferably 3 to 7, most preferably 3 to 6 carbon atoms. Preference is given to monocyclic cycloalkyl radicals having 3 to 7 carbon atoms. Non-limiting examples include cyclopropyl, cyclobutyl, cyclopentyl, cyclohexyl, cycloheptyl, bicyclo[2.2.1]heptyl, adamantyl.

Heterocycloalkyl in general represents a mono- or bicyclic, saturated heterocyclic radical having a total number of 3 to 10, preferably 4 to 7 ring atoms, including 2 to 8, preferably 3 to 6 carbon atoms and up to 2 heteroatoms and/or heterogroups independently selected from the group consisting of N, O, S, SO and SO$_2$, which ring system can be bonded via a ring carbon atom or, if possible, via a ring nitrogen atom. Non-limiting examples include aziridinyl, azetidinyl, oxetanyl, thietanyl, pyrrolidinyl, pyrazolidinyl, tetrahydrofuranyl, thiolanyl, sulfolanyl, 1,3-dioxolanyl, 1,3-oxazolidinyl, 1,3-thiazolidinyl, piperidinyl, piperazinyl, tetrahydropyranyl, tetrahydrothiopyranyl, 1,3-dioxanyl, 1,4-dioxanyl, morpholinyl, thiomorpholinyl, 1,1-dioxidothiomorpholinyl, perhydroazepinyl, perhydro-1,4-diazepinyl, perhydro-1,4-oxazepinyl, perhydroazocinyl, octahydropyrrolo[3,4-b]pyrrolyl, octahydroisoindolyl, octahydropyrrolo[3,4-b]pyridyl, octahydropyrrolo[1,2-a]pyrazinyl, decahydroisochinolinyl, 7-azabicyclo[2.2.1]heptyl, 3-azabicyclo[3.2.0]heptyl, 7-azabicyclo-[4.1.0]heptyl, 2,5-diazabicyclo[2.2.1]heptyl, 2-oxa-5-azabicyclo[2.2.1]heptyl, 2-azabicyclo-[2.2.2]octyl, 3-azabicyclo[3.2.1]octyl, 8-azabicyclo[3.2.1]octyl, 8-oxa-3-azabicyclo[3.2.1]octyl, 3-oxa-9-azabicyclo[3.3.1]nonyl. Particular preference is given to 5- to 7-membered monocyclic heterocycloalkyl radicals having up to 2 heteroatoms selected from the group consisting of N, O and S, such as illustratively and preferably tetrahydrofuranyl, 1,3-dioxolanyl, pyrrolidinyl, tetrahydropyranyl, 1,4-dioxanyl, piperidinyl, piperazinyl, morpholinyl, thiomorpholinyl, perhydroazepinyl, perhydro-1,4-diazepinyl and perhydro-1,4-oxazepinyl.

Heteroaryl in general represents a monocyclic, aromatic heterocyclic radical having 5 or 6 ring atoms, including up to 3 heteroatoms independently selected from the group consisting of N, O and S, which ring system can be bonded via a ring carbon atom or, if possible, via a ring nitrogen atom. Preference is given to 6-membered heteroaryl radicals having up to 2 nitrogen atoms, such as pyridyl, pyrimidyl, pyridazinyl and pyrazinyl, and to 5-membered heteroaryl radicals having up to 3 heteroatoms selected from the group consisting of N, O and S, such as illustratively and preferably thienyl, furyl, pyrrolyl, thiazolyl, oxazolyl, isothiazolyl, isoxazolyl, pyrazolyl, imidazolyl, oxadiazolyl, thiadiazolyl, triazolyl.

Halogen represents fluorine, chlorine, bromine and iodine.
Oxo represents a doubly bonded oxygen atom.

Throughout this document, for the sake of simplicity, the use of singular language is given preference over plural language, but is generally meant to include the plural language if not otherwise stated. E.g., the expression "A method of treating a disease in a patient, comprising administering to a patient an effective amount of a compound of formula (I)" is meant to include the simultaneous treatment of more than one disease as well as the administration of more than one compound of formula (I).

In a preferred embodiment, the present invention relates to compounds of general formula (I), wherein L is —C(=O)—, p is 0, and $R^7$ and $R^8$ both are hydrogen.

In another preferred embodiment, the present invention relates to compounds of general formula (I), wherein A is C—CN.

In another likewise preferred embodiment, the present invention relates to compounds of general formula (I), wherein D is —CH(CH$_3$)—.

In another likewise preferred embodiment, the present invention relates to compounds of general formula (I), wherein E is O.

In another likewise preferred embodiment, the present invention relates to compounds of general formula (I), wherein m and n both are 1.

In another likewise preferred embodiment, the present invention relates to compounds of general formula (I), wherein m is 2 and n is 1.

In another likewise preferred embodiment, the present invention relates to compounds of general formula (I), wherein m and n both are 2.

In another likewise preferred embodiment, the present invention relates to compounds of general formula (I), wherein m is 1 and n is 3.

In another likewise preferred embodiment, the present invention relates to compounds of general formula (I), wherein $R^4$ is hydroxy.

In a further preferred embodiment, the present invention relates to compounds of general formula (I), wherein
A is N,
D is absent or is —CH(CH$_3$)—,
E is S,
L is —C(=O)—,
m is 1,
n is 2,
p is 0,
$R^1$ represents hydrogen, fluoro or chloro,
$R^2$ represents hydrogen, fluoro, chloro or methyl,
$R^3$ represents hydrogen, fluoro, chloro, cyano, methyl, ethyl, methoxy or ethinyl,
$R^4$ represents hydrogen, fluoro, chloro, cyano, methyl, ethyl, hydroxy, methoxy or ethinyl,
$R^5$ represents hydrogen, fluoro, chloro, cyano or methyl,
or
$R^5$ is a group of the formula ♦-O—CH$_2$—$R^{14}$, wherein
  ♦ denotes the point of attachment,
  and
  $R^{14}$ represents phenyl or pyridyl which are optionally substituted with one or two substituents independently selected from the group consisting of fluoro, chloro, methyl and methoxy,
or
$R^4$ and $R^5$ are linked together and form a fused heterocyclic moiety of the formula

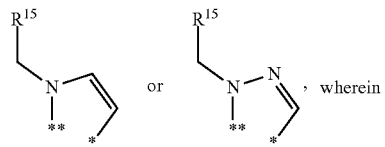

, wherein

* indicates the point of attachment to the phenyl ring in $R^4$ position,
** indicates the point of attachment to the phenyl ring in $R^5$ position,
and
$R^{15}$ represents phenyl or pyridyl which are optionally substituted with one or two substituents independently selected from the group consisting of fluoro, chloro, methyl and methoxy,
$R^7$ and $R^8$ both are hydrogen,
$R^9$ is hydrogen,
$R^{10}$ represents hydrogen, (C$_1$-C$_6$)-alkyl or (C$_3$-C$_7$)-cycloalkyl, wherein said (C$_1$-C$_6$)-alkyl and (C$_3$-C$_7$)-cycloalkyl are optionally substituted with one or two substituents independently selected from the group consisting of hydroxy, (C$_1$-C$_4$)-alkoxy, amino, mono-(C$_1$-C$_4$)-alkylamino and di-(C$_1$-C$_4$)-alkylamino,
and
$R^{11}$ represents (C$_1$-C$_6$)-alkyl which is substituted with one or two substituents independently selected from the group consisting of fluoro, cyano, (C$_1$-C$_4$)-alkoxy, amino, (C$_1$-C$_4$)-alkylcarbonylamino, (C$_1$-C$_4$)-alkoxycarbonylamino, hydroxycarbonyl, (C$_1$-C$_4$)-alkoxycarbonyl, aminocarbonyl, mono-(C$_1$-C$_4$)-alkylaminocarbonyl, di-(C$_1$-C$_4$)-alkylaminocarbonyl, (C$_1$-C$_4$)-alkylsulfonyl, S—(C$_1$-C$_4$)-alkylsulfonimidoyl, (C$_3$-C$_7$)-cycloalkyl, phenyl, 5- or 6-membered heteroaryl and 4- to 7-membered heterocycloalkyl,
  and which may be further substituted with hydroxy, mono-(C$_1$-C$_4$)-alkylamino or di-(C$_1$-C$_4$)-alkylamino,
    wherein said (C$_3$-C$_7$)-cycloalkyl, phenyl, 5- or 6-membered heteroaryl and 4- to 7-membered heterocycloalkyl substituents in turn are optionally substituted with one or two residues independently selected from the group consisting of fluoro, chloro, trifluoromethyl, (C$_1$-C$_4$)-alkyl, hydroxy, (C$_1$-C$_4$)-alkoxy, amino, mono-(C$_1$-C$_4$)-alkylamino and di-(C$_1$-C$_4$)-alkylamino,
or
$R^{11}$ represents (C$_3$-C$_7$)-cycloalkyl which is substituted with one or two substituents independently selected from the group consisting of (C$_1$-C$_4$)-alkyl, oxo, (C$_1$-C$_4$)-alkoxy and amino,
  and which may be further substituted with hydroxy, mono-(C$_1$-C$_4$)-alkylamino or di-(C$_1$-C$_4$)-alkylamino,
or
represents adamantyl,
or
$R^{11}$ represents 4- to 7-membered heterocycloalkyl which is optionally substituted with one or two substituents independently selected from the group consisting of (C$_1$-C$_4$)-alkyl, oxo, hydroxy, (C$_1$-C$_4$)-alkoxy, amino, mono-(C$_1$-C$_4$)-alkylamino and di-(C$_1$-C$_4$)-alkylamino.

In a further preferred embodiment, the present invention relates to compounds of general formula (I), wherein
A is N,
D is absent or is —CH(CH$_3$)—,
E is S,
L is —C(=O)—, m is 1,
n is 2,
p is 0,
$R^1$ represents hydrogen, fluoro or chloro,
$R^2$ represents hydrogen, fluoro, chloro or methyl,
$R^3$ represents hydrogen, fluoro, chloro, cyano, methyl, ethyl, methoxy or ethinyl,
$R^4$ represents hydrogen, fluoro, chloro, cyano, methyl, ethyl, hydroxy, methoxy or ethinyl,
$R^5$ represents hydrogen, fluoro, chloro, cyano or methyl,
or
$R^5$ is a group of the formula ◆-O—CH$_2$—R$^{14}$, wherein
◆ denotes the point of attachment,
and
$R^{14}$ represents phenyl or pyridyl which are optionally substituted with one or two substituents independently selected from the group consisting of fluoro, chloro, methyl and methoxy,
or
$R^4$ and $R^5$ are linked together and form a fused heterocyclic moiety of the formula

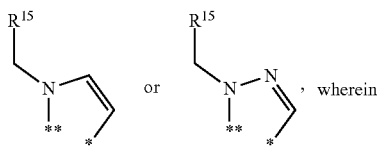

, wherein

* indicates the point of attachment to the phenyl ring in $R^4$ position,
** indicates the point of attachment to the phenyl ring in $R^5$ position,
and
$R^{15}$ represents phenyl or pyridyl which are optionally substituted with one or two substituents independently selected from the group consisting of fluoro, chloro, methyl and methoxy,
$R^7$ and $R^8$ both are hydrogen,
$R^9$ is hydrogen,
and
$R^{10}$ and $R^{11}$ are joined, and taken together with the nitrogen atom to which they are attached, form a heterocycloalkyl group of the formula

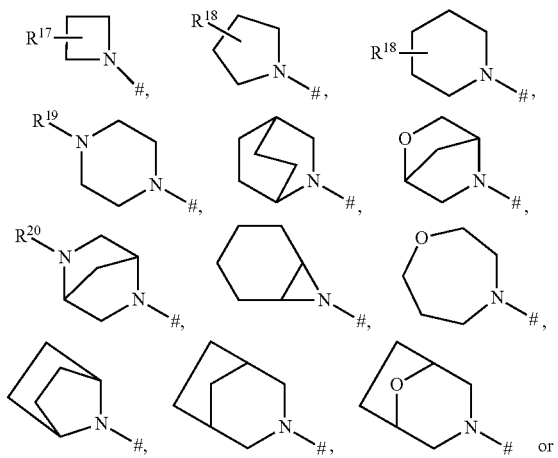

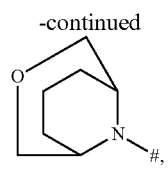

wherein
# denotes the point of attachment to the CHR$^9$ group,
$R^{17}$ represents hydrogen, (C$_1$-C$_4$)-alkoxy, (C$_1$-C$_4$)-alkylcarbonyl, (C$_1$-C$_4$)-alkoxycarbonyl, aminocarbonyl, mono-(C$_1$-C$_4$)-alkylaminocarbonyl, di-(C$_1$-C$_4$)-alkylaminocarbonyl, (C$_3$-C$_6$)-cycloalkyl, phenyl or phenoxy,
wherein said phenyl and phenoxy are optionally substituted with one or two residues independently selected from the group consisting of fluoro, chloro, (C$_1$-C$_4$)-alkyl and (C$_1$-C$_4$)-alkoxy,
or
represents (C$_1$-C$_4$)-alkyl which is optionally substituted with hydroxy, (C$_1$-C$_4$)-alkoxy, amino, mono-(C$_1$-C$_4$)-alkylamino or di-(C$_1$-C$_4$)-alkylamino,
$R^{18}$ represents (C$_1$-C$_4$)-alkylcarbonyl, (C$_1$-C$_4$)-alkoxycarbonyl, aminocarbonyl, mono(C$_1$-C$_4$)-alkylaminocarbonyl, di-(C$_1$-C$_4$)-alkylaminocarbonyl, (C$_3$-C$_6$)-cycloalkyl or phenyl,
or
represents (C$_1$-C$_4$)-alkyl which is substituted with (C$_1$-C$_4$)-alkoxy, amino, mono(C$_1$-C$_4$)-alkylamino, di-(C$_1$-C$_4$)-alkylamino, (C$_1$-C$_4$)-alkylcarbonylamino, (C$_1$-C$_4$)-alkoxycarbonyl, aminocarbonyl, mono-(C$_1$-C$_4$)-alkylaminocarbonyl or di-(C$_1$-C$_4$)-alkylaminocarbonyl,
$R^{19}$ represents hydrogen, (C$_1$-C$_4$)-alkylcarbonyl, (C$_1$-C$_4$)-alkylsulfonyl, (C$_1$-C$_4$)-alkoxycarbonyl, aminocarbonyl, mono-(C$_1$-C$_4$)-alkylaminocarbonyl, di-(C$_1$-C$_4$)-alkylaminocarbonyl, (C$_3$-C$_6$)-cycloalkyl, phenyl or 5- or 6-membered heteroaryl,
wherein said (C$_3$-C$_6$)-cycloalkyl, phenyl and 5- or 6-membered heteroaryl are optionally substituted with one or two residues independently selected from the group consisting of fluoro, chloro, (C$_1$-C$_4$)-alkyl, hydroxy and (C$_1$-C$_4$)-alkoxy,
or
represents (C$_1$-C$_4$)-alkyl which is substituted with one or two residues independently selected from the group consisting of hydroxy, (C$_1$-C$_4$)-alkoxy, oxo, amino, mono-(C$_1$-C$_4$)-alkylamino, di-(C$_1$-C$_4$)-alkylamino, (C$_1$-C$_4$)-alkoxycarbonyl, aminocarbonyl, mono-(C$_1$-C$_4$)-alkylaminocarbonyl, di-(C$_1$-C$_4$)-alkylaminocarbonyl and 5- to 7-membered heterocycloalkyl,
wherein said (C$_1$-C$_4$)-alkoxy residue in turn is optionally substituted with hydroxy, methoxy or ethoxy,
and
$R^{20}$ represents hydrogen, (C$_1$-C$_4$)-alkylcarbonyl, (C$_1$-C$_4$)-alkylsulfonyl, (C$_1$-C$_4$)-alkoxycarbonyl or di-(C$_1$-C$_4$)-alkylaminocarbonyl,
or
represents (C$_1$-C$_4$)-alkyl which is optionally substituted with hydroxy or (C$_1$-C$_4$)-alkoxy.
In a further preferred embodiment, the present invention relates to compounds of general formula (I), wherein
A is N,
D is absent or is —CH(CH$_3$)—,
E is S,
L is —C(=O)—, m is 1,
n is 2,
p is 0,
$R^1$ represents hydrogen, fluoro or chloro,
$R^2$ represents hydrogen, fluoro, chloro or methyl,
$R^3$ represents hydrogen, fluoro, chloro, cyano, methyl, ethyl, methoxy or ethinyl,
$R^4$ represents hydrogen, fluoro, chloro, cyano, methyl, ethyl, hydroxy, methoxy or ethinyl,
$R^5$ represents hydrogen, fluoro, chloro, cyano or methyl,
or
$R^5$ is a group of the formula ♦-O—$CH_2$—$R^{14}$, wherein
  ♦ denotes the point of attachment,
  and
  $R^{14}$ represents phenyl or pyridyl which are optionally substituted with one or two substituents independently selected from the group consisting of fluoro, chloro, methyl and methoxy,
or
$R^4$ and $R^5$ are linked together and form a fused heterocyclic moiety of the formula

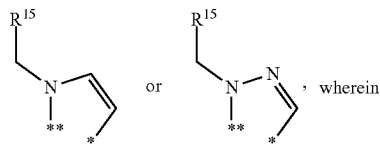, wherein

* indicates the point of attachment to the phenyl ring in $R^4$ position,
** indicates the point of attachment to the phenyl ring in $R^5$ position,
and
$R^{15}$ represents phenyl or pyridyl which are optionally substituted with one or two substituents independently selected from the group consisting of fluoro, chloro, methyl and methoxy,
$R^7$ and $R^8$ both are hydrogen,
$R^9$ and $R^{10}$ are joined, and taken together with the atoms to which they are attached, form a pyrrolidine or piperidine ring which is optionally substituted with one or two substituents independently selected from the group consisting of $(C_1-C_4)$-alkyl, hydroxy and $(C_1-C_4)$-alkoxy,
and
$R^{11}$ represents hydrogen or $(C_1-C_4)$-alkyl.

In a particularly preferred embodiment, the present invention relates to compounds of general formula (I), wherein
A is N,
D is absent,
E is S,
L is —C(═O)—,
m is 1,
n is 2,
p is 0,
$R^1$ represents hydrogen, fluoro or chloro,
$R^2$ represents hydrogen, fluoro or chloro,
$R^3$ represents hydrogen, fluoro, chloro or ethinyl,
$R^4$ represents hydrogen, fluoro, chloro or hydroxy,
$R^5$ represents hydrogen, fluoro or chloro,
or
$R^5$ is a group of the formula ♦-O—$CH_2$—$R^{14}$, wherein
  ♦ denotes the point of attachment,
  and
  $R^{14}$ represents phenyl which is optionally substituted with one or two fluoro atoms, or represents pyridyl, or
$R^4$ and $R^5$ are linked together and form a fused heterocyclic moiety of the formula

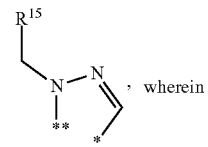, wherein

* indicates the point of attachment to the phenyl ring in $R^4$ position,
** indicates the point of attachment to the phenyl ring in $R^5$ position,
and
$R^{15}$ represents phenyl which is optionally substituted with one or two fluoro atoms, or represents pyridyl,
$R^7$ and $R^8$ both are hydrogen,
$R^9$ is hydrogen,
$R^{10}$ represents hydrogen, $(C_1-C_4)$-alkyl or cyclopropyl, wherein said $(C_1-C_4)$-alkyl is optionally substituted with hydroxy or $(C_1-C_4)$-alkoxy,
and
$R^{11}$ represents $(C_1-C_4)$-alkyl which is substituted with a group selected from $(C_1-C_4)$-alkoxy, hydroxycarbonyl, $(C_1-C_4)$-alkoxycarbonyl, di-$(C_1-C_4)$-alkylaminocarbonyl, $(C_1-C_4)$-alkylsulfonyl, 5- or 6-membered heteroaryl and 4- to 7-membered heterocycloalkyl,
  wherein said 5- or 6-membered heteroaryl and 4- to 7-membered heterocycloalkyl groups in turn are optionally substituted with one or two $(C_1-C_4)$-alkyl residues,
or
$R^{10}$ and $R^{11}$ are joined, and taken together with the nitrogen atom to which they are attached, form a heterocycloalkyl group of the formula

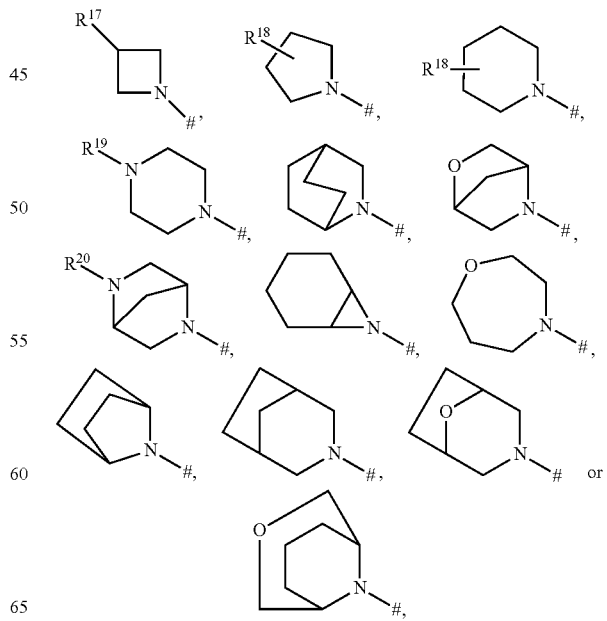

wherein
# denotes the point of attachment to the CHR$^9$ group,
R$^{17}$ represents hydrogen or phenoxy which is optionally substituted with one or two residues independently selected from the group consisting of fluoro, chloro, methyl and methoxy,
R$^{18}$ represents (C$_1$-C$_4$)-alkoxycarbonyl, aminocarbonyl, mono-(C$_1$-C$_4$)-alkylaminocarbonyl or di-(C$_1$-C$_4$)-alkylaminocarbonyl,
or
represents (C$_1$-C$_4$)-alkyl which is substituted with (C$_1$-C$_4$)-alkoxy, (C$_1$-C$_4$)-alkylcarbonylamino or (C$_1$-C$_4$)-alkoxycarbonyl,
R$^{19}$ represents (C$_1$-C$_4$)-alkylcarbonyl, (C$_1$-C$_4$)-alkylsulfonyl, (C$_1$-C$_4$)-alkoxycarbonyl, aminocarbonyl, mono-(C$_1$-C$_4$)-alkylaminocarbonyl, di-(C$_1$-C$_4$)-alkylaminocarbonyl, phenyl, pyridyl or pyrimidinyl,
wherein said phenyl is optionally substituted with hydroxy or methoxy,
or
represents (C$_1$-C$_4$)-alkyl which is substituted with a group selected from hydroxy, (C$_1$-C$_4$)-alkoxy, di-(C$_1$-C$_4$)-alkylamino, (C$_1$-C$_4$)-alkoxycarbonyl, aminocarbonyl, mono-(C$_1$-C$_4$)-alkylaminocarbonyl and di-(C$_1$-C$_4$)-alkylaminocarbonyl,
and
R$^{20}$ represents di-(C$_1$-C$_4$)-alkylaminocarbonyl, or (C$_1$-C$_4$)-alkyl which is optionally substituted with hydroxy or (C$_1$-C$_4$)-alkoxy.

In another particularly preferred embodiment, the present invention relates to compounds of general formula (I), wherein
A is N,
D is absent,
E is S,
L is —C(=O)—,
m is 1,
n is 2,
p is 0,
R$^1$ represents hydrogen, fluoro or chloro,
R$^2$ represents hydrogen, fluoro or chloro,
R$^3$ represents hydrogen, fluoro, chloro or ethinyl,
R$^4$ represents hydroxy,
R$^5$ represents hydrogen, fluoro, chloro or methyl,
R$^7$ and R$^8$ both are hydrogen,
R$^9$ is hydrogen,
R$^{10}$ represents hydrogen, (C$_1$-C$_4$)-alkyl or cyclopropyl, wherein said (C$_1$-C$_4$)-alkyl is optionally substituted with hydroxy, mono-(C$_1$-C$_4$)-alkylamino or di-(C$_1$-C$_4$)-alkylamino,
and
R$^{11}$ represents (C$_1$-C$_6$)-alkyl or (C$_3$-C$_6$)-cycloalkyl which are optionally substituted with one or two substituents independently selected from the group consisting of hydroxy, mono-(C$_1$-C$_4$)-alkylamino and di-(C$_1$-C$_4$)-alkylamino,
or
R$^{10}$ and R$^{11}$ are joined, and taken together with the nitrogen atom to which they are attached, form a heterocycloalkyl group of the formula wherein
# denotes the point of attachment to the CHR$^9$ group,
s is 0, 1 or 2,
R$^{18}$ represents hydrogen, (C$_1$-C$_4$)-alkyl, hydroxy, (C$_1$-C$_4$)-alkoxy, amino, mono-(C$_1$-C$_4$)-alkylamino or di-(C$_1$-C$_4$)-alkylamino,
and
R$^{19}$ represents (C$_1$-C$_4$)-alkyl.

In another particularly preferred embodiment, the present invention relates to compounds of general formula (I), wherein
A is C—CN,
D is absent,
E is S,
L is —C(=O)—,
m is 1,
n is 1 or 2,
p is 0,
R$^1$ represents hydrogen, fluoro or chloro,
R$^2$ represents hydrogen, fluoro or chloro,
R$^3$ represents hydrogen, fluoro, chloro or ethinyl,
R$^4$ represents hydrogen, fluoro, chloro or hydroxy,
R$^5$ represents hydrogen, fluoro or chloro,
or
R$^5$ is a group of the formula ♦-O—CH$_2$—R$^{14}$, wherein
♦ denotes the point of attachment,
and
R$^{14}$ represents phenyl which is optionally substituted with one or two fluoro atoms, or represents pyridyl,
or
R$^4$ and R$^5$ are linked together and form a fused heterocyclic moiety of the formula , wherein

* indicates the point of attachment to the phenyl ring in R$^4$ position,
** indicates the point of attachment to the phenyl ring in R$^5$ position,
and
R$^{15}$ represents phenyl which is optionally substituted with one or two fluoro atoms, or represents pyridyl,
R$^7$ and R$^8$ both are hydrogen,
R$^9$ is hydrogen,
R$^{10}$ represents hydrogen, (C$_1$-C$_4$)-alkyl or cyclopropyl, wherein said (C$_1$-C$_4$)-alkyl is optionally substituted with hydroxy or (C$_1$-C$_4$)-alkoxy,
and
R$^{11}$ represents (C$_1$-C$_4$)-alkyl or (C$_3$-C$_6$)-cycloalkyl, wherein
(i) said (C$_1$-C$_4$)-alkyl is optionally substituted with a group selected from hydroxy, (C$_1$-C$_4$)-alkoxy, amino, mono-(C$_1$-C$_4$)-alkylamino, di-(C$_1$-C$_4$)-alkylamino, hydroxycarbonyl, (C$_1$-C$_4$)-alkoxycarbonyl, di-(C$_1$-C$_4$)-alkylaminocarbonyl, $(C_1-C_4)$-alkylsulfonyl, 5- or 6-membered heteroaryl and 4- to 7-membered heterocycloalkyl,
  wherein said 5- or 6-membered heteroaryl and 4- to 7-membered heterocycloalkyl groups in turn are optionally substituted with one or two $(C_1-C_4)$-alkyl residues,
  and
(ii) said $(C_3-C_6)$-cycloalkyl is optionally substituted with one or two substituents independently selected from the group consisting of $(C_1-C_4)$-alkyl, hydroxy and $(C_1-C_4)$-alkoxy,
or
$R^{10}$ and $R^{11}$ are joined, and taken together with the nitrogen atom to which they are attached, form a heterocycloalkyl group of the formula

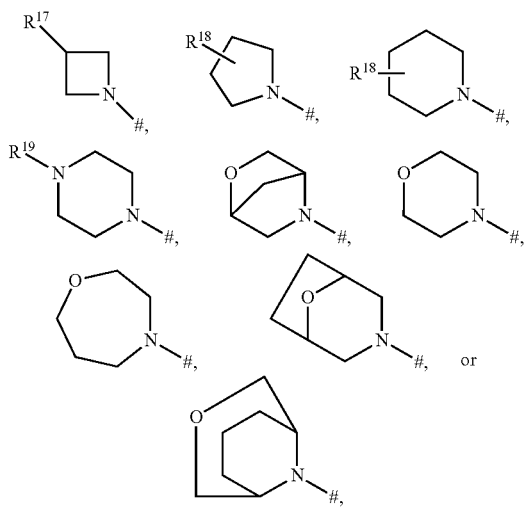

wherein
# denotes the point of attachment to the $CHR^9$ group,
$R^{17}$ represents hydrogen or phenoxy which is optionally substituted with one or two residues independently selected from the group consisting of fluoro, chloro, methyl and methoxy,
$R^{18}$ represents hydrogen, hydroxy, $(C_1-C_4)$-alkoxy, amino, mono-$(C_1-C_4)$-alkylamino, di-$(C_1-C_4)$-alkylamino, $(C_1-C_4)$-alkoxycarbonyl, aminocarbonyl, mono-$(C_1-C_4)$-alkylaminocarbonyl or di-$(C_1-C_4)$-alkylaminocarbonyl,
  or
  represents $(C_1-C_4)$-alkyl which is optionally substituted with hydroxy, $(C_1-C_4)$-alkoxy, amino, mono-$(C_1-C_4)$-alkylamino, di-$(C_1-C_4)$-alkylamino, $(C_1-C_4)$-alkylcarbonylamino or $(C_1-C_4)$-alkoxycarbonyl,
and
$R^{19}$ represents hydrogen, $(C_1-C_4)$-alkylcarbonyl, $(C_1-C_4)$-alkylsulfonyl, $(C_1-C_4)$-alkoxycarbonyl, aminocarbonyl, mono-$(C_1-C_4)$-alkylaminocarbonyl, di-$(C_1-C_4)$-alkylaminocarbonyl, phenyl, pyridyl or pyrimidinyl,
  wherein said phenyl is optionally substituted with hydroxy or methoxy,
  or
  represents $(C_1-C_4)$-alkyl which is optionally substituted with hydroxy, $(C_1-C_4)$-alkoxy, amino, mono-$(C_1-C_4)$-alkylamino, di-$(C_1-C_4)$-alkylamino, $(C_1-C_4)$-alkoxycarbonyl, aminocarbonyl, mono-$(C_1-C_4)$-alkylaminocarbonyl or di-$(C_1-C_4)$-alkylaminocarbonyl.

In another particularly preferred embodiment, the present invention relates to compounds of general formula (I), wherein
A is N or C—CN,
D is absent,
E is O,
L is —C(=O)—,
m is 1,
n is 2,
p is 0,
$R^1$ represents hydrogen, fluoro or chloro,
$R^2$ represents hydrogen, fluoro or chloro,
$R^3$ represents hydrogen, fluoro, chloro or ethinyl,
$R^4$ represents hydrogen, fluoro, chloro or hydroxy,
$R^5$ represents hydrogen, fluoro or chloro,
or
$R^5$ is a group of the formula ♦-O—CH$_2$—$R^{14}$, wherein
  ♦ denotes the point of attachment,
  and
  $R^{14}$ represents phenyl which is optionally substituted with one or two fluoro atoms, or represents pyridyl,
or
$R^4$ and $R^5$ are linked together and form a fused heterocyclic moiety of the formula

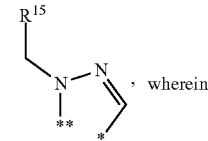, wherein

* indicates the point of attachment to the phenyl ring in $R^4$ position,
** indicates the point of attachment to the phenyl ring in $R^5$ position,
and
$R^{15}$ represents phenyl which is optionally substituted with one or two fluoro atoms, or represents pyridyl,
$R^7$ and $R^8$ both are hydrogen,
$R^9$ is hydrogen,
$R^{10}$ represents hydrogen, $(C_1-C_4)$-alkyl or cyclopropyl, wherein said $(C_1-C_4)$-alkyl is optionally substituted with hydroxy or $(C_1-C_4)$-alkoxy,
and
$R^{11}$ represents $(C_1-C_4)$-alkyl or $(C_3-C_6)$-cycloalkyl, wherein
  (i) said $(C_1-C_4)$-alkyl is optionally substituted with a group selected from hydroxy, $(C_1-C_4)$-alkoxy, amino, mono-$(C_1-C_4)$-alkylamino, di-$(C_1-C_4)$-alkylamino, hydroxycarbonyl, $(C_1-C_4)$-alkoxycarbonyl, di-$(C_1-C_4)$-alkylaminocarbonyl, $(C_1-C_4)$-alkylsulfonyl, 5- or 6-membered heteroaryl and 4- to 7-membered heterocycloalkyl,
    wherein said 5- or 6-membered heteroaryl and 4- to 7-membered heterocycloalkyl groups in turn are optionally substituted with one or two $(C_1-C_4)$-alkyl residues,
    and
  (ii) said $(C_3-C_6)$-cycloalkyl is optionally substituted with one or two substituents independently selected from the group consisting of $(C_1-C_4)$-alkyl, hydroxy and $(C_1-C_4)$-alkoxy.

In another particularly preferred embodiment, the present invention relates to compounds of general formula (I), wherein
A is N,
D is absent,
E is S,
L is —C(=O)—,
m is 1,
n is 1,
p is 0,
$R^1$ represents hydrogen, fluoro or chloro,
$R^2$ represents hydrogen, fluoro or chloro,
$R^3$ represents hydrogen, fluoro, chloro or ethinyl,
$R^4$ represents hydrogen, fluoro, chloro or hydroxy,
$R^5$ represents hydrogen, fluoro or chloro,
or
$R^5$ is a group of the formula ♦-O—CH$_2$—R$^{14}$, wherein
  ♦ denotes the point of attachment,
  and
  $R^{14}$ represents phenyl which is optionally substituted with one or two fluoro atoms, or represents pyridyl,
or
$R^4$ and $R^5$ are linked together and form a fused heterocyclic moiety of the formula

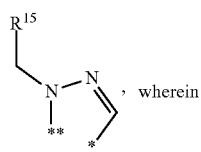, wherein

* indicates the point of attachment to the phenyl ring in $R^4$ position,
** indicates the point of attachment to the phenyl ring in $R^5$ position,
and
$R^{15}$ represents phenyl which is optionally substituted with one or two fluoro atoms, or represents pyridyl,
$R^7$ and $R^8$ both are hydrogen,
$R^9$ is hydrogen,
$R^{10}$ represents hydrogen, (C$_1$-C$_4$)-alkyl or cyclopropyl, wherein said (C$_1$-C$_4$)-alkyl is optionally substituted with hydroxy or (C$_1$-C$_4$)-alkoxy,
and
$R^{11}$ represents (C$_1$-C$_4$)-alkyl or (C$_3$-C$_6$)-cycloalkyl, wherein
  (i) said (C$_1$-C$_4$)-alkyl is optionally substituted with a group selected from hydroxy, (C$_1$-C$_4$)-alkoxy, amino, mono-(C$_1$-C$_4$)-alkylamino, di-(C$_1$-C$_4$)-alkylamino, hydroxycarbonyl, (C$_1$-C$_4$)-alkoxycarbonyl, di-(C$_1$-C$_4$)-alkylaminocarbonyl, (C$_1$-C$_4$)-alkyl sulfonyl, 5- or 6-membered heteroaryl and 4- to 7-membered heterocycloalkyl,
    wherein said 5- or 6-membered heteroaryl and 4- to 7-membered heterocycloalkyl groups in turn are optionally substituted with one or two (C$_1$-C$_4$)-alkyl residues,
  and
  (ii) said (C$_3$-C$_6$)-cycloalkyl is optionally substituted with one or two substituents independently selected from the group consisting of (C$_1$-C$_4$)-alkyl, hydroxy and (C$_1$-C$_4$)-alkoxy.

In another embodiment, the present invention relates to a process for preparing the compounds of general formula (I), comprising

[A] Reacting a Compound of Formula (II)

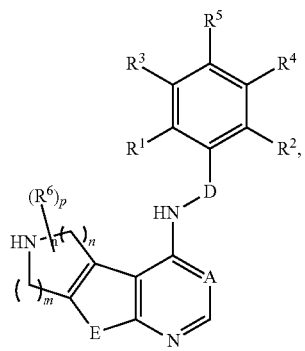

wherein A, D, E, $R^1$ to $R^6$, m, n and p have the meanings described above,
in the presence of an amide coupling reagent and/or a base, with a compound of formula (III)

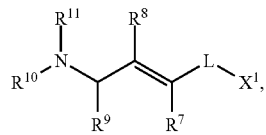

wherein L and $R^7$ to $R^{11}$ have the meanings described above,
and
$X^1$ represents hydroxy or a leaving group such as chloro or bromo,
or
[B] Reacting a Compound of Formula (IV)

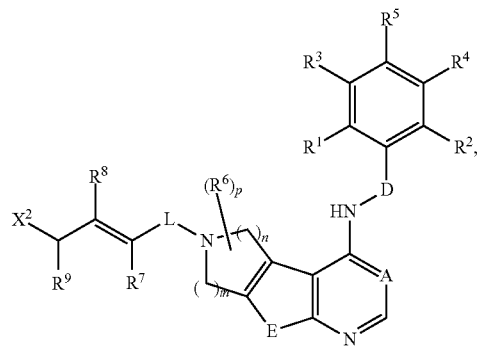

wherein A, D, E, L, $R^1$ to $R^9$, m, n and p have the meanings described above, and
$X^2$ represents a leaving group such as chloro, bromo, iodo, mesylate or tosylate, optionally in the presence of an auxiliary base, with a compound of formula (V)

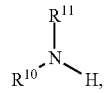

wherein $R^{10}$ and $R^{11}$ have the meanings described above, or

[C] Reacting a Compound of Formula (VI)

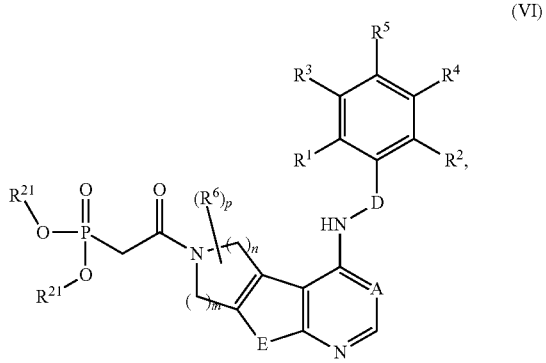

(VI)

wherein A, D, E, $R^1$ to $R^6$, m, n and p have the meanings described above,
and
$R^{21}$ represents $(C_1-C_4)$-alkyl,
in the presence of a base, with a compound of formula (VII)

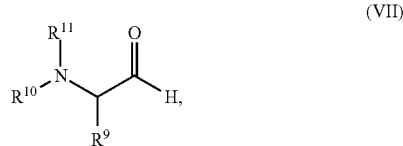

(VII)

wherein $R^9$, $R^{10}$ and $R^{11}$ have the meanings described above, or

[D] Reacting a Compound of Formula (VIII)

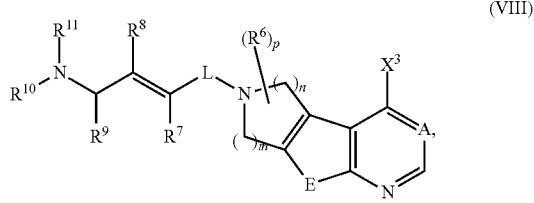

(VIII)

wherein A, E, L, $R^6$ to $R^{11}$, m, n and p have the meanings described above,
and
$X^3$ represents a leaving group such as chloro, bromo or iodo,
in the presence of an acid or base or by means of a palladium catalyst, with a compound of formula (IX)

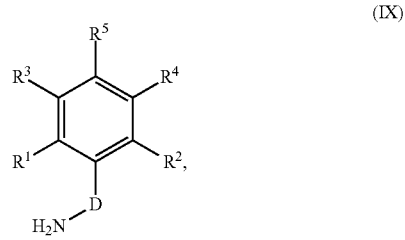

(IX)

wherein D and $R^1$ to $R^5$ have the meanings described above,
and optionally converting the resulting compounds of formula (I) into their hydrates, solvates, salts and/or hydrates or solvates of the salts by treatment with the corresponding solvents and/or acids or bases.

If not mentioned otherwise, the reactions described above are usually carried out in inert organic solvents which do not change under the reactions conditions.

Suitable solvents for process [A] include ethers such as diethyl ether, diisopropyl ether, methyl tert-butyl ether, 1,2-dimethoxyethane, 1,4-dioxan, tetrahydrofuran and bis-(2-methoxyethyl)-ether, hydrocarbons such as pentane, hexane, cyclohexane, benzene, toluene and xylene, halogenated hydrocarbons such as dichloromethane, trichloromethane, carbon tetrachloride, 1,2-dichloroethane, chlorobenzene and chlorotoluene, or other solvents such as pyridine, acetonitrile, dimethylsulfoxide (DMSO), N,N-dimethylformamide (DMF), N-methylpyrrolidinone (NMP) and N,N'-dimethylpropylene urea (DMPU). It is also possible to use mixtures of these solvents. Preferred solvents are tetrahydrofuran, dichloromethane and N,N-dimethylformamide.

Suitable bases for process [A] ($X^1$=Cl or Br) are customary organic bases. These include $(C_1-C_4)$-trialkylamines such as triethylamine and N,N-diisopropylethylamine, or cyclic tertiary amines such as N-methylpiperidine, N-methylmorpholine, pyridine and 4-N,N-dimethylaminopyridine. Preferred bases are triethylamine, N,N-diisopropylethylamine and pyridine.

Suitable condensing (amide coupling) reagents for process [A] ($X^1$=OH) include carbodiimides such as N,N'-diethyl-, N,N'-dipropyl-, N,N'-diisopropyl-, N,N'-dicyclohexylcarbodiimide (DCCI) or N-(3-dimethylaminoisopropyl)-N'-ethylcarbodiimide (EDCI), phosgene derivatives such as N,N'-carbonyldiimidazole (CDI), chloroformates such as isobutyl chloroformate, phosphonic acid derivatives such as propanephosphonic acid anhydride or cyanophosphonic acid diethylester, or other reagents such as bis-(2-oxo-3-oxazolidinyl) phosphoryl chloride, benzotriazol-1-yloxy-tris(dimethylamino)phosphonium hexafluorophosphate, benzotriazol-1-yloxy-tris(pyrrolidino)phosphonium hexafluorophosphate (PyBOP), O-(benzotriazol-1-yl)-N,N,N',N'-tetramethyluronium tetrafluoroborate (TBTU), O-(benzotriazol-1-yl)-N,N,N',N'-tetramethyluronium hexafluorophosphate (HBTU), 2-(2-oxo-1-(2H)-pyridyl)-1,1,3,3-tetramethyluronium tetrafluoroborate (TPTU), O-(7-azabenzotriazol-1-yl)-N,N,N',N'-tetramethyluronium hexafluorophosphate (HATU) or O-(1H-6-chlorobenzotriazol-1-yl)-1,1,3,3-tetramethyluronium tetrafluoroborate (TCTU), optionally in combination with further auxiliary agents such as 1-hydroxybenzotriazole (HOBt) or N-hydroxysuccinimide (HOSu), and bases such as alkali carbonates, e.g. sodium or potassium carbonate, or organic bases such as triethylamine, N-methylmorpholine, N-methylpiperidine, N,N-diisopropylethylamine or 4-N,N-dimethylaminopyridine. Preferred as coupling reagent is O-(benzotriazol-1-yl)-N,N,N',N'-tetramethyluronium tetrafluoroborate (TBTU).

Process [A] is usually performed at a temperature range from −20° C. to +60° C., preferably from 0° C. to +40° C., at normal pressure. However, it is also possible to run the reaction at elevated pressure or at reduced pressure (for example in a range from 0.5 to 5 bar).

Suitable solvents for process [B] include ethers such as diethyl ether, diisopropyl ether, methyl tert-butyl ether, 1,2-dimethoxyethane, 1,4-dioxan, tetrahydrofuran and bis-(2-methoxyethyl)-ether, halogenated hydrocarbons such as dichloromethane, trichloromethane, carbon tetrachloride, 1,2-dichloroethane, chlorobenzene and chlorotoluene, or other solvents such as pyridine, acetone, acetonitrile, dimethylsulfoxide (DMSO), N,N-dimethylformamide (DMF), N-methylpyrrolidinone (NMP) and N,N'-dimethylpropylene urea (DMPU). It is also possible to use mixtures of these solvents. N,N-Dimethylformamide is preferably used as solvent.

Suitable auxiliary bases for process [B] are $(C_1-C_4)$-trialkylamines such as triethylamine and N,N-diisopropylethylamine, or cyclic amines such as N-methylpiperidine, N-methylmorpholine, pyridine and 4-N,N-dimethylaminopyridine. Preferred bases are triethylamine and N,N-diisopropylethylamine.

Process [B] is usually performed at a temperature range from 0° C. to +100° C., preferably from +20° C. to +60° C., at normal pressure. However, it is also possible to run the reaction at elevated pressure or at reduced pressure (for example in a range from 0.5 to 5 bar).

Process [C] is usually carried out in ether solvents such as diethyl ether, diisopropyl ether, methyl tert-butyl ether, 1,2-dimethoxyethane or tetrahydrofuran. As base, sodium hydride is preferably used. The reaction is generally performed at a temperature range from −78° C. to +30° C. at normal pressure.

Suitable solvents for process [D] include ethers such as diethyl ether, diisopropyl ether, methyl tert-butyl ether, 1,2-dimethoxyethane, 1,4-dioxan, tetrahydrofuran and bis-(2-methoxyethyl)-ether, alcohols such as methanol, ethanol, n-propanol, isopropanol, n-butanol, tert-butanol and 2-methoxyethanol, or other solvents such as acetonitrile, dimethylsulfoxide (DMSO), N,N-dimethylformamide (DMF), N-methylpyrrolidinone (NMP) and N,N'-dimethylpropylene urea (DMPU), as well as water. It is also possible to use mixtures of these solvents. Preferred solvents are isopropanol, 2-methoxyethanol, tetrahydrofuran, N,N-dimethylformamide, and their mixtures.

In process [D], when A in formula (VIII) is N and D in formula (IX) is absent, the reaction can be favorably carried out in the presence of an acid, such as hydrochloric acid, acetic acid, trifluoroacetic acid, methanesulfonic acid, p-toluenesulfonic acid or pyridinium hydrochloride.

When A in formula (VIII) is N and D in formula (IX) represents —CH$_2$— or —CH(CH$_3$)—, process [D] is preferably performed in the presence of an organic base, such as triethylamine or N,N-diisopropylethylamine.

When A in formula (VIII) is C—CN and D in formula (IX) is absent, process [D] is carried out by means of palladium catalysis using, for example, tris(dibenzylideneacetone)dipalladium(0), tetrakis(triphenylphosphine)palladium(0), bis(triphenylphosphine)palladium(II)chloride, bis(acetonitrile)palladium(II)chloride, [1,1'-bis(diphenylphosphino)ferrocene]palladium(II) chloride or palladium(II) acetate as catalyst, optionally in combination with additional phosphane ligands such as, for example, dicyclohexyl[2',4',6'-tris(1-methylethyl)biphenyl-2-yl]phosphane (XPHOS).

Process [D] is usually performed at a temperature range from +20° C. to +120° C., preferably from +50° C. to +100° C., at normal pressure. However, it is also possible to run the reaction at elevated pressure or at reduced pressure (for example in a range from 0.5 to 5 bar).

The compounds of the invention and their respective precursors and intermediates, such as compounds (II), (III), (IV), (VI), (VIII) and (IX) described above, may be prepared by use of known chemical reactions and procedures. It will be also understood that starting materials are commercially available or are readily prepared by standard methods well known in the art. Such methods include, but are not limited to the transformations listed herein.

Nevertheless, the following general preparative methods are presented to aid the reader in synthesizing said compounds, with more detailed particular examples being presented below in the experimental section describing the Examples. The preparation of the compounds of the invention can be illustrated by means of the following synthetic schemes A-F:

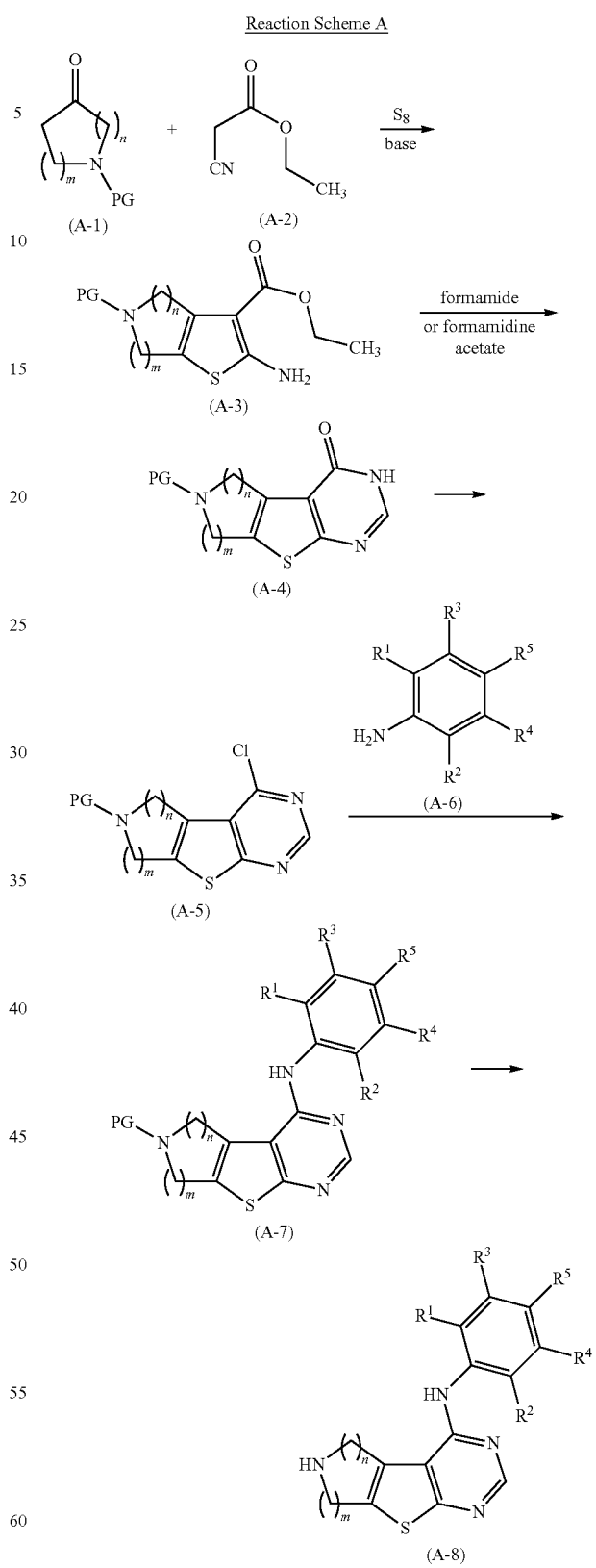

[PG = protecting group].

As shown in Scheme A, a cyclic ketone (A-1) is coupled with an appropriate cyanoacetic ester (A-2) in the presence of elemental sulfur and a base such as morpholine, triethylamine, diisopropylethylamine or diethylamine, preferably at room temperature, to yield the aminothiophene ester of formula (A-3) according to the procedure of Gewald, *J. Heterocyclic Chem.* 1999, 36, 333-345. The aminothiophene ester (A-3) is then converted to a compound of formula (A-4) by reaction with a formamide-containing reagent such as neat formamide or formamidine acetate, in a polar solvent such as DMF, with heat, preferably to 100° C. or above. Heating the compound of formula (A-4) with a chlorinating agent such as phosphorous oxychloride, preferably in sulfolane as solvent, provides compound (A-5) which is subsequently reacted with an aniline (A-6) in the presence of a catalytic amount of concentrated acid, such as hydrochloric acid, and a protic solvent, such as ethanol or isopropanol, to yield compound (A-7). Cleavage of the protecting group PG then affords compounds of formula (A-8).

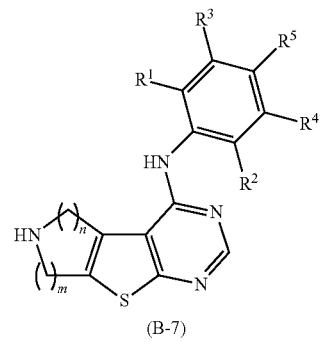

(B-7)

As an alternative to the procedure depicted in Scheme A, the ketone (B-1) may be cyclized with malonodinitrile (B-2) instead of cyanoacetic ester (A-2) in the presence of elemental sulfur and a base such as morpholine, triethylamine, diisopropylethylamine or diethylamine, preferably at room temperature, to yield the aminothiophene nitrile of formula (B-3), as depicted in Scheme B. The condensation with DMF dimethylacetal yields the [(dimethylamino)methylidene]amino-substituted compound (B-4), which is subsequently cyclized with aniline (B-5) in a protic solvent, preferably a acetonitrile/acetic acid mixture, to yield the compound (B-6), as described by D. S. Yoon et al., *Org. Lett.* 2004, 6, 4775-4778. Cleavage of the protecting group PG then affords compounds of formula (B-7).

Reaction Scheme B

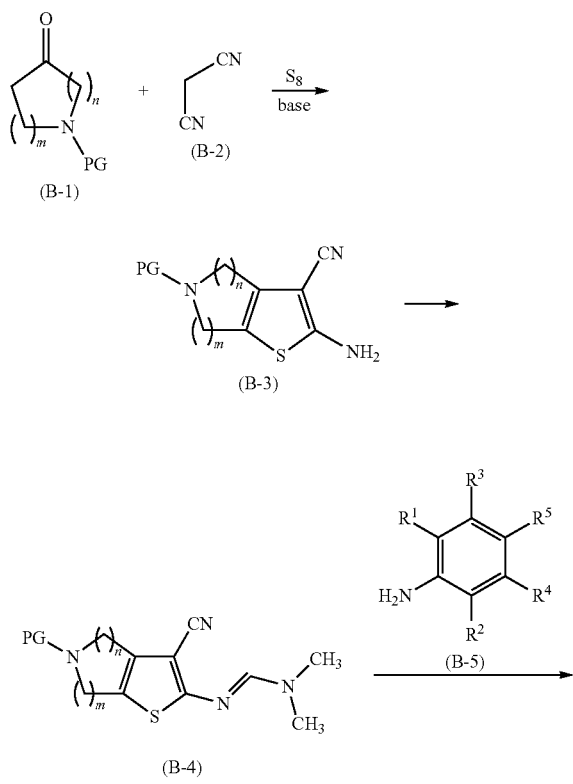

Reaction Scheme C

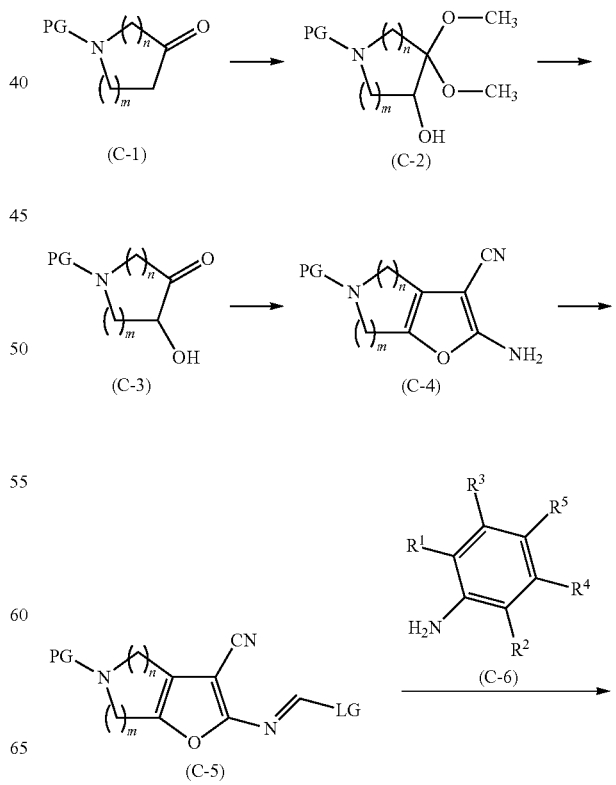

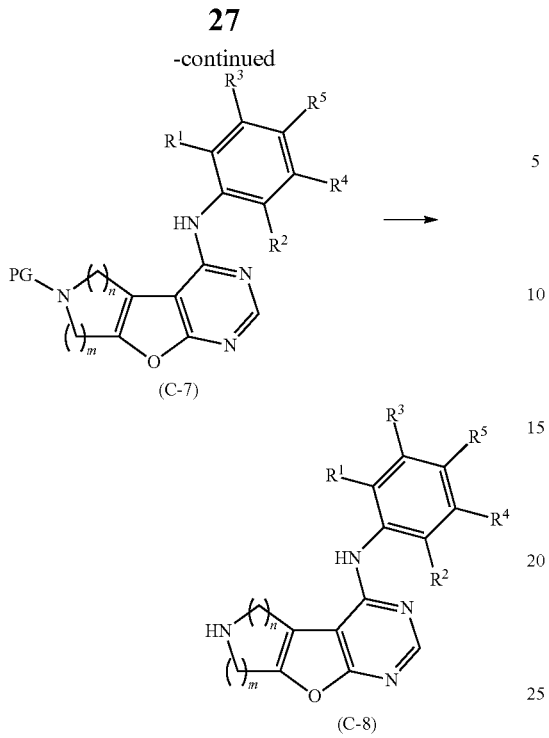

(C-7)

(C-8)

[LG = leaving group].

Furane containing compounds can be synthesized by hydroxylation of cyclic ketones (C-1) with potassium hydroxide and iodine in methanol and subsequent acidic cleavage of the acetal, following a method described by M. J. Zacuto and D. Cai, *Tetrahedron Lett.* 2005, 46, 447-450. The reaction of hydroxyketone (C-3) with malonodinitrile in alcoholic solution and in the presence of a base, preferably diethylamine, diisopropylethylamine, triethylamine or morpholine, yields the aminofurane (C-4). The latter is condensed to a compound (C-5) with DMF dimethylacetal (LG=NMe$_2$), triethyl orthoester (LG=OEt) or trimethyl orthoester (LG=OMe), which can be cyclized with an aniline (C-6) to compound (C-7) similarly to the reaction of (B-4) in Scheme B. Cleavage of the protecting group PG then affords compound (C-8).

Reaction Scheme D

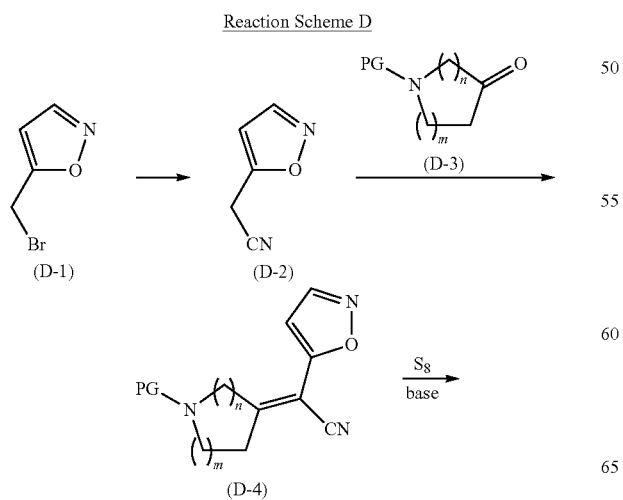

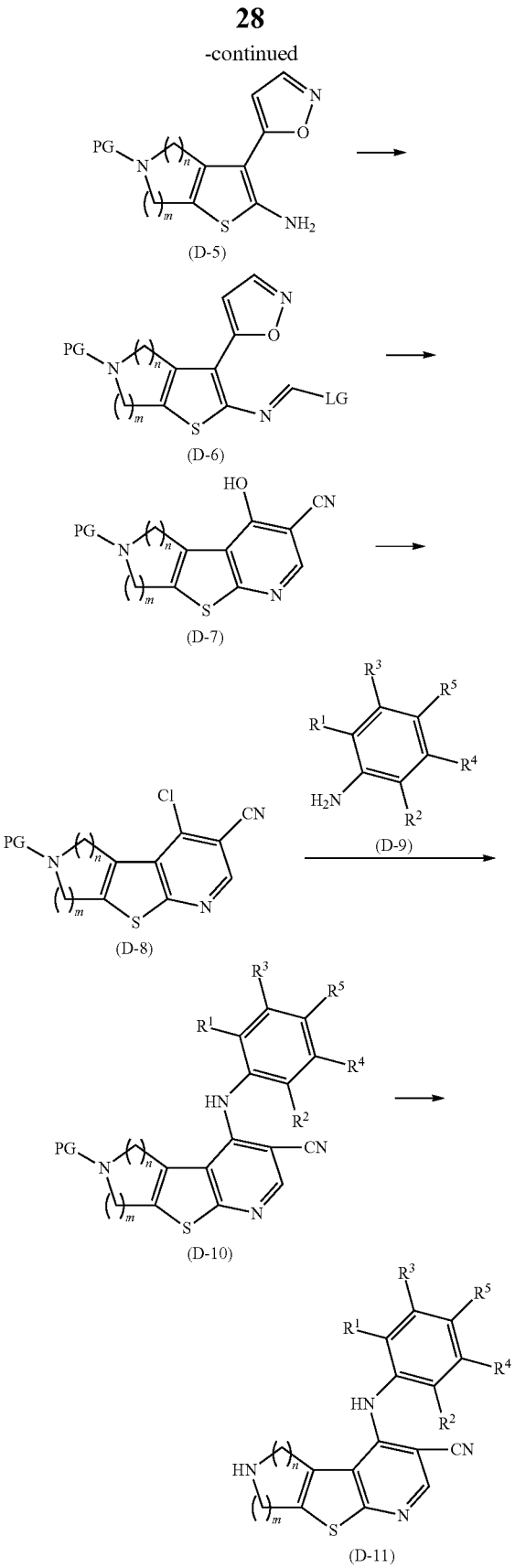

3-Cyanopyridine containing compounds can be synthesized starting from 5-(bromomethyl)isoxazole (D-1) [P. DeShong, J. A. Cipollina, N. K. Lowmaster, *J. Org. Chem.* 1988, 53, 1356-1364]. The bromide is reacted in DMSO/water with potassium cyanide to yield nitrile (D-2). The condensation reaction with ketone (D-3) under buffered conditions like ammonium acetate in toluene at elevated temperature yields compound (D-4), which reacts with elemental sulfur in an alcoholic solution in the presence of a base, preferably triethylamine, diisopropylethylamine, morpholine or diethylamine, to aminothiophene (D-5). The latter is condensated to a compound (D-6) with DMF dimethylacetal (LG=NMe$_2$), triethyl orthoester (LG=OEt) or trimethyl orthoester (LG=OMe), which cyclizes spontaneously to compound (D-7) upon treatment with base, preferably an alcoholic sodium alcoholate solution. Chlorination to (D-8) may be achieved with a reagent such as phosphorous oxychloride, preferably in sulfolane as solvent. (D-8) is reacted with aniline (D-9) under palladium catalysis to yield (D-10), which is then deprotected to compound (D-11).

Reaction Scheme F

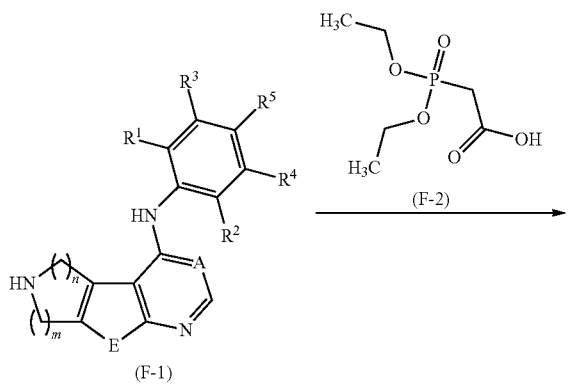

Reaction Scheme E

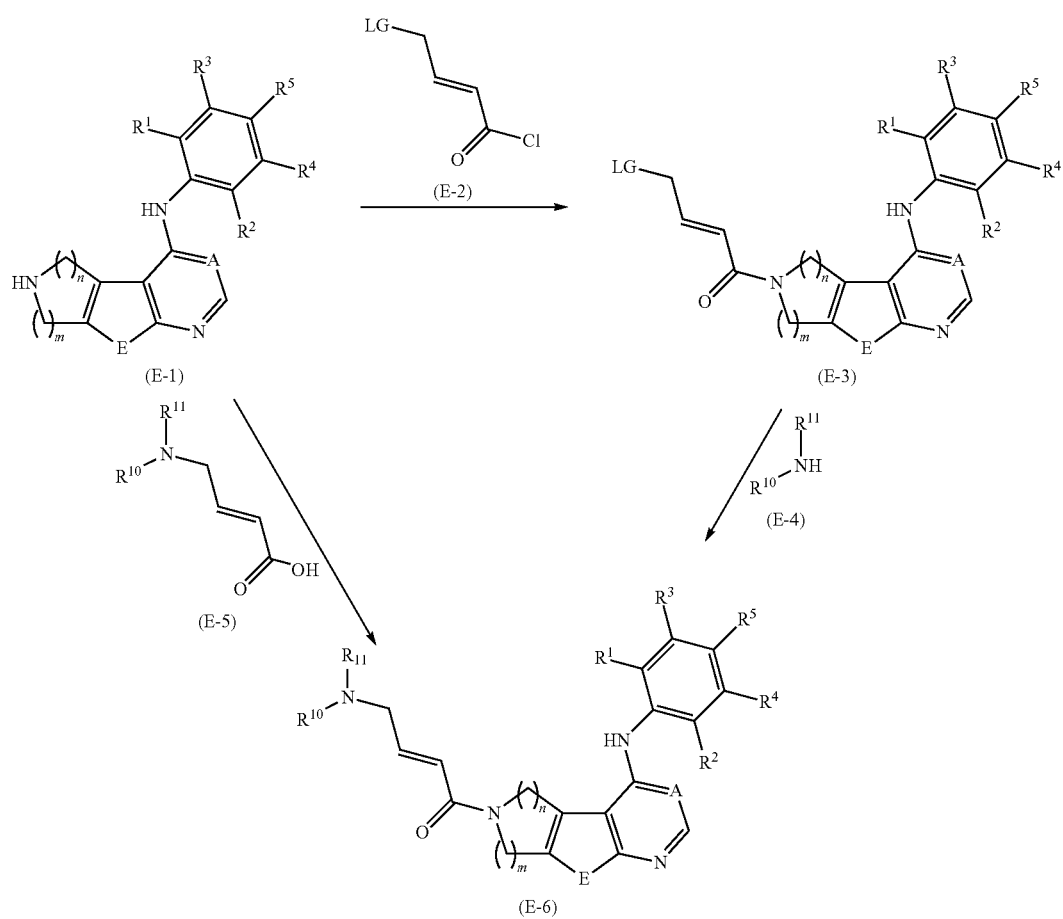

As depicted in Scheme E, the unsaturated side chain may be introduced by the reaction of a compound (E-1) with a butenoic acid chloride (E-2), which may be obtained from the corresponding acid by treatment with thionyl chloride. The amine residue can be introduced by nucleophilic displacement of an appropriate leaving group LG, preferably chloride or bromide. In an alternative pathway, the amine may be introduced prior to amide formation, yielding a reagent (E-5), which is then coupled to compound (E-1) by means of a coupling reagent, preferably O-(benzotriazol-1-yl)N,N,N', N'-tetramethyluronium tetrafluoroborate (TBTU).

-continued

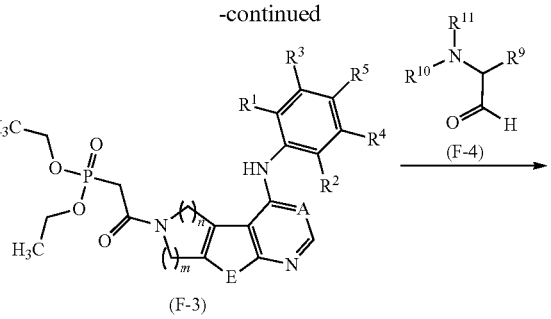

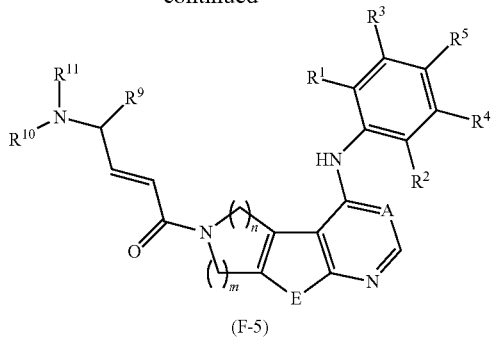

(F-5)

As an alternative procedure, the unsaturated side chain may be introduced by means of a Horner-Wadsworth-Emmons reaction as depicted in Scheme F. Compound (F-1) can be reacted with (diethoxyphosphoryl)acetic acid (F-2) in the presence of a coupling reagent, preferably TBTU, to yield phosphonate (F-3). Upon deprotonation, preferably with sodium hydride, the reaction with an aldehyde (F-4) yields the target compound (F-5).

Methods of Use

The compounds of the present invention may be used to inhibit the activity of tyrosine kinases, particularly including HER1 (EGFR) and HER2. Therefore, the compounds of formula (I) are expected to be valuable as therapeutic agents. Accordingly, in another embodiment, the present invention provides a method of treating a cell proliferative disorder in a patient in need of such treatment, comprising administering to the patient an effective amount of a compound of formula (I) as defined above. In certain embodiments, the cell proliferative disorder is cancer.

The term "treating" or "treatment" as stated throughout this document is used conventionally, e.g., the management or care of a subject for the purpose of combating, alleviating, reducing, relieving, improving the condition of a disease or disorder, such as a carcinoma.

The term "subject" or "patient" includes organisms which are capable of suffering from a cell proliferative disorder or who could otherwise benefit from the administration of a compound of the invention, such as human and non-human animals. Preferred humans include human patients suffering from or prone to suffering from a cell proliferative disorder or associated state, as described herein. The term "non-human animals" includes vertebrates, e.g., mammals, such as non-human primates, sheep, cow, dog, cat and rodents, e.g., mice, and non-mammals, such as chickens, amphibians, reptiles, etc.

The term "cell proliferative disorder" includes disorders involving the undesired or uncontrolled proliferation of a cell. The compounds of the present invention can be utilized to prevent, inhibit, block, reduce, decrease, control, etc., cell proliferation and/or cell division, and/or produce apoptosis. This method comprises administering to a subject in need thereof, including a mammal, including a human, an amount of a compound of this invention, or a pharmaceutically acceptable salt, isomer, polymorph, metabolite, hydrate or solvate thereof which is effective to treat or prevent the disorder.

Cell proliferative or hyper-proliferative disorders in the context of this invention include, but are not limited to, e.g., psoriasis, keloids and other hyperplasias affecting the skin, endometriosis, skeletal disorders, angiogenic or blood vessel proliferative disorders, pulmonary hypertension, fibrotic disorders, mesangial cell proliferative disorders, colonic polyps, polycystic kidney disease, benign prostate hyperplasia (BPH), and solid tumors, such as cancers of the breast, respiratory tract, brain, reproductive organs, digestive tract, urinary tract, eye, liver, skin, head and neck, thyroid, parathyroid, and their distant metastases. Those disorders also include lymphomas, sarcomas and leukemias.

Examples of breast cancer include, but are not limited to invasive ductal carcinoma, invasive lobular carcinoma, ductal carcinoma in situ, and lobular carcinoma in situ.

Examples of cancers of the respiratory tract include, but are not limited to small-cell and non-small-cell lung carcinoma, as well as bronchial adenoma and pleuropulmonary blastoma.

Examples of brain cancers include, but are not limited to brain stem and hypothalmic glioma, cerebellar and cerebral astrocytoma, glioblastoma, medulloblastoma, ependymoma, as well as neuroectodermal and pineal tumor.

Tumors of the male reproductive organs include, but are not limited to prostate and testicular cancer. Tumors of the female reproductive organs include, but are not limited to endometrial, cervical, ovarian, vaginal and vulvar cancer, as well as sarcoma of the uterus.

Tumors of the digestive tract include, but are not limited to anal, colon, colorectal, esophageal, gallbladder, gastric, pancreatic, rectal, small-intestine, and salivary gland cancers.

Tumors of the urinary tract include, but are not limited to bladder, penile, kidney, renal pelvis, ureter, urethral and human papillary renal cancers.

Eye cancers include, but are not limited to intraocular melanoma and retinoblastoma.

Examples of liver cancers include, but are not limited to hepatocellular carcinoma (liver cell carcinomas with or without fibrolamellar variant), cholangiocarcinoma (intrahepatic bile duct carcinoma), and mixed hepatocellular cholangiocarcinoma.

Skin cancers include, but are not limited to squamous cell carcinoma, Kaposi's sarcoma, malignant melanoma, Merkel cell skin cancer, and non-melanoma skin cancer.

Head-and-neck cancers include, but are not limited to laryngeal, hypopharyngeal, nasopharyngeal, oropharyngeal cancer, lip and oral cavity cancer, and squamous cell cancer.

Lymphomas include, but are not limited to AIDS-related lymphoma, non-Hodgkin's lymphoma, cutaneous T-cell lymphoma, Burkitt lymphoma, Hodgkin's disease, and lymphoma of the central nervous system.

Sarcomas include, but are not limited to sarcoma of the soft tissue, osteosarcoma, malignant fibrous histiocytoma, lymphosarcoma, and rhabdomyosarcoma.

Leukemias include, but are not limited to acute myeloid leukemia, acute lymphoblastic leukemia, chronic lymphocytic leukemia, chronic myelogenous leukemia, and hairy cell leukemia.

Fibrotic proliferative disorders, i.e. the abnormal formation of extracellular matrices, that may be treated with the compounds and methods of the present invention include atherosclerosis, restenosis, hepatic cirrhosis, and mesangial cell proliferative disorders, including renal diseases such as glomerulonephritis, diabetic nephropathy, malignant nephrosclerosis, thrombotic microangiopathy syndromes, transplant rejection, and glomerulopathies.

Other conditions in humans or other mammals that may be treated by administering a compound of the present invention include tumor growth, retinopathy, including diabetic retinopathy, ischemic retinal-vein occlusion, retinopathy of prematurity and age-related macular degeneration, rheumatoid arthritis, psoriasis, and bullous disorders associated with subepidermal blister formation, including bullous pemphigoid, erythema multiforme and dermatitis herpetiformis.

The compounds of the present invention may also be used to prevent and treat diseases of the airways and the lung, diseases of the gastrointestinal tract as well as diseases of the bladder and bile duct.

The disorders mentioned above have been well characterized in humans, but also exist with a similar etiology in other animals, including mammals, and can be treated by administering pharmaceutical compositions of the present invention.

Compounds of formula (I) may be administered as the sole pharmaceutical agent or in combination with one or more additional therapeutic agents where the combination causes no unacceptable adverse effects. This combination therapy includes administration of a single pharmaceutical dosage formulation which contains a compound of formula (I) and one or more additional therapeutic agents, as well as administration of the compound of formula (I) and each additional therapeutic agent in its own separate pharmaceutical dosage formulation. For example, a compound of formula (I) and a therapeutic agent may be administered to the patient together in a single oral dosage composition such as a tablet or capsule, or each agent may be administered in separate dosage formulations.

Where separate dosage formulations are used, the compound of formula (I) and one or more additional therapeutic agents may be administered at essentially the same time (e.g., concurrently) or at separately staggered times (e.g., sequentially).

In particular, the compounds of the present invention may be used in fixed or separate combination with other anti-tumor agents such as alkylating agents, anti-metabolites, plant-derived anti-tumor agents, hormonal therapy agents, topoisomerase inhibitors, camptothecin derivatives, kinase inhibitors, targeted drugs, antibodies, interferons and/or biological response modifiers, anti-angiogenic compounds, and other anti-tumor drugs. In this regard, the following is a non-limiting list of examples of secondary agents that may be used in combination with the compounds of the present invention:

Alkylating agents include, but are not limited to, nitrogen mustard N-oxide, cyclophosphamide, ifosfamide, thiotepa, ranimustine, nimustine, temozolomide, altretamine, apaziquone, brostallicin, bendamustine, carmustine, estramustine, fotemustine, glufosfamide, mafosfamide, bendamustin, and mitolactol; platinum-coordinated alkylating compounds include, but are not limited to, cisplatin, carboplatin, eptaplatin, lobaplatin, nedaplatin, oxaliplatin, and satraplatin;

Anti-metabolites include, but are not limited to, methotrexate, 6-mercaptopurine riboside, mercaptopurine, 5-fluorouracil alone or in combination with leucovorin, tegafur, doxifluridine, carmofur, cytarabine, cytarabine ocfosfate, enocitabine, gemcitabine, fludarabin, 5-azacitidine, capecitabine, cladribine, clofarabine, decitabine, eflornithine, ethynylcytidine, cytosine arabinoside, hydroxyurea, melphalan, nelarabine, nolatrexed, ocfosfate, disodium premetrexed, pentostatin, pelitrexol, raltitrexed, triapine, trimetrexate, vidarabine, vincristine, and vinorelbine;

Hormonal therapy agents include, but are not limited to, exemestane, Lupron, anastrozole, doxercalciferol, fadrozole, formestane, 11-beta hydroxysteroid dehydrogenase 1 inhibitors, 17-alpha hydroxylase/17,20 lyase inhibitors such as abiraterone acetate, 5-alpha reductase inhibitors such as finasteride and episteride, anti-estrogens such as tamoxifen citrate and fulvestrant, Trelstar, toremifene, raloxifene, lasofoxifene, letrozole, anti-androgens such as bicalutamide, flutamide, mifepristone, nilutamide, Casodex, and anti-progesterones and combinations thereof;

Plant-derived anti-tumor substances include, e.g., those selected from mitotic inhibitors, for example epothilones such as sagopilone, ixabepilone and epothilone B, vinblastine, vinflunine, docetaxel, and paclitaxel;

Cytotoxic topoisomerase inhibiting agents include, but are not limited to, aclarubicin, doxorubicin, amonafide, belotecan, camptothecin, 10-hydroxycamptothecin, 9-aminocamptothecin, diflomotecan, irinotecan, topotecan, edotecarin, epimbicin, etoposide, exatecan, gimatecan, lurtotecan, mitoxantrone, pirambicin, pixantrone, rubitecan, sobuzoxane, tafluposide, and combinations thereof;

Immunologicals include interferons such as interferon alpha, interferon alpha-2a, interferon alpha-2b, interferon beta, interferon gamma-1a and interferon gamma-n1, and other immune enhancing agents such as L19-IL2 and other IL2 derivatives, filgrastim, lentinan, sizofilan, TheraCys, ubenimex, aldesleukin, alemtuzumab, BAM-002, dacarbazine, daclizumab, denileukin, gemtuzumab, ozogamicin, ibritumomab, imiquimod, lenograstim, lentinan, melanoma vaccine (Corixa), molgramostim, sargramostim, tasonermin, tecleukin, thymalasin, tositumomab, Vimlizin, epratuzumab, mitumomab, oregovomab, pemtumomab, and Provenge;

Biological response modifiers are agents that modify defense mechanisms of living organisms or biological responses such as survival, growth or differentiation of tissue cells to direct them to have anti-tumor activity; such agents include, e.g., krestin, lentinan, sizofuran, picibanil, ProMune, and ubenimex;

Anti-angiogenic compounds include, but are not limited to, acitretin, aflibercept, angiostatin, aplidine, asentar, axitinib, recentin, bevacizumab, brivanib alaninat, cilengtide, combretastatin, DAST, endostatin, fenretinide, halofuginone, pazopanib, ranibizumab, rebimastat, removab, revlimid, sorafenib, vatalanib, squalamine, sunitinib, telatinib, thalidomide, ukrain, and vitaxin;

Antibodies include, but are not limited to, trastuzumab, cetuximab, bevacizumab, rituximab, ticilimumab, ipilimumab, lumiliximab, catumaxomab, atacicept, oregovomab, and alemtuzumab;

VEGF inhibitors such as, e.g., sorafenib, DAST, bevacizumab, sunitinib, recentin, axitinib, aflibercept, telatinib, brivanib alaninate, vatalanib, pazopanib, and ranibizumab;

EGFR (HER1) inhibitors such as, e.g., cetuximab, panitumumab, vectibix, gefitinib, erlotinib, and Zactima;

HER2 inhibitors such as, e.g., lapatinib, tratuzumab, and pertuzumab;

mTOR inhibitors such as, e.g., temsirolimus, sirolimus/Rapamycin, and everolimus;

cMet inhibitors;

PI3K and AKT inhibitors;

CDK inhibitors such as roscovitine and flavopiridol;

Spindle assembly checkpoints inhibitors and targeted anti-mitotic agents such as PLK inhibitors, Aurora inhibitors (e.g. Hesperadin), checkpoint kinase inhibitors, and KSP inhibitors;

HDAC inhibitors such as, e.g., panobinostat, vorinostat, MS275, belinostat, and LBH589;

HSP90 and HSP70 inhibitors;

Proteasome inhibitors such as bortezomib and carfilzomib;

Serine/threonine kinase inhibitors including MEK inhibitors and Raf inhibitors such as sorafenib;

Farnesyl transferase inhibitors such as, e.g., tipifarnib;

Tyrosine kinase inhibitors including, e.g., dasatinib, nilotibib, DAST, bosutinib, sorafenib, bevacizumab, sunitinib, AZD2171, axitinib, aflibercept, telatinib, imatinib mesylate, brivanib alaninate, pazopanib, ranibizumab, vatalanib, cetuximab, panitumumab, vectibix, gefitinib, erlotinib, lapatinib, tratuzumab, pertuzumab, and c-Kit inhibitors;

Vitamin D receptor agonists;

Bcl-2 protein inhibitors such as obatoclax, oblimersen sodium, and gossypol;

Cluster of differentiation 20 receptor antagonists such as, e.g., rituximab;

Ribonucleotide reductase inhibitors such as, e.g., gemcitabine;

Tumor necrosis apoptosis inducing ligand receptor 1 agonists such as, e.g., mapatumumab;

5-Hydroxytryptamine receptor antagonists such as, e.g., rEV598, xaliprode, palonosetron hydrochloride, granisetron, Zindol, and AB-1001;

Integrin inhibitors including alpha5-beta1 integrin inhibitors such as, e.g., E7820, JSM 6425, voloximab, and endostatin;

Androgen receptor antagonists including, e.g., nandrolone decanoate, fluoxymesterone, Android, Prost-aid, andromustine, bicalutamide, flutamide, apo-cyproterone, apo-flutamide, chlormadinone acetate, Androcur, Tabi, cyproterone acetate, and nilutamide;

Aromatase inhibitors such as, e.g., anastrozole, letrozole, testolactone, exemestane, aminoglutethimide, and formestane;

Matrix metalloproteinase inhibitors;

Other anti-cancer agents including, e.g., alitretinoin, ampligen, atrasentan bexarotene, bortezomib, bosentan, calcitriol, exisulind, fotemustine, ibandronic acid, miltefosine, mitoxantrone, I-asparaginase, procarbazine, dacarbazine, hydroxycarbamide, pegaspargase, pentostatin, tazaroten, velcade, gallium nitrate, canfosfamide, darinaparsin, and tretinoin.

In a preferred embodiment, the compounds of the present invention may be used in combination with chemotherapy (i.e. cytotoxic agents), anti-hormones and/or targeted therapies such as other kinase inhibitors, mTOR inhibitors and angiogenesis inhibitors.

The compounds of the present invention may also be employed in cancer treatment in conjunction with radiation therapy and/or surgical intervention.

Furthermore, the compounds of formula (I) may be utilized, as such or in compositions, in research and diagnostics, or as analytical reference standards, and the like, which are well known in the art.

Pharmaceutical Compositions and Methods of Treatment

In another aspect, the invention provides a pharmaceutical composition comprising a compound of formula (I) as defined above, together with a pharmaceutically acceptable carrier.

In still another aspect, the invention provides a process for preparing a pharmaceutical composition. The process includes the step of comprising combining at least one compound of formula (I) as defined above with at least one pharmaceutically acceptable carrier, and bringing the resulting combination into a suitable administration form.

The active component of formula (I) can act systemically and/or locally. For this purpose, it can be applied in a suitable manner, for example orally, parenterally, pulmonally, nasally, sublingually, lingually, buccally, rectally, transdermally, conjunctivally, otically, or as an implant or stent.

For these application routes, the active component of formula (I) can be administered in suitable application forms.

Useful oral application forms include application forms which release the active component rapidly and/or in modified form, such as, for example, tablets (non-coated and coated tablets, for example with an enteric coating), capsules, sugar-coated tablets, granules, pellets, powders, emulsions, suspensions, solutions and aerosols.

Parenteral application can be carried out with avoidance of an absorption step (intravenously, intraarterially, intracardially, intraspinally or intralumbarly) or with inclusion of an absorption (intramuscularly, subcutaneously, intracutaneously, percutaneously or intraperitoneally). Useful parenteral application forms include injection and infusion preparations in the form of solutions, suspensions, emulsions, lyophilisates and sterile powders.

Forms suitable for other application routes include, for example, inhalatory pharmaceutical forms (including powder inhalers, nebulizers), nasal drops, solutions or sprays, tablets or capsules to be administered lingually, sublingually or buccally, suppositories, ear and eye preparations, vaginal capsules, aqueous suspensions (lotions, shake mixtures), lipophilic suspensions, ointments, creams, milk, pastes, dusting powders, implants or stents.

In a preferred embodiment, the pharmaceutical composition comprising a compound of formula (I) as defined above is provided in a form suitable for oral administration. In another preferred embodiment, the pharmaceutical composition comprising a compound of formula (I) as defined above is provided in a form suitable for intravenous administration.

The active component of formula (I) can be converted into the recited application forms in a manner known per se. This is carried out using inert non-toxic, pharmaceutically suitable excipients. These include, inter alia, carriers (for example microcrystalline cellulose), solvents (for example liquid polyethylene glycols), emulsifiers (for example sodium dodecyl sulphate), dispersing agents (for example polyvinylpyrrolidone), synthetic and natural biopolymers (for example albumin), stabilizers (for example antioxidants such as ascorbic acid), colorants (for example inorganic pigments such as iron oxides) or taste and/or odor corrigents.

In another embodiment, the invention provides a method of treating a cell proliferative disorder in a patient in need of such treatment, comprising administering to the patient an effective amount of a compound of formula (I) as defined above. In certain embodiments, the cell proliferative disorder is cancer.

In still another aspect, the invention provides use of a compound of formula (I) as defined above for manufacturing a pharmaceutical composition for the treatment or prevention of a cell proliferative disorder. In certain embodiments, the cell proliferative disorder is cancer.

When the compounds of the present invention are administered as pharmaceuticals, to humans and animals, they can be given per se or as a pharmaceutical composition containing, for example, 0.1 to 99.5% (more preferably, 0.5 to 90%) of active ingredient in combination with a pharmaceutically-acceptable carrier.

Regardless of the route of administration selected, the compounds of the invention, which may be used in a suitable hydrated form, and/or the pharmaceutical compositions of the present invention, are formulated into pharmaceutically-acceptable dosage forms by conventional methods known to those of skill in the art.

Actual dosage levels and time course of administration of the active ingredients in the pharmaceutical compositions of the invention may be varied so as to obtain an amount of the active ingredient which is effective to achieve the desired therapeutic response for a particular patient, composition, and mode of administration, without being toxic to the patient. An exemplary dose range is from 0.01 to 100 mg/kg per day or 0.1 to 150 mg/kg per day.

In certain embodiments, the compound of the invention can be used in combination therapy with conventional cancer chemotherapeutics. Conventional treatment regimens for leukemia and for other tumors include radiation, drugs, or a combination of both.

Determination of a therapeutically effective anti-proliferative amount or a prophylactically effective anti-proliferative amount of the compounds of the invention can be readily made by the physician or veterinarian (the "attending clinician"), as one skilled in the art, by the use of known techniques and by observing results obtained under analogous circumstances. The dosages may be varied depending upon the requirements of the patient in the judgment of the attending clinician; the severity of the condition being treated and the particular compound being employed. In determining the therapeutically effective anti-proliferative amount or dose, and the prophylactically effective anti-proliferative amount or dose, a number of factors are considered by the attending clinician, including, but not limited to: the specific cell proliferative disorder involved; pharmacodynamic characteristics of the particular agent and its mode and route of administration; the desired time course of treatment; the species of mammal; its size, age, and general health; the specific disease involved; the degree of or involvement or the severity of the disease; the response of the individual patient; the particular compound administered; the mode of administration; the bioavailability characteristics of the preparation administered; the dose regimen selected; the kind of concurrent treatment (i.e., the interaction of the compound of the invention with other coadministered therapeutics); and other relevant circumstances.

Treatment can be initiated with smaller dosages, which are less than the optimum dose of the compound. Thereafter, the dosage may be increased by small increments until the optimum effect under the circumstances is reached. For convenience, the total daily dosage may be divided and administered in portions during the day if desired. A therapeutically effective anti-proliferative amount and a prophylactically effective anti-proliferative amount of a compound of the invention may be expected to vary from about 0.01 milligram per kilogram of body weight per day (mg/kg/day) to about 100 mg/kg/day.

A preferred dose of the compound of the invention for the present invention is the maximum that a patient can tolerate and not develop serious side effects. Illustratively, the compound of the present invention is administered at a dose of about 0.01 mg/kg to about 100 mg/kg of body weight, about 0.01 mg/kg to about 10 mg/kg of body weight or about 0.1 mg/kg to about 10 mg/kg of body weight. Ranges intermediate to the above-recited values are also intended to be part of the invention.

The percentages in the tests and examples which follows are, unless otherwise stated, by weight; parts are by weight. Solvent ratios, dilution ratios and concentrations reported for liquid/liquid solutions are each based on volume.

A. EXAMPLES

Abbreviations and Acronyms

Boc tert-butoxycarbonyl
$CDCl_3$ chloroform-d
$CD_2Cl_2$ dichloromethane-$d_2$
Celite® registered trademark of Celite Corp. brand of diatomaceous earth
conc. concentrated
DCI direct chemical ionization (MS)
DCM dichloromethane
DIPEA diisopropylethylamine
DMAP 4-N,N-dimethylaminopyridine
DMF N,N-dimethylformamide
DMSO dimethylsulfoxide
DMSO-$d_6$ dimethylsulfoxide-$d_6$
EDCI N-(3-dimethylaminoisopropyl)-N'-ethylcarbodiimide
equiv. equivalent(s)
ESI electro-spray ionization (MS)
Et ethyl
EtOAc ethyl acetate
GC/MS gas chromatography-coupled mass spectroscopy
h hour(s)
$^1$H-NMR proton nuclear magnetic resonance spectroscopy
Hex hexanes
HPLC high performance liquid chromatography
IPA isopropyl alcohol
LC/MS liquid chromatography-coupled mass spectroscopy
Me methyl
MeOH methanol
min minute(s)
MS mass spectroscopy
MTBE methyl tert-butyl ether
NMP N-methylpyrrolidinone
PE petroleum ether
$R_f$ TLC retention factor
rt room temperature
$R_t$ retention time (HPLC)
satd. saturated
TBTU O-benzotriazol-1-yl-N,N,N',N'-tetramethyluronium tetrafluoroborate
tBu tert-butyl
TFA trifluoroacetic acid
THF tetrahydrofuran
TLC thin layer chromatography
XPHOS dicyclohexyl[2',4',6'-tris(1-methylethyl)biphenyl-2-yl]phosphane
GC/MS and LC/MS Methods:
Method 1 (GC/MS):
  Instrument: Micromass GCT, GC6890; column: Restek RTX-35, 15 m×200 μm×0.33 μm; constant flow with helium: 0.88 mL/min; oven: 70° C.; inlet: 250° C.; gradient: 70° C., 30° C./min→310° C. (keep for 3 min).
Method 2 (LC/MS):
  Instrument: Micromass QuattroPremier with Waters HPLC Acquity; column: Thermo Hypersil GOLD 1.9μ, 50 mm×1 mm; eluent A: 1 L water+0.5 mL 50% formic acid, eluent B: 1 L acetonitrile+0.5 ml 50% formic acid; gradient: 0.0 min 90% A→0.1 min 90% A→1.5 min 10% A→2.2 min 10% A; oven: 50° C.; flow rate: 0.33 mL/min; UV detection: 210 nm.
Method 3 (LC/MS):
  Instrument: Micromass Quattro Micro MS with HPLC Agilent Series 1100; column: Thermo Hypersil GOLD 3μ, 20 mm×4 mm; eluent A: 1 L water+0.5 mL 50% formic acid, eluent B: 1 L acetonitrile+0.5 mL 50% formic acid; gradient: 0.0 min 100% A→3.0 min 10% A→4.0 min 10% A→4.01 min 100% A (flow 2.5 mL/min)→5.00 min 100% A; oven: 50° C.; flow rate: 2 mL/min; UV detection: 210 nm.
Method 4 (LC/MS):
  Instrument: Micromass ZQ with HPLC HP 1100 series; UV DAD; column: Phenomenex Gemini 3μ, 30 mm×3.00 mm; eluent A: 1 L water+0.5 mL 50% formic acid, eluent B: 1 L acetonitrile+0.5 mL 50% formic acid; gradient: 0.0 min 90% A→2.5 min 30% A→3.0 min 5% A→4.5 min 5% A; flow rate: 0.0 min 1 mL/min, 2.5 min/3.0 min/4.5 min 2 mL/min; oven: 50° C.; UV detection: 210 nm Method 5 (LC/MS):

Instrument: Waters ZQ with HPLC Agilent 1100 Series; UV DAD; column: Thermo Hypersil GOLD 3µ, 20 mm×4 mm; eluent A: 1 L water+0.5 mL 50% formic acid, eluent B: 1 L acetonitrile+0.5 mL 50% formic acid; gradient: 0.0 min 100% A→3.0 min 10% A→4.0 min 10% A→4.1 min 100% A (flow 2.5 mL/min)→5.0 min 100% A; oven: 55° C.; flow rate: 2 mL/min; UV detection: 210 nm.

Method 6 (LC/MS):

Instrument: Micromass ZQ with HPLC Waters Alliance 2795; column: Phenomenex Synergi 2.5µ MAX-RP 100A Mercury, 20 mm×4 mm; eluent A: 1 L water+0.5 mL 50% formic acid, eluent B: 1 L acetonitrile+0.5 mL 50% formic acid; gradient: 0.0 min 90% A→0.1 min 90% A→3.0 min 5% A→4.0 min 5% A→4.01 min 90% A; flow rate: 2 mL/min; oven: 50° C.; UV detection: 210 nm.

Method 7 (LC/MS):

Instrument: Waters ZQ 2000 with HPLC Agilent 1100, 2 column set-up, autosampler HTC PAL; column: YMC-ODS-AQ 3.0 µm, 50 mm×4.6 mm; eluent A: water+0.1% formic acid, eluent B: acetonitrile+0.1% formic acid; gradient: 0.0 min 100% A→0.1 min 95% A→0.8 min 25% A→0.9 min 5% A→1.8 min 5% A→1.81 min 100% A→1.9 min 100% A; oven: 40° C.; flow rate: 3.0 mL/min; UV detection: 210 nm.

Starting Materials and Intermediates

Example 1A (2E)-4-(Dimethylamino)but-2-enoic acid hydrochloride

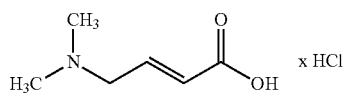

Methyl (2E)-4-(dimethylamino)but-2-enoate (3.4 g, 23.7 mmol) was dissolved in methanol (25 mL). A solution of sodium hydroxide (0.95 g, 23.7 mmol) in water (7 mL) was added, and the mixture was heated to 50° C. for 1 h. The pH was then adjusted to 2 with conc. hydrochloric acid. The solution was concentrated to dryness, and the residue was triturated with ethanol (30 mL). It was filtered, and the solution was concentrated in vacuo. The residue was triturated with 2-propanol, and the precipitate was collected by suction filtration and dried to yield 2.00 g (51%) of the title compound.

$^1$H-NMR (400 MHz, DMSO-d$_6$): δ=2.73 (s, 6H), 3.89 (d, 2H), 6.18 (d, 1H), 6.81 (dt, 1H), 10.8 (br. s, 1H), 12.8 (br. s, 1H).

Example 2A (2E)-4-[Methyl(1-methylethyl)amino]but-2-enoic acid hydrochloride

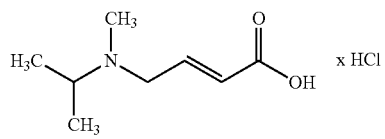

In analogy to Example 1A, the title compound was obtained from methyl (2E)-4-[methyl(1-methylethyl)amino]but-2-enoate (3.90 g, 22.8 mmol) to yield 2.00 g (45%).

$^1$H-NMR (400 MHz, DMSO-d$_6$): δ=1.25 (dd, 6H), 2.58 (s, 3H), 3.49 (sept, 1H), 3.76-3.99 (m, 2H), 6.21 (d, 1H), 6.90 (dt, 1H), 10.89 (br. s, 1H), 12.75 (br. s, 1H).

Example 3A

2-Chloro-1-[(3-fluorobenzyl)oxy]-4-nitrobenzene

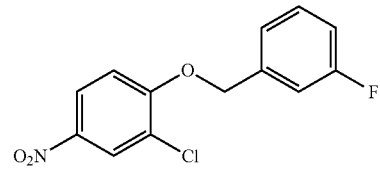 [SMILES: O=[N+]([O-])c1ccc(OCc2cccc(F)c2)c(Cl)c1]

To a mixture of 3-fluorobenzyl alcohol (7.88 g, 62.5 mmol), Aliquot 336 (8.08 g, 20.0 mmol), potassium hydroxide (3.51 g, 62.5 mmol) and water (40 mL) were added toluene (80 mL) and 1,2-dichloro-4-nitrobenzene (10.0 g, 52.1 mmol). The mixture was heated to 60° C. overnight with vigorous stirring. The mixture was diluted with ethyl acetate and washed with water. The organic layer was dried over sodium sulfate, and the solvent was removed in vacuo. The residue was triturated with hot petroleum ether and tert-butyl methyl ether to yield 9.20 g (63%) of the title compound.

$^1$H-NMR (400 MHz, DMSO-d$_6$): δ=5.42 (s, 2H), 7.21 (dt, 1H), 7.30-7.35 (m, 2H), 7.45-7.52 (m, 2H), 8.26 (dd, 1H), 8.36 (d, 1H).

GC/MS (method 1): R$_t$=7.76 min; MS (DCI): m/z=299 [M+NH$_4$]$^+$.

Example 4A

3-Chloro-4-[(3-fluorobenzyl)oxy]aniline

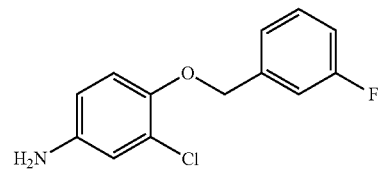

To a solution of 2-chloro-1-[(3-fluorobenzyl)oxy]-4-nitrobenzene from Example 3A (8.70 g, 25.1 mmol) in ethanol (150 mL) was added zinc powder (10.1 g, 154 mmol), and the mixture was heated to 60° C. A solution of ammonium chloride (3.30 g, 61.8 mmol) in water (30 mL) was added dropwise, and the reaction was stirred for additional 2 h at this temperature. The mixture was filtered through Celite®, and the solvent was removed in vacuo. The residue was triturated with water, and the precipitate was collected by suction filtration, washed with water and dried to yield 7.63 g (98%) of the aniline.

$^1$H-NMR (400 MHz, DMSO-$d_6$): δ=4.95 (br. s, 2H), 5.03 (s, 2H), 6.47 (dd, 1H), 6.65 (d, 1H), 6.91 (d, 1H), 7.11-7.18 (dt, 1H), 7.22-7.29 (m, 2H), 7.40-7.46 (m, 1H).

LC/MS (method 2): $R_t$=1.07 min; MS (ESIpos): m/z=252 [M+H]$^+$.

Example 5A

2-[(2-Chloro-4-nitrophenoxy)methyl]pyridine

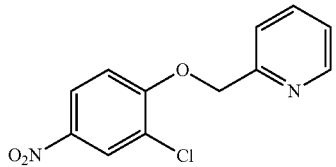 [SMILES: O=[N+]([O-])c1ccc(OCc2ccccn2)c(Cl)c1]

To a mixture of pyridin-2-ylmethanol (6.82 g, 62.5 mmol), Aliquat 336 (8.08 g, 20.0 mmol), potassium hydroxide (3.51 g, 62.5 mmol) and water (40 mL) were added toluene (80 mL) and 1,2-dichloro-4-nitrobenzene (10.0 g, 52.1 mmol). The mixture was heated to 60° C. overnight with vigorous stirring. The layers were separated, and the organic layer was diluted with ethyl acetate and washed with water. The organic layer was dried over sodium sulfate, and the solvent was removed in vacuo. The residue was triturated with petroleum ether and tert-butyl methyl ether to yield 6.66 g (48%) of the title compound.

$^1$H-NMR (400 MHz, DMSO-$d_6$): δ=5.47 (s, 2H), 7.39 (dd, 1H), 7.48 (d, 1H), 7.58 (d, 1H), 7.89 (dt, 1H), 8.24 (dd, 1H), 8.36 (d, 1H), 8.61 (d, 1H).

LC/MS (method 2): $R_t$=1.13 min; MS (EIpos): m/z=265 [M+H]$^+$.

Example 6A

3-Chloro-4-(pyridin-2-ylmethoxy)aniline

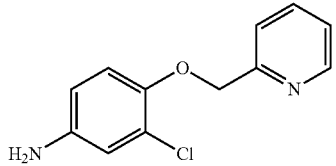

To a solution of 2-[(2-chloro-4-nitrophenoxy)methyl]pyridine from Example 5A (6.65 g, 25.1 mmol) in ethanol (120 mL) was added zinc powder (8.22 g, 126 mmol), and the mixture was heated to 60° C. A solution of ammonium chloride (2.67 g, 50.3 mmol) in water (24 mL) was added dropwise, and the reaction was stirred for additional 2 h at this temperature. The mixture was filtered through Celite®, and the solvent was removed in vacuo. The residue was triturated with water, and the precipitate was collected by suction filtration, washed with water and dried to yield 4.97 g (84%) of the aniline.

$^1$H-NMR (400 MHz, DMSO-$d_6$): δ=4.95 (br. s, 2H), 5.08 (s, 2H), 6.46 (dd, 1H), 6.66 (d, 1H), 6.91 (d, 1H), 7.33 (dd, 1H), 7.54 (d, 1H), 7.85 (dt, 1H), 8.56 (d, 1H).

LC/MS (method 3): $R_t$=1.17 min; MS (ESIpos): m/z=235 [M+H]$^+$.

Example 7A 1-(3-Fluorobenzyl)-5-nitro-1H-indazole

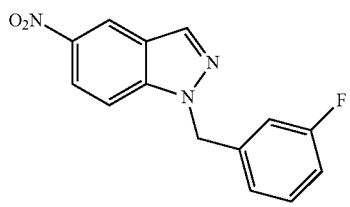 [SMILES: O=[N+]([O-])c1ccc2c(cnn2Cc2cccc(F)c2)c1]

5-Nitroindazol (10.0 g, 61.3 mmol) was dissolved in THF (100 mL). Potassium carbonate (25.4 g, 184 mmol) and 3-fluorobenzylbromide (12.7 g, 67.4 mmol) were added, and the mixture was heated to reflux for 3 h. The solvent was removed in vacuo, and the residue was dissolved in ethyl acetate (150 mL) and extracted with water (200 mL). The aqueous layer was extracted twice with ethyl acetate (100 mL each). The combined organic layers were dried over sodium sulfate, and the solvent was removed in vacuo. The residue was purified by column chromatography on silica gel (eluent: cyclohexane/ethyl acetate 3:1) to yield 6.55 g (39%) of the title compound (less polar component) and 5.84 g (35%) of the regioisomeric 2H-indazole derivative (more polar component).

$^1$H-NMR (400 MHz, DMSO-$d_6$): δ=5.80 (s, 2H), 7.04-7.15 (m, 3H), 7.37 (dt, 1H), 7.98 (d, 1H), 8.25 (dd, 1H), 8.48 (s, 1H), 8.86 (d, 1H).

LC/MS (method 2): $R_t$=1.23 min; MS (ESIpos): m/z=272 [M+H]$^+$.

Example 8A 1-(3-Fluorobenzyl)-1H-indazol-5-amine

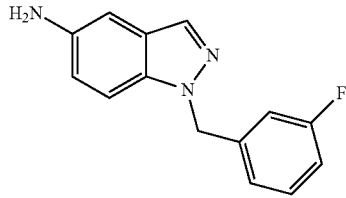

1-(3-Fluorobenzyl)-5-nitro-1H-indazole from Example 7A (500 mg) was dissolved in ethanol (40 mL) and was hydrogenated in an H-Cube™ (room temperature, 1 bar, 1 mL/min, 10% Pd/C catalyst). After removal of the solvent and trituration with tert-butyl methyl ether, 287 mg (64%) of the title compound were obtained.

$^1$H-NMR (400 MHz, DMSO-$d_6$): δ=4.83 (br. s, 2H), 5.55 (s, 2H), 6.75 (d, 1H), 6.79 (dd, 1H), 6.93-6.98 (m, 1H), 6.99

(d, 1H), 7.07 (dt, 1H), 7.33 (dt, 1H), 7.37 (d, 1H), 7.77 (s, 1H). LC/MS (method 4): R$_t$=1.17 min; MS (ESIpos): m/z=242 [M+H]$^+$.

Example 9A 6-tert-Butyl 3-ethyl 2-amino-4,7-dihydrothieno[2,3-c]pyridine-3,6(5H)-dicarboxylate

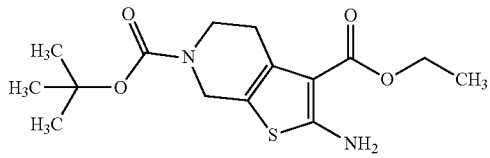 [SMILES: CCOC(=O)c1c(N)sc2c1CCN(C(=O)OC(C)(C)C)C2]

tert-Butyl 4-oxopiperidine-1-carboxylate (101 g, 505 mmol) was dissolved in ethanol (806 mL), and ethyl cyanoacetate (57.2 g, 505 mmol) and sulfur (17.0 g, 531 mmol) were added. The mixture was stirred for a couple of minutes, and then morpholine (44.0 g, 505 mmol) was added. The reaction was stirred at rt overnight. The precipitate was collected by suction filtration and washed with ethanol to yield 142 g (86%) of the title compound.

$^1$H-NMR (400 MHz, DMSO-d$_6$): δ=1.25 (t, 3H), 1.41 (s, 9H), 2.63-2.68 (m, 2H), 3.51 (t, 2H), 4.15 (q, 2H), 4.24 (br. s, 2H), 7.32 (s, 2H).

LC/MS (method 5): R$_t$=2.40 min; MS (ESIpos): m/z=327 [M+H]$^+$.

Example 10A tert-Butyl 4-oxo-3,5,6,8-tetrahydropyrido[4',3':4,5]thieno[2,3-d]pyrimidine-7(4H)-carboxylate

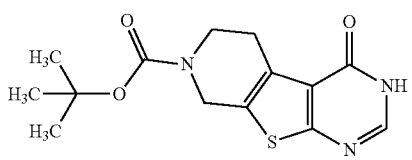 [SMILES: CC(C)(C)OC(=O)N1CCc2c(sc3nc[nH]c(=O)c23)C1]

To a solution of 6-tert-butyl 3-ethyl 2-amino-4,7-dihydrothieno[2,3-c]pyridine-3,6(5H)-dicarboxylate from Example 9A (1.23 kg, 3.77 mol) in DMF (10.3 L) was added formamidine acetate (588 g, 5.65 mol). The mixture was heated to 100° C. overnight. The solvent was removed in vacuo. The residue was stirred with ethyl acetate (3 L) for 2 h. The precipitate was collected by suction filtration and rinsed with ethyl acetate. The solid was dried to yield 1.02 kg (88%) of the title compound.

$^1$H-NMR (400 MHz, DMSO-d$_6$): δ=1.43 (s, 9H), 2.91-2.96 (m, 2H), 3.62 (t, 2H), 4.58 (s, 2H), 8.05 (s, 1H), 12.38 (br. s, 1H).

LC/MS (method 4): R$_t$=2.03 min; MS (ESIpos): m/z=308 [M+H]$^+$.

Example 11A tert-Butyl 4-chloro-5,8-dihydropyrido[4',3':4,5]thieno[2,3-d]pyrimidine-7(6H)-carboxylate

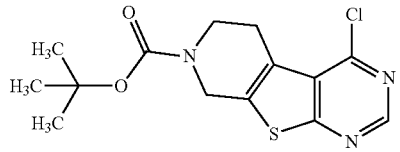 [SMILES: CC(C)(C)OC(=O)N1CCc2c(sc3ncnc(Cl)c23)C1]

To sulfolane (3.19 L) was added phosphoryl chloride (785 g, 5.12 mol) at rt. Triethylamine (518 g, 5.12 mol) was added dropwise with water-bath cooling. tert-Butyl 4-oxo-3,5,6,8-tetrahydropyrido[4',3':4,5]thieno[2,3-d]pyrimidine-7(4H)-carboxylate from Example 10A (525.5 g, 1.706 mol) and additional sulfolane (1.34 L) were added, and the mixture was heated to 70° C. for 2.5 h. The mixture was cooled to it, and triethylamine (967 g, 9.56 mol) was added. A semi-saturated aqueous sodium chloride solution (10 L) was added during which the mixture was cooled with an ice-bath. After stirring at rt for 2 h, the precipitate was collected by suction filtration and washed three times with water (1.5 L). The residue was dried to yield 517 g (93%) of the title compound.

$^1$H-NMR (400 MHz, DMSO-d$_6$): δ=1.44 (s, 9H), 3.07-3.12 (m, 2H), 3.71 (t, 2H), 4.75 (s, 2H), 8.86 (s, 1H).

LC/MS (method 4): R$_t$=2.66 min; MS (ESIpos): m/z=326 [M+H]$^+$.

Example 12A

N-(3-Chloro-4-fluorophenyl)-5,6,7,8-tetrahydropyrido[4',3':4,5]thieno[2,3-d]pyrimidin-4-amine

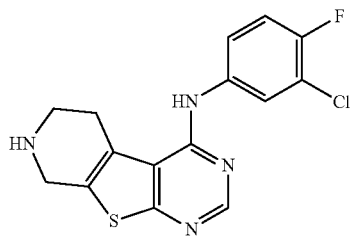

tert-Butyl 4-chloro-5,8-dihydropyrido[4',3':4,5]thieno[2,3-d]pyrimidine-7(6H)-carboxylate from Example 11A (407.5 g, 1.251 mol) was dissolved in 2-propanol (5.7 L). 3-Chloro-4-fluoroaniline (191.2 g, 1.313 mol) and a 4 M solution of gaseous hydrogen chloride in dioxane (17.4 mL, 63 mmol) were added. The mixture was heated to 80° C. for 3 days. The thick suspension was then diluted with additional 2-propanol (1 L), and further 4 M hydrogen chloride in dioxane (695 mL, 2.5 mol) was added. The mixture was again heated to 80° C. for 3 h. The solvent was then removed in vacuo, and the residue was treated with 1 M aqueous sodium hydroxide solution (12 L). The precipitate was collected by suction filtration and washed with water. The product was dried for 2 days at 50° C., then triturated with tert-butyl methyl ether and collected by suction filtration to yield 397 g (95%) of the title compound.

$^1$H-NMR (400 MHz, DMSO-d$_6$): δ=2.62 (br. s, 1H), 3.01-3.11 (m, 4H), 3.95 (s, 2H), 7.41 (t, 1H), 7.66 (ddd, 1H), 7.94 (dd, 1H), 8.25 (br. s, 1H), 8.42 (s, 1H).

LC/MS (method 2): $R_t$=0.78 min; MS (ESIpos): m/z=335 [M+H]$^+$.

Example 13A

Diethyl(2-{4-[(3-chloro-4-fluorophenyl)amino]-5,8-dihydropyrido[4',3':4,5]thieno[2,3-d]pyrimidin-7(6H)-yl}-2-oxoethyl)phosphonate

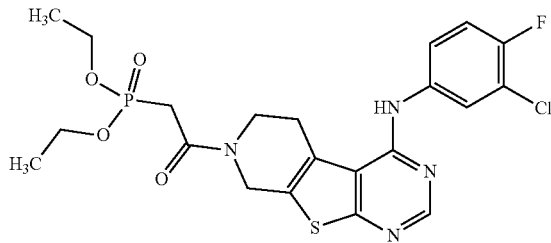 [SMILES: CCOP(=O)(CC(=O)N1CCc2c(sc3ncnc(Nc4ccc(F)c(Cl)c4)c23)C1)OCC]

N-(3-Chloro-4-fluorophenyl)-5,6,7,8-tetrahydropyrido[4',3':4,5]thieno[2,3-d]pyrimidin-4-amine from Example 12A (3.00 g, 8.96 mmol) and (diethoxyphosphoryl)acetic acid (2.46 g, 12.5 mmol) were dissolved in DMF (60 mL). DIPEA (3.47 g, 26.9 mmol) and TBTU (4.32 g, 13.4 mmol) were added, and the reaction was stirred overnight at rt. Subsequently, the mixture was concentrated in vacuo, and the residue was dissolved in ethyl acetate. The solution was extracted with 1 M aqueous sodium hydroxide solution, dried over sodium sulfate, and the solvent was removed in vacuo. The residue was triturated with tert-butyl methyl ether. The precipitate was collected by suction filtration to yield 4.31 g (94%) of the title compound as white crystals.

$^1$H-NMR (400 MHz, DMSO-d$_6$): δ=1.19 (t, 3H), 1.24 (t, 3H), 3.18-3.23 (m, 1H), 3.28-3.36 (m, 3H), 3.84 (t, 1H), 3.89 (t, 1H), 3.98-4.11 (m, 4H), 4.81 (s, 1H), 4.92 (s, 1H), 7.42 (dt, 1H), 7.59-7.68 (m, 1H), 7.90 (ddd, 1H), 8.34-8.40 (m, 1H), 8.46 (s, 1H).

LC/MS (method 2): $R_t$=1.13 min; MS (ESIpos): m/z=513 [M+H]$^+$.

Example 14A tert-Butyl (2S)-2-[(1E)-3-{4-[(3-chloro-4-fluorophenyl)amino]-5,8-dihydropyrido[4',3':4,5]thieno[2,3-d]pyrimidin-7(6H)-yl}-3-oxoprop-1-en-1-yl]pyrrolidine-1-carboxylate

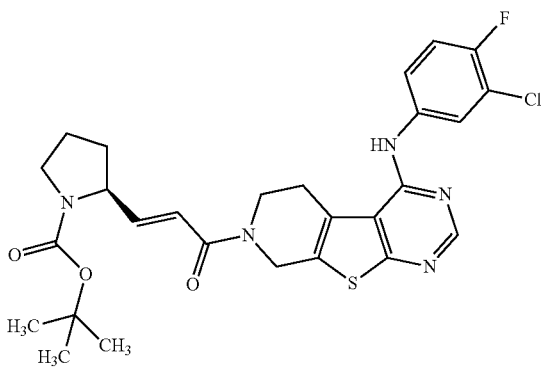 [SMILES: CC(C)(C)OC(=O)N1CCC[C@H]1/C=C/C(=O)N1CCc2c(sc3ncnc(Nc4ccc(F)c(Cl)c4)c23)C1]

A solution of diethyl(2-{4-[(3-chloro-4-fluorophenyl)amino]-5,8-dihydropyrido[4',3':4,5]thieno[2,3-d]-pyrimidin-7(6H)-yl}-2-oxoethyl)phosphonate from Example 13A (644 mg, 1.26 mmol) in THF (2.5 mL) was cooled to −78° C. Sodium hydride (60% in mineral oil, 50 mg, 1.26 mmol) was added, and the mixture was stirred for 15 min. Subsequently, a solution of tert-butyl (2S)-2-formylpyrrolidine-1-carboxylate (250 mg, 1.26 mmol) in THF (2.5 mL) was added dropwise. The mixture was slowly warmed to rt and stirred overnight. Methanol was added, and the solvent was removed in vacuo. The crude product was purified by preparative HPLC, and the title compound crystallized from PE/MTBE to yield 397 mg (56%).

$^1$H-NMR (400 MHz, DMSO-d$_6$): δ=1.30-1.45 (m, 9H), 1.69-1.85 (m, 3H), 1.99-2.12 (m, 1H), 3.20-3.41 (m, 4H), 3.80-3.95 (m, 2H), 4.30-4.43 (m, 1H), 4.80-4.99 (m, 2H), 6.42-6.55 (m, 1H), 6.56-6.67 (m, 1H), 7.42 (t, 1H), 7.58-7.68 (m, 1H), 7.86-7.94 (m, 1H), 8.30-8.40 (m, 1H), 8.46 (s, 1H).

LC/MS (method 2): $R_t$=1.38 min; MS (ESIpos): m/z=558 [M+H]$^+$.

Example 15A

N-(3,4-Dichlorophenyl)-5,6,7,8-tetrahydropyrido[4',3':4,5]thieno[2,3-d]pyrimidin-4-amine

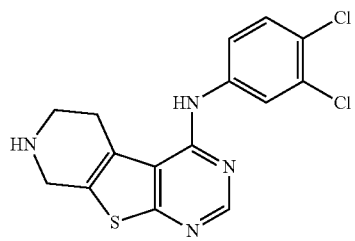

tert-Butyl 4-chloro-5,8-dihydropyrido[4',3':4,5]thieno[2,3-d]pyrimidine-7(6H)-carboxylate from Example 11A (407.5 g, 1.251 mol) was dissolved in 2-propanol (5.7 L). 3,4-Dichloroaniline (213.8 g, 1.313 mol) and a 4 M solution of gaseous hydrogen chloride in dioxane (17.4 mL, 63 mmol) were added. The mixture was heated to 80° C. for 3 days. The thick suspension was then diluted with additional 2-propanol (1 L), and further 4 M hydrogen chloride in dioxane (695 mL, 2.5 mol) was added. The mixture was again heated to 80° C. for 3 h. The solvent was then removed in vacuo, and the residue was treated with 1 M aqueous sodium hydroxide solution (12 L). The precipitate was collected by suction filtration and washed with water. The product was dried for 2 days at 50° C., then triturated with tert-butyl methyl ether and collected by suction filtration to yield 413 g (92%) of the title compound.

$^1$H-NMR (400 MHz, DMSO-d$_6$): δ=2.61 (br. s, 1H), 3.00-3.11 (m, 4H), 3.96 (s, 2H), 7.59 (d, 1H), 7.71 (dd, 1H), 8.04 (d, 1H), 8.34 (br. s, 1H), 8.47 (s, 1H).

LC/MS (method 2): $R_t$=0.87 min; MS (ESIpos): m/z=351 [M+H]$^+$.

Example 16A 3-(5,6,7,8-Tetrahydropyrido[4',3':4,5]thieno[2,3-d]pyrimidin-4-ylamino)phenol

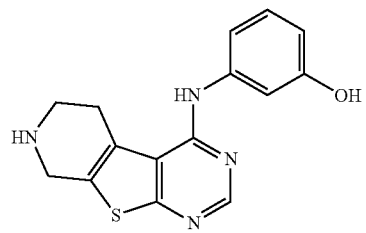 [SMILES: Oc1cccc(Nc2ncnc3sc4c(c23)CCNC4)c1]

tert-Butyl 4-chloro-5,8-dihydropyrido[4',3':4,5]thieno[2,3-d]pyrimidine-7(6H)-carboxylate from Example 11A (1.00 g, 3.07 mmol) was dissolved in 2-propanol (10 mL). 3-Aminophenol (352 mg, 3.22 mmol) and a 4 M solution of gaseous hydrogen chloride in dioxane (38 µL, 0.15 mmol) were added, and the mixture was heated to 80° C. for 20 h. Subsequently, further 4 M hydrogen chloride in dioxane (1.54 mL, 6.14 mmol) was added, and the mixture was heated for additional 3 h. The precipitate was collected by suction filtration to yield 1.21 g of the title compound as hydrochloride salt. An analytical amount was dissolved in 1 M aqueous sodium hydroxide solution which was then concentrated in vacuo. The precipitate was collected by suction filtration and dried to yield the product as free base.

$^1$H-NMR (400 MHz, DMSO-d$_6$): δ=2.60 (br. s, 1H), 3.00-3.10 (m, 4H), 3.32 (s, 2H), 6.50 (dd, 1H), 7.03-7.07 (m, 1H), 7.12 (t, 1H), 7.20-7.23 (m, 1H), 8.01 (br. s, 1H), 8.40 (s, 1H), 9.39 (br. s, 1H).

LC/MS (method 3): R$_t$=0.96 min; MS (ESIpos): m/z=299 [M+H]$^+$.

Example 17A tert-Butyl 4-{[(1R)-1-phenylethyl]amino}-5,8-dihydropyrido[4',3':4,5]thieno[2,3-d]pyrimidine-7(6H)-carboxylate

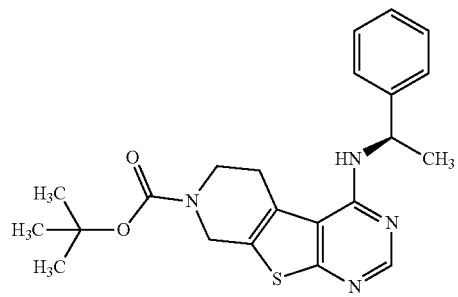 [SMILES: C[C@@H](Nc1ncnc2sc3c(c12)CCN(C(=O)OC(C)(C)C)C3)c1ccccc1]

tert-Butyl 4-chloro-5,8-dihydropyrido[4',3':4,5]thieno[2,3-d]pyrimidine-7(6H)-carboxylate from Example 11A (500 mg, 1.54 mmol) was dissolved in 2-methoxyethanol (5 mL), and (R)-methylbenzylamine (223 mg, 1.84 mmol) and triethylamine (621 mg, 6.14 mmol) were added. The mixture was heated to 100° C. for 2 h, then diluted with ethyl acetate and washed with water. The organic layer was dried over sodium sulfate, and the solvent was removed in vacuo. The crude product was purified by column chromatography on silica gel (eluent: cyclohexane/ethyl acetate 3:1) to yield 474 mg (75%) of the title compound.

$^1$H-NMR (400 MHz, DMSO-d$_6$): δ=1.44 (s, 9H), 1.56 (d, 3H), 3.13-3.19 (m, 2H), 3.64-3.76 (m, 2H), 4.57-4.69 (m, 2H), 5.46 (quint, 1H), 6.52 (d, 1H), 7.21 (tt, 1H), 7.31 (t, 2H), 7.45 (d, 2H), 8.24 (s, 1H).

LC/MS (method 4): R$_t$=2.77 min; MS (ESIpos): m/z=411 [M]$^+$.

Example 18A

N-[(1R)-1-Phenylethyl]-5,6,7,8-tetrahydropyrido[4',3':4,5]thieno[2,3-d]pyrimidin-4-amine

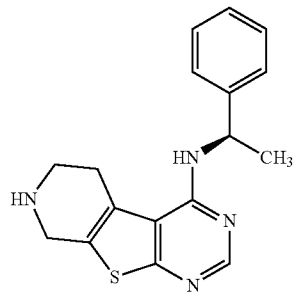 [SMILES: C[C@@H](Nc1ncnc2sc3c(c12)CCNC3)c1ccccc1]

tert-Butyl 4-{[(1R)-1-phenylethyl]amino}-5,8-dihydropyrido[4',3':4,5]thieno[2,3-d]pyrimidine-7(6H)-carboxylate from Example 17A (413 mg, 1.00 mmol) was dissolved in 2-propanol (4 mL), and 4 M gaseous hydrogen chloride in dioxane (0.5 mL, 2 mmol) was added. The mixture was heated to 80° C. for 3 h. Further hydrogen chloride solution (0.5 mL) was added, and the mixture was heated to 80° C. for further 30 min. Subsequently, the solution was diluted with ethyl acetate, washed with satd. aqueous sodium carbonate solution, dried over sodium sulfate, and the solvent was removed in vacuo. The product was purified by column chromatography on silica gel (eluent: DCM/MeOH 10:1) to yield 244 mg (78%) of the title compound.

$^1$H-NMR (400 MHz, DMSO-d$_6$): δ=1.56 (d, 3H), 2.77 (br. s, 1H), 3.03 (s, 4H), 3.90 (s, 2H), 5.46 (quint, 1H), 6.40 (d, 1H), 7.19-7.24 (m, 1H), 7.31 (t, 2H), 7.42-7.46 (m, 2H), 8.21 (s, 1H).

LC/MS (method 4): R$_t$=1.17 min; MS (ESIpos): m/z=311 [M+H]$^+$.

Example 19A

Diethyl 2-amino-4,6-dihydro-5H-thieno[2,3-c]pyrrole-3,5-dicarboxylate

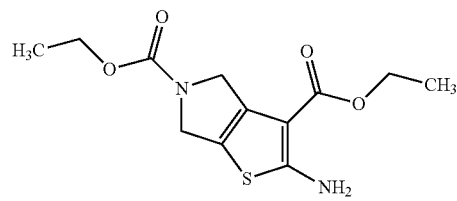 [SMILES: CCOC(=O)c1c(N)sc2c1CN(C(=O)OCC)C2]

Ethyl 3-oxopyrrolidine-1-carboxylate (14.0 g, 89.1 mmol), ethyl cyanoacetate (10.1 g, 89.1 mmol) and sulfur (2.86 g, 89.1 mmol) in ethanol (44 mL) were cooled to 0-5° C., and triethylamine (9.01 g, 89.1 mmol) was added dropwise. Subsequently, the mixture was warmed to rt and stirred overnight. The solvent was removed in vacuo, and the product was isolated after column chromatography on silica gel (eluent: cyclohexane/ethyl acetate 2:1) to yield 4.04 g (15%) of the title compound.

$^1$H-NMR (400 MHz, DMSO-d$_6$): δ=1.18-1.26 (m, 6H), 4.05-4.13 (m, 2H), 4.12-4.19 (m, 2H), 4.35-4.43 (m, 4H), 7.34-7.38 (m, 2H).

LC/MS (method 2): R$_t$=1.07 min; MS (ESIpos): m/z=285 [M+H]$^+$.

Example 20A

Ethyl 4-oxo-3,4,5,7-tetrahydro-6H-pyrrolo[3',4':4,5]thieno[2,3-d]pyrimidine-6-carboxylate

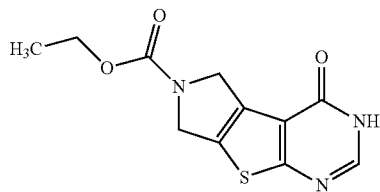 [SMILES: CCOC(=O)N1Cc2sc3nc[nH]c(=O)c3c2C1]

Diethyl 2-amino-4,6-dihydro-5H-thieno[2,3-c]pyrrole-3,5-dicarboxylate from Example 19A (3.60 g, 12.7 mmol) was dissolved in formamide (72 mL), and ammonium formiate (2.11 g, 20.3 mmol) was added. The mixture was heated to 140° C. overnight, then diluted with water and extracted with ethyl acetate. The organic layer was dried over sodium sulfate, and the solvent was removed in vacuo. The precipitate in the aqueous layer was collected by suction filtration and combined with the organic extracts. The product was purified by column chromatography on silica gel (eluent: DCM/MeOH 100:3) and subsequently triturated with tert-butyl methyl ether to yield 1.74 g (52%) of the title compound.

$^1$H-NMR (400 MHz, DMSO-d$_6$): δ=1.21-1.27 (m, 3H), 4.08-4.16 (m, 2H), 4.59-4.70 (m, 4H), 8.10 (s, 1H), 12.61 (br. s, 1H).

LC/MS (method 4): R$_t$=1.65 min; MS (ESIpos): m/z=266 [M+H]$^+$.

Example 21A

Ethyl 4-chloro-5,7-dihydro-6H-pyrrolo[3',4':4,5]thieno[2,3-d]pyrimidine-6-carboxylate

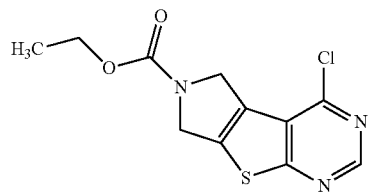 [SMILES: CCOC(=O)N1Cc2sc3ncnc(Cl)c3c2C1]

In analogy to Example 11A, ethyl 4-oxo-3,4,5,7-tetrahydro-6H-pyrrolo[3',4':4,5]thieno[2,3-d]pyrimidine-6-carboxylate from Example 20A (1.70 g, 6.41 mmol) was reacted with phosphoryl chloride to yield 1.23 g (67%) of the title compound.

$^1$H-NMR (400 MHz, DMSO-d$_6$): δ=1.23-1.28 (m, 3H), 4.16 (q, 2H), 4.79-4.87 (m, 4H), 8.92 (s, 1H).

LC/MS (method 2): R$_t$=1.04 min; MS (ESIpos): m/z=284 [M+H]$^+$.

Example 22A

Ethyl 4-[(3-chloro-4-fluorophenyl)amino]-5,7-dihydro-6H-pyrrolo[3',4':4,5]thieno[2,3-d]pyrimidine-6-carboxylate

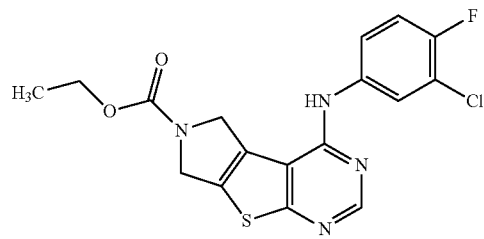 [SMILES: CCOC(=O)N1Cc2sc3ncnc(Nc4ccc(F)c(Cl)c4)c3c2C1]

Ethyl 4-chloro-5,7-dihydro-6H-pyrrolo[3',4':4,5]thieno[2,3-d]pyrimidine-6-carboxylate from Example 21A (250 mg, 0.88 mmol) was dissolved in 2-propanol (2 mL). 3-Chloro-4-fluoroanilin (135 mg, 0.93 mmol) and a 4 M solution of gaseous hydrogen chloride in dioxane (11 μL, 0.04 mmol) were added, and the mixture was heated to 80° C. overnight. The precipitate was collected by suction filtration to yield 419 mg of the crude product (70% purity, 83% yield), which was used in the next step without purification.

LC/MS (method 2): R$_t$=1.28 min; MS (ESIpos): m/z=393 [M+H]$^+$.

Example 23A

N-(3-Chloro-4-fluorophenyl)-6,7-dihydro-5H-pyrrolo[3',4':4,5]thieno[2,3-d]pyrimidin-4-amine

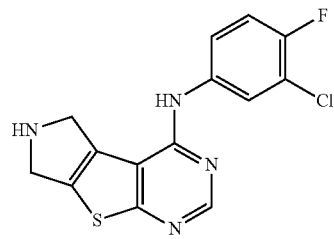 [SMILES: Fc1ccc(Nc2ncnc3sc4c(c23)CNC4)cc1Cl]

To a solution of ethyl 4-[(3-chloro-4-fluorophenyl)amino]-5,7-dihydro-6H-pyrrolo[3',4':4,5]thieno[2,3-d]pyrimidine-6-carboxylate from Example 22A (413 mg, 1.05 mmol) in ethanol (4 mL) was added a 10 M aqueous potassium hydroxide solution (2 mL), and the mixture was stirred for 14 h at 80° C. Subsequently, water was added, and the mixture was extracted with ethyl acetate. The organic layer was washed twice with water, dried over sodium sulfate, and the solvent was removed in vacuo. The residue was triturated with tert-butyl methyl ether, and the precipitate was collected by suction filtration to yield 126 mg (38%) of the title compound. The mother liquor was concentrated in vacuo and purified by preparative HPLC to yield further 35 mg (10%).

¹H-NMR (400 MHz, DMSO-d₆): δ=3.60 (br. s, 1H), 4.18 (t, 2H), 4.38 (t, 2H), 7.42 (t, 1H), 7.66 (ddd, 1H), 7.94 (dd, 1H), 8.42 (br. s, 1H), 8.44 (s, 1H).

LC/MS (method 6): $R_t$=0.88 min; MS (ESIpos): m/z=321 [M+H]⁺.

Example 24A

Ethyl 4-[(3,4-dichlorophenyl)amino]-5,7-dihydro-6H-pyrrolo[3',4':4,5]thieno[2,3-d]pyrimidine-6-carboxylate

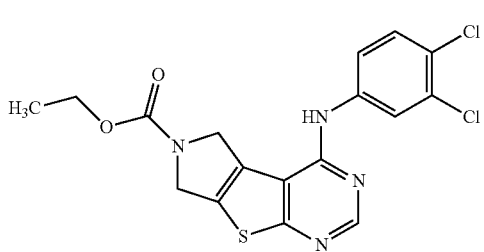

In analogy to Example 22A, the title compound was prepared from ethyl 4-chloro-5,7-dihydro-6H-pyrrolo[3',4':4,5]thieno[2,3-d]pyrimidine-6-carboxylate from Example 21A (250 mg, 0.88 mmol) and 3,4-dichloroaniline (150 mg, 0.93 mmol) to yield 324 mg (64% purity, 57% yield), which was used in the next step without purification.

LC/MS (method 2): $R_t$=1.38 min; MS (ESIpos): m/z=409 [M+H]⁺.

Example 25A

N-(3,4-Dichlorophenyl)-6,7-dihydro-5H-pyrrolo[3',4':4,5]thieno[2,3-d]pyrimidin-4-amine

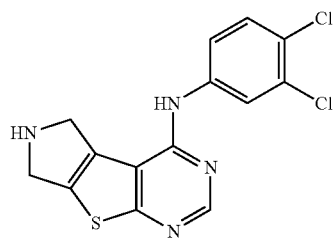

In analogy to Example 23A, ethyl 4-[(3,4-dichlorophenyl)amino]-5,7-dihydro-6H-pyrrolo[3',4':4,5]thieno[2,3-d]pyrimidine-6-carboxylate from Example 24A (324 mg, 0.79 mmol) was treated with aqueous potassium hydroxide solution to yield 157 mg (59%) of the title compound.

¹H-NMR (400 MHz, DMSO-d₆): δ=3.72 (br. s, 1H), 4.19 (t, 2H), 4.40 (t, 2H), 7.61 (d, 1H), 7.73 (dd, 1H), 8.06 (d, 1H), 8.49 (br. s, 2H).

LC/MS (method 4): $R_t$=1.44 min; MS (ESIpos): m/z=337 [M+H]⁺.

Example 26A

Ethyl 4-[(3-ethynylphenyl)amino]-5,7-dihydro-6H-pyrrolo[3',4':4,5]thieno[2,3-d]pyrimidine-6-carboxylate

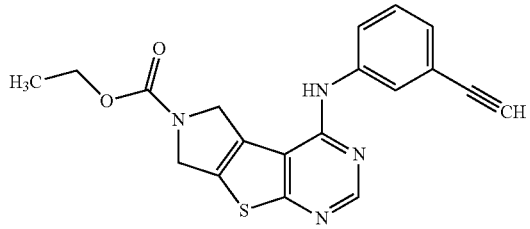 [SMILES: C#Cc1cccc(Nc2ncnc3sc4c(c23)CN(C(=O)OCC)C4)c1]

In analogy to Example 22A, ethyl 4-chloro-5,7-dihydro-6H-pyrrolo[3',4':4,5]thieno[2,3-d]pyrimidine-6-carboxylate from Example 21A (235 mg, 0.83 mmol) and 3-ethynylaniline (102 mg, 0.87 mmol) were reacted to the title compound to yield 211 mg (67%).

¹H-NMR (400 MHz, DMSO-d₆): δ=1.23-1.29 (m, 3H), 4.12-4.20 (m, 2H), 4.20-4.22 (m, 1H), 4.72-4.78 (m, 2H), 5.00 (t, 2H), 7.21-7.25 (m, 1H), 7.38 (t, 1H), 7.67-7.73 (m, 1H), 7.75-7.81 (m, 1H), 8.47 (s, 1H), 8.61 (s, 1H).

LC/MS (method 4): $R_t$=2.56 min; MS (ESIpos): m/z=365 [M+H]⁺.

Example 27A

N-(3-Ethynylphenyl)-6,7-dihydro-5H-pyrrolo[3',4':4,5]thieno[2,3-d]pyrimidin-4-amine

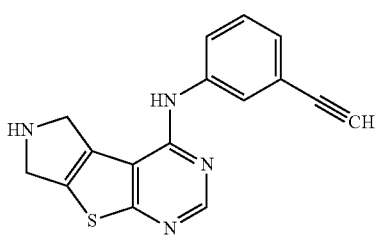 [SMILES: C#Cc1cccc(Nc2ncnc3sc4c(c23)CNC4)c1]

In analogy to Example 23A, ethyl 4-[(3-ethynylphenyl)amino]-5,7-dihydro-6H-pyrrolo[3',4':4,5]thieno[2,3-d]pyrimidine-6-carboxylate from Example 26A (180 mg, 0.49 mmol) was reacted to the title compound to yield 41 mg (25%).

¹H-NMR (400 MHz, DMSO-d₆): δ=3.70 (br. s, 1H), 4.17-4.19 (m, 2H), 4.20 (s, 1H), 4.38-4.41 (m, 2H), 7.19-7.22 (m, 1H), 7.37 (t, 1H), 7.71-7.76 (m, 1H), 7.82-7.85 (m, 1H), 8.36 (s, 1H), 8.45 (s, 1H).

LC/MS (method 5): $R_t$=1.17 min; MS (ESIpos): m/z=293 [M+H]⁺.

Example 28A

Ethyl 4-({3-chloro-4-[(3-fluorobenzyl)oxy]phenyl}amino)-5,7-dihydro-6H-pyrrolo[3',4':4,5]thieno[2,3-d]pyrimidine-6-carboxylate

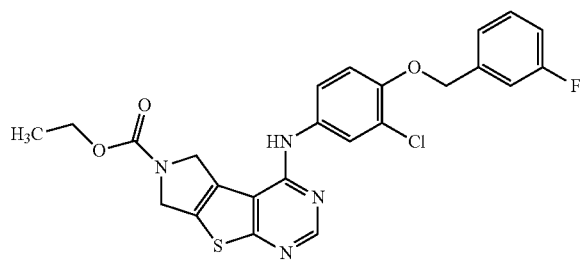 [SMILES: CCOC(=O)N1Cc2sc3ncnc(Nc4ccc(OCc5cccc(F)c5)c(Cl)c4)c3c2C1]

In analogy to Example 22A, the title compound was prepared from ethyl 4-chloro-5,7-dihydro-6H-pyrrolo[3',4':4,5]thieno[2,3-d]pyrimidine-6-carboxylate from Example 21A (100 mg, 0.35 mmol) and 3-chloro-4-[(3-fluorobenzyl)oxy]aniline from Example 4A (93 mg, 0.37 mmol) to give 157 mg (72% purity, 65% yield), which was used in the next step without purification.

LC/MS (method 6): $R_t$=2.40 min; MS (ESIpos): m/z=499 [M+H]⁺.

Example 29A

N-{3-Chloro-4-[(3-fluorobenzyl)oxy]phenyl}-6,7-dihydro-5H-pyrrolo[3',4':4,5]thieno[2,3-d]pyrimidin-4-amine

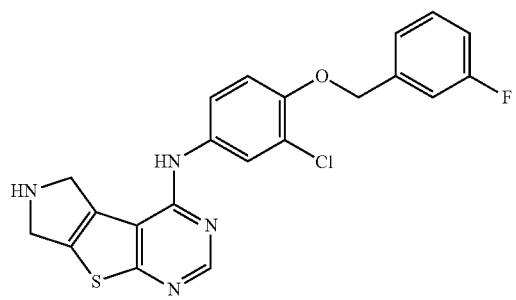 [SMILES: Fc1cccc(COc2ccc(Nc3ncnc4sc5c(c34)CNC5)cc2Cl)c1]

In analogy to Example 23A, ethyl 4-({3-chloro-4-[(3-fluorobenzyl)oxy]phenyl}amino)-5,7-dihydro-6H-pyrrolo[3',4':4,5]thieno[2,3-d]pyrimidine-6-carboxylate from Example 28A (157 mg, 0.314 mmol) was reacted to the title compound to yield 51 mg (38%).

¹H-NMR (400 MHz, DMSO-d₆): δ=3.68 (br. s, 1H), 4.17 (t, 2H), 4.36 (t, 2H), 5.25 (s, 2H), 7.18 (dt, 1H), 7.23 (d, 1H), 7.28-7.35 (m, 2H), 7.47 (dt, 1H), 7.53 (dd, 1H), 7.78 (d, 1H), 8.29 (br. s, 1H), 8.38 (s, 1H).

LC/MS (method 6): $R_t$=1.30 min; MS (ESIpos): m/z=427 [M+H]⁺.

Example 30A

Ethyl 4-{[3-chloro-4-(pyridin-2-ylmethoxy)phenyl]amino}-5,7-dihydro-6H-pyrrolo[3',4':4,5]thieno[2,3-d]pyrimidine-6-carboxylate

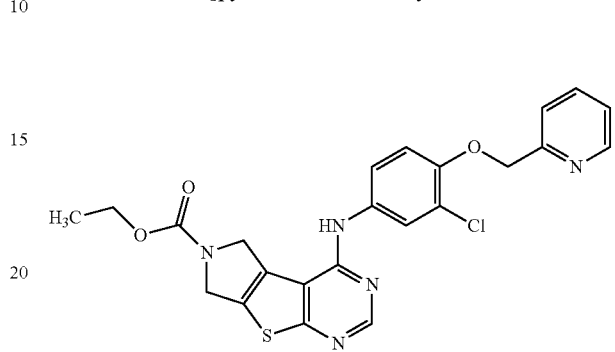

In analogy to Example 22A, ethyl 4-chloro-5,7-dihydro-6H-pyrrolo[3',4':4,5]thieno[2,3-d]pyrimidine-6-carboxylate from Example 21A (100 mg, 0.35 mmol) and 3-chloro-4-(pyridin-2-ylmethoxy)aniline from Example 6A (87 mg, 0.37 mmol) were reacted to the title compound to give 158 mg of a crude product (72% purity, 67% yield), which was used in the next step without further purification.

LC/MS (method 6): $R_t$=1.92 min; MS (ESIpos): m/z=482 [M+H]⁺.

Example 31A

N-[3-Chloro-4-(pyridin-2-ylmethoxy)phenyl]-6,7-dihydro-5H-pyrrolo[3',4':4,5]thieno[2,3-d]pyrimidin-4-amine

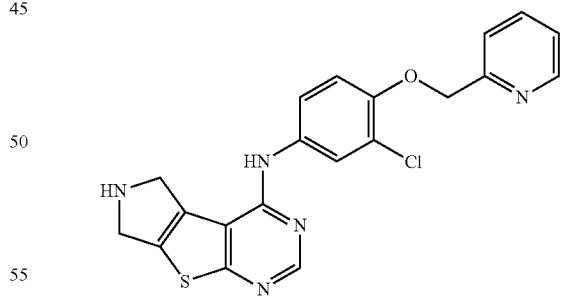

In analogy to Example 23A, ethyl 4-{[3-chloro-4-(pyridin-2-ylmethoxy)phenyl]amino}-5,7-dihydro-6H-pyrrolo[3',4':4,5]thieno[2,3-d]pyrimidine-6-carboxylate from Example 30A (158 mg, 0.237 mmol) was reacted to the title compound to yield 43 mg (44%).

¹H-NMR (400 MHz, DMSO-d₆): δ=3.63 (br. s, 1H), 4.17 (t, 2H), 4.36 (t, 2H), 5.29 (s, 2H), 7.24 (d, 1H), 7.37 (dd, 1H), 7.52 (dd, 1H), 7.58 (d, 1H), 7.79 (d, 1H), 7.88 (dt, 1H), 8.28 (br. s, 1H), 8.38 (s, 1H), 8.58-8.61 (m, 1H).

LC/MS (method 2): $R_t$=0.74 min; MS (ESIpos): m/z=410 [M+H]$^+$.

Example 32A

Ethyl 4-{[1-(3-fluorobenzyl)-1H-indazol-5-yl]amino}-5,7-dihydro-6H-pyrrolo[3',4':4,5]thieno[2,3-d]pyrimidine-6-carboxylate

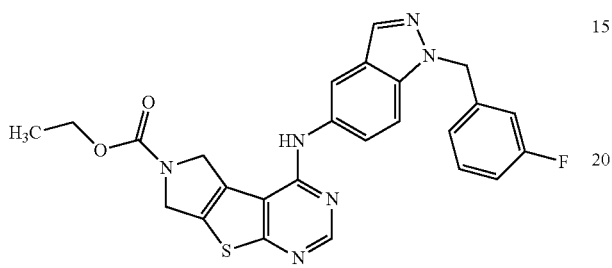

In analogy to Example 22A, ethyl 4-chloro-5,7-dihydro-6H-pyrrolo[3',4':4,5]thieno[2,3-d]pyrimidine-6-carboxylate from Example 21A (100 mg, 0.35 mmol) and 1-(3-fluorobenzyl)-1H-indazol-5-amine from Example 8A (89 mg, 0.37 mmol) were reacted to the title compound to yield 120 mg (68%).

LC/MS (method 2): $R_t$=1.25 min; MS (ESIpos): m/z=489 [M+H]$^+$.

Example 33A

N-[1-(3-Fluorobenzyl)-1H-indazol-5-yl]-6,7-dihydro-5H-pyrrolo[3',4':4,5]thieno[2,3-d]pyrimidin-4-amine

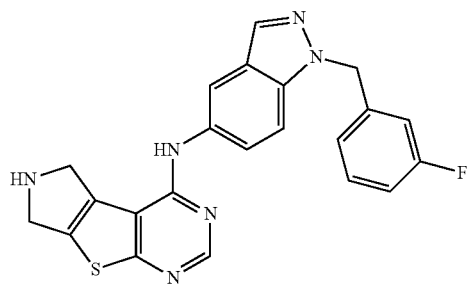 [SMILES: Fc1cccc(Cn2ncc3cc(Nc4ncnc5sc6c(c45)CNC6)ccc32)c1]

In analogy to Example 23A, ethyl 4-{[1-(3-fluorobenzyl)-1H-indazol-5-yl]amino}-5,7-dihydro-6H-pyrrolo[3',4':4,5]thieno[2,3-d]pyrimidine-6-carboxylate from Example 32A (118 mg, 0.17 mmol) was reacted to the title compound to yield 60 mg (83%).

$^1$H-NMR (400 MHz, DMSO-d$_6$): δ=3.80 (br. s, 1H), 4.17 (t, 2H), 4.35 (t, 2H), 5.70 (s, 2H), 7.00-7.05 (m, 2H), 7.07-7.13 (m, 1H), 7.33-7.39 (m, 1H), 7.52 (dd, 1H), 7.71 (d, 1H), 8.00 (d, 1H), 8.13 (s, 1H), 8.33 (s, 1H), 8.41 (s, 1H).

LC/MS (method 6): $R_t$=1.01 min; MS (ESIpos): m/z=417 [M+H]$^+$.

Example 34A

Ethyl 3-hydroxy-4,4-dimethoxypiperidine-1-carboxylate

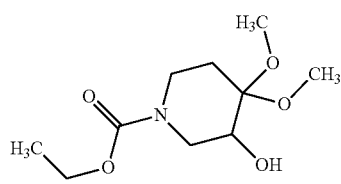 [SMILES: CCOC(=O)N1CCC(OC)(OC)C(O)C1]

Potassium hydroxide powder (3.97 g, 60.2 mmol) was dissolved in methanol (50 mL) and cooled to 0-5° C. Ethyl 4-oxopiperidine-1-carboxylate (4.29 g, 25.1 mmol) was added, and the mixture was stirred for 15 min. A solution of iodine (7.00 g, 27.6 mmol) in methanol (50 mL) was added within 2 h. The reaction was warmed to rt and stirred for further 4 h. The mixture was then concentrated in vacuo, and the residue was triturated with toluene and filtered. The solvent was removed in vacuo to yield 5.40 g of an orange oil (91% purity, 84% yield), which was used in the next step without purification.

GC/MS (method 1): $R_t$=5.78 min; MS (ESIpos): m/z=233 [M]$^+$.

Example 35A

Ethyl 3-hydroxy-4-oxopiperidine-1-carboxylate

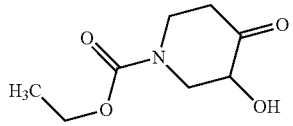

Ethyl 3-hydroxy-4,4-dimethoxypiperidine-1-carboxylate from Example 34A (5.00 g, 21.4 mmol) was dissolved in THF (50 mL), and trifluoroacetic acid (15.9 mL, 214 mmol) was added. The mixture was stirred for 3.5 h at rt. The solvent was then removed in vacuo. Twice, toluene was added and again removed in vacuo. The residue was dissolved in dichloromethane, dried over sodium sulfate, and the solvent was removed in vacuo to yield 4.70 g (95%) of an oil, which was used without further purification.

GC/MS (method 1): $R_t$=4.93 min; MS (ESIpos): m/z=187 [M]+.

Example 36A

Ethyl 2-amino-3-cyano-4,7-dihydrofuro[2,3-c]pyridine-6(5H)-carboxylate

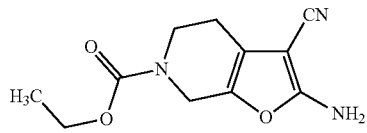 [SMILES: CCOC(=O)N1CCc2c(oc(N)c2C#N)C1]

Ethyl 3-hydroxy-4-oxopiperidine-1-carboxylate from Example 35A (4.00 g, 21.4 mmol) was dissolved in ethanol (10 mL), and propanedinitrile (1.41 g, 21.4 mmol) was added. Within 10 min, diethylamine (1.56 g, 21.4 mmol) was added dropwise, whilst the temperature was kept below 35° C. Subsequently, the reaction mixture was stirred for 20 h at rt. The precipitate was collected by suction filtration and washed with ethanol and diethyl ether to yield 2.00 g (39%) of the title compound.

$^1$H-NMR (400 MHz, DMSO-$d_6$): δ=1.19 (t, 3H), 2.32-2.38 (m, 2H), 3.57 (t, 2H), 4.07 (q, 2H), 4.24 (br. s, 2H), 7.34 (s, 2H).

GC/MS (method 1): $R_t$=7.92 min; MS (ESIpos): m/z=235 [M]+.

Example 37A

Ethyl 3-cyano-2-{[(1E)-(dimethylamino)methylidene]amino}-4,7-dihydrofuro[2,3-c]pyridine-6(5H)-carboxylate

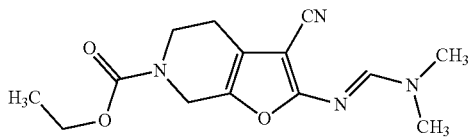

Ethyl 2-amino-3-cyano-4,7-dihydrofuro[2,3-c]pyridine-6(5H)-carboxylate from Example 36A (7.00 g, 29.8 mmol) was heated in dimethylformamide dimethylacetal (14.7 mL, 110 mmol) for 30 min to 110° C. The mixture was then concentrated in vacuo, and the residue was triturated with petroleum ether, the solvent was decanted, and the trituration was repeated. The remaining solid was then triturated with diethyl ether/petroleum ether (1:1), and the precipitate was collected by suction filtration to yield 8.5 g (98%) of the title compound.

$^1$H-NMR (400 MHz, DMSO-$d_6$): δ=1.20 (t, 3H), 2.40-2.46 (m, 2H), 2.99 (s, 3H), 3.11 (s, 3H), 3.60 (t, 2H), 4.08 (q, 2H), 4.33 (br. s, 2H), 8.22 (s, 1H).

LC/MS (method 6): $R_t$=1.61 min; MS (ESIpos): m/z=291 [M+H]+.

Example 38A

Ethyl 4-[(3-chloro-4-fluorophenyl)amino]-5,8-dihydropyrido[4',3':4,5]furo[2,3-d]pyrimidine-7(6H)-carboxylate

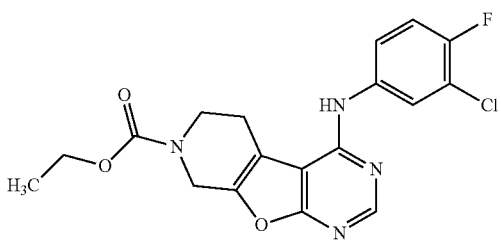 [SMILES: CCOC(=O)N1CCc2c(oc3ncnc(Nc4ccc(F)c(Cl)c4)c23)C1]

Ethyl 3-cyano-2-{[(1E)-(dimethylamino)methylidene]amino}-4,7-dihydrofuro[2,3-c]pyridine-6(5H)-carboxylate from Example 37A (1.20 g, 4.14 mmol) and 3-chloro-4-fluoroaniline (1.20 g, 8.27 mmol) were heated in a mixture of acetonitrile (20 mL) and acetic acid (10 mL) in a microwave oven for 30 min to 160° C. The mixture was then concentrated in vacuo, diluted with water, basified with aqueous sodium hydroxide solution and extracted with ethyl acetate. The organic layer was dried over sodium sulfate, and the solvent was evaporated. The residue was triturated with dichloromethane and left to stand for 20 h. The precipitate was collected by suction filtration. Subsequently, the solid was triturated with methanol. The crystals were collected by suction filtration and washed with diethyl ether to yield 360 mg (22%) of the title compound. A second batch of 159 mg (10%) was obtained from the mother liquor after purification by preparative HPLC.

$^1$H-NMR (400 MHz, DMSO-$d_6$): δ=1.23 (t, 3H), 2.95 (t, 2H), 3.71 (t, 2H), 4.12 (q, 2H), 4.62 (br. s, 2H), 7.42 (t, 1H), 7.62-7.69 (m, 1H), 7.91-7.96 (m, 1H), 8.39 (s, 1H), 8.70 (br. s, 1H).

LC/MS (method 6): $R_t$=2.08 min; MS (ESIpos): m/z=391 [M+H]+.

Example 39A

N-(3-Chloro-4-fluorophenyl)-5,6,7,8-tetrahydropyrido[4',3':4,5]furo[2,3-d]pyrimidin-4-amine

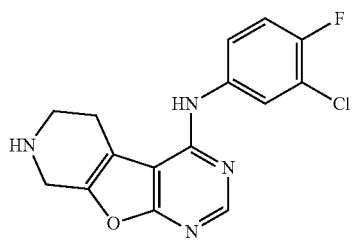 [SMILES: Fc1ccc(Nc2ncnc3oc4c(c23)CCNC4)cc1Cl]

In analogy to Example 23A, ethyl 4-[(3-chloro-4-fluorophenyl)amino]-5,8-dihydropyrido[4',3':4,5]-furo[2,3-d]pyrimidine-7(6H)-carboxylate from Example 38A (1.00 g, 2.56 mmol) was reacted to the title compound to yield 775 mg (95%).

¹H-NMR (400 MHz, DMSO-d₆): δ=2.67 (br. s, 1H), 2.95 (t, 2H), 3.33 (s, 2H), 3.83 (s, 2H), 7.40 (s, 1H), 7.66 (ddd, 1H), 7.94 (dd, 1H), 8.35 (s, 1H), 8.57 (s, 1H).

LC/MS (method 4): $R_t$=1.24 min; MS (ESIpos): m/z=319 [M+H]⁺.

Example 40A

Ethyl 4-[(3,4-dichlorophenyl)amino]-5,8-dihydropyrido[4',3':4,5]furo[2,3-d]pyrimidine-7(6H)carboxylate

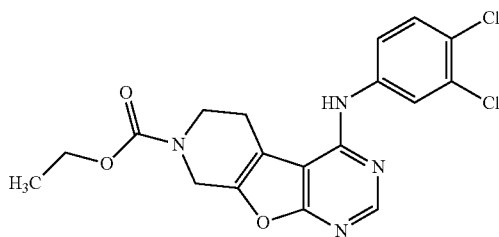

Ethyl 3-cyano-2-{[(1E)-(dimethylamino)methylidene]amino}-4,7-dihydrofuro[2,3-c]pyridine-6(5H)-carboxylate from Example 37A (1.00 g, 4.14 mmol) and 3,4-dichloroaniline (1.12 g, 6.89 mmol) were heated in a mixture of acetonitrile (20 mL) and acetic acid (2 mL) for 20 h under reflux. The mixture was then half-concentrated in vacuo and heated for further 20 h. Subsequently, it was diluted with water, basified with aqueous sodium hydroxide solution and extracted with ethyl acetate. The organic layer was dried over sodium sulfate, and the solvent was evaporated. The residue was triturated with methanol. The precipitate was collected by suction filtration to yield 542 mg (34%) of the title compound. A second batch of 50 mg (4%) was obtained from the mother liquor after purification by preparative HPLC.

¹H-NMR (400 MHz, DMSO-d₆): δ=1.23 (t, 3H), 2.95-3.00 (m, 2H), 3.71 (t, 2H), 4.12 (q, 2H), 4.63 (s, 2H), 7.60 (d, 1H), 7.73 (dd, 1H), 8.05 (d, 1H), 8.44 (s, 1H), 8.76 (br. s, 1H).

LC/MS (method 4): $R_t$=2.86 min; MS (ESIpos): m/z=407 [M+H]⁺.

Example 41A

N-(3,4-Dichlorophenyl)-5,6,7,8-tetrahydropyrido[4',3':4,5]furo[2,3-d]pyrimidin-4-amine

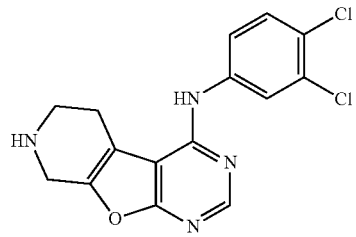

In analogy to Example 23A, ethyl 4-[(3,4-dichlorophenyl)amino]-5,8-dihydropyrido[4',3':4,5]furo-[2,3-d]pyrimidine-7(6H)-carboxylate from Example 40A (288 mg, 0.71 mmol) was reacted to the title compound to yield 203 mg (82%).

¹H-NMR (400 MHz, DMSO-d₆): δ=2.70 (br. s, 1H), 2.82-2.87 (m, 2H), 2.95 (t, 2H), 3.83-3.85 (m, 2H), 7.59 (d, 1H), 7.74 (dd, 1H), 8.07 (d, 1H), 8.40 (s, 1H), 8.66 (br. s, 1H).

LC/MS (method 5): $R_t$=1.56 min; MS (ESIpos): m/z=335 [M+H]⁺.

Example 42A

Ethyl 4-[(3-ethynylphenyl)amino]-5,8-dihydropyrido[4',3':4,5]furo[2,3-d]pyrimidine-7(6H)-carboxylate

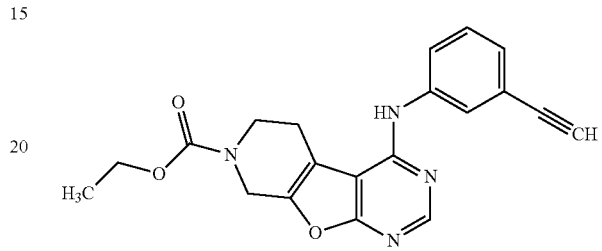

In analogy to Example 38A, the title compound was prepared from ethyl 3-cyano-2-{[(1E)(dimethylamino)methylidene]amino}-4,7-dihydrofuro[2,3-c]pyridine-6(5H)-carboxylate from Example 37A (1.20 g, 4.14 mmol) and 3-ethynylaniline (968 mg, 8.27 mmol) to yield 443 mg (28%).

¹H-NMR (400 MHz, DMSO-d₆): δ=1.23 (t, 3H), 2.92-2.98 (m, 2H), 3.70 (t, 2H), 4.12 (q, 2H), 4.19 (s, 1H), 4.62 (br. s, 2H), 7.20 (d, 1H), 7.37 (t, 1H), 7.70-7.75 (m, 1H), 7.80-7.83 (m, 1H), 8.38-8.40 (m, 1H), 8.64 (br. s, 1H).

LC/MS (method 6): $R_t$=1.95 min; MS (ESIpos): m/z=363 [M+H]⁺.

Example 43A

N-(3-Ethynylphenyl)-5,6,7,8-tetrahydropyrido[4',3':4,5]furo[2,3-d]pyrimidin-4-amine

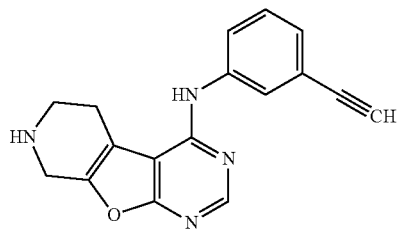 [SMILES: C#Cc1cccc(Nc2ncnc3oc4c(c23)CCNC4)c1]

In analogy to Example 23A, ethyl 4-[(3-ethynylphenyl)amino]-5,8-dihydropyrido[4',3':4,5]furo-[2,3-d]pyrimidine-7(6H)-carboxylate from Example 42A (863 mg, 2.38 mmol) was reacted to the title compound to yield 485 mg (68%).

¹H-NMR (400 MHz, DMSO-d₆): δ=2.61 (br. s, 1H), 2.80-2.85 (m, 2H), 2.95 (t, 2H), 3.82-3.84 (m, 2H), 4.19 (s, 1H), 7.18 (dt, 1H), 7.36 (t, 1H), 7.71-7.76 (m, 1H), 7.82-7.85 (m, 1H), 8.35-8.36 (m, 1H), 8.52 (br. s, 1H).

LC/MS (method 4): $R_t$=1.15 min; MS (ESIpos): m/z=291 [M+H]$^+$.

Example 44A tert-Butyl 3-hydroxy-4,4-dimethoxypiperidine-1-carboxylate

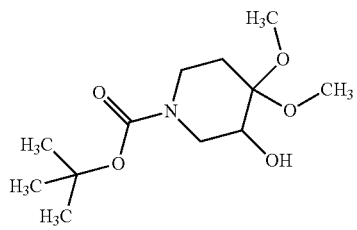 [SMILES: COC1(OC)CCN(C(=O)OC(C)(C)C)CC1O]

Potassium hydroxide powder (4.75 g, 72.0 mmol) was dissolved in methanol (60 mL) and cooled to 0-5° C. tert-Butyl 4-oxopiperidine-1-carboxylate (5.98 g, 30.0 mmol) was added, and the mixture was stirred for 15 min. A solution of iodine (8.38 g, 33.0 mmol) in methanol (60 mL) was added within 2 h. The reaction mixture was warmed to rt and stirred for further 5 h. The solution was then concentrated in vacuo, and the residue was triturated with toluene and filtered. The solvent was removed in vacuo to yield 5.24 g of a brown oil (88% purity, 59% yield) which was used in the next step without purification.

GC/MS (method 1): $R_t$=5.78 min; MS (DCI): m/z=262 [M+H]$^+$.

Example 45A tert-Butyl 3-hydroxy-4-oxopiperidine-1-carboxylate

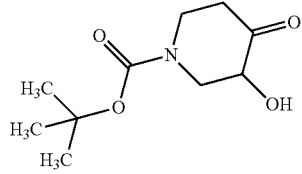

tert-Butyl 3-hydroxy-4,4-dimethoxypiperidine-1-carboxylate from Example 44A (5.24 g, 20.1 mmol) was dissolved in acetone (100 mL), and p-toluene sulfonic acid (173 mg, 1.00 mmol) was added. The mixture was stirred at rt for 3 days, then filtered, and the filtrate was concentrated. The residue was dissolved in tert-butyl methyl ether and extracted with satd. aqueous sodium bicarbonate solution. The organic layer was dried over sodium sulfate, and the solvent was removed in vacuo to yield 4.67 g of an oil (64% purity, 69% yield), which was used in the next step without further purification.

GC/MS (method 1): $R_t$=4.95 min; MS (ESIpos): m/z=159 [M−tBu]$^+$.

Example 46A tert-Butyl 2-amino-3-cyano-4,7-dihydrofuro[2,3-c]pyridine-6(5H)-carboxylate

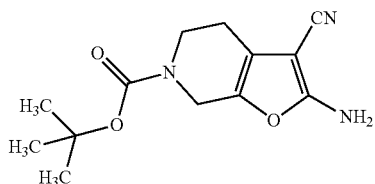

tert-Butyl 3-hydroxy-4-oxopiperidine-1-carboxylate from Example 45A (3.88 g, 64% purity, 11.5 mmol) was dissolved in ethanol (10 mL), and propanedinitrile (758 mg, 11.5 mmol) was added. Within 10 min, diethylamine (0.84 g, 11.5 mmol) was added dropwise, whilst the temperature was kept below 30° C. Subsequently, the reaction mixture was stirred for 20 h at rt. The solvent was removed in vacuo, and the residue was purified by column chromatography on silica gel (eluent: cyclohexane/ethyl acetate 2:1). The product was triturated with petroleum ether/tert-butyl methyl ether (3:1) to yield 1.45 g (47%) of the title compound as yellow crystals.

$^1$H-NMR (400 MHz, DMSO-d$_6$): δ=1.41 (s, 9H), 2.31-2.36 (m, 2H), 3.52 (t, 2H), 4.19 (s, 2H), 7.33 (s, 2H).

LC/MS (method 2): $R_t$=1.05 min; MS (ESIpos): m/z=206 [M−tBu]$^+$.

Example 47A tert-Butyl 3-cyano-2-[(1-methoxymethylidene)amino]-4,7-dihydrofuro[2,3-c]pyridine-6(5H)-carboxylate

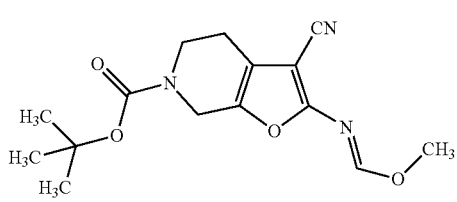 [SMILES: CO/C=N/c1oc2c(c1C#N)CCN(C(=O)OC(C)(C)C)C2]

tert-Butyl 2-amino-3-cyano-4,7-dihydrofuro[2,3-c]pyridine-6(5H)-carboxylate from Example 46A (200 mg, 0.76 mmol) was heated in trimethyl orthoformiate (1.7 mL) for 15 min to 100° C. Volatiles were removed in vacuo, and the crude product was used in the next step without further purification.

LC/MS (method 6): $R_t$=2.06 and 2.10 min; MS (ESIpos): m/z=306 [M+H]$^+$.

Example 48A

Isoxazol-5-ylacetonitrile

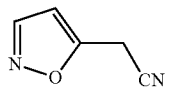

5-(Bromomethyl)isoxazole [P. DeShong, J. A. Cipollina, N. K. Lowmaster, *J. Org. Chem.* 1988, 53, 1356-1364] (42 g, 259 mmol) was dissolved in DMSO (420 mL). Water was added (145 mL), and the mixture was cooled with an ice-bath. Potassium cyanide (21.9 g, 337 mmol) was added, and the reaction was stirred at rt for 3 h. Subsequently, it was diluted with water (2 L), and the mixture was extracted three times with ethyl acetate (1 L each). The combined organic layers were washed with brine, dried over sodium sulfate, and the solvent was evaporated. The crude product was purified by column chromatography on silica gel (eluent: cyclohexane/ethyl acetate 2:1) to yield 15.5 g (55%) of the title product as an oil.

$^1$H-NMR (500 MHz, DMSO-d$_6$): δ=4.45 (s, 2H), 6.52-6.54 (m, 1H), 8.60 (d, 1H).

GC/MS (method 1): $R_t$=3.13 min; MS (ESIpos): m/z=108 [M]$^+$.

Example 49A tert-Butyl 4-[cyano(isoxazol-5-yl)methylidene]piperidine-1-carboxylate

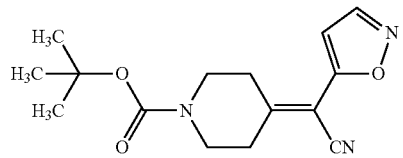 [SMILES: CC(C)(C)OC(=O)N1CCC(=C(C#N)c2ccno2)CC1]

A mixture of isoxazol-5-ylacetonitrile from Example 48A (3.00 g, 27.8 mmol), tert-butyl 4-oxopiperidine-1-carboxylate (5.53 g, 27.8 mmol) and ammonium acetate (4.28 g, 55.5 mmol) in toluene (50 mL) was heated for 8 h to reflux. Subsequently, the mixture was extracted with water, dried over sodium sulfate, and the solvent was removed in vacuo. The crude product was purified by column chromatography on silica gel (eluent: cyclohexane/ethyl acetate 2:1) to yield an oil, which precipitated upon treatment with petroleum ether/tert-butyl methyl ether to yield 4.38 g (54.6%) of the title compound as yellowish crystals.

$^1$H-NMR (500 MHz, DMSO-d$_6$): δ=1.42 (s, 9H), 2.73-2.79 (m, 4H), 3.47 (t, 2H), 3.55 (t, 2H), 6.79 (d, 1H), 8.73 (d, 1H).

LC/MS (method 2): $R_t$=1.14 min; MS (ESIpos): m/z=322 [M+H]$^+$.

Example 50A tert-Butyl 2-amino-3-isoxazol-5-yl-4,7-dihydrothieno[2,3-c]pyridine-6(5H)-carboxylate

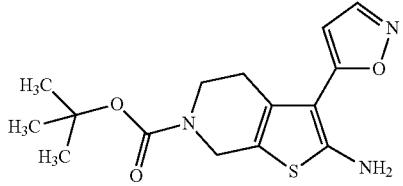 [SMILES: CC(C)(C)OC(=O)N1CCc2c(sc(N)c2-c2ccno2)C1]

To a solution of tert-butyl 4-[cyano(isoxazol-5-yl)methylidene]piperidine-1-carboxylate from Example 49A (2.10 g, 7.26 mmol) in ethanol (5.0 mL) were added sulfur (233 mg, 7.26 mmol) and triethylamine (734 mg, 7.26 mmol), and the mixture was stirred for 15 h at rt. The precipitate was collected by suction filtration and washed with diethyl ether to yield 916 mg (39%) of the title compound. The mother liquor was concentrated in vacuo, and the residue was purified by preparative HPLC to give a second batch of 454 mg (19%).

$^1$H-NMR (400 MHz, DMSO-d$_6$): δ=1.42 (s, 9H), 2.60-2.66 (m, 2H), 3.57 (t, 2H), 4.32 (s, 2H), 6.34 (s, 2H), 6.42 (d, 1H), 8.52 (d, 1H).

LC/MS (method 2): $R_t$=1.14 min; MS (ESIpos): m/z=322 [M+H]$^+$.

Example 51A tert-Butyl 3-isoxazol-5-yl-2-{[(1E)-methoxymethylidene]amino}-4,7-dihydrothieno[2,3-c]pyridine-6 (5H)-carboxylate

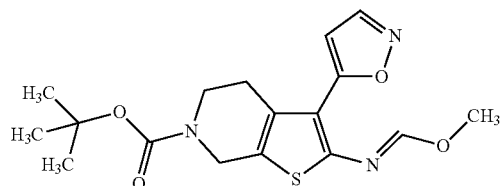

tert-Butyl 2-amino-3-isoxazol-5-yl-4,7-dihydrothieno[2,3-c]pyridine-6(5H)-carboxylate from Example 50A (1.76 g, 5.48 mmol) was heated in trimethyl orthoformiate (12 mL) for 15 min to 100° C. The mixture was then concentrated in vacuo, and the residue was triturated with dichloromethane to yield reddish crystals which were collected by suction filtration to yield 1.70 g (85%) of the title compound.

¹H-NMR (400 MHz, DMSO-d₆): δ=1.43 (s, 9H), 2.80-2.85 (m, 2H), 3.60-3.65 (m, 2H), 3.89 (s, 3H), 4.49 (s, 2H), 6.80 (d, 1H), 8.29 (s, 1H), 8.58 (d, 1H).

Example 52A tert-Butyl 3-cyano-4-hydroxy-5,8-dihydrothieno[2,3-b:5,4-c']dipyridine-7(6H)-carboxylate

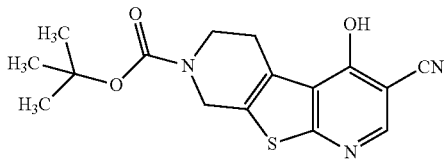 [SMILES: CC(C)(C)OC(=O)N1CCc2c(sc3ncc(C#N)c(O)c23)C1]

To a suspension of tert-butyl 3-isoxazol-5-yl-2-{[(1E)-methoxymethylidene]amino}-4,7-dihydrothieno[2,3-e]pyridine-6(5H)-carboxylate from Example 51A (1.80 g, 4.95 mmol) in methanol (10 mL) was added a 5.4 M solution of sodium methanolate in methanol (25 mL, 135 mmol), and the mixture was stirred for 15 min. It was then concentrated in vacuo. Water was added, and the mixture was neutralized with diluted aqueous hydrochloric acid. The mixture was extracted with dichloromethane. The organic phase was dried over sodium sulfate, and the solvent was evaporated. The residue was purified by column chromatography on silica gel (eluent: DCM/MeOH 9:1) to yield 1.00 g (56%) of the title compound.

¹H-NMR (400 MHz, DMSO-d₆): δ=1.42 (s, 9H), 2.95-3.00 (m, 2H), 3.59 (t, 2H), 4.55 (s, 2H), 8.55 (s, 1H), 13.38 (br. s, 1H).

LC/MS (method 2): $R_t$=0.92 min; MS (ESIpos): m/z=332 [M+H]⁺.

Example 53A tert-Butyl 4-chloro-3-cyano-5,8-dihydrothieno[2,3-b:5,4-c']dipyridine-7(6H)-carboxylate

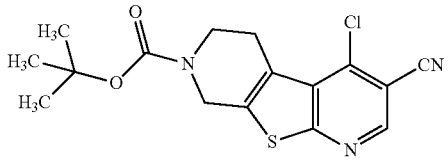 [SMILES: CC(C)(C)OC(=O)N1CCc2c(sc3ncc(C#N)c(Cl)c23)C1]

To sulfolane (10 mL) was added phosphoryl chloride (1.39 g, 9.05 mmol) at rt. Triethylamine (0.92 g, 9.05 mmol) was added dropwise with cooling. tert-Butyl 3-cyano-4-hydroxy-5,8-dihydrothieno[2,3-b:5,4-c']dipyridine-7(6H)-carboxylate from Example 52A (1.00 g, 3.02 mol) was added, and the mixture was heated to 70° C. for 1.5 h. The mixture was cooled to rt, and triethylamine (2.3 mL) was added. A semi-saturated aqueous sodium chloride solution (10 L) was added whilst cooling with an ice-bath. The mixture was stirred at rt for 30 min and then extracted with ethyl acetate. The organic layer was washed with water, dried over sodium sulfate, and the solvent was removed in vacuo. Toluene was added, and the mixture was washed with water. The organic layer was again dried over sodium sulfate, and the solvent was removed in vacuo. After crystallization, the product was triturated with water, collected by suction filtration and dried to yield 543 mg (51%) of the title compound.

¹H-NMR (400 MHz, DMSO-d₆): δ=1.44 (s, 9H), 3.13-3.18 (m, 2H), 3.68-3.73 (m, 2H), 4.74-4.76 (m, 2H), 8.93 (s, 1H).

LC/MS (method 6): $R_t$=2.28 min; MS (ESIpos): m/z=350 [M+H]⁺.

Example 54A tert-Butyl 4-[(3-chloro-4-fluorophenyl)amino]-3-cyano-5,8-dihydrothieno[2,3-b:5,4-c']dipyridine-7(6H)-carboxylate

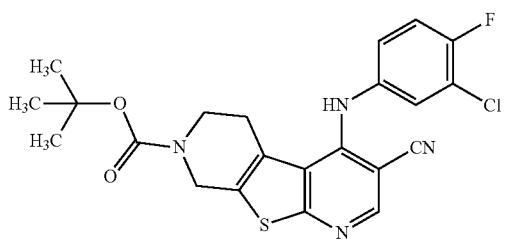 [SMILES: CC(C)(C)OC(=O)N1CCc2c(sc3ncc(C#N)c(Nc4ccc(F)c(Cl)c4)c23)C1]

To a solution of tert-butyl 4-chloro-3-cyano-5,8-dihydrothieno[2,3-b:5,4-c']dipyridine-7(6H)-carboxylate from Example 53A (150 mg, 0.43 mmol) in a degassed mixture of DMF (1.5 mL) and THF (1.5 mL) were added 3-chloro-4-fluoroaniline (62 mg, 0.43 mmol), XPHOS (4.1 mg, 0.009 mmol), caesium carbonate (196 mg, 0.60 mmol) and tris (dibenzylideneacetone)dipalladium(0) (24 mg, 0.026 mmol). The mixture was heated to 90° C. for 1 h. The solvent was removed in vacuo, and the residue was purified by column chromatography on silica gel (eluent: DCM/MeOH 50:1) to yield 190 mg (70% purity, 68% yield) of the title compound, which was used in the next step without further purification.

LC/MS (method 3): $R_t$=2.62 min; MS (ESIpos): m/z=459 [M+H]⁺.

Example 55A

4-[(3-Chloro-4-fluorophenyl)amino]-5,6,7,8-tetrahydrothieno[2,3-b:5,4-c']dipyridine-3-carbonitrile

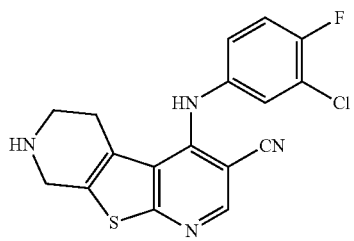 [SMILES: N#Cc1cnc2sc3c(c2c1Nc1ccc(F)c(Cl)c1)CCNC3]

tert-Butyl 4-[(3-chloro-4-fluorophenyl)amino]-3-cyano-5,8-dihydrothieno[2,3-b:5,4-c']dipyridine-7(6H)-carboxylate from Example 54A (250 mg, 0.365 mmol) was dissolved in 2-propanol (2 mL), and 4 M gaseous hydrogen chloride in dioxane (0.18 mL, 0.72 mmol) was added. The mixture was stirred at 80° C. for 1.5 h. The solvent was removed, and the residue was treated with 1 M aqueous sodium hydroxide solution (5 mL). The precipitate was collected by suction filtration, washed with water and dried in vacuo to yield 138 mg (99%) of the title compound.

$^1$H-NMR (400 MHz, DMSO-d$_6$): δ=3.00-3.05 (m, 2H), 3.13-3.17 (t, 2H), 4.22 (s, 2H), 7.03 (ddd, 1H), 7.25 (dd, 1H), 7.34 (t, 1H), 8.62 (s, 1H), 8.81 (br. s, 1H).

LC/MS (method 2): R$_t$=0.79 min; MS (ESIpos): m/z=359 [M+H]$^+$.

Example 56A tert-Butyl 4-{[3-chloro-4-(pyridin-2-ylmethoxy)phenyl]amino}-3-cyano-5,8-dihydrothieno[2,3-b:5,4-c']dipyridine-7(6H)-carboxylate

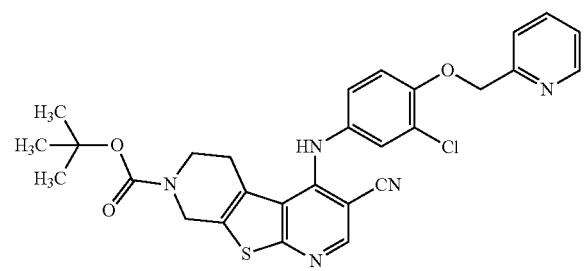 [SMILES: CC(C)(C)OC(=O)N1CCc2c(sc3ncc(C#N)c(Nc4ccc(OCc5ccccn5)c(Cl)c4)c23)C1]

In analogy to Example 54A, the title compound was synthesized from tert-butyl 4-chloro-3-cyano-5,8-dihydrothieno[2,3-b:5,4-c']dipyridine-7(6H)-carboxylate from Example 53A (190 mg, 0.54 mmol) and 3-chloro-4-(pyridin-2-ylmethoxy)aniline from Example 6A (127 mg, 0.54 mmol) to yield 215 mg (88% purity, 64% yield), which were used without further purification.

$^1$H-NMR (400 MHz, DMSO-d$_6$): δ=1.42 (s, 9H), 2.93-3.01 (m, 2H), 3.58 (t, 2H), 4.67 (br. s, 2H), 5.25 (s, 2H), 7.04 (dd, 1H), 7.20 (d, 1H), 7.25 (d, 1H), 7.35-7.39 (m, 1H), 7.55-7.58 (d, 1H), 7.87 (dt, 1H), 8.50 (s, 2H), 8.57-8.60 (m, 1H).

LC/MS (method 2): R$_t$=1.37 min; MS (ESIpos): m/z=548 [M+H]$^+$.

Example 57A

4-{[3-Chloro-4-(pyridin-2-ylmethoxy)phenyl]amino}-5,6,7,8-tetrahydrothieno[2,3-b:5,4-c']dipyridine-3-carbonitrile

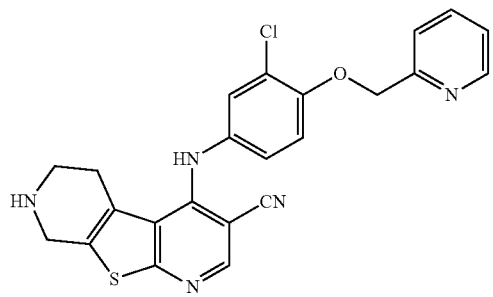 [SMILES: N#Cc1cnc2sc3c(c2c1Nc1ccc(OCc2ccccn2)c(Cl)c1)CCNC3]

tert-Butyl 4-{[3-chloro-4-(pyridin-2-ylmethoxy)phenyl]amino}-3-cyano-5,8-dihydrothieno[2,3-b:5,4-c']dipyridine-7(6H)-carboxylate from Example 56A (210 mg, 0.34 mmol) was dissolved in 2-propanol, and 4 M gaseous hydrogen chloride in dioxane (0.17 mL, 0.67 mmol) was added. The mixture was heated to 80° C. for 3 h. The precipitate was collected by suction filtration and dissolved in diluted aqueous sodium hydroxide solution. Some methanol was added, and the mixture was extracted with ethyl acetate. The organic layer was dried over sodium sulfate, and the solvent was evaporated. The title compound was crystallized from dichloromethane/diethyl ether to yield 116 mg (77%).

$^1$H-NMR (400 MHz, DMSO-d$_6$): δ=2.75 (br. s, 1H), 2.85-2.90 (m, 2H), 2.91-2.96 (m, 2H), 3.96 (s, 2H), 5.24 (s, 2H), 7.02 (dd, 1H), 7.19 (d, 1H), 7.25 (d, 1H), 7.36 (dd, 1H), 7.56 (d, 1H), 7.87 (dt, 1H), 8.40 (br. s, 1H), 8.48 (s, 1H), 8.59 (m, 1H).

LC/MS (method 4): R$_t$=1.33 min; MS (ESIpos): m/z=448 [M+H]$^+$.

Example 58A

7-[(2E)-4-Bromobut-2-enoyl]-N-(3-chloro-4-fluorophenyl)-5,6,7,8-tetrahydropyrido[4',3':4,5]thieno[2,3-d]pyrimidin-4-amine and 7-[(2E)-4-Chlorobut-2-enoyl]-N-(3-chloro-4-fluorophenyl)-5,6,7,8-tetrahydropyrido[4',3':4,5]thieno[2,3-d]pyrimidin-4-amine

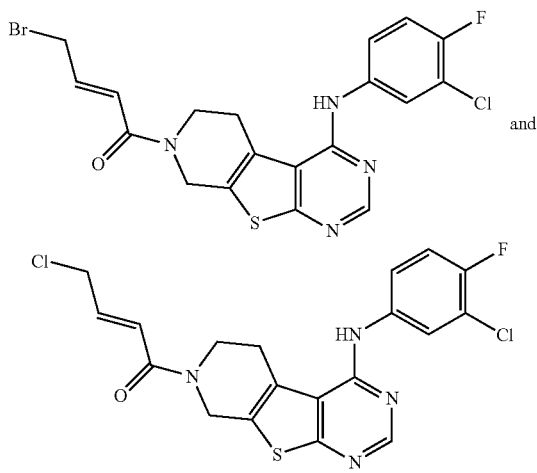

(2E)-4-Bromobut-2-enoic acid (1.48 g, 7.17 mmol) was stirred in thionylchloride (10 mL, 137 mmol) for 4 h. The mixture was then concentrated in vacuo. Twice, toluene was added and again removed in vacuo. The residue was dissolved in dichloromethane (14 mL). This solution was added to a solution of N-(3-chloro-4-fluorophenyl)-5,6,7,8-tetrahydropyrido[4',3':4,5]thieno[2,3-d]-pyrimidin-4-amine from Example 12A (2.00 g, 5.97 mmol) and DIPEA (1.93 g, 14.9 mmol) in DMF (35 mL) at −10° C. The mixture was stirred for 1.5 h at −10° C. and subsequently for 15 h at rt. The mixture was then diluted with water. Ethyl acetate was added, and the precipitate was collected by suction filtration to yield 1.50 g of a solid, which was identified by LC/MS as a mixture of the bromo- and chloro-allylic compound. It was used in the next step without further purification or separation.

LC/MS (method 4):
$R_t$=2.62 min; MS (ESIpos): m/z=437 $[M_{Cl}+H]^+$;
$R_t$=2.66 min; MS (ESIpos): m/z=481 $[M_{Br}+H]^+$.

Example 59A

7-[(2E)-4-Bromobut-2-enoyl]-N-(3,4-dichlorophenyl)-5,6,7,8-tetrahydropyrido[4',3':4,5]thieno[2,3-d]pyrimidin-4-amine and 7-[(2E)-4-Chlorobut-2-enoyl]-N-(3,4-dichlorophenyl)-5,6,7,8-tetrahydropyrido[4',3':4,5]thieno[2,3-d]pyrimidin-4-amine

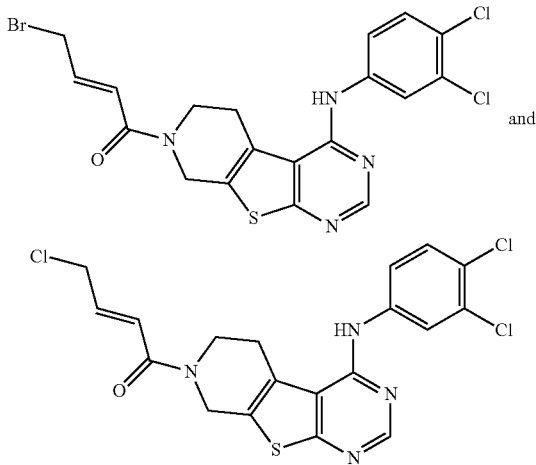

(2E)-4-Bromobut-2-enoic acid (1.33 g, 6.83 mmol) was dissolved in petroleum ether (25 mL). Thionylchloride (2.65 mL, 36.6 mmol) was added, and the mixture was heated to reflux for 4 h. The mixture was then concentrated in vacuo. Toluene was added and again removed in vacuo. The residue was dissolved in dichloromethane (14 mL). This solution was added to a solution of N-(3,4-dichlorophenyl)-5,6,7,8-tetrahydropyrido[4',3':4,5]thieno[2,3-d]pyrimidin-4-amine from Example 15A (2.00 g, 5.69 mmol) and DIPEA (1.25 g, 9.68 mmol) in DMF (20 mL) at −10° C. The mixture was warmed to rt and stirred overnight. The precipitate was collected by suction filtration and washed with water to yield 1.52 g of a solid, which was used in the next step without further purification or separation.

Example 60A

5-Nitro-1-(pyridin-2-ylmethyl)-1H-indazole

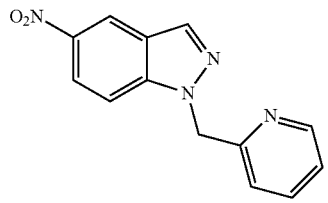 [SMILES: O=[N+]([O-])c1ccc2c(cnn2Cc2ccccn2)c1]

5-Nitroindazole (10.0 g, 61.3 mmol) was dissolved in THF (100 mL), and 2-(chloromethyl)pyridine hydrochloride (8.60 g, 52.4 mmol) and potassium carbonate (24.4 g, 184 mmol) were added. The mixture was heated for 4 h to 75° C. Water was added, and the mixture was extracted with ethyl acetate. The organic layer was dried over sodium sulfate, and the solvent was removed in vacuo. The crude product was purified by column chromatography on silica gel (eluent: gradient cyclohexane/ethyl acetate 1:1 to ethyl acetate) to yield 6.73 g (43%) of the title compound.
$^1$H-NMR (400 MHz, DMSO-$d_6$): δ=5.77 (s, 2H), 7.03 (d, 1H), 7.22 (dd, 1H), 7.54 (d, 1H), 7.62 (dt, 1H), 8.24 (dd, 1H), 8.27 (s, 1H), 8.58 (d, 1H), 8.74 (d, 1H).
LC/MS (method 2): $R_t$=0.95 min; MS (ESIpos): m/z=255 $[M+H]^+$.

Example 61A 1-(Pyridin-2-ylmethyl)-1H-indazol-5-amine

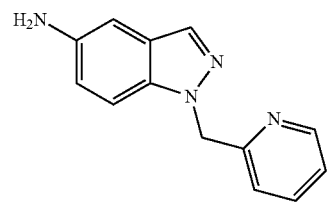

A solution of the compound from Example 60A (6.73 g, 26.5 mmol) in ethanol (70 mL) was stirred with platinum dioxide (200 mg) under a hydrogen atmosphere at normal pressure for 3 h. The catalyst was removed by suction filtration, and the solvent was removed in vacuo. The residue was triturated with tert-butyl methyl ether, and the product was collected by suction filtration to yield 5.1 g (86%) as white crystals.
$^1$H-NMR (400 MHz, DMSO-$d_6$): δ=4.83 (s, 2H), 5.61 (s, 2H), 6.76-6.83 (m, 3H), 7.26 (dd, 1H), 7.32 (d, 1H), 7.68 (dt, 1H), 7.78 (s, 1H), 8.51 (d, 1H).
LC/MS (method 2): $R_t$=0.25 min; MS (ESIpos): m/z=225 $[M+H]^+$.

Example 62A

N-[1-(Pyridin-2-ylmethyl)-1H-indazol-5-yl]-5,6,7,8-tetrahydropyrido[4',3':4,5]thieno[2,3-d]-pyrimidin-4-amine

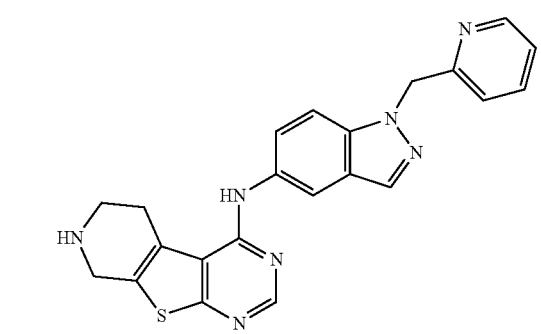 [SMILES: c1ccc(Cn2ncc3cc(Nc4ncnc5sc6c(c45)CCNC6)ccc32)nc1]

The title compound was synthesized in analogy to Example 12A from tert-butyl 4-chloro-5,8-dihydropyrido[4',3':4,5]thieno[2,3-d]pyrimidine-7(6H)-carboxylate from Example 11A (4.84 g, 14.5 mmol) and 1-(pyridin-2-ylmethyl)-1H-indazol-5-amine from Example 61A (3.50 g, 15.6 mmol) to yield 4.39 g (71%).

$^1$H-NMR (400 MHz, DMSO-$d_6$): δ=2.61 (br. s, 1H), 3.02-3.06 (m, 2H), 3.09-3.14 (m, 2H), 3.95 (s, 2H), 5.76 (s, 2H), 6.95 (d, 1H), 7.29 (dd, 1H), 7.53 (dd, 1H), 7.64 (d, 1H), 7.72 (dt, 1H), 8.04 (d, 1H), 8.11 (s, 1H), 8.20 (s, 1H), 8.32 (s, 1H), 8.51-8.53 (m, 1H).

LC/MS (method 2): $R_t$=0.61 min; MS (ESIpos): m/z=414 [M+H]$^+$.

Example 63A

3-Chloro-5-nitrophenol

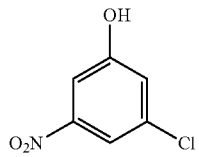

To a mixture of 1,3-dichloro-5-nitrobenzene (5.00 g, 26.0 mmol), potassium hydroxide (3.44 g, 52.1 mmol), tris(dibenzylideneacetone)dipalladium(0) (539 mg, 0.52 mmol), and 2-(di-tert-butylphosphino)-2,4,6-triisopropylbiphenyl (885 mg, 2.08 mmol) was added a degassed mixture of dioxane (25 mL) and water (15 mL). The mixture was heated for 30 min to 80° C., then diluted with water/ethyl acetate and acidified with diluted hydrochloric acid. The mixture was extracted three times with ethyl acetate. The combined organic layers were dried over sodium sulfate, and the solvent was removed in vacuo. The crude product was purified by column chromatography on silica gel (eluent: cyclohexane/ethyl acetate 3:1). The product was then triturated with petroleum ether/tert-butyl methyl ether and collected by suction filtration to yield 3.06 g (66%) of the title compound as yellowish crystals.

$^1$H-NMR (400 MHz, DMSO-$d_6$): δ=7.27 (t, 1H), 7.52 (t, 1H), 7.69 (t, 1H), 10.97 (br. s, 1H).

LC/MS (method 4): $R_t$=2.06 min; MS (ESIpos): m/z=174 [M+H]$^+$.

Example 64A

3-Amino-5-chlorophenol

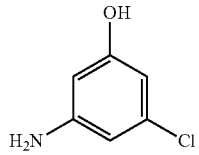 [SMILES: O=[N+]([O-])c1cc(O)cc(Cl)c1]

3-Chloro-5-nitrophenol from Example 63A (3.00 g, 17.3 mmol) and zinc powder (5.65 g, 86.4 mmol) in ethanol (80 mL) were heated to 60° C., and a solution of ammonium chloride (1.85 g, 34.6 mmol) in water (16 mL) was added dropwise. The reaction was stirred for further 3 h at 60° C. It was then filtered through Celite®, and the solvent was removed in vacuo. The residue was dissolved in water and extracted with ethyl acetate. The organic layer was dried over sodium sulfate, and the solvent was removed in vacuo. The residue was triturated with DCM, and the precipitate was collected by suction filtration to yield 1.97 g (77%) of the title compound as yellowish crystals.

$^1$H-NMR (400 MHz, DMSO-$d_6$): δ=5.25 (br. s, 2H), 5.92 (d, 2H), 6.03 (t, 1H), 9.29 (s, 1H).

LC/MS (method 4): $R_t$=1.07 min; MS (ESIpos): m/z=144 [M+H]$^+$.

Example 65A

3-Chloro-5-(5,6,7,8-tetrahydropyrido[4',3':4,5]thieno[2,3-d]pyrimidin-4-ylamino)phenol hydrochloride

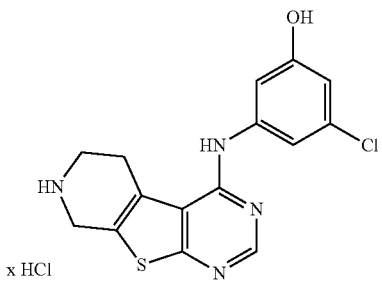 [SMILES: Oc1cc(Cl)cc(Nc2ncnc3sc4c(c23)CCNC4)c1]

tert-Butyl 4-chloro-5,8-dihydropyrido[4',3':4,5]thieno[2,3-d]pyrimidine-7(6H)-carboxylate from Example 11A (3.24 g, 9.95 mmol) was dissolved in 2-propanol (40 mL). 3-Amino-5-chlorophenol (1.50 g, 10.4 mmol) from Example 64A and a 4 M solution of gaseous hydrogen chloride in dioxane (124 µL, 0.50 mmol) were added, and the mixture was heated to 80° C. for 20 h. Subsequently, further hydrogen chloride in dioxane (5.0 mL, 20 mmol) was added, and the mixture was heated for additional 3 h. The resulting precipitate was collected by suction filtration to yield 3.63 g (99%) of the title compound.

$^1$H-NMR (400 MHz, DMSO-$d_6$): δ=3.46 (s, 4H), 4.50 (br. s, 3H), 6.57 (t, 1H), 7.16 (t, 1H), 7.21 (t, 1H), 8.51 (br. s, 1H), 8.53 (s, 1H), 9.83 (br. s, 2H).

LC/MS (method 6): $R_t$=0.76 min; MS (ESIpos): m/z=332 [M+H]$^+$.

Example 66A tert-Butyl(3,4,5-trichlorophenyl)carbamate

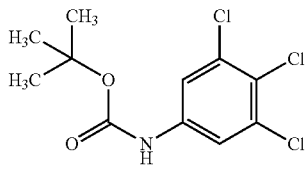 [SMILES: CC(C)(C)OC(=O)Nc1cc(Cl)c(Cl)c(Cl)c1]

3,4,5-Trichloroaniline (2.00 g, 10.2 mmol) was dissolved in THF (23 mL), and triethylamine (2.58 g, 25.5 mmol), di-tert-butyl dicarbonate (2.44 g, 11.2 mmol) and DMAP (124 mg, 1.02 mmol) were added. The mixture was stirred overnight at rt. Further di-tert-butyl dicarbonate (889 mg, 4.07 mmol) was added, and the mixture was heated to reflux overnight. The solvent was then removed in vacuo. The residue was dissolved in ethyl acetate and washed with satd. aqueous ammonium chloride solution. The organic layer was dried over sodium sulfate. The solvent was removed in vacuo, and the crude product was purified by column chromatography on silica gel (eluent: cyclohexane/ethyl acetate 3:1) to yield 2.81 g (82%) of the title compound.

$^1$H-NMR (400 MHz, DMSO-d$_6$): δ=1.48 (s, 9H), 7.71 (s, 2H), 9.86 (s, 1H).

LC/MS (method 2): R$_t$=1.57 min; MS (ESIpos): m/z=296 [M+H]$^+$.

Example 67A tert-Butyl(3,4-dichloro-5-hydroxyphenyl)carbamate

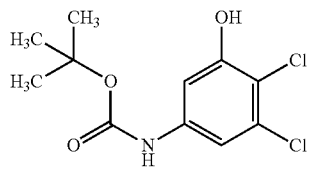 [SMILES: CC(C)(C)OC(=O)Nc1cc(O)c(Cl)c(Cl)c1]

In analogy to Example 63A, tert-butyl(3,4,5-trichlorophenyl)carbamate from Example 66A (3.98 g, 13.4 mmol) was reacted with potassium hydroxide (1.77 g, 26.8 mmol). The reaction mixture was heated to 80° C. overnight and subsequently to 90° C. for 3 h. The product was isolated by preparative HPLC to yield 760 mg (20%).

$^1$H-NMR (400 MHz, DMSO-d$_6$): δ=1.47 (s, 9H), 7.16 (d, 1H), 7.22 (d, 1H), 9.53 (s, 1H), 10.55 (br. s, 1H).

LC/MS (method 2): R$_t$=1.23 min; MS (ESIneg): m/z=276 [M–H]$^-$.

Example 68A

5-Amino-2,3-dichlorophenol hydrochloride

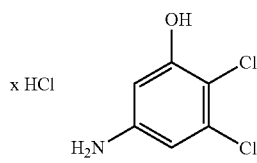

tert-Butyl(3,4-dichloro-5-hydroxyphenyl)carbamate from Example 67A (960 mg, 3.45 mmol) was dissolved in 2-propanol (16 mL), and 4 M gaseous hydrogen chloride in dioxane (5.0 mL, 20 mmol) was added. The mixture was heated to 80° C. for 1.5 h. Subsequently, the solvent was removed in vacuo to yield 700 mg (90%) of the title compound.

$^1$H-NMR (400 MHz, DMSO-d$_6$): δ=6.73 (s, 2H), 7.40 (br. s, 3H), 10.9 (br. s, 1H).

LC/MS (method 3): R$_t$=1.54 min; MS (ESIpos): m/z=178 [M+H]$^+$.

Example 69A 2,3-Dichloro-5-(5,6,7,8-tetrahydropyrido[4',3':4,5]thieno[2,3-d]pyrimidin-4-ylamino)phenol hydrochloride

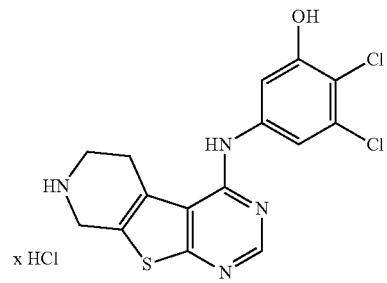 [SMILES: Oc1cc(Nc2ncnc3sc4c(c23)CCNC4)cc(Cl)c1Cl]

The title compound was prepared in analogy to Example 65A from tert-butyl 4-chloro-5,8-dihydropyrido[4',3':4,5]thieno[2,3-d]pyrimidine-7(6H)-carboxylate from Example 11A (300 mg, 0.92 mmol) and 5-amino-2,3-dichlorophenol hydrochloride from Example 68A (296 mg, 1.38 mmol) to yield 395 mg (99%).

$^1$H-NMR (400 MHz, DMSO-d$_6$): δ=3.46 (s, 4H), 4.46 (s, 2H), 7.40 (s, 1H), 7.46 (s, 1H), 8.54 (s, 1H), 8.62 (br. s, 1H), 9.88 (br. s, 2H), 10.75 (br. s, 1H).

LC/MS (method 4): R$_t$=1.30 min; MS (ESIpos): m/z=367 [M+H]$^+$.

Example 70A

4-Chloro-3-(5,6,7,8-tetrahydropyrido[4',3':4,5]thieno[2,3-d]pyrimidin-4-ylamino)phenol hydrochloride

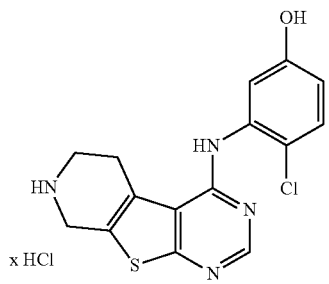 [SMILES: Oc1ccc(Cl)c(Nc2ncnc3sc4c(c23)CCNC4)c1]

The title compound was prepared in analogy to Example 65A from tert-butyl 4-chloro-5,8-dihydropyrido[4',3':4,5]thieno[2,3-d]pyrimidine-7(6H)-carboxylate from Example 11A (2.16 g, 6.63 mmol) and 3-amino-4-chlorophenol (1.00 g, 6.97 mmol) to yield 2.26 g (87%).

$^1$H-NMR (400 MHz, DMSO-d$_6$): δ=3.34-3.50 (m, 4H), 4.46 (br. s, 2H), 6.55 (br. s, 1H), 6.70 (dd, 1H), 7.31 (d, 1H), 7.39 (d, 1H), 8.46 (br. s, 2H), 10.04 (br. s, 2H).

LC/MS (method 3): $R_t$=1.12 min; MS (ESIpos): m/z=333 [M+H]$^+$.

Example 71A 2,4-Difluoro-5-(5,6,7,8-tetrahydropyrido[4',3':4,5]thieno[2,3-d]pyrimidin-4-ylamino)phenol hydrochloride

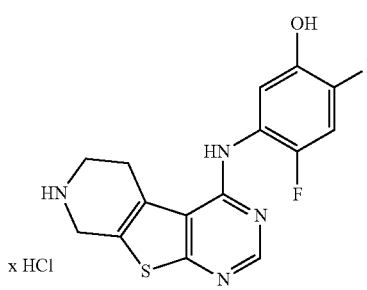

The title compound was prepared in analogy to Example 65A from tert-butyl 4-chloro-5,8-dihydropyrido[4',3':4,5]thieno[2,3-d]pyrimidine-7(6H)-carboxylate from Example 11A (4.00 g, 12.3 mmol) and 5-amino-2,4-difluorophenol (1.87 g, 12.9 mmol) to yield 740 mg (16%).

$^1$H-NMR (400 MHz, DMSO-d$_6$): δ=3.36-3.41 (m, 2H), 3.47-3.51 (m, 2H), 4.47 (s, 2H), 7.20 (dd, 1H), 7.28 (t, 1H), 8.34 (br. s, 1H), 8.38 (s, 1H), 9.59 (br. s, 2H), 9.95 (s, 1H).

LC/MS (method 3): $R_t$=1.05 min; MS (ESIpos): m/z=335 [M+H]$^+$.

Example 72A

4-Fluoro-2-methyl-5-(5,6,7,8-tetrahydropyrido[4',3':4,5]thieno[2,3-d]pyrimidin-4-ylamino)phenol hydrochloride

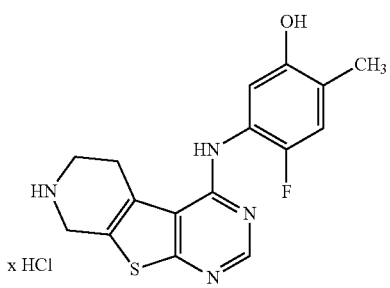 [SMILES: Cc1cc(F)c(Nc2ncnc3sc4c(c23)CCNC4)cc1O]

The title compound was prepared in analogy to Example 65A from tert-butyl 4-chloro-5,8-dihydropyrido[4',3':4,5]thieno[2,3-d]pyrimidine-7(6H)-carboxylate from Example 11A (2.20 g, 6.75 mmol) and 5-amino-4-fluoro-2-methylphenol (1.00 g, 7.09 mmol) to yield 2.69 g (100%).

$^1$H-NMR (400 MHz, DMSO-d$_6$): δ=2.13 (s, 3H), 3.38-3.43 (m, 2H), 3.44-3.50 (m, 2H), 4.45 (s, 2H), 5.25 (br. s, 1H), 6.99 (d, 1H), 7.07 (d, 1H), 8.38 (s, 2H), 9.88 (br. s, 2H).

LC/MS (method 4): $R_t$=0.71 min; MS (ESIpos): m/z=331 [M+H]$^+$.

Example 73A 5-tert-Butyl 3-ethyl 2-amino-6,7-dihydrothieno[3,2-c]pyridine-3,5(4H)-dicarboxylate

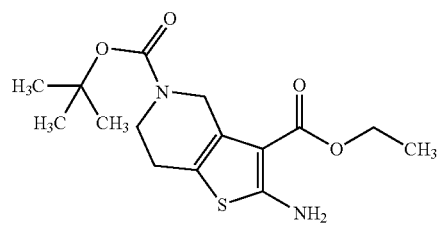 [SMILES: CCOC(=O)c1c(N)sc2c1CN(C(=O)OC(C)(C)C)CC2]

A mixture of tert-butyl 3-oxopiperidine-1-carboxylate (4.93 g, 24.7 mmol), ethyl cyanoacetate (2.80 g, 24.7 mmol) and sulfur (0.79 g, 24.7 mmol) in ethanol (10 mL) was cooled to −5° C. Triethylamine (1.81 g, 24.7 mmol) was added dropwise, and the reaction mixture was stirred at rt for 20 h. The solvent was then removed in vacuo, and the residue was purified by column chromatography on silica gel (eluent: cyclohexane/ethyl acetate 2:1). The product thus obtained was further purified by preparative HPLC to yield 780 mg (9%) of the title compound.

$^1$H-NMR (400 MHz, DMSO-d$_6$): δ=1.26 (t, 3H), 1.41 (s, 9H), 2.45-2.55 (m, 2H), 3.55 (t, 2H), 4.16 (q, 2H), 4.40 (s, 2H), 7.33 (s, 2H).

LC/MS (method 2): $R_t$=1.27 min; MS (ESIpos): m/z=327 [M+H]$^+$.

Example 74A tert-Butyl 4-oxo-3,4,7,8-tetrahydropyrido[3',4':4,5]thieno[2,3-d]pyrimidine-6(5H)-carboxylate

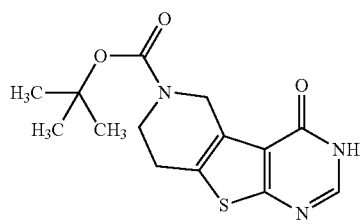 [SMILES: CC(C)(C)OC(=O)N1CCc2sc3nc[nH]c(=O)c3c2C1]

5-tert-Butyl 3-ethyl 2-amino-6,7-dihydrothieno[3,2-c]pyridine-3,5(4H)-dicarboxylate from Example 73A (780 mg, 2.39 mmol) was dissolved in DMF (8 mL), and formamidine acetate (373 mg, 3.58 mmol) was added. The reaction mixture was heated to 100° C. overnight. The solvent was then removed in vacuo, and the residue was dissolved in ethyl acetate. The organic layer was washed with water, dried over sodium sulfate, and the solvent was removed in vacuo. The residue was triturated with tert-butyl methyl ether, and the precipitate was collected by suction filtration to yield 414 mg (56%) of the title compound as a tan solid. The mother liquor was concentrated and purified by preparative HPLC to yield a second batch of 36 mg (5%).

$^1$H-NMR (400 MHz, DMSO-d$_6$): δ=1.43 (s, 9H), 2.80-2.85 (m, 2H), 3.67 (t, 2H), 4.67 (s, 2H), 8.06 (s, 1H), 12.48 (s, 1H).

LC/MS (method 2): $R_t$=0.99 min; MS (ESIpos): m/z=308 [M+H]$^+$.

Example 75A tert-Butyl 4-chloro-7,8-dihydropyrido[3',4':4,5]thieno[2,3-d]pyrimidine-6(5H)-carboxylate

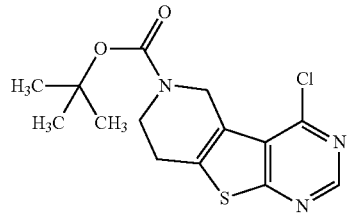 [SMILES: CC(C)(C)OC(=O)N1CCc2sc3ncnc(Cl)c3c2C1]

The title compound was prepared in analogy to Example 80A from tert-butyl 4-oxo-3,4,7,8-tetrahydropyrido[3',4':4,5]thieno[2,3-d]pyrimidine-6(5H)-carboxylate from Example 74A (193 mg, 0.63 mmol) to yield 125 mg (61%).

$^1$H-NMR (400 MHz, DMSO-d$_6$): δ=1.44 (s, 9H), 2.97-3.02 (m, 2H), 3.73 (t, 2H), 4.87 (s, 2H), 8.88 (s, 1H).

LC/MS (method 4): $R_t$=2.54 min; MS (ESIpos): m/z=326 [M+H]$^+$.

Example 76A

N-(3,4-Dichlorophenyl)-5,6,7,8-tetrahydropyrido[3',4':4,5]thieno[2,3-d]pyrimidin-4-amine

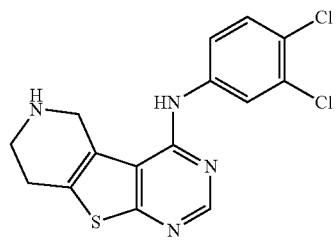 [SMILES: Clc1ccc(Nc2ncnc3sc4c(c23)CNCC4)cc1Cl]

The title compound was prepared in analogy to Example 12A from tert-butyl 4-chloro-7,8-dihydropyrido[3',4':4,5]thieno[2,3-d]pyrimidine-6(5H)-carboxylate from Example 75A (122 mg, 0.37 mmol) and 3,4-dichloroaniline (64 mg, 0.39 mmol) to yield 127 mg (91%).

$^1$H-NMR (400 MHz, DMSO-d$_6$): δ=2.7 (br. s, 1H), 2.78-2.83 (m, 2H), 3.03 (t, 2H), 4.27 (s, 2H), 7.59 (d, 1H), 7.66 (dd, 1H), 8.00 (d, 1H), 8.24 (s, 1H), 8.48 (s, 1H).

LC/MS (method 4): $R_t$=1.37 min; MS (ESIpos): m/z=351 [M+H]$^+$.

Example 77A 7-tert-Butyl 3-ethyl 2-amino-4,5,6,8-tetrahydro-7H-thieno[2,3-c]azepine-3,7-dicarboxylate and 6-tert-Butyl 3-ethyl 2-amino-4,5,7,8-tetrahydro-6H-thieno[2,3-d]azepine-3,6-dicarboxylate

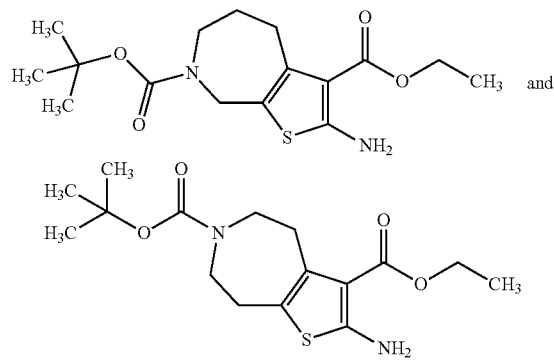

A mixture of tert-butyl 4-oxoazepane-1-carboxylate [cf. WO 2006/029154, Example 1b)] (13.7 g, 64.2 mmol), ethyl cyanoacetate (7.27 g, 64.2 mmol) and sulfur (2.06 g, 64.2 mmol) in ethanol (32 mL) was cooled to −5° C. Triethylamine (6.50 g, 64.2 mmol) was added dropwise, and the reaction mixture was stirred at rt for 20 h. The solvent was then removed in vacuo, and the residue was purified by column chromatography on silica gel (eluent: DCM/methanol 50:1). The product thus obtained was further purified by preparative HPLC to yield 12.5 g (57%) of an inseparable mixture of the two regioisomeric title compounds which was used as such in the following synthetic step.

LC/MS (method 4): $R_t$=2.48 min; MS (ESIpos): m/z=341 [M+H]$^+$.

Example 78A and Example 79A tert-Butyl 4-oxo-3,4,5,6,7,9-hexahydro-8H-pyrimido[5',4':4,5]thieno[2,3-c]azepine-8-carboxylate (Example 78A) and tert-Butyl 4-oxo-3,4,5,6,8,9-hexahydro-7H-pyrimido[5',4':4,5]thieno[2,3-d]azepine-7-carboxylate (Example 79A)

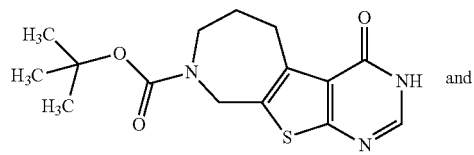

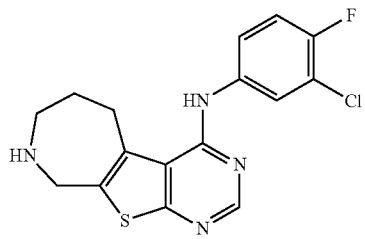 [SMILES: Fc1ccc(Nc2ncnc3sc4c(c23)CCCNC4)cc1Cl]

The mixture of 7-tert-butyl 3-ethyl 2-amino-4,5,6,8-tetrahydro-7H-thieno[2,3-c]azepine-3,7-dicarboxylate and 6-tert-butyl 3-ethyl 2-amino-4,5,7,8-tetrahydro-6H-thieno[2,3-d]azepine-3,6-dicarboxylate from Example 77A (12.5 g, 36.8 mmol) was dissolved in DMF (120 mL), and formamidine acetate (5.75 g, 55.2 mmol) was added. The reaction mixture was heated to 100° C. overnight. The solvent was then removed in vacuo, and the residue was dissolved in ethyl acetate. The organic layer was washed with water, dried over sodium sulfate, and the solvent was removed in vacuo. The remaining orange oil was triturated with tert-butyl methyl ether, and the precipitate was collected by suction filtration to yield 8.23 g of a tan solid. The mother liquor was concentrated and purified by column chromatography on silica gel (eluent: DCM/methanol 100:1) to give a second batch (0.74 g). The regioisomers were separated by preparative HPLC to afford 7.35 g (62%) of tert-butyl 4-oxo-3,4,5,6,7,9-hexahydro-8H-pyrimido[5',4':4,5]thieno[2,3-c]azepine-8-carboxylate (Example 78A) and 1.35 g (11%) of tert-butyl 4-oxo-3,4,5,6,8,9-hexahydro-7H-pyrimido[5',4':4,5]thieno[2,3-d]azepine-7-carboxylate (Example 79A).

Example 78A $^1$H-NMR (400 MHz, DMSO-$d_6$): δ=1.33 and 1.36 (s, Σ9H), 1.67-1.79 (m, 2H), 3.33-3.39 (m, 2H), 3.63-3.68 (m, 2H), 4.48 and 4.50 (s, Σ2H), 8.03 (s, 1H), 12.38 (br. s, 1H).
LC/MS (method 3): $R_t$=1.81 min; MS (ESIpos): m/z=322 [M+H]$^+$.

Example 79A $^1$H-NMR (400 MHz, DMSO-$d_6$): δ=1.42 (s, 9H), 2.95-3.01 (m, 2H), 3.32-3.38 (m, 2H), 3.50-3.58 (m, 4H), 8.02 (s, 1H), 12.37 (br. s, 1H).
LC/MS (method 3): $R_t$=1.85 min; MS (ESIpos): m/z=322 [M+H]$^+$.

Example 80A tert-Butyl 4-chloro-5,6,7,9-tetrahydro-8H-pyrimido[5',4':4,5]thieno[2,3-c]azepine-8-carboxylate

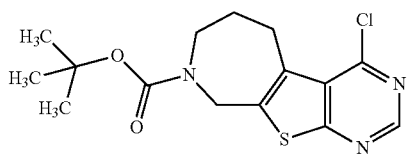 [SMILES: CC(C)(C)OC(=O)N1CCCc2c(sc3ncnc(Cl)c23)C1]

To sulfolane (20 mL) was added phosphoryl chloride (7.40 g, 48.3 mmol). Triethylamine (4.88 g, 48.3 mmol) was added dropwise, and the mixture was stirred for 30 min at rt. Subsequently, tert-butyl 4-oxo-3,4,5,6,7,9-hexahydro-8H-pyrimido[5',4':4,5]thieno[2,3-c]azepine-8-carboxylate from Example 78A (5.17 g, 16.1 mmol) was added, and the reaction mixture was heated for 2 h to 65° C. The mixture was then cooled to rt, and triethylamine (7.0 mL) was added. It was diluted with toluene and cooled to 0° C. Half-saturated aqueous sodium chloride solution was added, and the mixture was stirred for 20 min. The organic layer was separated, washed with water and dried over sodium sulfate, and the solvent was removed in vacuo. The residue was triturated with tert-butyl methyl ether, and the precipitate was collected by suction filtration to yield 4.40 g (80%) of the title compound.
$^1$H-NMR (400 MHz, DMSO-$d_6$): δ=1.31 and 1.36 (s, Σ9H), 1.86-2.00 (m, 2H), 3.35-3.42 (m, 2H), 3.67-3.72 (m, 2H), 4.67 and 4.70 (s, Σ2H), 8.85 (s, 1H).
LC/MS (method 6): $R_t$=2.11 min; MS (ESIpos): m/z=340 [M+H]$^+$.

Example 81A

N-(3-Chloro-4-fluorophenyl)-6,7,8,9-tetrahydro-5H-pyrimido[5',4':4,5]thieno[2,3-c]azepin-4-amine

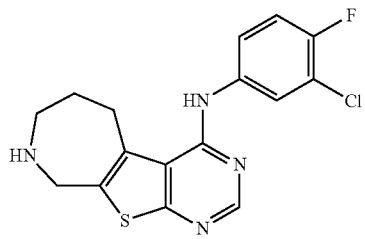 [SMILES: Fc1ccc(Nc2ncnc3sc4c(c23)CCCNC4)cc1Cl]

The title compound was synthesized in analogy to Example 12A from tert-butyl 4-chloro-5,6,7,9-tetrahydro-8H-pyrimido[5',4':4,5]thieno[2,3-c]azepine-8-carboxylate from Example 80A (349 mg, 0.40 mmol) and 3-chloro-4-fluoroaniline (61 mg, 0.42 mmol) to yield 169 mg (68% purity, 82% yield), which was used without further purification.
LC/MS (method 6): $R_t$=0.98 min; MS (ESIpos): m/z=349 [M+H]$^+$.

Example 82A

N-(3,4-Dichlorophenyl)-6,7,8,9-tetrahydro-5H-pyrimido[5',4':4,5]thieno[2,3-c]azepin-4-amine

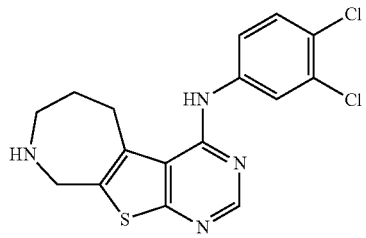

The title compound was synthesized in analogy to Example 12A from tert-butyl 4-chloro-5,6,7,9-tetrahydro-8H-pyrimido[5',4':4,5]thieno[2,3-c]azepine-8-carboxylate from Example 80A (1.74 g, 5.11 mmol) and 3,4-dichloroaniline (870 mg, 5.37 mmol) to yield 820 mg (44%).

¹H-NMR (400 MHz, DMSO-d₆): δ=1.76-1.84 (m, 2H), 2.56 (br. s, 1H), 3.07 (dd, 2H), 3.22-3.26 (m, 2H), 3.96 (s, 2H), 7.56-7.64 (m, 2H), 7.95 (d, 1H), 8.44 (s, 1H), 8.81 (s, 1H).

LC/MS (method 4): $R_t$=1.42 min; MS (ESIpos): m/z=365 [M+H]⁺.

Example 83A

N-[1-(3-Fluorobenzyl)-1H-indazol-5-yl]-6,7,8,9-tetrahydro-5H-pyrimido[5',4':4,5]thieno[2,3-c]-azepin-4-amine

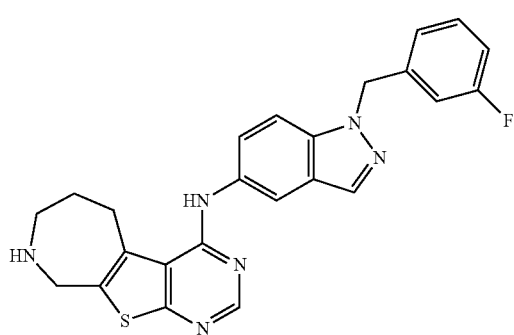 [SMILES: Fc1cccc(Cn2ncc3cc(Nc4ncnc5sc6c(c45)CCCNC6)ccc32)c1]

The title compound was synthesized in analogy to Example 12A from tert-butyl 4-chloro-5,6,7,9-tetrahydro-8H-pyrimido[5',4':4,5]thieno[2,3-c]azepine-8-carboxylate from Example 80A (200 mg, 0.59 mmol) and 1-(3-fluorobenzyl)-1H-indazol-5-amine from Example 8A (149 mg, 0.62 mmol) to yield 213 mg (77% purity, 63% yield), which was used without further purification.

LC/MS (method 4): $R_t$=1.41 min; MS (ESIpos): m/z=445 [M+H]⁺.

Example 84A tert-Butyl 4-chloro-5,6,8,9-tetrahydro-7H-pyrimido[5',4':4,5]thieno[2,3-d]azepine-7-carboxylate

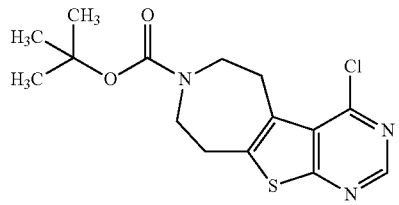 [SMILES: CC(C)(C)OC(=O)N1CCc2sc3ncnc(Cl)c3c2CC1]

The title compound was prepared in analogy to Example 80A from tert-butyl 4-oxo-3,4,5,6,8,9-hexahydro-7H-pyrimido[5',4':4,5]thieno[2,3-d]azepine-7-carboxylate from Example 79A (1.35 g, 4.20 mmol) to yield 1.37 g (96%).

¹H-NMR (400 MHz, DMSO-d₆): δ=1.39 (s, 9H), 3.20-3.26 (m, 2H), 3.36-3.45 (m, 2H), 3.60-3.66 (m, 2H), 3.68-3.73 (m, 2H), 8.84 (s, 1H).

LC/MS (method 4): $R_t$=2.49 min; MS (ESIpos): m/z=340 [M+H]⁺.

Example 85A

N-(3-Chloro-4-fluorophenyl)-6,7,8,9-tetrahydro-5H-pyrimido[5',4':4,5]thieno[2,3-d]azepin-4-amine

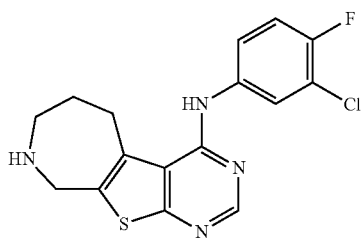 [SMILES: Fc1ccc(Nc2ncnc3sc4c(c23)CCCNC4)cc1Cl]

The title compound was prepared in analogy to Example 12A from tert-butyl 4-chloro-5,6,8,9-tetrahydro-7H-pyrimido[5',4':4,5]thieno[2,3-d]azepine-7-carboxylate from Example 84A (680 mg, 2.00 mmol) and 3-chloro-4-fluoroaniline (306 mg, 2.10 mmol) to yield 419 mg (60%).

¹H-NMR (400 MHz, DMSO-d₆): δ=2.73 (br. s, 1H), 2.87-2.94 (m, 4H), 2.96-3.01 (m, 2H), 3.19-3.24 (m, 2H), 7.39 (t, 1H), 7.53-7.57 (m, 1H), 7.81 (dd, 1H), 8.39 (s, 1H), 8.65 (br. s, 1H).

LC/MS (method 2): $R_t$=0.78 min; MS (ESIpos): m/z=349 [M+H]⁺.

Example 86A tert-Butyl 4-({3-chloro-4-[(3-fluorobenzyl)oxy]phenyl}amino)-5,8-dihydropyrido[4',3':4,5]furo-[2,3-d]pyrimidine-7(6H)-carboxylate

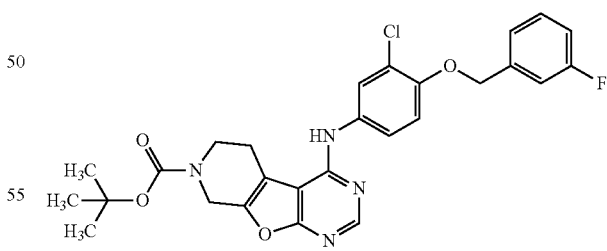

tert-Butyl 3-cyano-2-[(1-methoxymethylidene)amino]-4,7-dihydrofuro[2,3-c]pyridine-6(5H)-carboxylate from Example 47A (134 mg, 0.44 mmol) and 3-chloro-4-[(3-fluorobenzyl)oxy]aniline from Example 4A (221 mg, 0.88 mmol) were heated in methanol (3.0 mL) in a microwave oven for 1 h at 160° C. The title compound was isolated by preparative HPLC to yield 18 mg (8%).

LC/MS (method 4): $R_t$=3.05 min; MS (ESIpos): m/z=525 [M+H]$^+$.

Example 87A tert-Butyl 3-cyano-4-[(3,4-dichlorophenyl)amino]-5,8-dihydrothieno[2,3-b:5,4-c']dipyridine-7(6H)-carboxylate

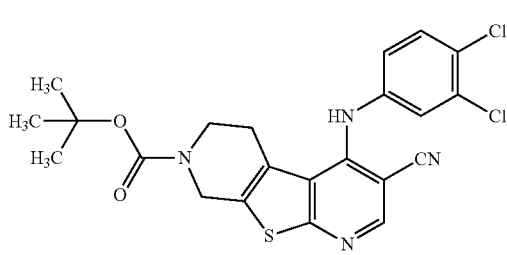 [SMILES: CC(C)(C)OC(=O)N1CCc2c(sc3ncc(C#N)c(Nc4ccc(Cl)c(Cl)c4)c23)C1]

In analogy to Example 54A, the title compound was synthesized from 3,4-dichloroaniline (116 mg, 0.72 mmol) and tert-butyl 4-chloro-3-cyano-5,8-dihydrothieno[2,3-b:5,4-c']dipyridine-7(6H)-carboxylate (250 mg, 0.72 mmol) from Example 53A to yield 207 mg (61%).

$^1$H-NMR (400 MHz, DMSO-$d_6$): δ=1.41 (s, 9H), 2.80-2.95 (m, 2H), 3.57 (t, 2H), 4.70 (s, 2H), 6.92 (dd, 1H), 7.19 (d, 1H), 7.49 (d, 1H), 8.70 (s, 1H), 8.96 (br. s, 1H).

LC/MS (method 2): $R_t$=1.51 min; MS (ESIpos): m/z=475 [M+H]$^+$.

Example 88A

4-[(3,4-Dichlorophenyl)amino]-5,6,7,8-tetrahydrothieno[2,3-b:5,4-c']dipyridine-3-carbonitrile

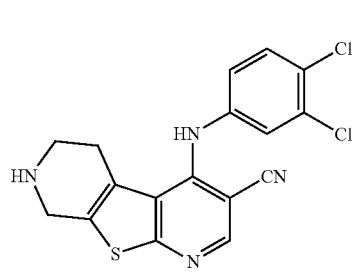 [SMILES: N#Cc1cnc2sc3c(c2c1Nc1ccc(Cl)c(Cl)c1)CCNC3]

In analogy to Example 55A, the title compound was obtained by deprotection of the Boc-protected amine from Example 87A (200 mg, 0.42 mmol) to yield 157 mg (99%).

$^1$H-NMR (400 MHz, DMSO-$d_6$): δ=2.65 (br. s, 1H), 2.76-2.81 (m, 2H), 2.91 (t, 2H), 3.97 (s, 2H), 6.88 (dd, 1H), 7.15 (d, 1H), 7.47 (d, 1H), 8.68 (s, 1H), 8.88 (br. s, 1H).

LC/MS (method 6): $R_t$=1.10 min; MS (ESIpos): m/z=375 [M+H]$^+$.

Example 89A tert-Butyl 4-({3-chloro-4-[(3-fluorobenzyl)oxy]phenyl}amino)-3-cyano-5,8-dihydrothieno[2,3-b:5,4-c']dipyridine-7(6H)-carboxylate

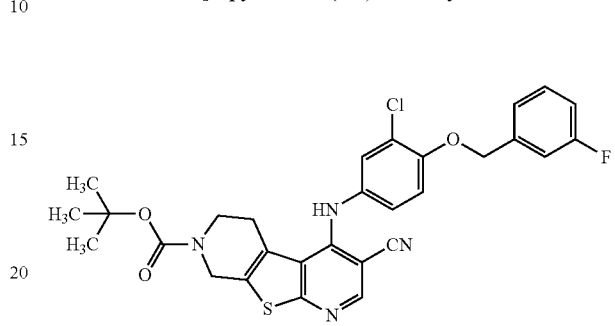

In analogy to Example 54A, the title compound was synthesized from 3-chloro-4-[(3-fluorobenzyl)oxy]aniline from Example 4A (180 mg, 0.72 mmol) and tert-butyl 4-chloro-3-cyano-5,8-dihydrothieno[2,3-b:5,4-c']dipyridine-7(6H)-carboxylate (250 mg, 0.72 mmol) from Example 53A to yield 258 mg (64%).

$^1$H-NMR (400 MHz, DMSO-$d_6$): δ=1.44 (s, 9H), 2.95-3.03 (m, 2H), 3.60 (t, 2H), 4.70 (s, 2H), 5.24 (s, 2H), 7.07 (dd, 1H), 7.16-7.23 (m, 2H), 7.27 (d, 1H), 7.29-7.35 (m, 2H), 7.48 (dt, 1H), 8.50-8.53 (m, 2H).

LC/MS (method 6): $R_t$=2.64 min; MS (ESIpos): m/z=565 [M+H]$^+$.

Example 90A 4-({3-Chloro-4-[(3-fluorobenzyl)oxy]phenyl}amino)-5,6,7,8-tetrahydrothieno[2,3-b:5,4-c']dipyridine-3-carbonitrile

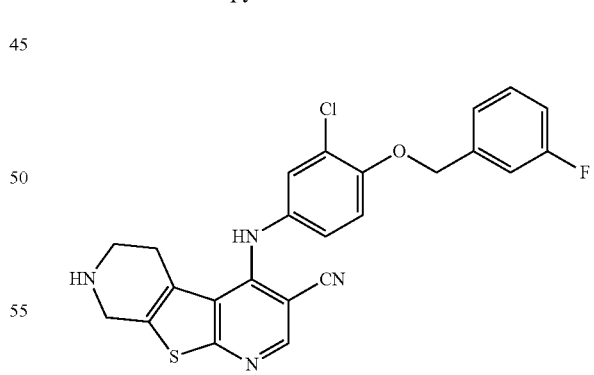

In analogy to Example 55A, the title compound was obtained by deprotection of the Boc-protected amine from Example 89A (250 mg, 0.44 mmol) to yield 170 mg (83%).

$^1$H-NMR (400 MHz, DMSO-$d_6$): δ=2.62 (br. s, 1H), 2.84-2.89 (m, 2H), 2.90-2.95 (m, 2H), 3.95 (s, 2H), 5.21 (s, 2H), 7.00-7.04 (m, 1H), 7.14-7.19 (m, 2H), 7.22-7.24 (m, 1H), 7.27-7.32 (m, 2H), 7.42-7.48 (m, 1H), 8.38 (s, 1H), 8.47 (s, 1H).

LC/MS (method 4): $R_t$=1.70 min; MS (ESIpos): m/z=465 [M+H]$^+$.

Example 91A tert-Butyl 3-cyano-4-{[1-(pyridin-2-ylmethyl)-1H-indazol-5-yl]amino}-5,8-dihydrothieno[2,3-b:5,4-c']dipyridine-7(6H)-carboxylate

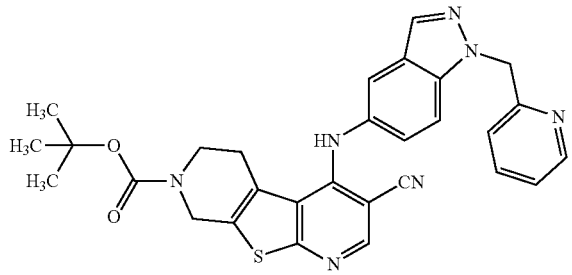 [SMILES: CC(C)(C)OC(=O)N1CCc2c(sc3ncc(C#N)c(Nc4ccc5c(cnn5Cc5ccccn5)c4)c23)C1]

In analogy to Example 54A, the compound was synthesized from tert-butyl 4-chloro-3-cyano-5,8-dihydrothieno[2,3-b:5,4-c']dipyridine-7(6H)-carboxylate from Example 53A (220 mg, 0.63 mmol) and 1-(pyridin-2-ylmethyl)-1H-indazol-5-amine from Example 61A (141 mg, 0.63 mmol) to yield 177 mg (52%).

$^1$H-NMR (400 MHz, DMSO-d$_6$): δ=1.40 (s, 9H), 2.98 (t, 2H), 3.56 (t, 2H), 4.67 (s, 2H), 5.76 (s, 2H), 6.84-6.91 (m, 1H), 7.25-7.31 (m, 2H), 7.46 (d, 1H), 7.66 (d, 1H), 7.67-7.73 (m, 1H), 8.06 (s, 1H), 8.45 (s, 1H), 8.51-8.55 (m, 2H).

LC/MS (method 6): $R_t$=2.01 min; MS (ESIpos): m/z=538 [M+H]$^+$.

Example 92A

4-{[1-Pyridin-2-ylmethyl)-1H-indazol-5-yl]amino}-5,6,7,8-tetrahydrothieno[2,3-b:5,4-c']-dipyridine-3-carbonitrile

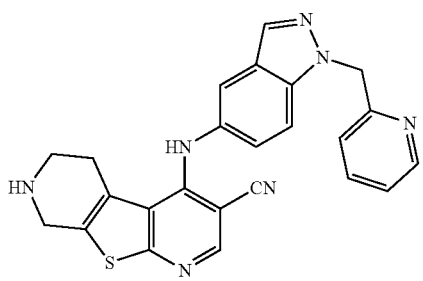 [SMILES: N#Cc1cnc2sc3c(c2c1Nc1ccc2c(cnn2Cc2ccccn2)c1)CCNC3]

In analogy to Example 55A, the title compound was obtained by deprotection of the Boc-protected amine from Example 91A (170 mg, 0.32 mmol) to yield 135 mg (98%).

$^1$H-NMR (400 MHz, DMSO-d$_6$): δ=2.56 (br. s, 1H), 2.91 (s, 4H), 3.95 (s, 2H), 5.75 (s, 2H), 6.87 (d, 1H), 7.25-7.30 (m, 2H), 7.45 (d, 1H), 7.65 (d, 1H), 7.69 (dt, 1H), 8.05 (s, 1H), 8.41-8.43 (m, 2H), 8.51-8.53 (m, 1H).

LC/MS (method 2): $R_t$=0.69 min; MS (ESIpos): m/z=438 [M+H]$^+$.

Example 93A tert-Butyl 3-cyano-4-{[1-(3-fluorobenzyl)-1H-indazol-5-yl]amino}-5,8-dihydrothieno[2,3-b:5,4-c']-dipyridine-7(6H)-carboxylate

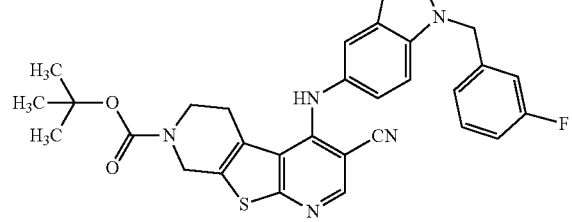

In analogy to Example 54A, the title compound was synthesized from 1-(3-fluorobenzyl)-1H-indazol-5-amine from Example 8A (138 mg, 0.57 mmol) and tert-butyl 4-chloro-3-cyano-5,8-dihydrothieno[2,3-b:5,4-c']dipyridine-7(6H)-carboxylate (200 mg, 0.57 mmol) from Example 53A to yield 234 mg (74%).

$^1$H-NMR (400 MHz, DMSO-d$_6$): δ=1.39 (s, 9H), 2.94-3.05 (m, 2H), 3.57 (t, 2H), 4.67 (s, 2H), 5.69 (s, 2H), 6.95-7.03 (m, 2H), 7.06-7.12 (m, 1H), 7.26-7.30 (m, 1H), 7.31-7.38 (m, 1H), 7.49 (s, 1H), 7.71 (d, 1H), 8.07 (s, 1H), 8.44 (s, 1H), 8.53 (s, 1H).

LC/MS (method 6): $R_t$=2.38 min; MS (ESIpos): m/z=555 [M+H]$^+$.

Example 94A

4-{[1-(3-Fluorobenzyl)-1H-indazol-5-yl]amino}-5,6,7,8-tetrahydrothieno[2,3-b:5,4-c']dipyridine-3-carbonitrile

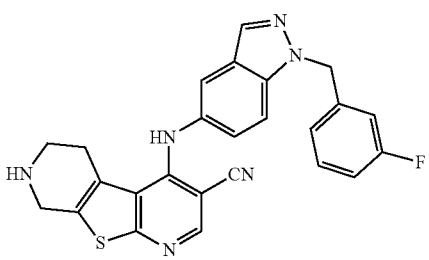 [SMILES: N#Cc1cnc2sc3c(c2c1Nc1ccc2c(cnn2Cc2cccc(F)c2)c1)CCNC3]

In analogy to Example 55A, the title compound was obtained by deprotection of the Boc-protected amine from Example 93A (230 mg, 0.42 mmol) to yield 185 mg (98%).

$^1$H-NMR (400 MHz, DMSO-d$_6$): δ=2.54 (br. s, 1H), 2.92 (s, 4H), 3.95 (s, 2H), 5.69 (s, 2H), 6.95-6.99 (m, 1H), 7.01 (d, 1H), 7.08 (dt, 1H), 7.28 (dd, 1H), 7.34 (dt, 1H), 7.46 (d, 1H), 7.70 (d, 1H), 8.06 (s, 1H), 8.40-8.41 (m, 2H).

LC/MS (method 4): R$_t$=1.48 min; MS (ESIpos): m/z=455 [M+H]$^+$.

Preparation Examples

Example 1

7-[(2E)-4-Azetidin-1-ylbut-2-enoyl]-N-(3-chloro-4-fluorophenyl)-5,6,7,8-tetrahydropyrido[4',3':4,5]thieno[2,3-d]pyrimidin-4-amine

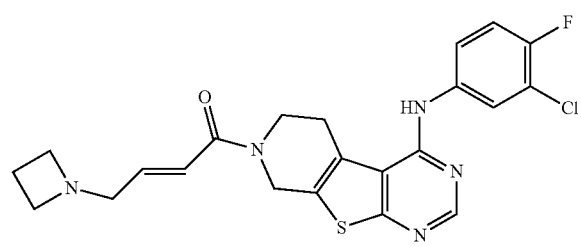 [SMILES: O=C(/C=C/CN1CCC1)N1CCc2c(sc3ncnc(Nc4ccc(F)c(Cl)c4)c23)C1]

To a suspension of Example 58A (176 mg, 0.40 mmol) in DMF (2 mL) was added azetidine (28 mg, 0.48 mmol) and DIPEA (52 mg, 0.40 mmol), and the mixture was stirred at rt for 15 h. It was then diluted with methyl tert-butyl ether, washed with water and dried over sodium sulfate. The solvent was removed in vacuo, and the residue was purified by preparative HPLC to yield 80 mg (43%) of the title compound.

$^1$H-NMR (400 MHz, DMSO-d$_6$): δ=1.95-2.04 (m, 2H), 3.20-3.34 (m, 6H), 3.83-3.96 (m, 2H), 4.83-4.98 (m, 2H), 6.57-6.65 (m, 2H), 7.42 (t, 1H), 7.60-7.67 (m, 1H), 7.87-7.94 (m, 1H), 8.34 (br. s, 1H), 8.45 (s, 1H).

LC/MS (method 4): R$_t$=1.70 min; MS (ESIpos): m/z=458 [M+H]$^+$.

Example 2

Ethyl 4-[(2E)-4-{4-[(3-chloro-4-fluorophenyl)amino]-5,8-dihydropyrido[4',3':4,5]thieno[2,3-d]-pyrimidin-7(6H)-yl}-4-oxobut-2-en-1-yl]piperazine-1-carboxylate

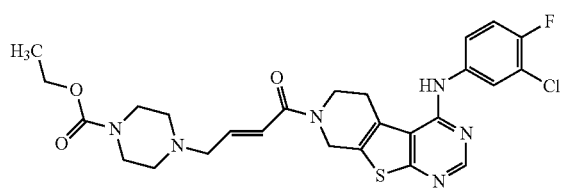 [SMILES: CCOC(=O)N1CCN(C/C=C/C(=O)N2CCc3c(sc4ncnc(Nc5ccc(F)c(Cl)c5)c34)C2)CC1]

To a suspension of Example 58A (100 mg, 0.23 mmol) in DMF (1.5 mL) was added ethyl piperazine-1-carboxylate (72 mg, 0.46 mmol), and the mixture was stirred at rt for 20 h. It was then directly purified by preparative HPLC. The product crystallized from dichloromethane to yield 67 mg (52%) of the title compound.

$^1$H-NMR (400 MHz, DMSO-d$_6$): δ=1.17 (t, 3H), 2.31-2.39 (m, 4H), 3.12-3.19 (m, 2H), 3.21-3.32 (m, 2H), 3.34-3.40 (m, 4H), 3.84-3.96 (m, 2H), 4.03 (q, 2H), 4.83-4.99 (m, 2H), 6.64-6.82 (m, 2H), 7.42 (t, 1H), 7.59-7.68 (m, 1H), 7.87-7.94 (m, 1H), 8.32-8.36 (m, 1H), 8.46 (s, 1H).

LC/MS (method 4): R$_t$=1.77 min; MS (ESIpos): m/z=559 [M+H]$^+$.

Example 3 tert-Butyl 4-[(2E)-4-{4-[(3-chloro-4-fluorophenyl)amino]-5,8-dihydropyrido[4',3':4,5]thieno[2,3-d]pyrimidin-7(6H)-yl}-4-oxobut-2-en-1-yl]piperazine-1-carboxylate

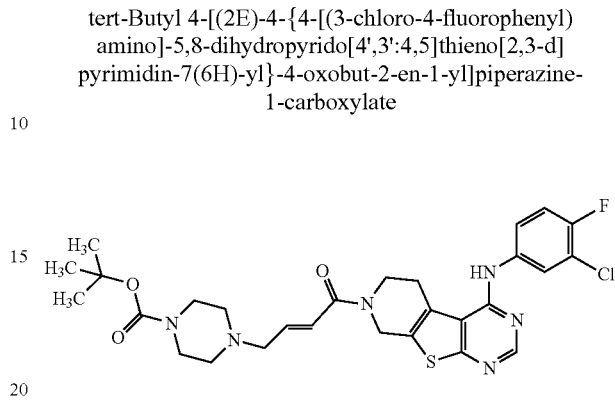

In analogy to Example 2, the title compound was prepared from Example 58A (200 mg, 0.46 mmol) and tert-butyl piperazine-1-carboxylate (170 mg, 0.92 mmol) to yield 182 mg (68%).

$^1$H-NMR (400 MHz, DMSO-d$_6$): δ=1.39 (s, 9H), 2.30-2.37 (m, 4H), 3.12-3.18 (m, 2H), 3.21-3.30 (m, 6H), 3.85-3.96 (m, 2H), 4.84-4.98 (m, 2H), 6.65-6.81 (m, 2H), 7.42 (t, 1H), 6.59-7.68 (m, 1H), 7.87-7.95 (m, 1H), 8.31-8.38 (m, 1H), 8.46 (s, 1H).

LC/MS (method 2): R$_t$=1.16 min; MS (ESIpos): m/z=587 [M+H]$^+$.

Example 4

N-(3-Chloro-4-fluorophenyl)-7-[(2E)-4-piperazin-1-ylbut-2-enoyl]-5,6,7,8-tetrahydropyrido[4',3':4,5]thieno[2,3-d]pyrimidin-4-amine

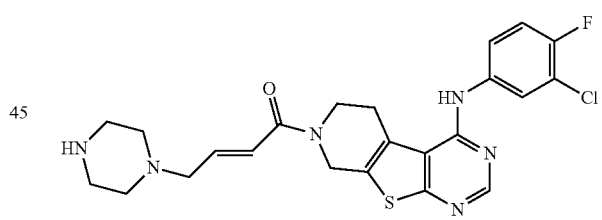

To a solution of tert-butyl 4-[(2E)-4-{4-[(3-chloro-4-fluorophenyl)amino]-5,8-dihydropyrido-[4',3':4,5]thieno[2,3-d]pyrimidin-7(6H)-yl}-4-oxobut-2-en-1-yl]piperazine-1-carboxylate from Example 3 (150 mg, 0.255 mmol) in dichloromethane (15 mL) was added TFA (1.0 mL, 13 mmol), and the mixture was stirred at rt for 5 h. The solvent was removed in vacuo. 1 M aqueous sodium hydroxide solution was added, and the mixture was extracted with ethyl acetate. The organic layer was dried over sodium sulfate, and the solvent was evaporated. The residue was crystallized from dichloromethane/diethyl ether to yield 108 mg (87%) of the title compound.

$^1$H-NMR (400 MHz, DMSO-d$_6$): δ=2.28-2.36 (m, 4H), 2.50 (br. s, 1H), 2.69-2.72 (m, 4H), 3.07-3.12 (m, 2H), 3.84-3.95 (m, 2H), 4.82-4.98 (m, 2H), 6.66-6.79 (m, 2H), 7.41 (t, 1H), 7.60-7.67 (m, 1H), 7.87-7.94 (m, 1H), 8.30-8.36 (m, 1H), 8.46 (s, 1H).

LC/MS (method 3): $R_t$=1.57 min; MS (ESIpos): m/z=487 [M+H]$^+$.

Example 5

N-(3-Chloro-4-fluorophenyl)-7-[(2E)-4-(1,4-oxazepan-4-yl)but-2-enoyl]-5,6,7,8-tetrahydropyrido[4',3':4,5]thieno[2,3-d]pyrimidin-4-amine

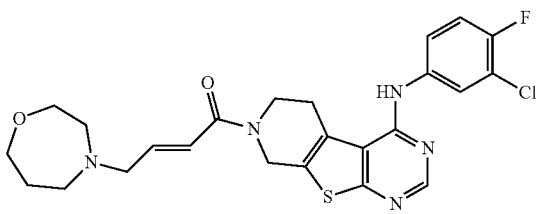 [SMILES: O=C(/C=C/CN1CCCOCC1)N1CCc2c(sc3ncnc(Nc4ccc(F)c(Cl)c4)c23)C1]

In analogy to Example 1, the title compound was prepared from Example 58A (100 mg, 0.23 mmol) and 1,4-oxazepane hydrochloride (63 mg, 0.46 mmol) to yield 76 mg (66%).

$^1$H-NMR (400 MHz, DMSO-d$_6$): δ=1.76-1.85 (m, 2H), 2.58-2.68 (m, 4H), 3.20-3.30 (m, 4H), 3.58-3.64 (m, 2H), 3.69 (t, 2H), 3.85-3.96 (m, 2H), 4.84-4.99 (m, 2H), 6.68-6.81 (m, 2H), 7.42 (t, 1H), 7.60-7.67 (m, 1H), 7.87-7.95 (m, 1H), 8.32-8.37 (m, 1H), 8.46 (s, 1H).

LC/MS (method 6): $R_t$=1.15 min; MS (ESIpos): m/z=502 [M+H]$^+$.

Example 6 trans-2-{4-[(2E)-4-{4-[(3-Chloro-4-fluorophenyl)amino]-5,8-dihydropyrido[4',3':4,5]thieno[2,3-d]pyrimidin-7(6H)-yl}-4-oxobut-2-en-1-yl]piperazin-1-yl}cyclohexanol

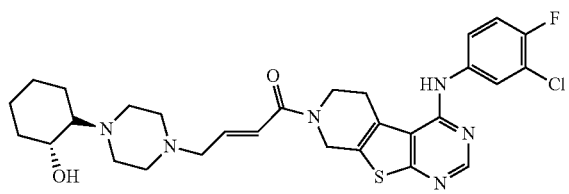

In analogy to Example 2, the title compound was prepared from Example 58A (100 mg, 0.23 mmol) and trans-piperazin-1-ylcyclohexanol (84 mg, 0.46 mmol) to yield 74 mg (55%).

$^1$H-NMR (400 MHz, DMSO-d$_6$): δ=1.08-1.16 (m, 4H), 1.55-1.75 (m, 4H), 1.86-1.92 (m, 1H), 2.10-2.16 (m, 1H), 2.30-2.48 (m, 5H), 2.61-2.70 (m, 3H), 3.08-3.15 (m, 2H), 3.21-3.30 (m, 2H), 3.84-3.96 (m, 3H), 4.84-4.98 (m, 2H), 6.64-6.80 (m, 2H), 7.42 (t, 1H), 7.60-7.67 (m, 1H), 7.87-7.94 (m, 1H), 8.31-8.37 (br. s, 1H), 8.46 (s, 1H).

LC/MS (method 4): $R_t$=1.73 min; MS (ESIpos): m/z=585 [M+H]$^+$.

Example 7

N-(3-Chloro-4-fluorophenyl)-7-{(2E)-4-[4-(2-oxo-2-pyrrolidin-1-ylethyl)piperazin-1-yl]but-2-enoyl}-5,6,7,8-tetrahydropyrido[4',3':4,5]thieno[2,3-d]pyrimidin-4-amine

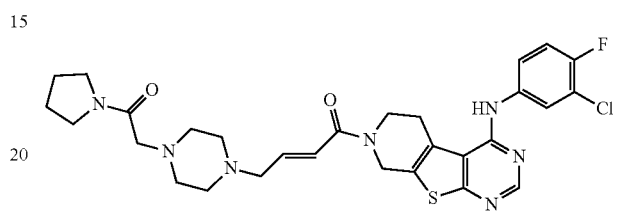

In analogy to Example 2, the title compound was prepared from Example 58A (100 mg, 0.23 mmol) and 1-(2-oxo-2-pyrrolidin-1-ylethyl)piperazine (90 mg, 0.46 mmol) to yield 97 mg (71%).

$^1$H-NMR (400 MHz, DMSO-d$_6$): δ=0.81-0.88 (m, 2H), 1.74 (quint, 2H), 1.84 (quint, 2H), 2.33-2.50 (m, 4H), 3.04-3.15 (m, 4H), 3.20-3.32 (m, 4H), 3.45 (t, 2H), 3.84-3.96 (m, 2H), 4.84-4.98 (m, 2H), 6.64-6.80 (m, 2H), 7.42 (t, 1H), 7.60-7.67 (m, 1H), 7.87-7.95 (m, 1H), 8.31-8.38 (m, 1H), 8.46 (s, 1H).

LC/MS (method 2): $R_t$=0.91 min; MS (ESIpos): m/z=598 [M+H]$^+$.

Example 8

N-(3-Chloro-4-fluorophenyl)-7-{(2E)-4-[3-(trifluoromethyl)-5,6-dihydro[1,2,4]triazolo[4,3-a]-pyrazin-7(8H)-yl]but-2-enoyl}-5,6,7,8-tetrahydropyrido[4',3':4,5]thieno[2,3-d]pyrimidin-4-amine

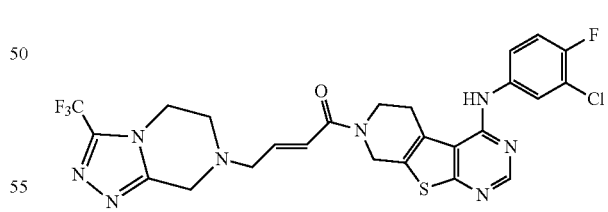

In analogy to Example 2, the title compound was prepared from Example 58A (100 mg, 0.23 mmol) and 3-(trifluoromethyl)-5,6,7,8-tetrahydro[1,2,4]triazolo[4,3-a]pyrazine hydrochloride (105 mg, 0.46 mmol) to yield 82 mg (60%).

$^1$H-NMR (400 MHz, DMSO-d$_6$): δ=2.93-3.00 (m, 2H), 3.22-3.28 (m, 2H), 3.40-3.48 (m, 2H), 3.86-3.99 (m, 4H), 4.16-4.22 (m, 2H), 4.86-5.01 (m, 2H), 6.69-6.92 (m, 2H), 7.42 (t, 1H), 7.60-7.68 (m, 1H), 7.88-7.94 (m, 1H), 8.35 (br. s, 1H), 8.46 (s, 1H).

Example 9

N-(3-Chloro-4-fluorophenyl)-7-[(2E)-4-{methyl[2-(methylsulfonyl)ethyl]amino}but-2-enoyl]-5,6,7,8-tetrahydropyrido[4',3':4,5]thieno[2,3-d]pyrimidin-4-amine

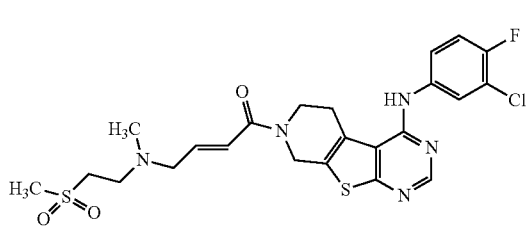 [SMILES: CN(C/C=C/C(=O)N1CCc2c(sc3ncnc(Nc4ccc(F)c(Cl)c4)c23)C1)CCS(C)(=O)=O]

In analogy to Example 17, the title compound was synthesized from Example 58A (80 mg, 0.18 mmol) and N-methyl-2-(methylsulfonyl)ethanamine (92 mg, 0.37 mmol) to yield 59 mg (58%).

$^1$H-NMR (400 MHz, DMSO-$d_6$): δ=2.19-2.25 (m, 3H), 2.72-2.80 (m, 2H), 3.02 (s, 3H), 3.18-3.33 (m, 6H), 3.85-3.99 (m, 2H), 4.85-5.00 (m, 2H), 6.64-6.85 (m, 2H), 7.42 (t, 1H), 7.59-7.68 (m, 1H), 7.87-7.95 (m, 1H), 8.34 (br. s, 1H), 8.46 (s, 1H).

LC/MS (method 6): $R_t$=1.59 min; MS (ESIpos): m/z=538 [M+H]$^+$.

Example 10

7-[(2E)-4-(7-Azabicyclo[2.2.1]hept-7-yl)but-2-enoyl]-N-(3-chloro-4-fluorophenyl)-5,6,7,8-tetrahydropyrido[4',3':4,5]thieno[2,3-d]pyrimidin-4-amine

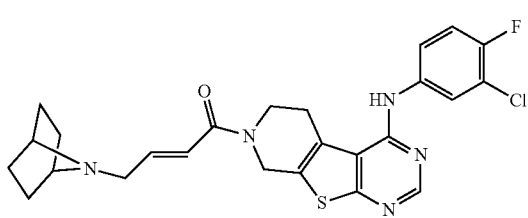 [SMILES: O=C(/C=C/CN1C2CCC1CC2)N1CCc2c(sc3ncnc(Nc4ccc(F)c(Cl)c4)c23)C1]

In analogy to Example 1, the title compound was prepared from Example 58A (80 mg, 0.18 mmol) and 7-azabicyclo[2.2.1]heptane hydrochloride (49 mg, 0.37 mmol) to yield 25 mg (27%).

$^1$H-NMR (400 MHz, DMSO-$d_6$): δ=1.20-1.29 (m, 4H), 1.61-1.70 (m, 4H), 3.07-3.30 (m, 6H), 3.84-3.96 (m, 2H), 4.84-4.98 (m, 2H), 6.68-6.77 (m, 2H), 7.42 (t, 1H), 7.59-7.67 (m, 1H), 7.87-7.95 (m, 1H), 8.32-8.37 (m, 1H), 8.46 (s, 1H).

LC/MS (method 2): $R_t$=0.95 min; MS (ESIpos): m/z=498 [M+H]$^+$.

Example 11

N-(3-Chloro-4-fluorophenyl)-7-{(2E)-4-[cyclopropyl(pyridin-3-ylmethyl)amino]but-2-enoyl}-5,6,7,8-tetrahydropyrido[4',3':4,5]thieno[2,3-d]pyrimidin-4-amine

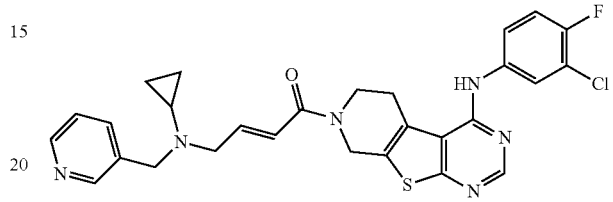

In analogy to Example 2, the title compound was prepared from Example 58A (100 mg, 0.23 mmol) and N-(pyridin-3-ylmethyl)cyclopropanamine (68 mg, 0.46 mmol) to yield 22 mg (18%).

$^1$H-NMR (400 MHz, DMSO-$d_6$): δ=0.27-0.32 (m, 2H), 0.41-0.47 (m, 2H), 1.84-1.91 (m, 1H), 3.21-3.30 (m, 4H), 3.72-3.76 (m, 2H), 3.85-3.95 (m, 2H), 4.84-4.96 (m, 2H), 6.64-6.83 (m, 2H), 7.32-7.36 (m, 1H), 7.42 (t, 1H), 7.60-7.71 (m, 2H), 7.87-7.94 (m, 1H), 8.32-8.37 (m, 1H), 8.44-8.50 (m, 3H).

LC/MS (method 6): $R_t$=1.39 min; MS (ESIpos): m/z=549 [M+H]$^+$.

Example 12

N-(3-Chloro-4-fluorophenyl)-7-{(2E)-4-[(1,1-dimethyl-2-morpholin-4-ylethyl)amino]but-2-enoyl}-5,6,7,8-tetrahydropyrido[4',3':4,5]thieno[2,3-d]pyrimidin-4-amine

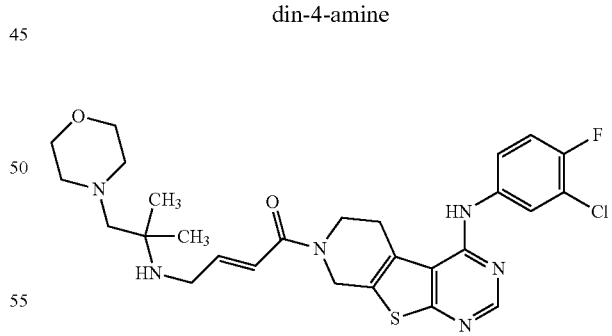

In analogy to Example 2, the title compound was prepared from Example 58A (100 mg, 0.23 mmol) and 2-methyl-1-morpholin-4-ylpropan-2-amine (72 mg, 0.46 mmol) to yield 14 mg (11%).

$^1$H-NMR (400 MHz, DMSO-$d_6$): δ=1.00 (s, 6H), 1.65 (br. s, 1H), 2.20 (s, 2H), 3.20-3.35 (m, 6H), 3.54-3.58 (m, 4H), 3.84-3.95 (m, 2H), 4.83-4.97 (m, 2H), 6.60-6.83 (m, 2H), 7.42 (t, 1H), 7.60-7.67 (m, 1H), 7.88-7.94 (m, 1H), 8.32-8.37 (m, 1H), 8.46 (s, 1H).

LC/MS (method 3): $R_t$=1.67 min; MS (ESIpos): m/z=559 [M+H]$^+$.

Example 13

N-(3-Chloro-4-fluorophenyl)-7-{(2E)-3-[(2S)-pyrrolidin-2-yl]prop-2-enoyl}-5,6,7,8-tetrahydropyrido[4',3':4,5]thieno[2,3-d]pyrimidin-4-amine

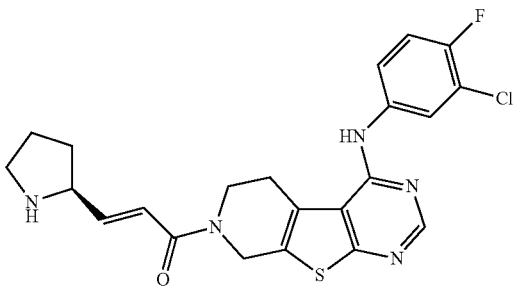 [SMILES: O=C(/C=C/[C@@H]1CCCN1)N1CCc2c(sc3ncnc(Nc4ccc(F)c(Cl)c4)c23)C1]

tert-Butyl (2S)-2-[(1E)-3-{4-[(3-chloro-4-fluorophenyl)amino]-5,8-dihydropyrido[4',3':4,5]thieno[2,3-d]pyrimidin-7(6H)-yl}-3-oxoprop-1-en-1-yl]pyrrolidine-1-carboxylate from Example 14A (397 mg, 0.712 mmol) was dissolved in 2-propanol (4 mL), and a 4 M solution of gaseous hydrogen chloride in dioxane (0.36 mL) was added. The mixture was stirred for 3 h at 70° C. The solvent was then removed in vacuo. The residue was dissolved in ethyl acetate and washed with 1 N aqueous sodium hydroxide solution. The organic layer was dried over sodium sulfate, and the solvent was evaporated. The crude product was purified by preparative HPLC to yield 139 mg (42%) of the title compound.

$^1$H-NMR (400 MHz, DMSO-d$_6$): δ=1.34-1.45 (m, 1H), 1.61-1.74 (m, 2H), 1.85-1.96 (m, 1H), 2.76-2.84 (m, 1H), 2.85-2.92 (m, 1H), 3.62-3.72 (m, 1H), 3.83-3.95 (m, 2H), 4.83-4.97 (m, 2H), 6.59-6.75 (m, 2H), 7.42 (t, 1H), 7.60-7.67 (m, 1H), 7.88-7.94 (m, 1H), 8.31-8.38 (m, 1H), 8.46 (s, 1H).

LC/MS (method 2): $R_t$=0.90 min; MS (ESIpos): m/z=458 [M+H]$^+$.

Example 14

N-(3-Chloro-4-fluorophenyl)-7-{(2E)-3-[(2S)-1-methylpyrrolidin-2-yl]prop-2-enoyl}-5,6,7,8-tetrahydropyrido[4',3':4,5]thieno[2,3-d]pyrimidin-4-amine

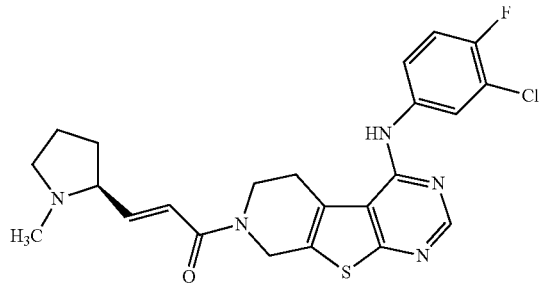 [SMILES: CN1CCC[C@H]1/C=C/C(=O)N1CCc2c(sc3ncnc(Nc4ccc(F)c(Cl)c4)c23)C1]

To a solution of N-(3-Chloro-4-fluorophenyl)-7-{(2E)-3-[(2S)-pyrrolidin-2-yl]prop-2-enoyl}-5,6,7,8-tetrahydropyrido[4',3':4,5]thieno[2,3-d]pyrimidin-4-amine from Example 13 (60 mg, 0.13 mmol) in DMF (1 mL) was added potassium carbonate (27 mg, 0.20 mmol) and iodomethane (20 mg, 0.14 mmol), and the mixture was stirred overnight at rt. The reaction mixture was diluted with ethyl acetate and extracted with water. The organic layer was dried over sodium sulfate, and the solvent was removed in vacuo. The crude product was purified by column chromatography on silica gel (eluent: DCM/MeOH 10:1) to yield 8 mg (13%) of the title compound.

$^1$H-NMR (400 MHz, DMSO-d$_6$): δ=1.50-1.61 (m, 1H), 1.66-1.80 (m, 2H), 1.90-2.03 (m, 1H), 2.12-2.22 (m, 4H), 2.73-2.82 (m, 1H), 2.97-3.05 (m, 1H), 3.84-3.97 (m, 2H), 4.85-5.00 (m, 2H), 6.52-6.60 (m, 1H), 6.65-6.76 (m, 1H), 7.42 (t, 1H), 7.60-7.67 (m, 1H), 7.88-7.94 (m, 1H), 8.32-8.37 (m, 1H), 8.46 (s, 1H).

LC/MS (method 2): $R_t$=0.93 min; MS (ESIpos): m/z=472 [M+H]$^+$.

Example 15

7-[(2E)-4-Azetidin-1-ylbut-2-enoyl]-N-(3,4-dichlorophenyl)-5,6,7,8-tetrahydropyrido[4',3':4,5]thieno[2,3-d]pyrimidin-4-amine

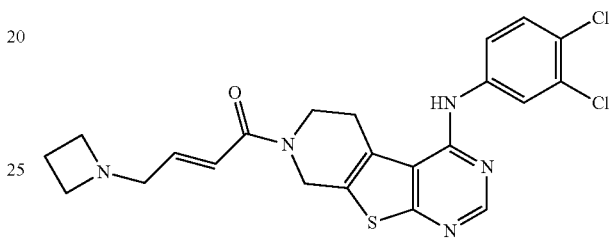

To a suspension of Example 59A (100 mg, 0.20 mmol) in DMF (2 mL) was added azetidine (23 mg, 0.40 mmol), and the mixture was heated to 50° C. for 1 h. It was then diluted with methyl tert-butyl ether, washed with water and dried over sodium sulfate. The solvent was removed in vacuo, and the residue was purified by preparative HPLC to yield 12.4 mg (13%) of the title compound.

$^1$H-NMR (400 MHz, DMSO-d$_6$): δ=1.95-2.05 (m, 2H), 3.11-3.19 (m, 6H), 3.21-3.30 (m, 2H), 3.82-3.95 (m, 2H), 4.82-4.99 (m, 2H), 6.56-6.70 (m, 2H), 7.58-7.63 (m, 1H), 7.66-7.73 (m, 1H), 7.99-8.05 (m, 1H), 8.40-8.47 (m, 1H), 8.51 (s, 1H).

LC/MS (method 4): $R_t$=1.63 min; MS (ESIpos): m/z=474 [M+H]$^+$.

Example 16

N-(3,4-Dichlorophenyl)-7-[(2E)-4-(1,4-oxazepan-4-yl)but-2-enoyl]-5,6,7,8-tetrahydropyrido[4',3':4,5]thieno[2,3-d]pyrimidin-4-amine

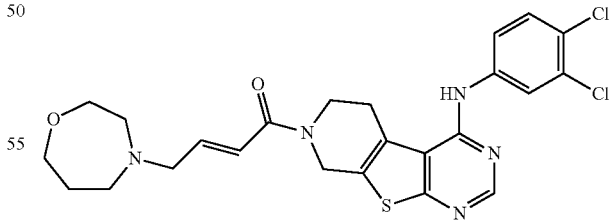

To a solution of Example 59A (100 mg, 0.201 mmol) in DMF (2 mL) and DIPEA (0.10 mL, 0.60 mmol) was added 1,4-oxazepane hydrochloride (55 mg, 0.40 mmol). The mixture was stirred for 1 h at rt and then heated for 1 h to 50° C. The reaction mixture was directly separated by preparative HPLC. The product crystallized upon trituration with dichloromethane. The solvent was removed in vacuo to yield 83 mg (80%) of the title compound.

¹H-NMR (400 MHz, DMSO-d₆): δ=1.76-1.85 (m, 2H), 2.58-2.67 (m, 4H), 3.20-3.32 (m, 4H), 3.58-3.64 (m, 2H), 3.69 (t, 2H), 3.84-3.96 (m, 2H), 4.87 (br. s, 1H), 4.97 (br. s, 1H), 6.68-6.81 (m, 2H), 7.58-7.63 (m, 1H), 7.66-7.73 (m, 1H), 7.98-8.05 (m, 1H), 8.40-8.47 (m, 1H), 8.51 (s, 1H).

LC/MS (method 4): $R_t$=1.67 min; MS (ESIpos): m/z=518 [M+H]⁺.

Example 17

N-(3,4-Dichlorophenyl)-7-[(2E)-4-(4-pyridin-2-ylpiperazin-1-yl)but-2-enoyl]-5,6,7,8-tetrahydropyrido[4',3':4,5]thieno[2,3-d]pyrimidin-4-amine

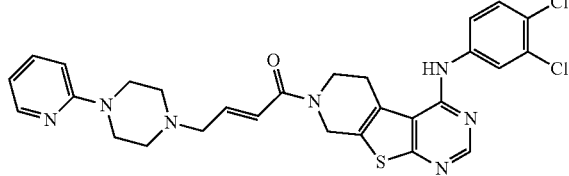

To a suspension of Example 59A (80 mg, 0.16 mmol) in DMF (1 mL) was added 1-pyridin-2-ylpiperazine (52 mg, 0.32 mmol), and the mixture was stirred at rt for 3 h and then heated to 50° C. for 4 h. After purification by preparative HPLC, the product crystallized upon trituration with dichloromethane to yield 74 mg (79%) of the title compound.

¹H-NMR (400 MHz, DMSO-d₆): δ=3.15-3.23 (m, 2H), 3.45-3.52 (m, 4H), 3.85-3.98 (m, 2H), 4.85-5.01 (m, 2H), 6.63 (dd, 1H), 6.71-6.85 (m, 3H), 7.52 (ddd, 1H), 7.59-7.62 (m, 1H), 7.66-7.74 (m, 1H), 7.99-8.05 (m, 1H), 8.10 (dd, 1H), 8.42-8.48 (m, 1H), 8.51 (s, 1H).

LC/MS (method 6): $R_t$=1.36 min; MS (ESIpos): m/z=580 [M+H]⁺.

Example 18

N-(3,4-Dichlorophenyl)-7-[(2E)-4-(1-methylhexahydropyrrolo[3,4-b]pyrrol-5(1H)-yl)but-2-enoyl]-5,6,7,8-tetrahydropyrido[4',3':4,5]thieno[2,3-d]pyrimidin-4-amine

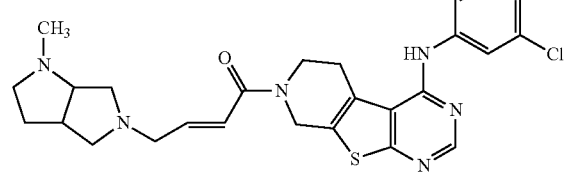

To a suspension of Example 59A (80 mg, 0.16 mmol) in DMF (1 mL) was added 1-methyloctahydropyrrolo[3,4-b]pyrrole (41 mg, 0.32 mmol), and the mixture was stirred at rt for 20 h. After purification by preparative HPLC, the title compound was crystallized from dichloromethane/petroleum ether to yield 12 mg (14%).

LC/MS (method 4): $R_t$=1.66 min; MS (ESIpos): m/z=543 [M+H]⁺.

Example 19

N-(3,4-Dichlorophenyl)-7-{(2E)-4-[4-(2-methoxyphenyl)piperazin-1-yl]but-2-enoyl}-5,6,7,8-tetrahydropyrido[4',3':4,5]thieno[2,3-d]pyrimidin-4-amine

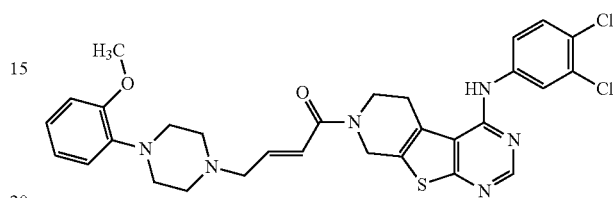

In analogy to Example 17, the title compound was synthesized from Example 59A (80 mg, 0.16 mmol) and 1-(2-methoxyphenyl)piperazine (62 mg, 0.32 mmol) to yield 71 mg (73%).

¹H-NMR (400 MHz, DMSO-d₆): δ=2.98 (br. s, 4H), 3.17-3.29 (m, 2H), 3.76 (s, 3H), 3.85-3.98 (m, 2H), 4.85-5.02 (m, 2H), 6.70-6.81 (m, 2H), 6.83-6.97 (m, 4H), 7.58-7.62 (m, 1H), 7.67-7.74 (m, 1H), 7.98-8.06 (m, 1H), 8.41-8.48 (m, 1H), 8.51 (s, 1H).

LC/MS (method 6): $R_t$=1.53 min; MS (ESIpos): m/z=609 [M+H]⁺.

Example 20

N-(3,4-Dichlorophenyl)-7-{(2E)-4-[methyl(2-morpholin-4-ylethyl)amino]but-2-enoyl}-5,6,7,8-tetrahydropyrido[4',3':4,5]thieno[2,3-d]pyrimidin-4-amine

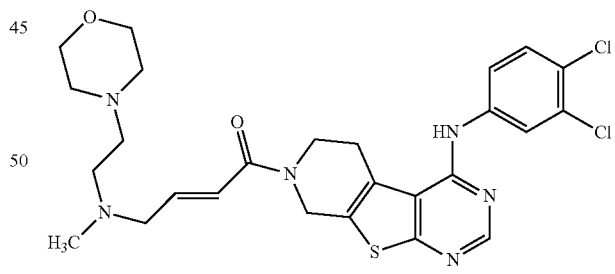

In analogy to Example 17, the title compound was synthesized from Example 59A (80 mg, 0.16 mmol) and N-methyl-2-morpholin-4-ylethanamine (46 mg, 0.32 mmol) to yield 62 mg (69%).

¹H-NMR (400 MHz, DMSO-d₆): δ=2.16-2.22 (s, 3H), 2.34-2.50 (m, 8H), 3.15-3.22 (m, 2H), 3.49-3.61 (m, 4H), 3.84-3.97 (m, 2H), 4.85-5.00 (m, 2H), 6.67-6.81 (m, 2H), 7.59-7.63 (m, 1H), 7.66-7.74 (m, 1H), 7.98-8.05 (m, 1H), 8.40-8.48 (m, 1H), 8.51 (s, 1H).

LC/MS (method 6): $R_t$=1.27 min; MS (ESIpos): m/z=561 [M+H]⁺.

Example 21

3-({7-[(2E)-4-(Dimethylamino)but-2-enoyl]-5,6,7,8-tetrahydropyrido[4',3':4,5]thieno[2,3-d]pyrimidin-4-yl}amino)phenol

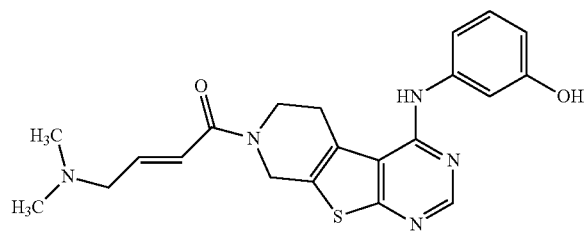 [SMILES: CN(C)C/C=C/C(=O)N1CCc2c(sc3ncnc(Nc4cccc(O)c4)c23)C1]

In analogy to Example 89, the title compound was prepared from 3-(5,6,7,8-tetrahydropyrido[4',3':4,5]thieno[2,3-d]pyrimidin-4-ylamino)phenol from Example 16A (52 mg, 0.18 mmol) and (2E)-4-(dimethylamino)but-2-enoic acid hydrochloride from Example 1A (41 mg, 0.25 mmol) to yield 7 mg (9%).

$^1$H-NMR (400 MHz, DMSO-$d_6$): δ=2.17 (s, 6H), 3.02-3.10 (m, 2H), 3.19-3.30 (m, 2H), 3.83-3.96 (m, 2H), 4.82-4.99 (m, 2H), 6.48-6.52 (m, 1H), 6.65-6.79 (m, 2H), 7.00-7.07 (m, 1H), 7.12 (s, 1H), 7.16-7.20 (m, 1H), 8.13 (br. s, 1H), 8.43 (s, 1H), 9.39 (s, 1H).

LC/MS (method 2): $R_t$=0.64 min; MS (ESIpos): m/z=410 [M+H]$^+$.

Example 22

3-[(7-{(2E)-4-[Methyl(1-methylethyl)amino]but-2-enoyl}-5,6,7,8-tetrahydropyrido[4',3':4,5]thieno[2,3-d]pyrimidin-4-yl)amino]phenol

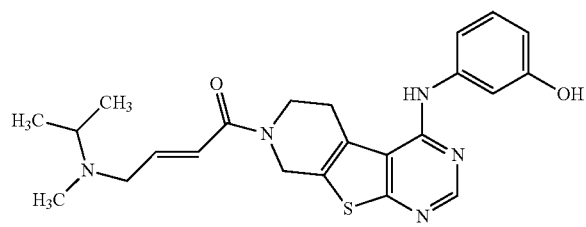 [SMILES: CC(C)N(C)C/C=C/C(=O)N1CCc2c(sc3ncnc(Nc4cccc(O)c4)c23)C1]

In analogy to Example 89, the title compound was prepared from 3-(5,6,7,8-tetrahydropyrido[4',3':4,5]thieno[2,3-d]pyrimidin-4-ylamino)phenol from Example 16A (100 mg, 0.25 mmol) and (2E)-4-[methyl(1-methylethyl)amino]but-2-enoic acid hydrochloride from Example 2A (68 mg, 0.35 mmol) to yield 35 mg (31%).

$^1$H-NMR (400 MHz, DMSO-$d_6$): δ=0.96 (d, 6H), 2.08-2.13 (m, 3H), 2.73-2.84 (m, 1H), 3.14-3.20 (m, 2H), 3.20-3.30 (m, 2H), 3.83-3.95 (m, 2H), 4.82-4.98 (m, 2H), 6.48-6.52 (m, 1H), 6.65-6.80 (m, 2H), 7.00-7.07 (m, 1H), 7.12 (t, 1H), 7.16-7.20 (m, 1H), 8.13 (br. s, 1H), 8.43 (s, 1H), 9.39 (s, 1H).

LC/MS (method 2): $R_t$=0.69 min; MS (ESIpos): m/z=438 [M+H]$^+$.

Example 23

7-[(2E)-4-(Dimethylamino)but-2-enoyl]-N-[(1R)-1-phenylethyl]-5,6,7,8-tetrahydropyrido[4',3':4,5]thieno[2,3-d]pyrimidin-4-amine

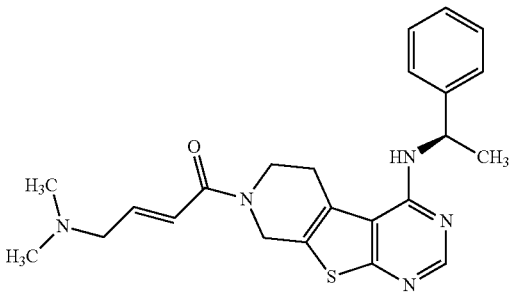 [SMILES: C[C@@H](Nc1ncnc2sc3c(c12)CCN(C(=O)/C=C/CN(C)C)C3)c1ccccc1]

In analogy to Example 89, the title compound was prepared from N-[(1R)-1-phenylethyl]-5,6,7,8-tetrahydropyrido[4',3':4,5]thieno[2,3-d]pyrimidin-4-amine from Example 18A (100 mg, 0.32 mmol) and (2E)-4-(dimethylamino)but-2-enoic acid hydrochloride from Example 1A (75 mg, 0.45 mmol) to yield 23 mg (17%).

$^1$H-NMR (400 MHz, DMSO-$d_6$): δ=1.55 (d, 3H), 2.13-2.18 (m, 6H), 3.02-3.09 (m, 2H), 3.15-3.27 (m, 2H), 3.83-3.98 (m, 2H), 4.74-4.93 (m, 2H), 5.44 (quint, 1H), 6.46-6.54 (m, 1H), 6.65-6.79 (m, 2H), 7.15-7.26 (m, 1H), 7.31 (t, 2H), 7.42-7.46 (m, 2H), 8.24 (s, 1H).

LC/MS (method 2): $R_t$=0.85 min; MS (ESIpos): m/z=422 [M+H]$^+$.

The following examples in Table 1 were prepared in analogy to Example 2 from Example 58A and the corresponding amine:

TABLE 1

| Example | Structure | LC/MS (method 7) $R_t$ [min] | LC/MS m/z [M + H]$^+$ |
|---|---|---|---|
| 24 | 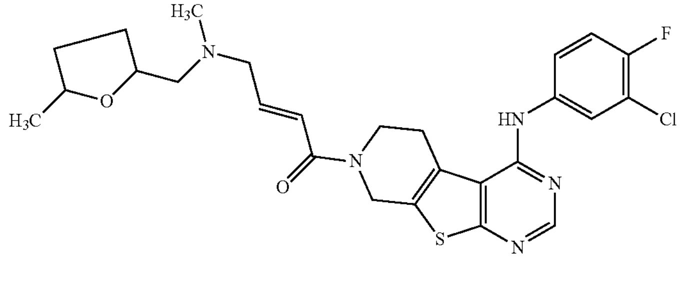 [SMILES: CC1CCC(CN(C)C/C=C/C(=O)N2CCc3c(sc4ncnc(Nc5ccc(F)c(Cl)c5)c34)C2)O1] | 1.81 | 530 |

TABLE 1-continued

| Example | Structure | LC/MS (method 7) R_t [min] | LC/MS m/z [M + H]+ |
|---|---|---|---|
| 25 | 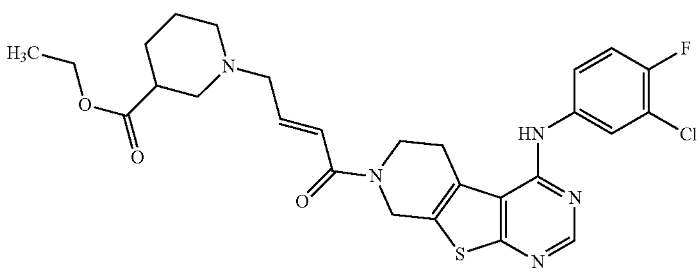 [SMILES: CCOC(=O)C1CCCN(C/C=C/C(=O)N2CCc3c(sc4ncnc(Nc5ccc(F)c(Cl)c5)c34)C2)C1] | 1.81 | 558 |
| 26 | 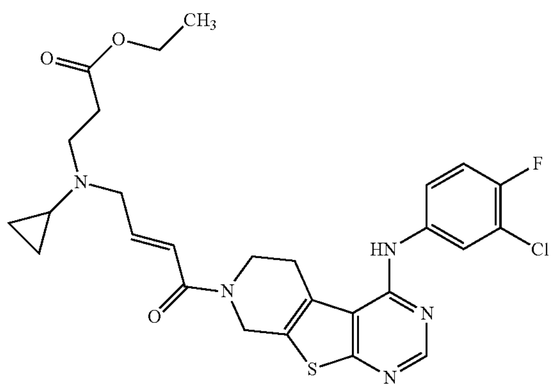 [SMILES: CCOC(=O)CCN(C/C=C/C(=O)N1CCc2c(sc3ncnc(Nc4ccc(F)c(Cl)c4)c23)C1)C1CC1] | 1.84 | 558 |
| 27 | 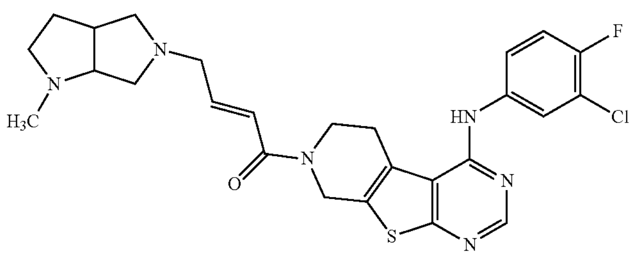 [SMILES: CN1CCC2CN(C/C=C/C(=O)N3CCc4c(sc5ncnc(Nc6ccc(F)c(Cl)c6)c45)C3)CC21] | 1.69 | 527 |
| 28 | 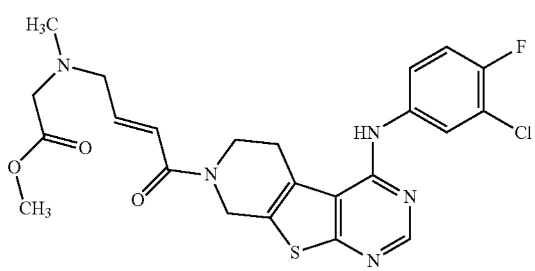 [SMILES: COC(=O)CN(C)C/C=C/C(=O)N1CCc2c(sc3ncnc(Nc4ccc(F)c(Cl)c4)c23)C1] | 1.75 | 504 |
| 29 | 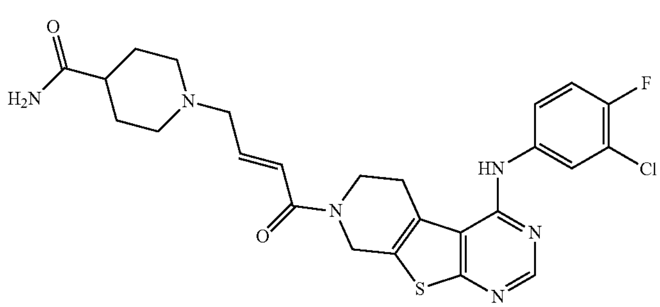 [SMILES: NC(=O)C1CCN(C/C=C/C(=O)N2CCc3c(sc4ncnc(Nc5ccc(F)c(Cl)c5)c34)C2)CC1] | 1.70 | 529 |

TABLE 1-continued

| Example | Structure | LC/MS (method 7) R$_t$ [min] | LC/MS m/z [M + H]$^+$ |
|---|---|---|---|
| 30 | 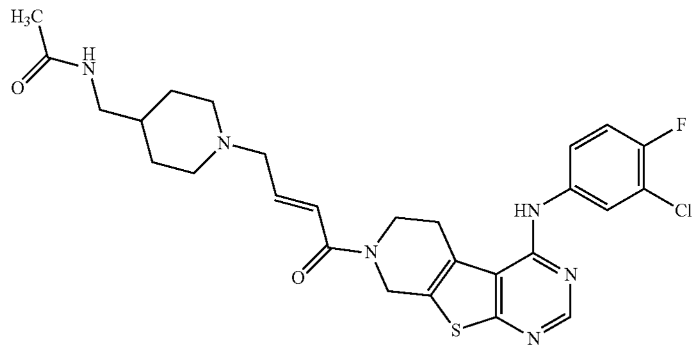 [SMILES: CC(=O)NCC1CCN(C/C=C/C(=O)N2CCc3c(sc4ncnc(Nc5ccc(F)c(Cl)c5)c34)C2)CC1] | 1.72 | 557 |
| 31 | 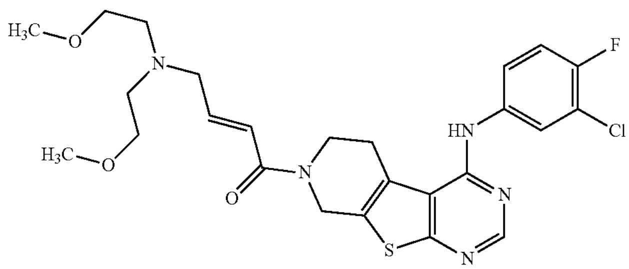 [SMILES: COCCN(C/C=C/C(=O)N1CCc2c(sc3ncnc(Nc4ccc(F)c(Cl)c4)c23)C1)CCOC] | 1.78 | 534 |
| 32 | 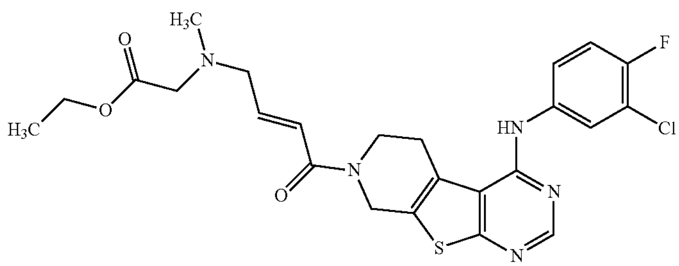 [SMILES: CCOC(=O)CN(C)C/C=C/C(=O)N1CCc2c(sc3ncnc(Nc4ccc(F)c(Cl)c4)c23)C1] | 1.78 | 518 |
| 33 | 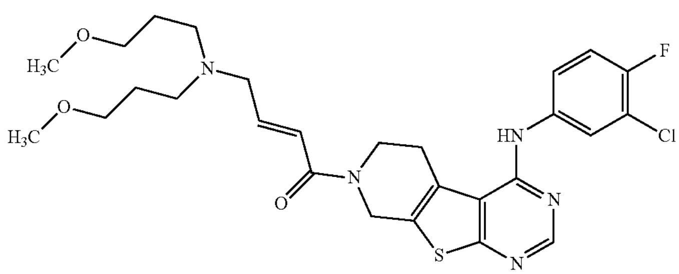 [SMILES: COCCCN(C/C=C/C(=O)N1CCc2c(sc3ncnc(Nc4ccc(F)c(Cl)c4)c23)C1)CCCOC] | 1.81 | 562 |
| 34 | 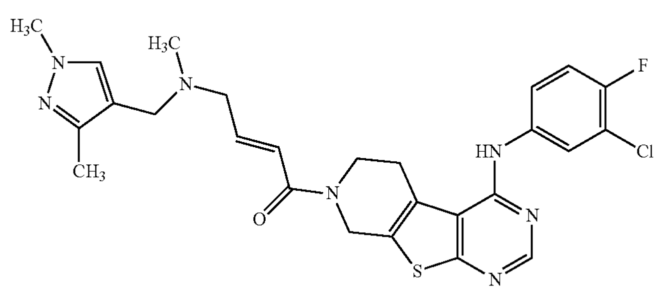 [SMILES: Cc1nn(C)cc1CN(C)C/C=C/C(=O)N1CCc2c(sc3ncnc(Nc4ccc(F)c(Cl)c4)c23)C1] | 1.75 | 540 |

TABLE 1-continued

| Example | Structure | LC/MS (method 7) R_t [min] | LC/MS m/z [M + H]+ |
|---|---|---|---|
| 35 | 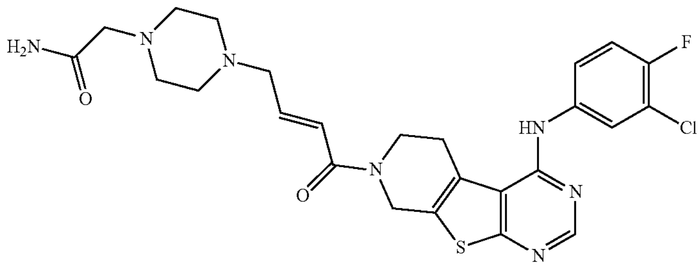 [SMILES: NC(=O)CN1CCN(C/C=C/C(=O)N2CCc3c(sc4ncnc(Nc5ccc(F)c(Cl)c5)c34)C2)CC1] | 1.70 | 544 |
| 36 | 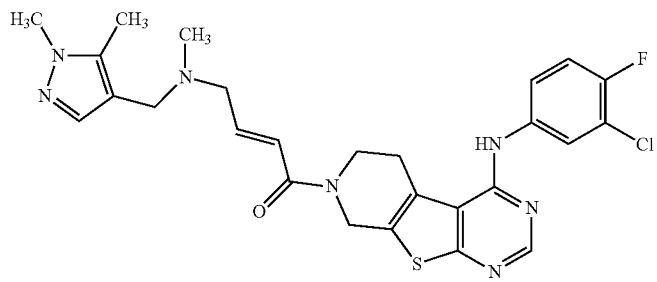 [SMILES: Cc1c(CN(C)C/C=C/C(=O)N2CCc3c(sc4ncnc(Nc5ccc(F)c(Cl)c5)c34)C2)cnn1C] | 1.76 | 540 |
| 37 | 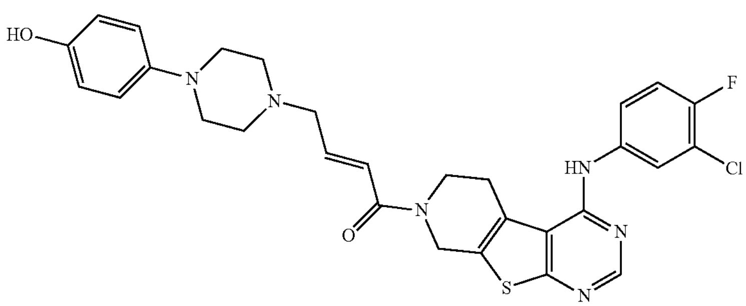 [SMILES: O=C(/C=C/CN1CCN(c2ccc(O)cc2)CC1)N1CCc2c(sc3ncnc(Nc4ccc(F)c(Cl)c4)c23)C1] | 1.75 | 579 |
| 38 | 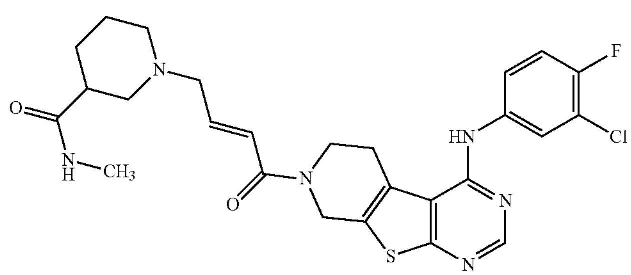 [SMILES: CNC(=O)C1CCCN(C/C=C/C(=O)N2CCc3c(sc4ncnc(Nc5ccc(F)c(Cl)c5)c34)C2)C1] | 1.73 | 543 |
| 39 | 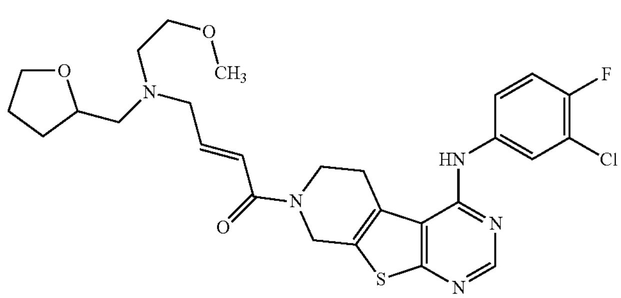 [SMILES: COCCN(C/C=C/C(=O)N1CCc2c(sc3ncnc(Nc4ccc(F)c(Cl)c4)c23)C1)CC1CCCO1] | 1.81 | 560 |

TABLE 1-continued
| Example | Structure | LC/MS (method 7) $R_t$ [min] | LC/MS m/z [M + H]+ |
|---|---|---|---|
| 40 | 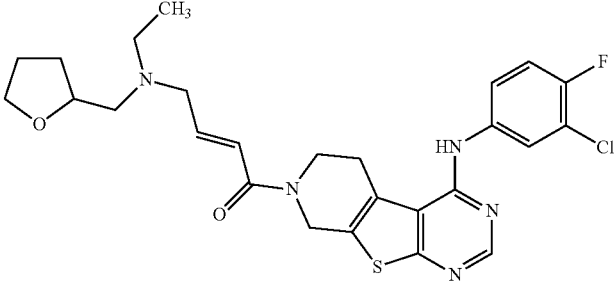 [SMILES: CCN(C/C=C/C(=O)N1CCc2c(sc3ncnc(Nc4ccc(F)c(Cl)c4)c23)C1)CC1CCCO1] | 1.79 | 530 |
| 41 | 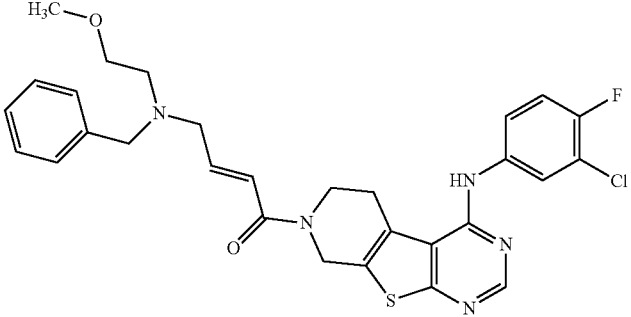 [SMILES: COCCN(C/C=C/C(=O)N1CCc2c(sc3ncnc(Nc4ccc(F)c(Cl)c4)c23)C1)Cc1ccccc1] | 1.86 | 566 |
| 42 | 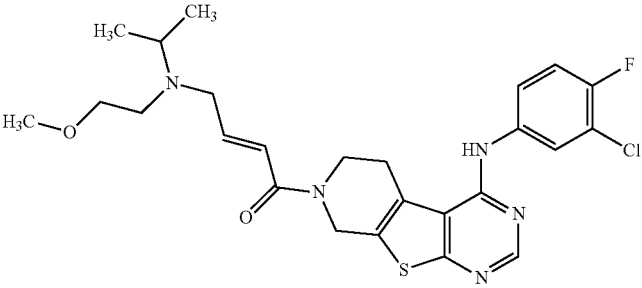 [SMILES: COCCN(C/C=C/C(=O)N1CCc2c(sc3ncnc(Nc4ccc(F)c(Cl)c4)c23)C1)C(C)C] | 1.78 | 518 |
| 43 | 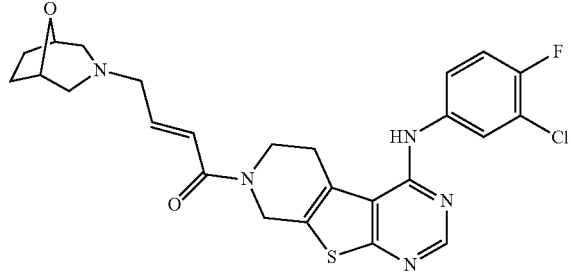 [SMILES: O=C(/C=C/CN1CC2CCC(C1)O2)N1CCc2c(sc3ncnc(Nc4ccc(F)c(Cl)c4)c23)C1] | 1.74 | 514 |
| 44 | 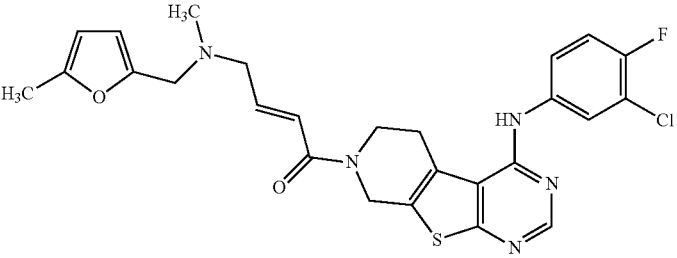 [SMILES: Cc1ccc(CN(C)C/C=C/C(=O)N2CCc3c(sc4ncnc(Nc5ccc(F)c(Cl)c5)c34)C2)o1] | 1.82 | 526 |

TABLE 1-continued

| Example | Structure | LC/MS (method 7) R_t [min] | LC/MS m/z [M + H]+ |
|---|---|---|---|
| 45 | 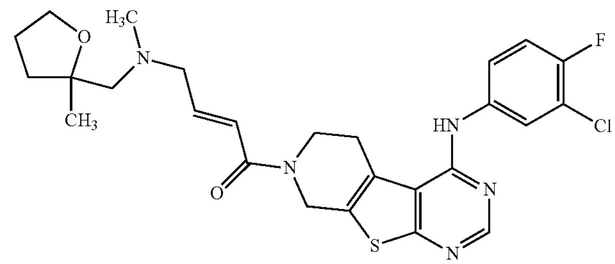 [SMILES: CN(C/C=C/C(=O)N1CCc2c(sc3ncnc(Nc4ccc(F)c(Cl)c4)c23)C1)CC1(C)CCCO1] | 1.79 | 530 |
| 46 | 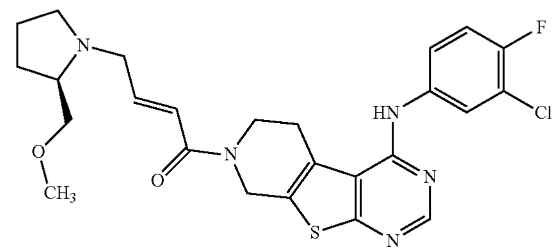 [SMILES: COC[C@H]1CCCN1C/C=C/C(=O)N1CCc2c(sc3ncnc(Nc4ccc(F)c(Cl)c4)c23)C1] | 1.78 | 516 |
| 47 | 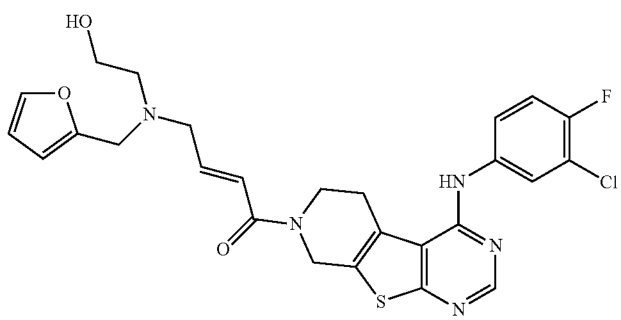 [SMILES: O=C(/C=C/CN(CCO)Cc1ccco1)N1CCc2c(sc3ncnc(Nc4ccc(F)c(Cl)c4)c23)C1] | 1.76 | 542 |
| 48 | 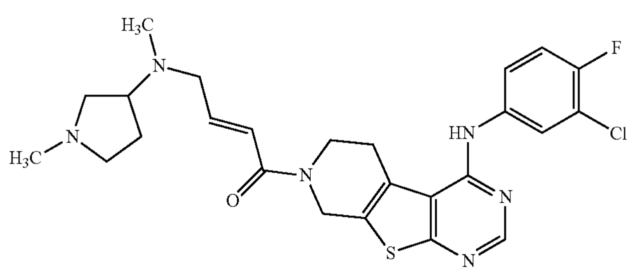 [SMILES: CN1CCC(N(C)C/C=C/C(=O)N2CCc3c(sc4ncnc(Nc5ccc(F)c(Cl)c5)c34)C2)C1] | 1.74 | 515 |
| 49 | 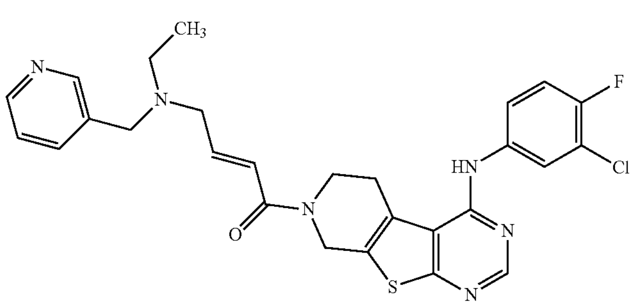 [SMILES: CCN(C/C=C/C(=O)N1CCc2c(sc3ncnc(Nc4ccc(F)c(Cl)c4)c23)C1)Cc1cccnc1] | 1.74 | 537 |

TABLE 1-continued

| Example | Structure | LC/MS (method 7) R_t [min] | LC/MS m/z [M + H]+ |
|---|---|---|---|
| 50 | 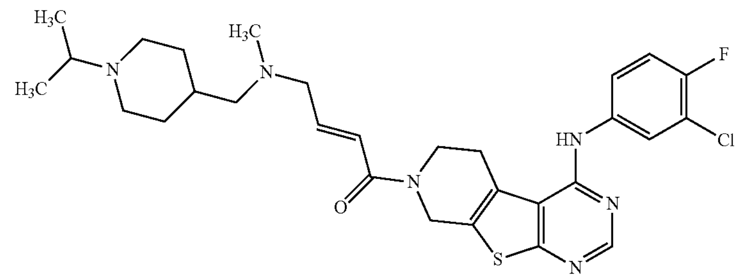 [SMILES: CC(C)N1CCC(CN(C)C/C=C/C(=O)N2CCc3c(sc4ncnc(Nc5ccc(F)c(Cl)c5)c34)C2)CC1] | 1.57 | 571 |
| 51 | 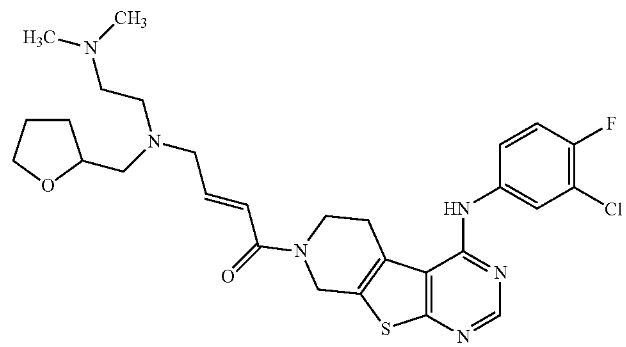 [SMILES: CN(C)CCN(C/C=C/C(=O)N1CCc2c(sc3ncnc(Nc4ccc(F)c(Cl)c4)c23)C1)CC1CCCO1] | 1.82 | 573 |
| 52 | 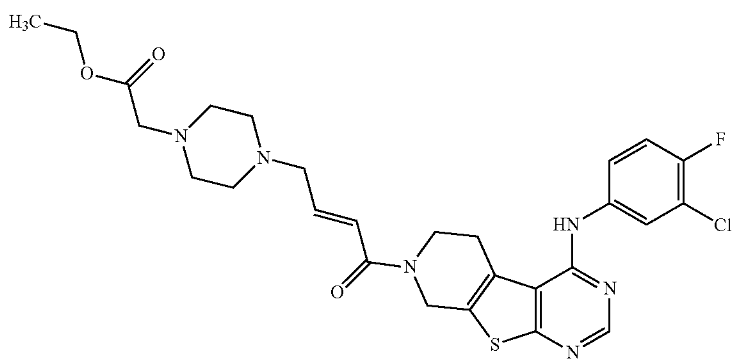 [SMILES: CCOC(=O)CN1CCN(C/C=C/C(=O)N2CCc3c(sc4ncnc(Nc5ccc(F)c(Cl)c5)c34)C2)CC1] | 1.77 | 573 |
| 53 | 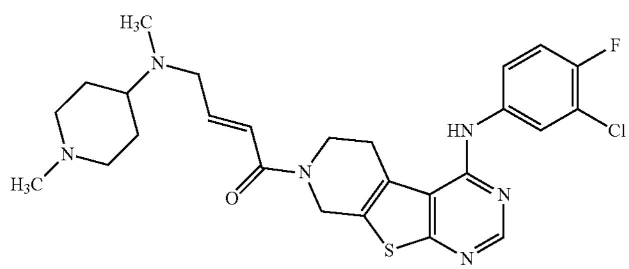 [SMILES: CN1CCC(N(C)C/C=C/C(=O)N2CCc3c(sc4ncnc(Nc5ccc(F)c(Cl)c5)c34)C2)CC1] | 1.54 | 529 |
| 54 | 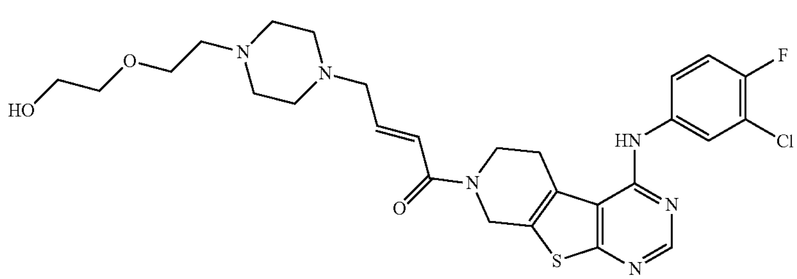 [SMILES: O=C(/C=C/CN1CCN(CCOCCO)CC1)N1CCc2c(sc3ncnc(Nc4ccc(F)c(Cl)c4)c23)C1] | 1.73 | 575 |

TABLE 1-continued

| Example | Structure | LC/MS (method 7) R$_t$ [min] | LC/MS m/z [M + H]$^+$ |
| --- | --- | --- | --- |
| 55 | 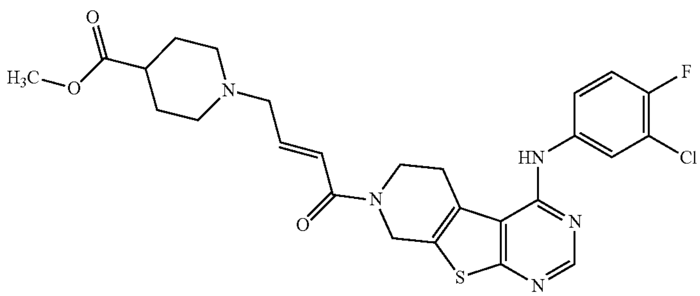 [SMILES: COC(=O)C1CCN(C/C=C/C(=O)N2CCc3c(sc4ncnc(Nc5ccc(F)c(Cl)c5)c34)C2)CC1] | 1.77 | 544 |
| 56 | 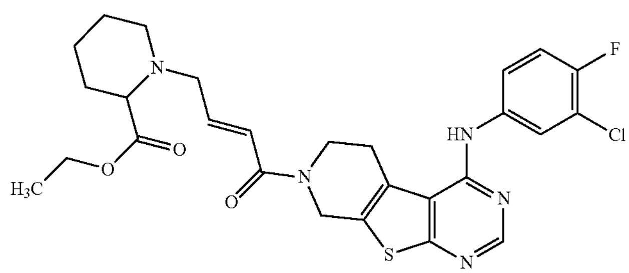 [SMILES: CCOC(=O)C1CCCCN1C/C=C/C(=O)N1CCc2c(sc3ncnc(Nc4ccc(F)c(Cl)c4)c23)C1] | 1.83 | 558 |
| 57 | 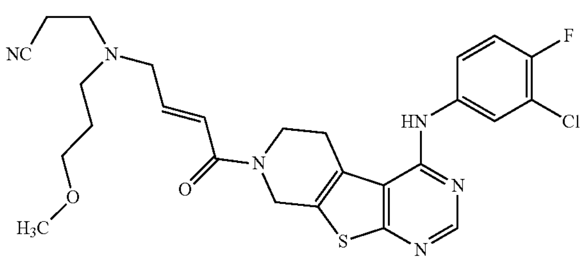 [SMILES: COCCCN(C/C=C/C(=O)N1CCc2c(sc3ncnc(Nc4ccc(F)c(Cl)c4)c23)C1)CCC#N] | 1.82 | 543 |
| 58 | 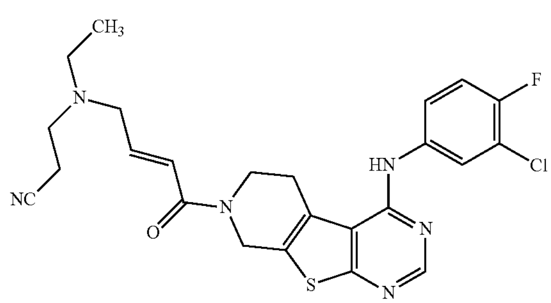 [SMILES: CCN(C/C=C/C(=O)N1CCc2c(sc3ncnc(Nc4ccc(F)c(Cl)c4)c23)C1)CCC#N] | 1.75 | 499 |
| 59 | 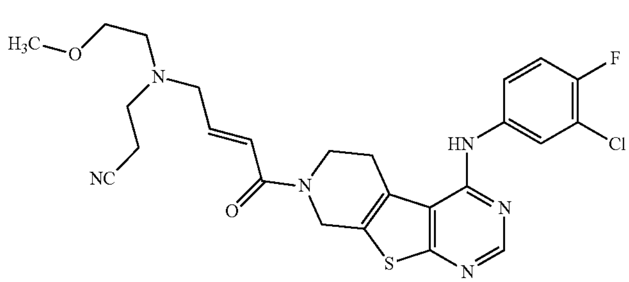 [SMILES: COCCN(C/C=C/C(=O)N1CCc2c(sc3ncnc(Nc4ccc(F)c(Cl)c4)c23)C1)CCC#N] | 1.85 | 529 |

TABLE 1-continued

| Example | Structure | LC/MS (method 7) R_t [min] | LC/MS m/z [M + H]+ |
|---|---|---|---|
| 60 | 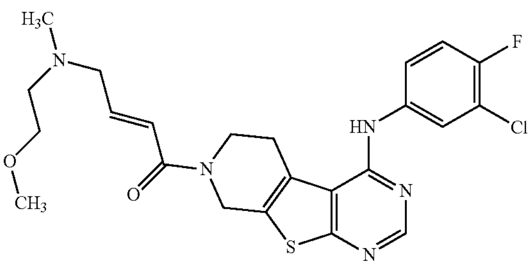 [SMILES: COCCN(C)C/C=C/C(=O)N1CCc2c(sc3ncnc(Nc4ccc(F)c(Cl)c4)c23)C1] | 1.73 | 490 |
| 61 | 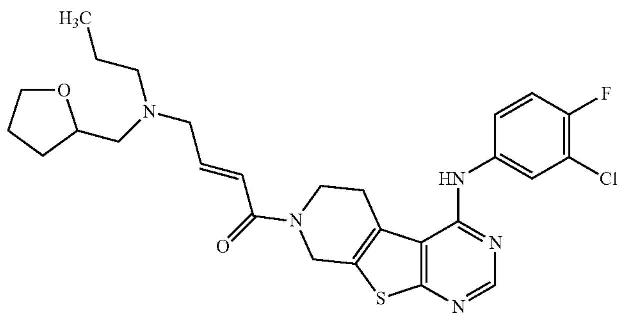 [SMILES: CCCN(C/C=C/C(=O)N1CCc2c(sc3ncnc(Nc4ccc(F)c(Cl)c4)c23)C1)CC1CCCO1] | 1.83 | 544 |
| 62 | 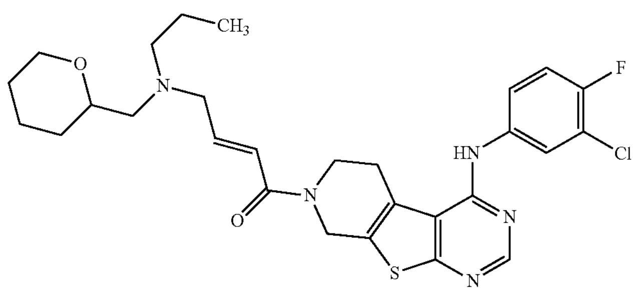 [SMILES: CCCN(C/C=C/C(=O)N1CCc2c(sc3ncnc(Nc4ccc(F)c(Cl)c4)c23)C1)CC1CCCCO1] | 1.85 | 558 |
| 63 | 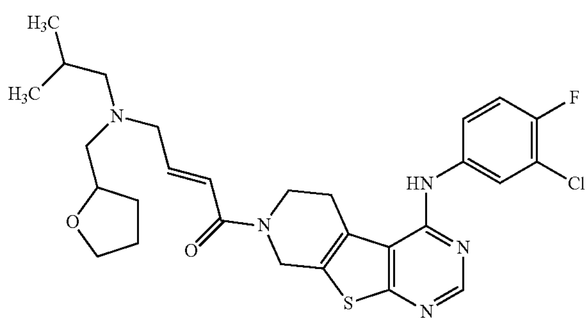 [SMILES: CC(C)CN(C/C=C/C(=O)N1CCc2c(sc3ncnc(Nc4ccc(F)c(Cl)c4)c23)C1)CC1CCCO1] | 1.86 | 558 |
| 64 | 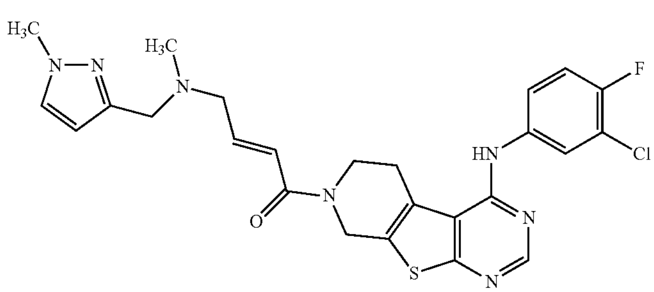 [SMILES: CN(C/C=C/C(=O)N1CCc2c(sc3ncnc(Nc4ccc(F)c(Cl)c4)c23)C1)Cc1ccn(C)n1] | 1.75 | 526 |

TABLE 1-continued

| Example | Structure | LC/MS (method 7) R_t [min] | LC/MS m/z [M + H]+ |
|---------|-----------|---------------------------|---------------------|
| 65 | 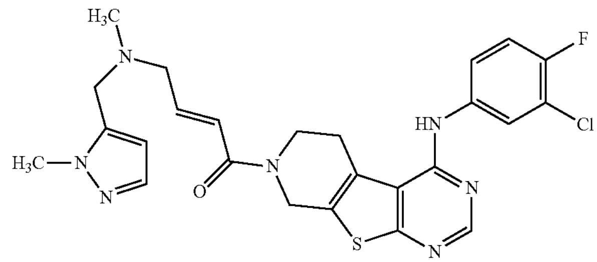 [SMILES: CN(C/C=C/C(=O)N1CCc2c(sc3ncnc(Nc4ccc(F)c(Cl)c4)c23)C1)Cc1ccnn1C] | 1.75 | 526 |
| 66 | 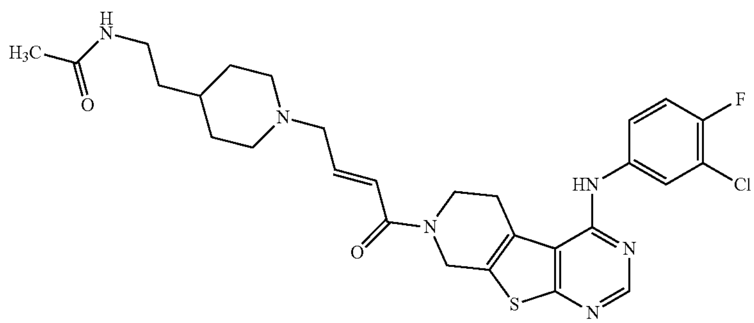 [SMILES: CC(=O)NCCC1CCN(C/C=C/C(=O)N2CCc3c(sc4ncnc(Nc5ccc(F)c(Cl)c5)c34)C2)CC1] | 1.73 | 571 |
| 67 | 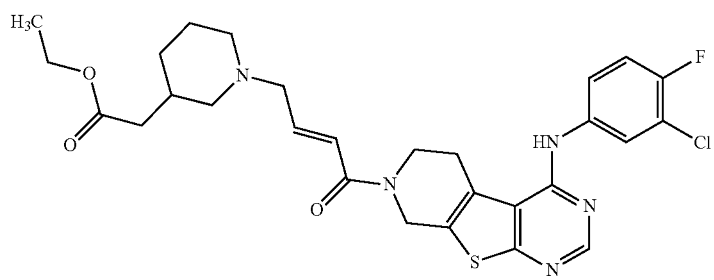 [SMILES: CCOC(=O)CC1CCCN(C/C=C/C(=O)N2CCc3c(sc4ncnc(Nc5ccc(F)c(Cl)c5)c34)C2)C1] | 1.82 | 572 |
| 68 | 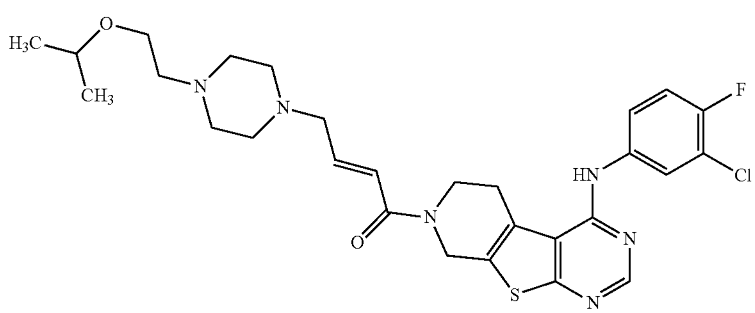 [SMILES: CC(C)OCCN1CCN(C/C=C/C(=O)N2CCc3c(sc4ncnc(Nc5ccc(F)c(Cl)c5)c34)C2)CC1] | 1.81 | 573 |
| 69 | 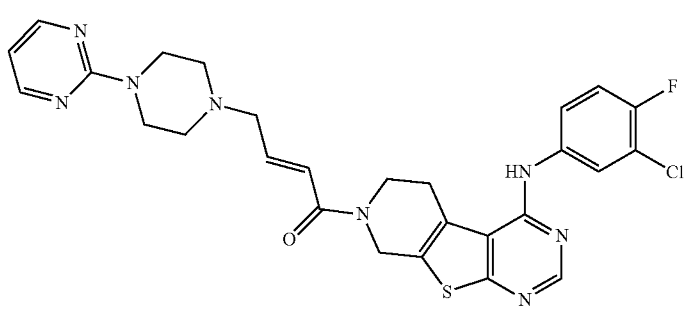 [SMILES: O=C(/C=C/CN1CCN(c2ncccn2)CC1)N1CCc2c(sc3ncnc(Nc4ccc(F)c(Cl)c4)c23)C1] | 1.77 | 565 |

TABLE 1-continued

| Example | Structure | LC/MS (method 7) R_t [min] | LC/MS m/z [M + H]+ |
|---|---|---|---|
| 70 | 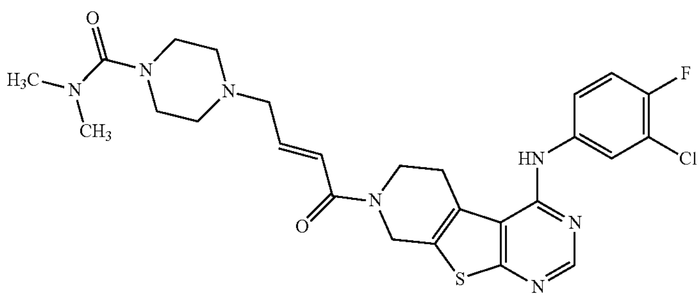 [SMILES: CN(C)C(=O)N1CCN(C/C=C/C(=O)N2CCc3c(sc4ncnc(Nc5ccc(F)c(Cl)c5)c34)C2)CC1] | 1.75 | 558 |
| 71 | 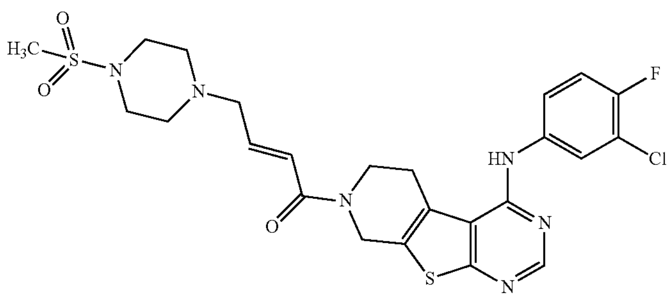 [SMILES: CS(=O)(=O)N1CCN(C/C=C/C(=O)N2CCc3c(sc4ncnc(Nc5ccc(F)c(Cl)c5)c34)C2)CC1] | 1.76 | 565 |
| 72 | 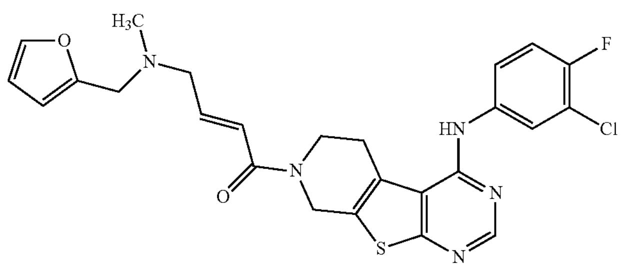 [SMILES: CN(C/C=C/C(=O)N1CCc2c(sc3ncnc(Nc4ccc(F)c(Cl)c4)c23)C1)Cc1ccco1] | 1.78 | 512 |
| 73 | 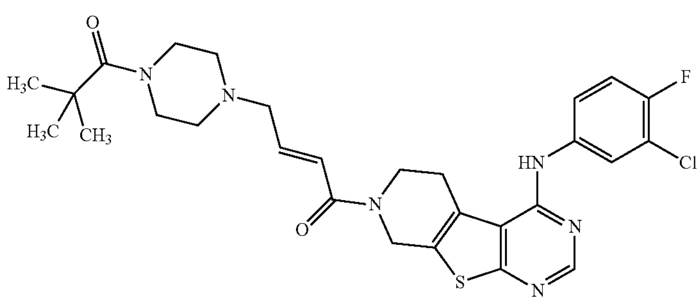 [SMILES: CC(C)(C)C(=O)N1CCN(C/C=C/C(=O)N2CCc3c(sc4ncnc(Nc5ccc(F)c(Cl)c5)c34)C2)CC1] | 1.79 | 571 |
| 74 | 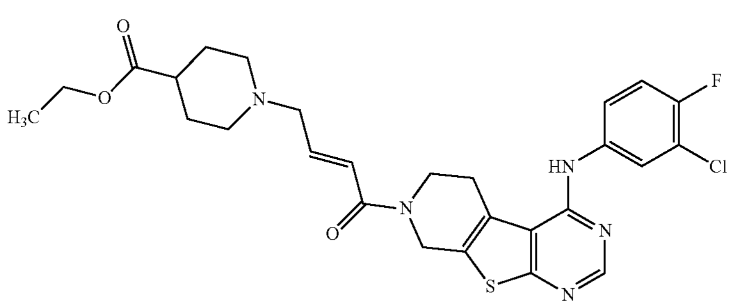 [SMILES: CCOC(=O)C1CCN(C/C=C/C(=O)N2CCc3c(sc4ncnc(Nc5ccc(F)c(Cl)c5)c34)C2)CC1] | 1.80 | 558 |

TABLE 1-continued

| Example | Structure | LC/MS (method 7) R_t [min] | LC/MS m/z [M + H]+ |
|---|---|---|---|
| 75 | 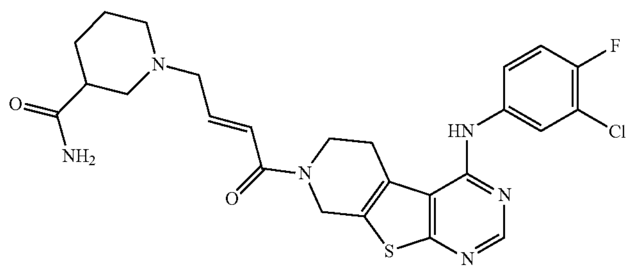 [SMILES: NC(=O)C1CCCN(C/C=C/C(=O)N2CCc3c(sc4ncnc(Nc5ccc(F)c(Cl)c5)c34)C2)C1] | 1.71 | 529 |
| 76 | 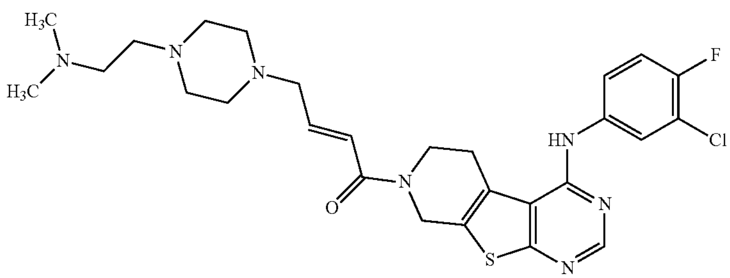 [SMILES: CN(C)CCN1CCN(C/C=C/C(=O)N2CCc3c(sc4ncnc(Nc5ccc(F)c(Cl)c5)c34)C2)CC1] | 1.56 | 558 |
| 77 | 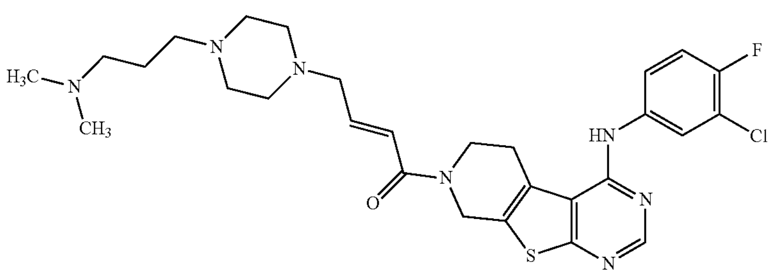 [SMILES: CN(C)CCCN1CCN(C/C=C/C(=O)N2CCc3c(sc4ncnc(Nc5ccc(F)c(Cl)c5)c34)C2)CC1] | 1.58 | 572 |
| 78 | 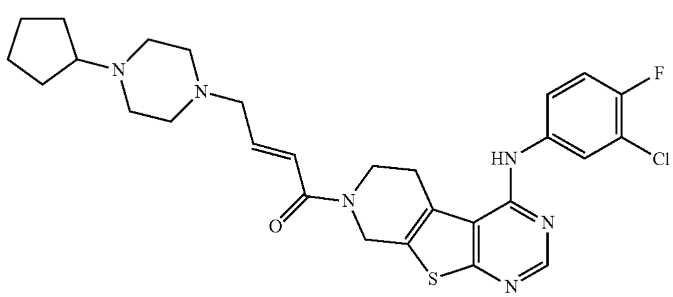 [SMILES: O=C(/C=C/CN1CCN(C2CCCC2)CC1)N1CCc2c(sc3ncnc(Nc4ccc(F)c(Cl)c4)c23)C1] | 1.77 | 555 |
| 79 | 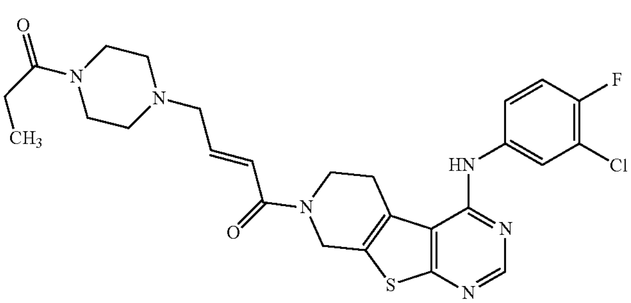 [SMILES: CCC(=O)N1CCN(C/C=C/C(=O)N2CCc3c(sc4ncnc(Nc5ccc(F)c(Cl)c5)c34)C2)CC1] | 1.73 | 543 |

TABLE 1-continued

| Example | Structure | LC/MS (method 7) R$_t$ [min] | LC/MS m/z [M + H]$^+$ |
|---|---|---|---|
| 80 | 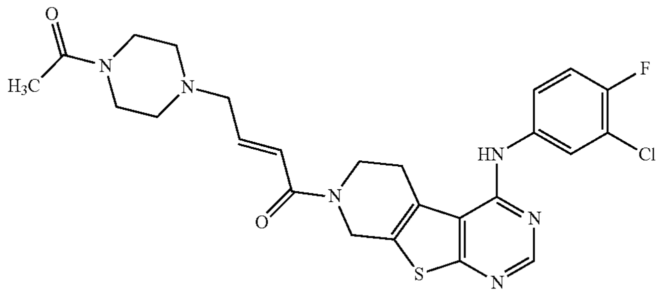 [SMILES: CC(=O)N1CCN(C/C=C/C(=O)N2CCc3c(sc4ncnc(Nc5ccc(F)c(Cl)c5)c34)C2)CC1] | 1.72 | 529 |

Example 81

N-(3-Chloro-4-fluorophenyl)-6-[(2E)-4-(dimethylamino)but-2-enoyl]-6,7-dihydro-5H-pyrrolo[3',4':4,5]thieno[2,3-d]pyrimidin-4-amine

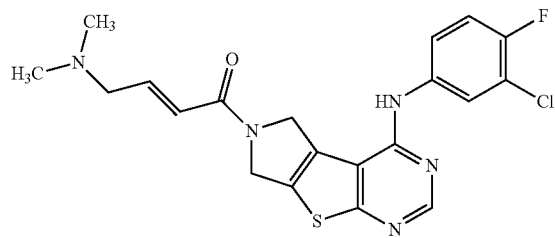 [SMILES: CN(C)C/C=C/C(=O)N1Cc2sc3ncnc(Nc4ccc(Cl)c(Cl)c4)c3c2C1]

In analogy to Example 89, the title compound was prepared from N-(3-chloro-4-fluorophenyl)-6,7-dihydro-5H-pyrrolo[3',4':4,5]thieno[2,3-d]pyrimidin-4-amine from Example 23A (60 mg, 0.19 mmol) and (2E)-4-(dimethylamino)but-2-enoic acid hydrochloride from Example 1A (43 mg, 0.26 mmol) to yield 17 mg (21%).

$^1$H-NMR (400 MHz, DMSO-d$_6$): δ=2.19 (s, 6H), 3.07-3.12 (m, 2H), 4.82 (t, 1H), 5.07 (s, 2H), 5.26 (t, 1H), 6.42-6.57 (m, 1H), 6.72-6.85 (m, 1H), 7.40-7.50 (m, 1H), 7.60-7.69 (m, 1H), 7.87-7.92 (m, 1H), 8.46-8.48 (m, 1H), 8.50-8.77 (m, 1H).

LC/MS (method 2): R$_t$=0.88 min; MS (ESIpos): m/z=432 [M+H]$^+$.

Example 82

N-(3-Chloro-4-fluorophenyl)-6-{(2E)-4-[isopropyl(methyl)amino]but-2-enoyl}-6,7-dihydro-5H-pyrrolo[3',4':4,5]thieno[2,3-d]pyrimidin-4-amine

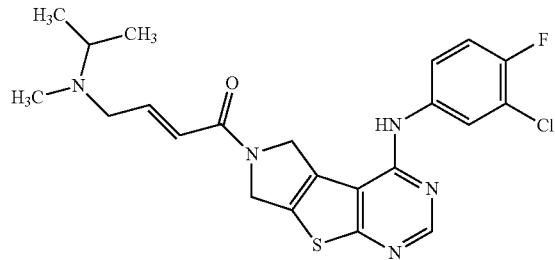 [SMILES: CC(C)N(C)C/C=C/C(=O)N1Cc2sc3ncnc(Nc4ccc(Cl)c(Cl)c4)c3c2C1]

In analogy to Example 89, the title compound was prepared from N-(3-chloro-4-fluorophenyl)-6,7-dihydro-5H-pyrrolo[3',4':4,5]thieno[2,3-d]pyrimidin-4-amine from Example 23A (60 mg, 0.19 mmol) and (2E)-4-[methyl(1-methylethyl)amino]but-2-enoic acid hydrochloride from Example 2A (51 mg, 0.26 mmol) to yield 30 mg (35%).

$^1$H-NMR (400 MHz, DMSO-d$_6$): δ=0.98 (d, 6H), 2.13 (s, 3H), 2.75-2.86 (m, 1H), 3.15-3.25 (m, 2H), 4.82 (br. s, 1H), 5.06 (br. s, 2H), 5.25 (br. s, 1H), 6.42-6.57 (m, 1H), 6.71-6.84 (m, 1H), 7.39-7.51 (m, 1H), 7.60-7.70 (m, 1H), 7.87-7.94 (m, 1H), 8.43-8.54 (m, 1H), 8.69-8.75 (m, 1H).

LC/MS (method 2): R$_t$=0.92 min; MS (ESIpos): m/z=460 [M+H]$^+$.

Example 83

N-(3,4-Dichlorophenyl)-6-[(2E)-4-(dimethylamino)but-2-enoyl]-6,7-dihydro-5H-pyrrolo[3',4':4,5]thieno[2,3-d]pyrimidin-4-amine

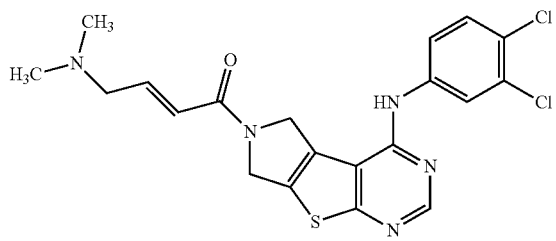

In analogy to Example 89, the title compound was prepared from N-(3,4-dichlorophenyl)-6,7-dihydro-5H-pyrrolo[3',4':4,5]thieno[2,3-d]pyrimidin-4-amine from Example 25A (65 mg, 0.19 mmol) and (2E)-4-(dimethylamino)but-2-enoic acid hydrochloride from Example 1A (45 mg, 0.27 mmol) to yield 24 mg (26%).

$^1$H-NMR (400 MHz, DMSO-d$_6$): δ=2.19 (s, 6H), 3.07-3.14 (m, 2H), 4.82 (s, 1H), 5.07 (s, 2H), 5.28 (s, 1H), 6.42-6.58 (m, 1H), 6.73-6.85 (m, 1H), 7.60-7.67 (m, 1H), 7.68-7.76 (m, 1H), 8.00-8.03 (m, 1H), 8.51+8.52 (s, Σ1H), 8.57+8.76 (br. s, Σ1H).

LC/MS (method 6): R$_t$=1.21 min; MS (ESIpos): m/z=448 [M+H]$^+$.

Example 84

N-(3,4-Dichlorophenyl)-6-{(2E)-4-[isopropyl(methyl)amino]but-2-enoyl}-6,7-dihydro-5H-pyrrolo[3',4':4,5]thieno[2,3-d]pyrimidin-4-amine

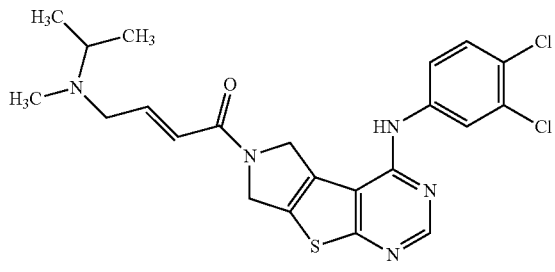

In analogy to Example 89, the title compound was prepared from N-(3,4-dichlorophenyl)-6,7-dihydro-5H-pyrrolo[3',4':4,5]thieno[2,3-d]pyrimidin-4-amine from Example 25A (65 mg, 0.19 mmol) and (2E)-4-[methyl(1-methylethyl)amino]but-2-enoic acid hydrochloride from Example 2A (52 mg, 0.27 mmol) to yield 34 mg (37%).

$^1$H-NMR (400 MHz, DMSO-$d_6$): δ=0.96-1.00 (m, 6H), 2.13+2.14 (s, Σ3H), 2.77-2.85 (m, 1H), 3.17-3.23 (m, 2H), 4.82 (t, 1H), 5.07 (s, 2H), 5.27 (t, 1H), 6.43-6.57 (m, 1H), 6.72-6.83 (m, 1H), 7.60-7.67 (m, 1H), 7.68-7.77 (m, 1H), 8.01-8.04 (m, 1H), 8.52+8.53 (s, Σ1H), 8.57+8.77 (br. s, Σ1H).

LC/MS (method 6): $R_t$=1.26 min; MS (ESIpos): m/z=476 [M+H]$^+$.

Example 85

6-[(2E)-4-(Dimethylamino)but-2-enoyl]-N-(3-ethynylphenyl)-6,7-dihydro-5H-pyrrolo[3',4':4,5]thieno[2,3-d]pyrimidin-4-amine

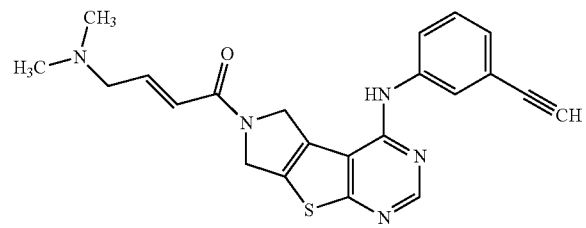 [SMILES: C#Cc1cccc(Nc2ncnc3sc4c(c23)CN(C(=O)/C=C/CN(C)C)C4)c1]

In analogy to Example 89, the title compound was prepared from N-(3-ethynylphenyl)-6,7-dihydro-5H-pyrrolo[3',4':4,5]thieno[2,3-d]pyrimidin-4-amine from Example 27A (40 mg, 0.12 mmol) and (2E)-4-(dimethylamino)but-2-enoic acid hydrochloride from Example 1A (27 mg, 0.17 mmol) to yield 11 mg (22%).

$^1$H-NMR (400 MHz, DMSO-$d_6$): δ=2.19 (s, 6H), 3.07-3.13 (m, 2H), 4.82 (t, 1H), 5.07 (s, 2H), 5.26 (t, 1H), 6.42-6.57 (m, 1H), 6.72-6.84 (m, 1H), 7.21-7.28 (m, 1H), 7.36-7.44 (m, 1H), 7.69-7.81 (m, 2H), 8.48 (s, 1H).

LC/MS (method 6): $R_t$=1.04 min; MS (ESIpos): m/z=404 [M+H]$^+$.

Example 86

N-{3-Chloro-4-[(3-fluorobenzyl)oxy]phenyl}-6-[(2E)-4-(dimethylamino)but-2-enoyl]-6,7-dihydro-5H-pyrrolo[3',4':4,5]thieno[2,3-d]pyrimidin-4-amine

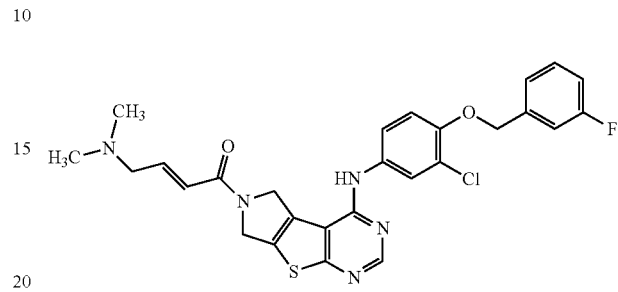

In analogy to Example 89, the title compound was prepared from N-{3-chloro-4-[(3-fluorobenzyl)oxy]phenyl}-6,7-dihydro-5H-pyrrolo[3',4':4,5]thieno[2,3-d]pyrimidin-4-amine from Example 29A (46 mg, 0.11 mmol) and (2E)-4-(dimethylamino)but-2-enoic acid hydrochloride from Example 1A (25 mg, 0.15 mmol) to yield 19 mg (33%).

$^1$H-NMR (400 MHz, DMSO-$d_6$): δ=2.15-2.19 (m, 6H), 3.09 (t, 2H), 4.80 (s, 1H), 5.05 (s, 2H), 5.22 (s, 1H), 5.25-5.29 (m, 2H), 6.42-6.55 (m, 1H), 6.72-6.84 (m, 1H), 7.15-7.21 (m, 1H), 7.22-7.28 (m, 1H), 7.29-7.35 (m, 2H), 7.44-7.50 (m, 1H), 7.50-7.55 (m, 1H), 7.72-7.75 (m, 1H), 8.41 (s, 1H), 8.43+8.62 (br. s, Σ1H).

LC/MS (method 6): $R_t$=1.38 min; MS (ESIpos): m/z=538 [M+H]$^+$.

Example 87

N-[3-Chloro-4-(pyridin-2-ylmethoxy)phenyl]-6-[(2E)-4-(dimethylamino)but-2-enoyl]-6,7-dihydro-5H-pyrrolo[3',4':4,5]thieno[2,3-d]pyrimidin-4-amine

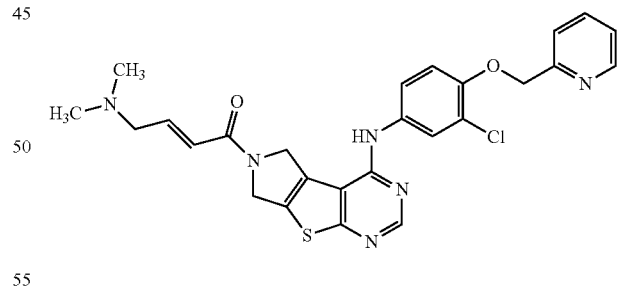

In analogy to Example 89, the title compound was prepared from N-[3-chloro-4-(pyridin-2-ylmethoxy)phenyl]-6,7-dihydro-5H-pyrrolo[3',4':4,5]thieno[2,3-d]pyrimidin-4-amine from Example 31A (38 mg, 0.094 mmol) and (2E)-4-(dimethylamino)but-2-enoic acid hydrochloride from Example 1A (22 mg, 0.13 mmol) to yield 18 mg (37%).

$^1$H-NMR (400 MHz, DMSO-$d_6$): δ=2.17-2.19 (m, 6H), 3.09 (t, 2H), 4.80 (t, 1H), 5.06 (s, 2H), 5.22 (t, 1H), 5.29-5.32 (m, 2H), 6.42-6.55 (m, 1H), 6.72-6.84 (m, 1H), 7.23-7.29 (m, 1H), 7.35-7.40 (m, 1H), 7.50-7.54 (m, 1H), 7.56-7.60 (m, 1H), 7.73-7.76 (m, 1H), 7.86-7.91 (m, 1H), 8.41-8.44+8.59-8.63 (m, Σ3H).

LC/MS (method 6): $R_t$=1.08 min; MS (ESIpos): m/z=521 [M+H]$^+$.

Example 88

6-[(2E)-4-(Dimethylamino)but-2-enoyl]-N-[1-(3-fluorobenzyl)-1H-indazol-5-yl]-6,7-dihydro-5H-pyrrolo[3',4':4,5]thieno[2,3-d]pyrimidin-4-amine

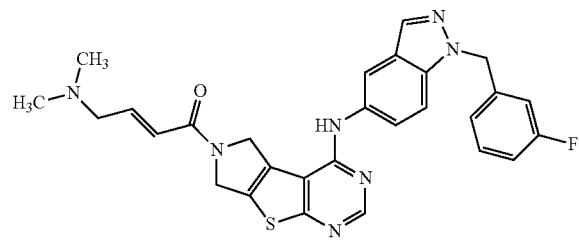 [SMILES: CN(C)C/C=C/C(=O)N1Cc2sc3ncnc(Nc4ccc5c(cnn5Cc5cccc(F)c5)c4)c3c2C1]

In analogy to Example 89, the title compound was prepared from N-[1-(3-fluorobenzyl)-1H-indazol-5-yl]-6,7-dihydro-5H-pyrrolo[3',4':4,5]thieno[2,3-d]pyrimidin-4-amine from Example 33A (51 mg, 0.12 mmol) and (2E)-4-(dimethylamino)but-2-enoic acid hydrochloride from Example 1A (29 mg, 0.17 mmol) to yield 30 mg (44%).

$^1$H-NMR (400 MHz, DMSO-d$_6$): δ=2.17+2.19 (s, Σ6H), 3.06-3.10 (m, 2H), 4.80 (t, 1H), 5.05 (s, 2H), 5.20 (t, 1H), 5.69-5.72 (m, 2H), 6.42-6.50 (m, 1H), 6.72-6.82 (m, 1H), 7.00-7.06 (m, 2H), 7.07-7.13 (m, 1H), 7.33-7.40 (m, 1H), 7.50-7.55 (m, 1H), 7.69-7.76 (m, 1H), 7.93-7.96 (m, 1H), 8.13-8.17 (m, 1H), 8.35-8.37 (m, 1H), 8.60+8.76 (s, Σ1H).

LC/MS (method 4): $R_t$=1.52 min; MS (ESIpos): m/z=528 [M+H]$^+$.

Example 89

N-(3-Chloro-4-fluorophenyl)-7-[(2E)-4-(dimethylamino)but-2-enoyl]-5,6,7,8-tetrahydropyrido[4',3':4,5]furo[2,3-d]pyrimidin-4-amine

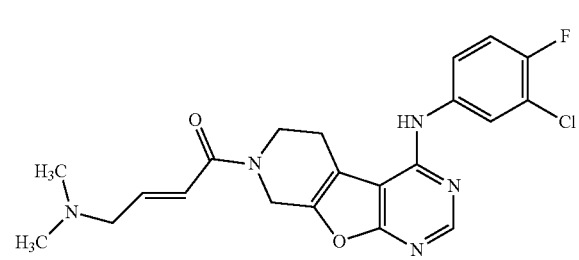 [SMILES: CN(C)C/C=C/C(=O)N1CCc2c(oc3ncnc(Nc4ccc(F)c(Cl)c4)c23)C1]

A suspension of N-(3-chloro-4-fluorophenyl)-5,6,7,8-tetrahydropyrido[4',3':4,5]furo[2,3-d]pyrimidin-4-amine from Example 39A (100 mg, 0.314 mmol) and (2E)-4-(dimethylamino)but-2-enoic acid hydrochloride from Example 1A (73 mg, 0.44 mmol) in THF (2 mL) was treated with DIPEA (160 mg, 1.26 mmol) and TBTU (150 mg, 0.47 mmol). The mixture was stirred at rt overnight and then purified directly by preparative HPLC. The product crystallized upon trituration with diethyl ether to afford 76 mg (56%) of the title compound.

$^1$H-NMR (400 MHz, DMSO-d$_6$): δ=2.17 (s, 6H), 2.91-3.01 (m, 2H), 3.03-3.10 (m, 2H), 3.82-3.92 (m, 2H), 4.71-4.88 (m, 2H), 6.63-6.79 (m, 2H), 7.42 (t, 1H), 7.61-7.68 (m, 1H), 7.91-7.96 (m, 1H), 8.39 (s, 1H), 8.72 (br. s, 1H).

LC/MS (method 4): $R_t$=1.49 min; MS (ESIpos): m/z=430 [M+H]$^+$.

Example 90

N-(3-Chloro-4-fluorophenyl)-7-{(2E)-4-[methyl(1-methylethyl)amino]but-2-enoyl}-5,6,7,8-tetrahydro-pyrido[4',3':4,5]furo[2,3-d]pyrimidin-4-amine

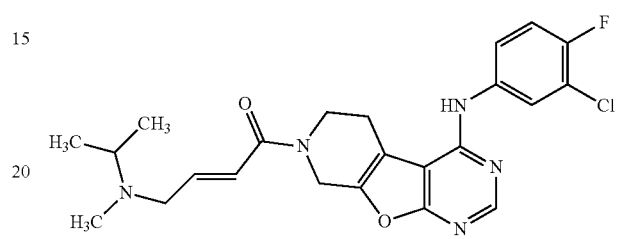

In analogy to Example 89, the title compound was prepared from N-(3-chloro-4-fluorophenyl)-5,6,7,8-tetrahydropyrido[4',3':4,5]furo[2,3-d]pyrimidin-4-amine from Example 39A (100 mg, 0.314 mmol) and (2E)-4-[methyl(1-methylethyl)amino]but-2-enoic acid hydrochloride from Example 2A (85 mg, 0.44 mmol) to yield 80 mg (53%).

$^1$H-NMR (400 MHz, DMSO-d$_6$): δ=0.98 (d, 6H), 2.12 (s, 3H), 2.74-2.84 (m, 1H), 2.91-3.01 (m, 2H), 3.14-3.21 (m, 2H), 3.82-3.91 (m, 2H), 4.71-4.87 (m, 2H), 6.63-6.80 (m, 2H), 7.42 (t, 1H), 7.61-7.68 (m, 1H), 7.90-7.96 (m, 1H), 8.38-8.40 (m, 1H), 8.72 (br. s, 1H).

LC/MS (method 6): $R_t$=1.14 min; MS (ESIpos): m/z=458 [M+H]$^+$.

Example 91

N-(3,4-Dichlorophenyl)-7-[(2E)-4-(dimethylamino)but-2-enoyl]-5,6,7,8-tetrahydropyrido[4',3':4,5]furo[2,3-d]pyrimidin-4-amine

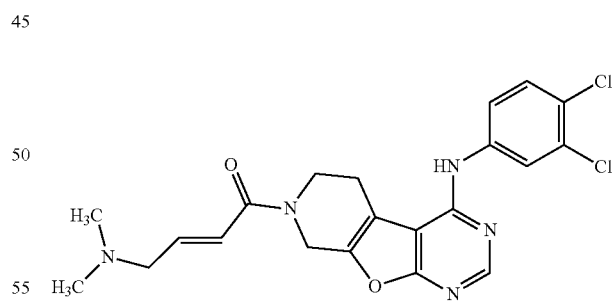

In analogy to Example 89, the title compound was prepared from N-(3,4-dichlorophenyl)-5,6,7,8-tetrahydropyrido[4',3':4,5]furo[2,3-d]pyrimidin-4-amine from Example 41A (100 mg, 0.30 mmol) and (2E)-4-(dimethylamino)but-2-enoic acid hydrochloride from Example 1A (69 mg, 0.42 mmol) to yield 75 mg (56%).

$^1$H-NMR (400 MHz, DMSO-d$_6$): δ=2.17 (s, 6H), 2.93-3.10 (m, 4H), 3.83-3.92 (m, 2H), 4.73-4.88 (m, 2H), 6.64-6.79 (m, 2H), 7.59-7.62 (m, 1H), 7.69-7.75 (m, 1H), 8.05 (br. s, 1H), 8.44 (s, 1H), 8.78 (br. s, 1H).

LC/MS (method 6): $R_t$=1.20 min; MS (ESIpos): m/z=446 [M+H]$^+$.

Example 92

N-(3,4-Dichlorophenyl)-7-{(2E)-4-[isopropyl(methyl)amino]but-2-enoyl}-5,6,7,8-tetrahydropyrido[4',3':4,5]furo[2,3-d]pyrimidin-4-amine

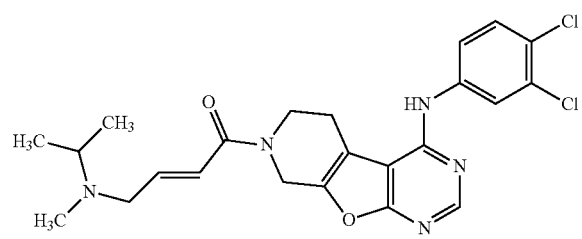 [SMILES: CC(C)N(C)C/C=C/C(=O)N1CCc2c(oc3ncnc(Nc4ccc(F)c(Cl)c4)c23)C1]

In analogy to Example 89, the title compound was prepared from N-(3,4-dichlorophenyl)-5,6,7,8-tetrahydropyrido[4',3':4,5]furo[2,3-d]pyrimidin-4-amine from Example 41A (100 mg, 0.30 mmol) and (2E)-4-[methyl(1-methylethyl)amino]but-2-enoic acid hydrochloride from Example 2A (81 mg, 0.42 mmol) to yield 86 mg (61%).

$^1$H-NMR (400 MHz, DMSO-d$_6$): δ=0.98 (d, 6H), 2.11 (s, 3H), 2.73-2.84 (m, 1H), 2.98-3.04 (m, 2H), 3.13-3.20 (m, 2H), 3.82-3.92 (m, 2H), 4.72-4.88 (m, 2H), 6.63-6.79 (m, 2H), 7.59-7.62 (m, 1H), 7.69-7.75 (m, 1H), 8.05 (br. s, 1H), 8.44 (s, 1H), 8.78 (s, 1H).

LC/MS (method 6): $R_t$=1.26 min; MS (ESIpos): m/z=474 [M+H]$^+$.

Example 93

7-[(2E)-4-(Dimethylamino)but-2-enoyl]-N-(3-ethynylphenyl)-5,6,7,8-tetrahydropyrido[4',3':4,5]furo[2,3-d]pyrimidin-4-amine

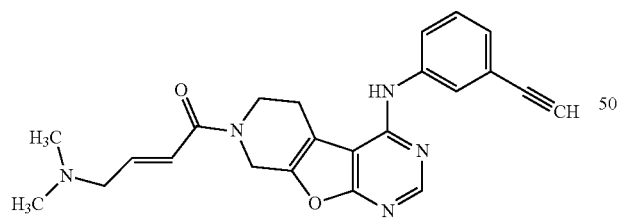

In analogy to Example 89, the title compound was prepared from N-(3-ethynylphenyl)-5,6,7,8-tetrahydropyrido[4',3':4,5]furo[2,3-d]pyrimidin-4-amine from Example 43A (100 mg, 0.344 mmol) and (2E)-4-(dimethylamino)but-2-enoic acid hydrochloride from Example 1A (80 mg, 0.48 mmol) to yield 66 mg (46%).

$^1$H-NMR (400 MHz, DMSO-d$_6$): δ=2.17 (s, 6H), 2.90-3.01 (m, 2H), 3.04-3.10 (m, 2H), 3.82-3.91 (m, 2H), 4.19 (s, 1H), 4.72-4.88 (m, 2H), 6.63-6.80 (m, 2H), 7.18-7.21 (m, 1H), 7.37 (t, 1H), 7.69-7.75 (m, 1H), 7.80-7.84 (m, 1H), 8.39-8.40 (m, 1H), 8.66 (br. s, 1H).

LC/MS (method 6): $R_t$=1.00 min; MS (ESIpos): m/z=402 [M+H]$^+$.

Example 94

N-(3-Ethynylphenyl)-7-{(2E)-4-[isopropyl(methyl)amino]but-2-enoyl}-5,6,7,8-tetrahydropyrido[4',3':4,5]furo[2,3-d]pyrimidin-4-amine

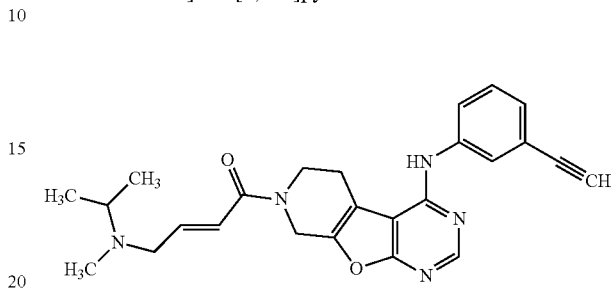

In analogy to Example 89, the title compound was prepared from N-(3-ethynylphenyl)-5,6,7,8-tetrahydropyrido[4',3':4,5]furo[2,3-d]pyrimidin-4-amine from Example 43A (100 mg, 0.344 mmol) and (2E)-4-[methyl(1-methylethyl)amino]but-2-enoic acid hydrochloride from Example 2A (93 mg, 0.48 mmol) to yield 82 mg (55%).

$^1$H-NMR (400 MHz, DMSO-d$_6$): δ=0.97 (d, 6H), 2.12 (s, 3H), 2.73-2.83 (m, 1H), 2.90-3.01 (m, 2H), 3.14-3.20 (m, 2H), 3.81-3.90 (m, 2H), 4.19 (s, 1H), 4.71-4.87 (m, 2H), 6.63-6.79 (m, 2H), 7.17-7.21 (m, 1H), 7.37 (t, 1H), 7.69-7.74 (m, 1H), 7.80-7.83 (m, 1H), 8.38-8.40 (m, 1H), 8.66 (br. s, 1H).

LC/MS (method 5): $R_t$=1.55 min; MS (ESIpos): m/z=430 [M+H]$^+$.

Example 95

4-[(3-Chloro-4-fluorophenyl)amino]-7-[(2E)-4-(dimethylamino)but-2-enoyl]-5,6,7,8-tetrahydrothieno[2,3-b:5,4-c']dipyridine-3-carbonitrile

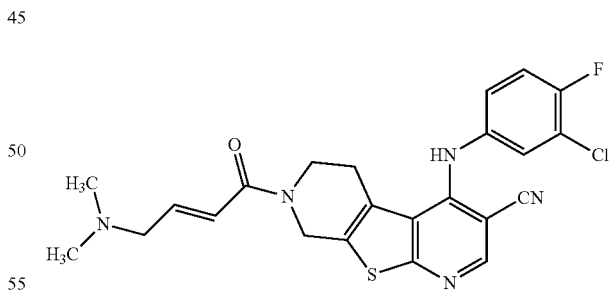

In analogy to Example 89, the title compound was prepared from 4-[(3-chloro-4-fluorophenyl)amino]-5,6,7,8-tetrahydrothieno[2,3-b:5,4-c']dipyridine-3-carbonitrile from Example 55A (100 mg, 0.28 mmol) and (2E)-4-(dimethylamino)but-2-enoic acid hydrochloride from Example 1A (65 mg, 0.39 mmol) to yield 53 mg (40%).

$^1$H-NMR (400 MHz, DMSO-d$_6$): δ=2.15 (s, 6H), 2.97-3.06 (m, 4H), 3.75-3.88 (m, 2H), 4.84-5.01 (m, 2H), 6.62-6.74 (m, 2H), 6.98-7.08 (m, 1H), 7.22-7.29 (m, 1H), 7.34 (t, 1H), 8.59-8.63 (m, 1H), 8.73 (s, 1H).

LC/MS (method 2): $R_t$=0.89 min; MS (ESIpos): m/z=470 [M+H]$^+$.

Example 96

4-{[3-Chloro-4-(pyridin-2-ylmethoxy)phenyl]amino}-7-[(2E)-4-(dimethylamino)but-2-enoyl]-5,6,7,8-tetrahydrothieno[2,3-b:5,4-c']dipyridine-3-carbonitrile

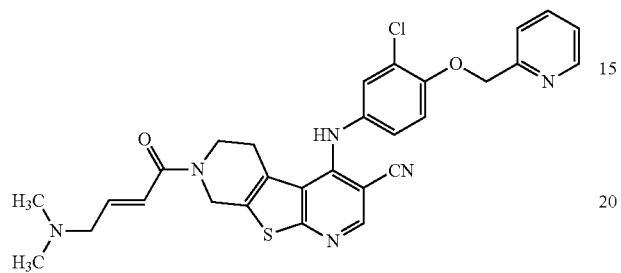

In analogy to Example 89, the title compound was prepared from 4-{[3-chloro-4-(pyridin-2-ylmethoxy)phenyl]amino}-5,6,7,8-tetrahydrothieno[2,3-b:5,4-c']dipyridine-3-carbonitrile from Example 57A (100 mg, 0.22 mmol) and (2E)-4-(dimethylamino)but-2-enoic acid hydrochloride from Example 1A (52 mg, 0.31 mmol) to yield 71 mg (53%).

$^1$H-NMR (400 MHz, DMSO-d$_6$): δ=1.11 (s, 6H), 3.00-3.08 (m, 4H), 3.75-3.87 (m, 2H), 4.84-4.98 (m, 2H), 5.24 (s, 2H), 6.63-6.73 (m, 2H), 7.00-7.07 (m, 1H), 7.17-7.21 (m, 1H), 7.24-7.28 (m, 1H), 7.36 (dd, 1H), 7.56 (d, 1H), 7.87 (dt, 1H), 8.48-8.60 (m, 3H).

LC/MS (method 2): $R_t$=0.87 min; MS (ESIpos): m/z=559 [M+H]$^+$.

Example 97 tert-Butyl N-[(2E)-4-{4-[(3-chloro-4-fluorophenyl)amino]-5,8-dihydropyrido[4',3':4,5]thieno[2,3-d]pyrimidin-7(6H)-yl}-4-oxobut-2-en-1-yl]-N-methylglycinate

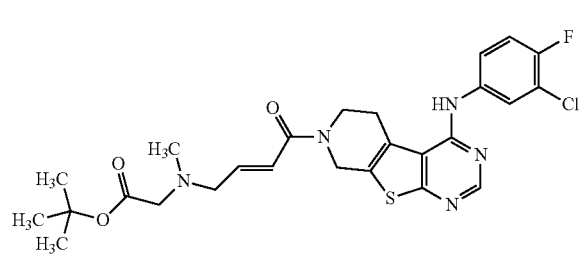 [SMILES: CN(C/C=C/C(=O)N1CCc2c(sc3ncnc(Nc4ccc(F)c(Cl)c4)c23)C1)CC(=O)OC(C)(C)C]

In analogy to Example 2, the title compound was synthesized from Example 58A (150 mg, 0.34 mmol) and 2-tert-butoxy-N-methyl-2-oxoethanaminium chloride (75 mg, 0.41 mmol) to yield 64 mg (34%).

$^1$H-NMR (400 MHz, DMSO-d$_6$): δ=1.42 (s, 9H), 2.29 (s, 3H), 3.15-3.19 (m, 2H), 4H under H$_2$O signal, 3.85-3.96 (m, 2H), 4.85-4.98 (m, 2H), 6.62-6.80 (m, 2H), 7.42 (t, 1H), 7.60-7.67 (m, 1H), 7.87-7.94 (m, 1H), 8.31-8.38 (m, 1H), 8.46 (s, 1H).

LC/MS (method 4): $R_t$=1.81 min; MS (ESIpos): m/z=546 [M+H]$^+$.

Example 98

N-[(2E)-4-{4-[(3-Chloro-4-fluorophenyl)amino]-5,8-dihydropyrido[4',3':4,5]thieno[2,3-d]-pyrimidin-7(6H)-yl}-4-oxobut-2-en-1-yl]-N-methylglycine

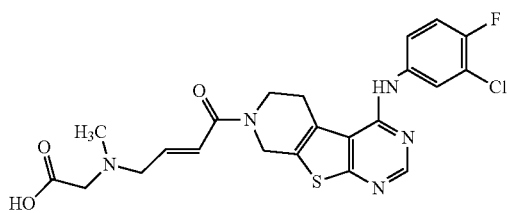 [SMILES: CN(C/C=C/C(=O)N1CCc2c(sc3ncnc(Nc4ccc(F)c(Cl)c4)c23)C1)CC(=O)O]

The compound of Example 97 (60 mg, 0.11 mmol) was dissolved in DCM (1.0 mL) and cooled to 0° C. TFA (0.30 mL) was added, and the mixture was warmed to rt and stirred overnight. Subsequently, the solvent was removed in vacuo, and the residue was purified by preparative HPLC to yield 43 mg (78%) of the title compound as white crystals.

$^1$H-NMR (400 MHz, DMSO-d$_6$): δ=2.32-2.39 (m, 3H), 3.00-3.50 (m, 7H), 3.85-3.96 (m, 2H), 4.84-4.99 (m, 2H), 6.64-6.85 (m, 2H), 7.42 (t, 1H), 7.60-7.67 (m, 1H), 7.88-7.94 (m, 1H), 8.32-8.40 (m, 1H), 8.46 (s, 1H).

LC/MS (method 4): $R_t$=1.80 min; MS (ESIpos): m/z=490 [M+H]$^+$.

Example 99

N-(3-Chloro-4-fluorophenyl)-7-[(2E)-4-(2-oxa-5-azabicyclo[2.2.1]hept-5-yl)but-2-enoyl]-5,6,7,8-tetrahydropyrido[4',3':4,5]thieno[2,3-d]pyrimidin-4-amine

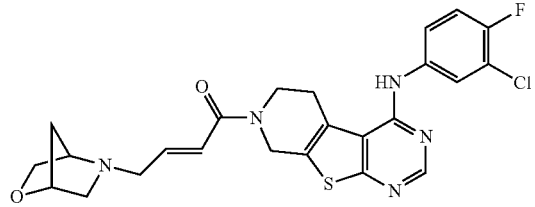 [SMILES: O=C(/C=C/CN1CC2CC1CO2)N1CCc2c(sc3ncnc(Nc4ccc(F)c(Cl)c4)c23)C1]

In analogy to Example 1, the title compound was synthesized from Example 58A (150 mg, 0.34 mmol) and 2-oxa-5-azabicyclo[2.2.1]heptane (41 mg, 0.41 mmol) in the presence of DIPEA (133 mg, 1.03 mmol) to yield 50 mg (29%).

$^1$H-NMR (400 MHz, DMSO-d$_6$): δ=1.52-1.65 (m, 1H), 1.70-1.81 (m, 1H), 1H under DMSO signal, 2.71-2.81 (m, 2H), 3.40-3.56 (m, 4H), 3.80-3.97 (m, 4H), 4.35 (br. s, 1H), 4.80-5.00 (m, 2H), 6.64-6.78 (m, 2H), 7.35-7.47 (m, 1H), 7.58-7.69 (m, 1H), 7.87-7.95 (m, 1H), 8.30-8.50 (m, 2H).

LC/MS (method 4): $R_t$=1.52 min; MS (ESIpos): m/z=500 [M+H]$^+$.

The following examples in Table 2 were prepared in analogy to Example 1 from Example 58A and the respective amine:

TABLE 2

| Example | Structure | LC/MS R$_t$ [min] (method) | LC/MS m/z [M + H]$^+$ |
| --- | --- | --- | --- |
| 100 | 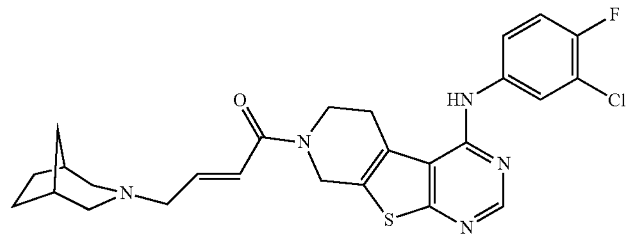 [SMILES: O=C(/C=C/CN1CC2CCC(C2)C1)N1CCc2c(sc3ncnc(Nc4ccc(F)c(Cl)c4)c23)C1] | 1.74 (3) | 512 |
| 101 | 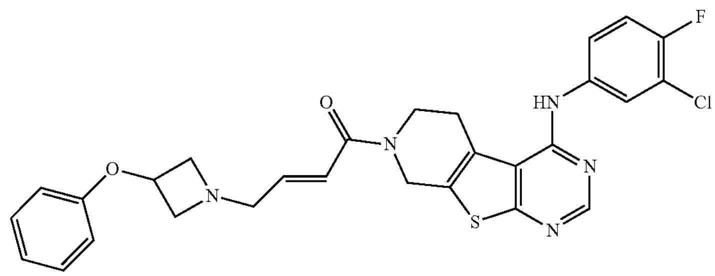 [SMILES: O=C(/C=C/CN1CC(Oc2ccccc2)C1)N1CCc2c(sc3ncnc(Nc4ccc(F)c(Cl)c4)c23)C1] | 1.09 (2) | 550 |
| 102 | 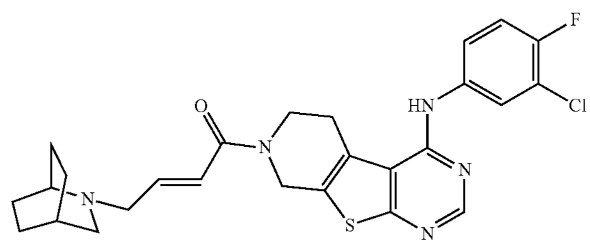 [SMILES: O=C(/C=C/CN1CC2CCC1CC2)N1CCc2c(sc3ncnc(Nc4ccc(F)c(Cl)c4)c23)C1] | 1.57 (4) | 512 |
| 103 | 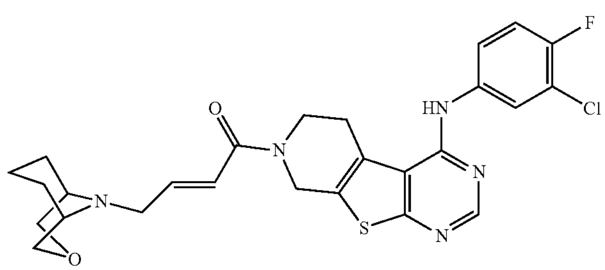 [SMILES: O=C(/C=C/CN1C2CCCC1COC2)N1CCc2c(sc3ncnc(Nc4ccc(F)c(Cl)c4)c23)C1] | 0.95 (2) | 528 |
| 104 | 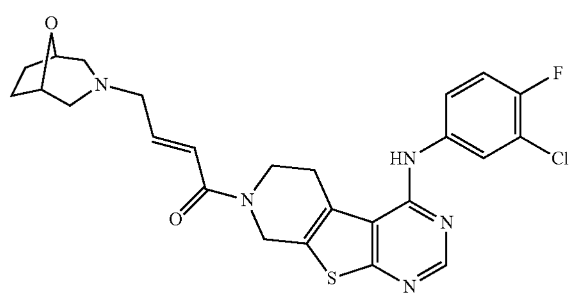 [SMILES: O=C(/C=C/CN1CC2CCC(C1)O2)N1CCc2c(sc3ncnc(Nc4ccc(F)c(Cl)c4)c23)C1] | 0.93 (2) | 514 |

TABLE 2-continued

| Example | Structure | LC/MS R_t [min] (method) | LC/MS m/z [M + H]+ |
|---|---|---|---|
| 105 | 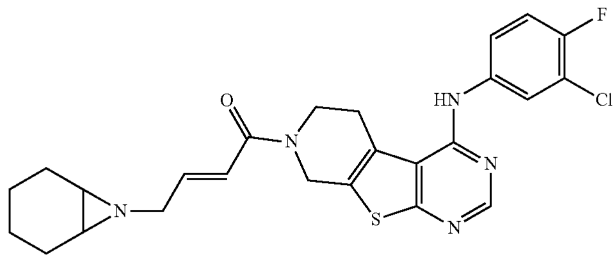 [SMILES: O=C(/C=C/CN1C2CCCCC21)N1CCc2c(sc3ncnc(Nc4ccc(F)c(Cl)c4)c23)C1] | 1.23 (6) | 498 |
| 106 | 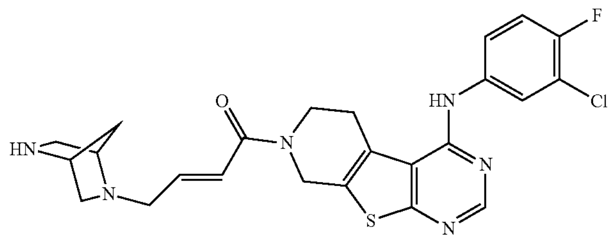 [SMILES: O=C(/C=C/CN1CC2CC1CN2)N1CCc2c(sc3ncnc(Nc4ccc(F)c(Cl)c4)c23)C1] | 1.31 (4) | 499 |

The following examples in Table 3 were prepared in analogy to Example 2 from Example 58A and the respective amine:

TABLE 3

| Example | Structure | LC/MS R_t [min] (method) | LC/MS m/z [M + H]+ |
|---|---|---|---|
| 107 | 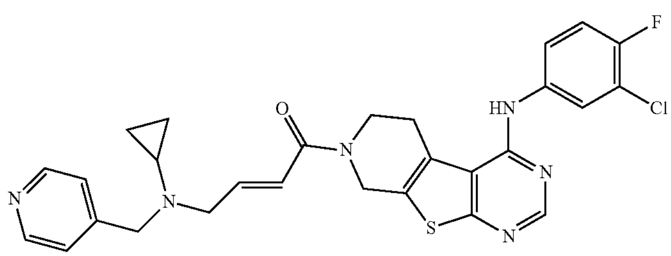 [SMILES: O=C(/C=C/CN(Cc1ccncc1)C1CC1)N1CCc2c(sc3ncnc(Nc4ccc(F)c(Cl)c4)c23)C1] | 1.43 (6) | 549 |
| 108 | 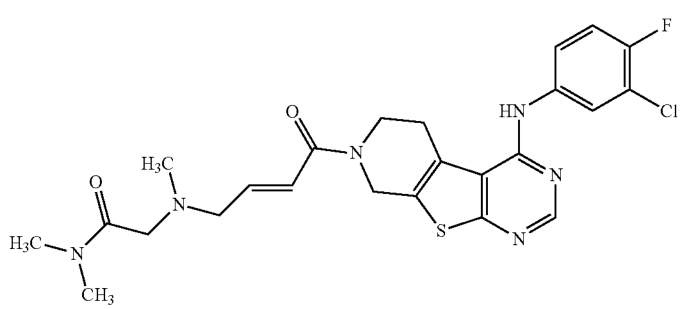 [SMILES: CN(C/C=C/C(=O)N1CCc2c(sc3ncnc(Nc4ccc(F)c(Cl)c4)c23)C1)CC(=O)N(C)C] | 0.91 (2) | 517 |

Example 109

N-(3-Chloro-4-fluorophenyl)-7-[(2E)-3-(1-methylpi-peridin-2-yl)prop-2-enoyl]-5,6,7,8-tetrahydropyrido[4',3':4,5]thieno[2,3-d]pyrimidin-4-amine

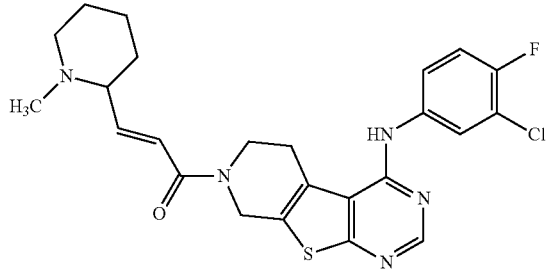 [SMILES: CN1CCCCC1/C=C/C(=O)N1CCc2c(sc3ncnc(Nc4ccc(F)c(Cl)c4)c23)C1]

DMSO (122 mg, 1.56 mmol) in DCM (0.5 mL) was cooled to −78° C., and trifluoroacetic acid anhydride (246 mg, 1.17 mmol) in DCM (0.5 mL) was added slowly. The mixture was stirred at −78° C. for 45 min. Subsequently, a solution of (1-methylpiperidin-2-yl)methanol (101 mg, 0.78 mmol) in DCM (1.0 mL) was added dropwise, and the mixture was kept at −78° C. for 1 h. Triethylamine (99 mg, 0.98 mmol) was added, and the mixture was slowly warmed to rt. The mixture was then diluted with tert-butyl methyl ether/DCM (1:1) and extracted with 1 N hydrochloric acid. The aqueous phase was washed twice with tert-butyl methyl ether, then basified with sodium carbonate solution and extracted with tert-butyl methyl ether. The organic phase was dried over sodium sulfate, and the solvent was carefully removed in vacuo. The residue was dissolved in THF (1.0 mL) to give solution A.

In a separate flask, diethyl (2-{4-[(3-chloro-4-fluorophenyl)amino]-5,8-dihydropyrido[4',3':4,5]thieno[2,3-d]pyrimidin-7(6H)-yl}-2-oxoethyl)phosphonate from Example 13A (400 mg, 0.78 mmol) was dissolved in THF (1.0 mL). The solution was cooled to −78° C., and sodium hydride (60% in mineral oil, 31 mg, 0.78 mmol) was added. The mixture was stirred for 15 min, then solution A was added slowly. The mixture was slowly warmed to rt and stirred overnight. Methanol was added, and the solvents were removed in vacuo. The residue was purified by preparative HPLC to yield 90 mg (24%) of the title compound.

$^1$H-NMR (400 MHz, DMSO-$d_6$): δ=1.17-1.40 (m, 2H), 1.40-1.62 (m, 3H), 1.63-1.72 (m, 1H), 2.06 and 2.09 (s, Σ3H), 2.50-2.62 (m, 1H), 2.76-2.84 (m, 1H), 3.20-3.31 (m, 2H), 3.77-3.97 (m, 2H), 4.81-4.99 (m, 2H), 6.60 (dd, 1H), 6.74 (t, 1H), 7.49 (t, 1H), 7.58-7.66 (m, 1H), 7.86-7.94 (m, 1H), 8.34 (s, 1H), 8.44 (s, 1H).

LC/MS (method 2): $R_t$=0.97 min; MS (ESIpos): m/z=486 [M+H]$^+$.

Example 110

7-[(2E)-4-(1,4-Oxazepan-4-yl)but-2-enoyl]-N-[1-(pyridin-2-ylmethyl)-1H-indazol-5-yl]-5,6,7,8-tetrahydropyrido[4',3':4,5]thieno[2,3-d]pyrimidin-4-amine

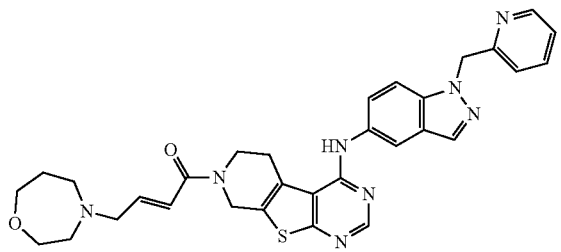 [SMILES: O=C(/C=C/CN1CCCOCC1)N1CCc2c(sc3ncnc(Nc4ccc5c(cnn5Cc5ccccn5)c4)c23)C1]

The title compound was synthesized in analogy to Example 130 from N-[1-(pyridin-2-ylmethyl)-1H-indazol-5-yl]-5,6,7,8-tetrahydropyrido[4',3':4,5]thieno[2,3-d]pyrimidin-4-amine from Example 62A (100 mg, 0.24 mmol), (2E)-4-bromobut-2-enoic acid (75 mg, 0.36 mmol) and 1,4-oxazepane hydrochloride (53 mg, 0.39 mmol) to yield 62 mg (42%).

$^1$H-NMR (400 MHz, DMSO-$d_6$): δ=1.77-1.85 (m, 2H), 2.59-2.67 (m, 4H), 3.02-3.14 (m, 2H), 3.22-3.30 (m, 2H), 3.59-3.63 (m, 2H), 3.68 (t, 2H), 3.85-3.97 (m, 2H), 4.86 (s, 1H), 4.96 (s, 1H), 5.76 (s, 2H), 6.67-6.81 (m, 2H), 6.95 (d, 1H), 7.29 (dd, 1H), 7.49-7.55 (m, 1H), 7.62-7.67 (m, 1H), 7.73 (dt, 1H), 8.00-8.04 (m, 1H), 8.12 (s, 1H), 8.29-8.35 (m, 2H), 8.52 (d, 1H).

LC/MS (method 2): $R_t$=0.75 min; MS (ESIpos): m/z=581 [M+H]$^+$.

Example 111

4-[(2E)-4-{4-[(3,4-Dichlorophenyl)amino]-5,8-dihydropyrido[4',3':4,5]thieno[2,3-d]pyrimidin-7(6H)-yl}-4-oxobut-2-en-1-yl]-N,N-dimethylpiperazine-1-carboxamide

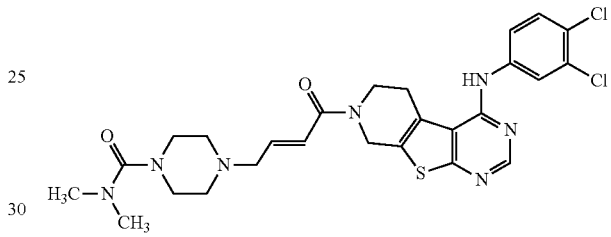

(2E)-4-Bromobut-2-enoic acid (106 mg, 0.64 mmol) and piperazine-1-carboxylic acid dimethylamide (107 mg, 0.68 mmol) were dissolved in DCM (5.0 mL), and DIPEA (111 mg, 0.85 mmol) was added. The mixture was stirred at rt for 2 h. Subsequently, the compound from Example 15A (150 mg, 0.43 mmol), DIPEA (55 mg, 0.43 mmol) and EDCI (82 mg, 0.43 mmol) were added. The reaction mixture was stirred at rt overnight. Then, water was added, and the mixture was extracted three times with DCM. The combined organic layers were dried over sodium sulfate. The solvent was removed in vacuo, and the residue was purified by preparative HPLC to yield 59 mg (24%) of the title compound.

$^1$H-NMR (400 MHz, DMSO-$d_6$): δ=2.34-2.42 (m, 4H), 2.72 (s, 6H), 3.08-3.19 (m, 6H), 3.21-3.31 (m, 2H), 3.84-3.96 (m, 2H), 4.87 (br. s, 1H), 4.97 (br. s, 1H), 6.65-6.82 (m, 2H), 7.60 (d, 1H), 7.66-7.73 (m, 1H), 7.98-8.05 (m, 1H), 8.40-8.47 (m, 1H), 8.51 (s, 1H).

LC/MS (method 2): $R_t$=1.02 min; MS (ESIpos): m/z=574 [M+H]$^+$.

Example 112

N-(3,4-Dichlorophenyl)-7-{(2E)-4-[4-(pyrrolidin-1-ylcarbonyl)piperazin-1-yl]but-2-enoyl}-5,6,7,8-tetrahydropyrido[4',3':4,5]thieno[2,3-d]pyrimidin-4-amine

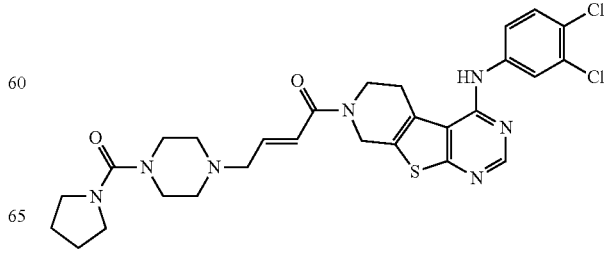

(2E)-4-Bromobut-2-enoic acid (106 mg, 0.64 mmol) and piperazin-1-yl(pyrrolidin-1-yl)methanone (125 mg, 0.68 mmol) were dissolved in DCM (5.0 mL), and DIPEA (111 mg, 0.85 mmol) was added. The mixture was stirred at rt for 2 h. Subsequently, the compound from Example 15A (150 mg, 0.43 mmol), DIPEA (55 mg, 0.43 mmol) and EDCI (82 mg, 0.43 mmol) were added. The reaction was stirred at 50° C. overnight. Then, water was added, and the mixture was extracted three times with DCM. The combined organic layers were dried over sodium sulfate. The solvent was removed in vacuo, and the residue was purified by preparative HPLC to yield 25 mg (10%) of the title compound.

$^1$H-NMR (400 MHz, DMSO-$d_6$): δ=1.70-1.76 (m, 4H), 2.34-2.42 (m, 4H), 3.13-3.19 (m, 6H), 3.22-3.27 (m, 6H), 3.84-3.96 (m, 2H), 4.85-4.99 (m, 2H), 6.65-6.82 (m, 2H), 7.60 (d, 1H), 7.66-7.73 (m, 1H), 7.98-8.05 (m, 1H), 8.40-8.47 (m, 1H), 8.51 (s, 1H).

LC/MS (method 6): $R_t$=1.36 min; MS (ESIpos): m/z=600 [M+H]$^+$.

The following examples in Table 4 were prepared in analogy to Example 17 from Example 59A and the respective amine:

TABLE 4

| Example | Structure | LC/MS $R_t$ [min] (method) | LC/MS m/z [M + H]$^+$ |
|---|---|---|---|
| 113 | (structure) | 1.61 (4) | 506 |
| 114 | (structure) | 1.69 (4) | 548 |
| 115 | (structure) | 1.67 (4) | 550 |
| 116 | (structure) | 1.43 (6) | 602 |

TABLE 4-continued
| Example | Structure | LC/MS R$_t$ [min] (method) | LC/MS m/z [M + H]$^+$ |
|---|---|---|---|
| 117 | 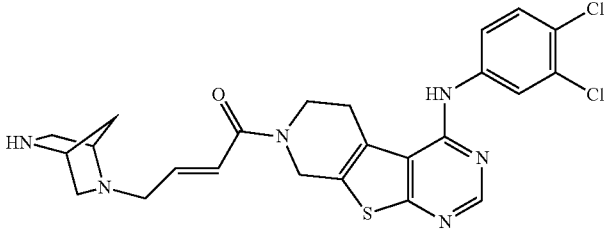 [SMILES: O=C(/C=C/CN1CC2CC1CN2)N1CCc2c(sc3ncnc(Nc4ccc(Cl)c(Cl)c4)c23)C1] | 0.92 (2) | 515 |
| 118 | 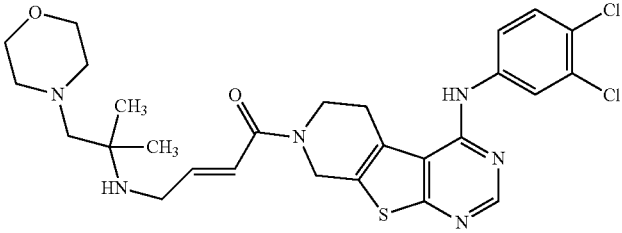 [SMILES: CC(C)(CN1CCOCC1)NC/C=C/C(=O)N1CCc2c(sc3ncnc(Nc4ccc(Cl)c(Cl)c4)c23)C1] | 1.08 (2) | 575 |
| 119 | 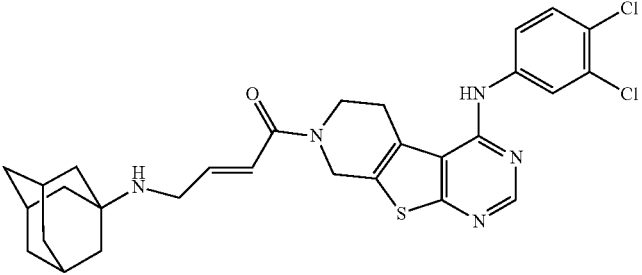 [SMILES: O=C(/C=C/CNC12CC3CC(CC(C3)C1)C2)N1CCc2c(sc3ncnc(Nc4ccc(Cl)c(Cl)c4)c23)C1] | 1.17 (2) | 568 |
| 120 | 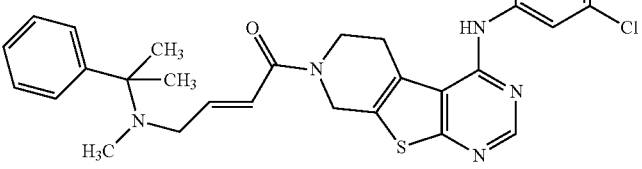 | 1.81 (4) | 566 |
| 121 | 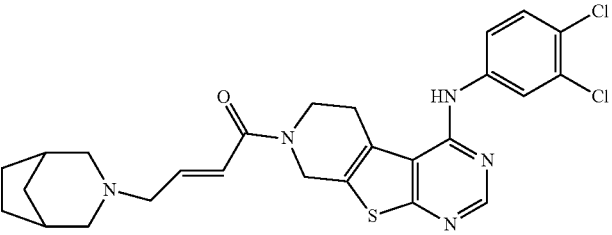 [SMILES: O=C(/C=C/CN1CC2CCC(C2)C1)N1CCc2c(sc3ncnc(Nc4ccc(Cl)c(Cl)c4)c23)C1] | 1.10 (2) | 528 |

Example 122

3-Chloro-5-({7-[(2E)-4-(dimethylamino)but-2-enoyl]-5,6,7,8-tetrahydropyrido[4',3':4,5]thieno[2,3-d]pyrimidin-4-yl}amino)phenol

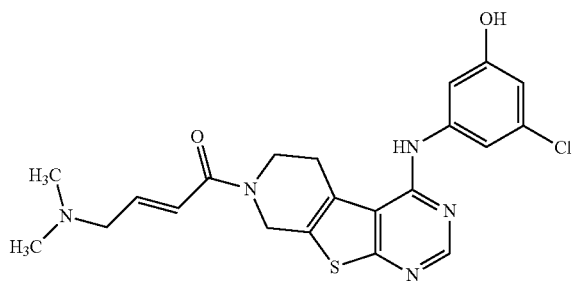 [SMILES: CN(C)C/C=C/C(=O)N1CCc2c(sc3ncnc(Nc4cc(O)cc(Cl)c4)c23)C1]

A solution of 3-chloro-5-(5,6,7,8-tetrahydropyrido[4',3':4,5]thieno[2,3-d]pyrimidin-4-ylamino)phenol hydrochloride from Example 65A (150 mg, 0.41 mmol) and (2E)-4-(dimethylamino)but-2-enoic acid hydrochloride from Example 1A (94 mg, 0.57 mmol) in a mixture of DMF (2 mL) and THF (4 mL) was treated with DIPEA (263 mg, 2.03 mmol) and TBTU (197 mg, 0.61 mmol). The mixture was stirred at rt overnight and then directly purified by preparative HPLC. The product was triturated with tert-butyl methyl ether and collected by suction filtration to yield 52 mg (29%) as tan crystals.

$^1$H-NMR (400 MHz, DMSO-$d_6$): δ=2.14-2.19 (m, 6H), 3.04-3.10 (m, 2H), 3.20-3.30 (m, 2H), 3.82-3.95 (m, 2H), 4.84-4.99 (m, 2H), 6.51-6.53 (m, 1H), 6.65-6.79 (m, 2H), 7.16-7.25 (m, 2H), 8.22-8.27 (m, 1H), 8.50 (s, 1H), 9.91 (s, 1H).

LC/MS (method 6): $R_t$=0.99 min; MS (ESIpos): m/z=444 [M+H]$^+$.

Example 123

3-Chloro-5-[(7-{(2E)-4-[methyl(1-methylethyl)amino]but-2-enoyl}-5,6,7,8-tetrahydropyrido[4',3':4,5]thieno[2,3-d]pyrimidin-4-yl)amino]phenol

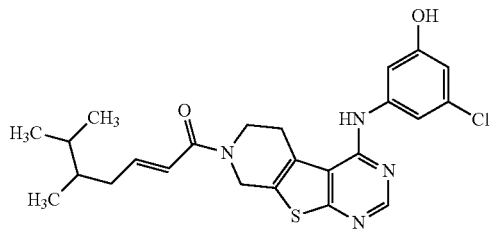 [SMILES: CC(C)C(C)C/C=C/C(=O)N1CCc2c(sc3ncnc(Nc4cc(O)cc(Cl)c4)c23)C1]

The title compound was prepared in analogy to Example 122 from 3-chloro-5-(5,6,7,8-tetrahydropyrido[4',3':4,5]thieno[2,3-d]pyrimidin-4-ylamino)phenol hydrochloride from Example 65A (100 mg, 0.27 mmol) and (2E)-4-[methyl(1-methylethyl)amino]but-2-enoic acid hydrochloride from Example 2A (73 mg, 0.38 mmol) to yield 24 mg (19%) as tan crystals.

$^1$H-NMR (400 MHz, DMSO-$d_6$): δ=0.97 (d, 6H), 2.12 (s, 3H), 2.72-2.85 (m, 1H), 3.12-3.30 (m, 4H), 3.83-3.95 (m, 2H), 4.83-4.99 (m, 2H), 6.51-6.53 (m, 1H), 6.64-6.81 (m, 2H), 7.16-7.26 (m, 2H), 8.22-8.28 (m, 1H), 8.50 (s, 1H), 9.91 (br. s, 1H).

LC/MS (method 6): $R_t$=1.07 min; MS (ESIpos): m/z=472 [M+H]$^+$.

Example 124

3-Chloro-5-[(7-{(2E)-4-[cyclopropyl(methyl)amino]but-2-enoyl}-5,6,7,8-tetrahydropyrido[4',3':4,5]thieno[2,3-d]pyrimidin-4-yl)amino]phenol

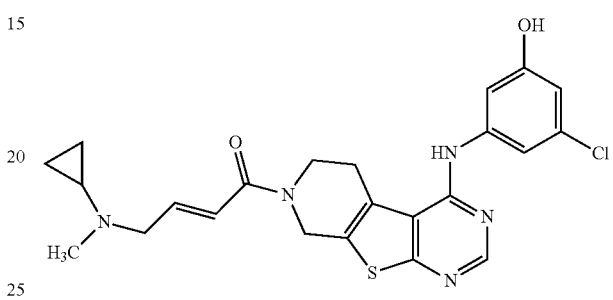

In analogy to Example 130, the title compound was prepared from (2K)-4-bromobut-2-enoic acid (125 mg, 0.61 mmol), 3-chloro-5-(5,6,7,8-tetrahydropyrido[4',3':4,5]thieno[2,3-d]pyrimidin-4-ylamino)phenol hydrochloride from Example 65A (150 mg, 0.41 mmol) and N-methylcyclopropanamine (116 mg, 1.63 mmol) to yield 10 mg (5%).

$^1$H-NMR (400 MHz, DMSO-$d_6$): δ=0.29-0.35 (m, 2H), 0.41-0.47 (m, 2H), 1.68-1.76 (m, 1H), 2.26 (s, 3H), 3.20-3.32 (m, 4H), 3.83-3.96 (m, 2H), 4.83-4.99 (m, 2H), 6.51-6.53 (m, 1H), 6.68-6.76 (m, 2H), 7.16-7.25 (m, 2H), 8.25 (br. s, 1H), 8.50 (s, 1H), 9.92 (br. s, 1H).

LC/MS (method 6): $R_t$=1.06 min; MS (ESIpos): m/z=470 [M+H]$^+$.

Example 125

3-Chloro-5-[(7-{(2E)-4-[(2-methoxyethyl)(methyl)amino]but-2-enoyl}-5,6,7,8-tetrahydropyrido[4',3':4,5]thieno[2,3-d]pyrimidin-4-yl)amino]phenol

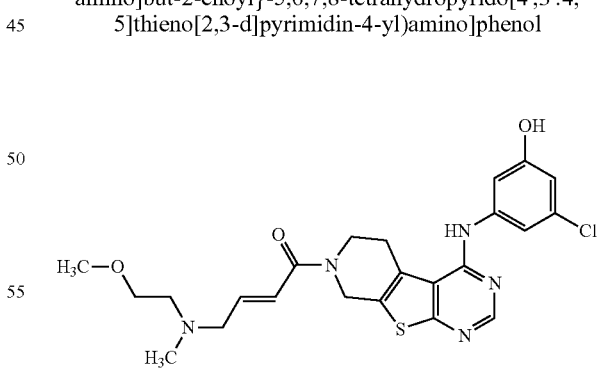

In analogy to Example 130, the title compound was prepared from (2E)-4-bromobut-2-enoic acid (84 mg, 0.41 mmol), 3-chloro-5-(5,6,7,8-tetrahydropyrido[4',3':4,5]thieno[2,3-d]pyrimidin-4-ylamino)phenol hydrochloride from Example 65A (100 mg, 0.27 mmol) and 2-methoxy-N-methylethanamine (39 mg, 0.43 mmol) to yield 24 mg (18%).

$^1$H-NMR (400 MHz, DMSO-$d_6$): δ=2.18-2.23 (m, 3H), 3.15-3.35 (m, 6H), 3.25 (s, 3H), 3.40-3.46 (m, 2H), 3.83-3.96

(m, 2H), 4.84-4.98 (m, 2H), 6.51-6.53 (m, 1H), 6.65-6.82 (m, 2H), 7.16-7.26 (m, 2H), 8.22-8.27 (m, 1H), 8.50 (s, 1H), 9.92 (s, 1H).

LC/MS (method 4): $R_t$=1.38 min; MS (ESIpos): m/z=488 [M+H]$^+$.

Example 126

3-[(7-{(2E)-4-[Bis(2-methoxyethyl)amino]but-2-enoyl}-5,6,7,8-tetrahydropyrido[4',3':4,5]thieno[2,3-d]pyrimidin-4-yl)amino]-5-chlorophenol

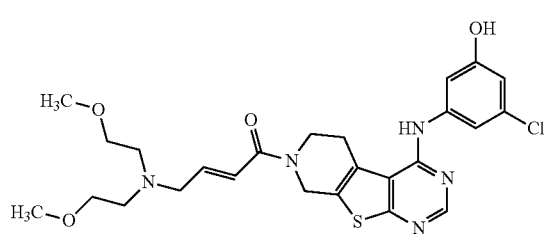 [SMILES: COCCN(C/C=C/C(=O)N1CCc2c(sc3ncnc(Nc4cc(O)cc(Cl)c4)c23)C1)CCOC]

In analogy to Example 130, the title compound was prepared from (2E)-4-bromobut-2-enoic acid (84 mg, 0.41 mmol), 3-chloro-5-(5,6,7,8-tetrahydropyrido[4',3':4,5]thieno[2,3-d]pyrimidin-4-ylamino)phenol hydrochloride from Example 65A (100 mg, 0.27 mmol) and bis(2-methoxyethyl)amine (58 mg, 0.43 mmol) to yield 42 mg (29%).

$^1$H-NMR (400 MHz, DMSO-d$_6$): δ=2.60-2.67 (m, 4H), 3.22-3.43 (m, 10H), 3.83-3.96 (m, 2H), 4.83-4.98 (m, 2H), 6.51-6.53 (m, 1H), 6.65-6.85 (m, 2H), 7.15-7.26 (m, 2H), 8.22-8.28 (m, 1H), 8.50 (s, 1H), 9.91 (s, 1H).

LC/MS (method 2): $R_t$=0.86 min; MS (ESIpos): m/z=532 [M+H]$^+$.

Example 127

3-Chloro-5-({7-[(2E)-4-(4-methoxypiperidin-1-yl)but-2-enoyl]-5,6,7,8-tetrahydropyrido[4',3':4,5]thieno[2,3-d]pyrimidin-4-yl}amino)phenol

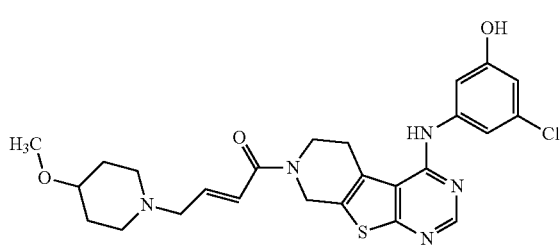 [SMILES: COC1CCN(C/C=C/C(=O)N2CCc3c(sc4ncnc(Nc5cc(O)cc(Cl)c5)c34)C2)CC1]

In analogy to Example 130, the title compound was prepared from (2E)-4-bromobut-2-enoic acid (84 mg, 0.41 mmol), 3-chloro-5-(5,6,7,8-tetrahydropyrido[4',3':4,5]thieno[2,3-d]pyrimidin-4-ylamino)phenol hydrochloride from Example 65A (100 mg, 0.27 mmol) and 4-methoxypiperidine (50 mg, 0.43 mmol) to yield 33 mg (23%).

$^1$H-NMR (400 MHz, DMSO-d$_6$): δ=1.37-1.49 (m, 2H), 1.77-1.87 (m, 2H), 2.04-2.15 (m, 2H), 2.60-2.70 (m, 2H), 3.08-3.30 (m, 5H), 3.22 (s, 3H), 3.83-3.99 (m, 2H), 4.83-4.98 (m, 2H), 6.51-6.53 (m, 1H), 6.67-6.79 (m, 2H), 7.16-7.25 (m, 2H), 8.22-8.27 (m, 1H), 8.50 (s, 1H), 9.93 (br. s, 1H).

LC/MS (method 4): $R_t$=1.39 min; MS (ESIpos): m/z=514 [M+H]$^+$.

Example 128

4-[(2E)-4-{4-[(3-Chloro-5-hydroxyphenyl)amino]-5,8-dihydropyrido[4',3':4,5]thieno[2,3-d]-pyrimidin-7(6H)-yl}-4-oxobut-2-en-1-yl]-N,N-dimethylpiperazine-1-carboxamide

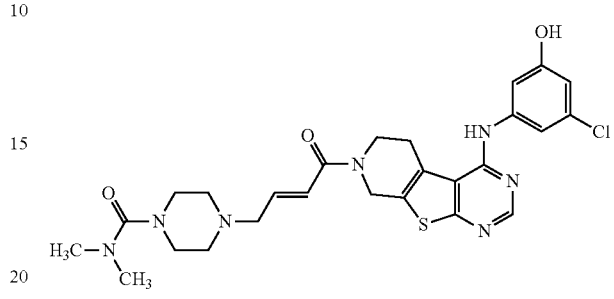

In analogy to Example 130, the title compound was prepared from (2E)-4-bromobut-2-enoic acid (84 mg, 0.41 mmol), 3-chloro-5-(5,6,7,8-tetrahydropyrido[4',3':4,5]thieno[2,3-d]pyrimidin-4-ylamino)phenol hydrochloride from Example 65A (100 mg, 0.27 mmol) and N,N-dimethylpiperazine-1-carboxamide (68 mg, 0.43 mmol) to yield 59 mg (38%).

$^1$H-NMR (400 MHz, DMSO-d$_6$): δ=2.34-2.42 (m, 4H), 2.72 (s, 6H), 3.05-3.30 (m, 8H), 3.83-3.97 (m, 2H), 4.84-4.98 (m, 2H), 6.51-6.53 (m, 1H), 6.65-6.82 (m, 2H), 7.16-7.26 (m, 2H), 8.13 and 8.24 (br. s, Σ1H), 8.46 and 8.50 (br. s, Σ1H), 9.93 (br. s, 1H).

LC/MS (method 2): $R_t$=0.83 min; MS (ESIpos): m/z=556 [M+H]$^+$.

Example 129

3-Chloro-5-({7-[(2E)-4-(1,4-oxazepan-4-yl)but-2-enoyl]-5,6,7,8-tetrahydropyrido[4',3':4,5]thieno[2,3-d]pyrimidin-4-yl}amino)phenol

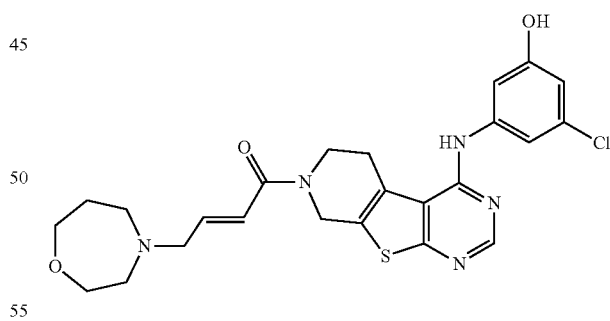

In analogy to Example 130, the title compound was prepared from (2E)-4-bromobut-2-enoic acid (84 mg, 0.41 mmol), 3-chloro-5-(5,6,7,8-tetrahydropyrido[4',3':4,5]thieno[2,3-d]pyrimidin-4-ylamino)phenol hydrochloride from Example 65A (100 mg, 0.27 mmol) and 1,4-oxazepane hydrochloride (60 mg, 0.43 mmol) to yield 30 mg (22%).

$^1$H-NMR (400 MHz, DMSO-d$_6$): δ=1.77-1.85 (m, 2H), 2.59-2.68 (m, 4H), 3.20-3.32 (m, 4H), 3.59-3.64 (m, 2H), 3.69 (t, 2H), 3.83-3.96 (m, 2H), 4.84-4.98 (m, 2H), 6.51-6.53 (m, 1H), 6.68-6.81 (m, 2H), 7.16-7.26 (m, 2H), 8.22-8.27 (m, 1H), 8.50 (s, 1H), 9.92 (br. s, 1H).

Example 130

3-Chloro-5-({7-[(2E)-4-(8-oxa-3-azabicyclo[3.2.1]oct-3-yl)but-2-enoyl]-5,6,7,8-tetrahydropyrido[4',3':4,5]thieno[2,3-d]pyrimidin-4-yl}amino)phenol

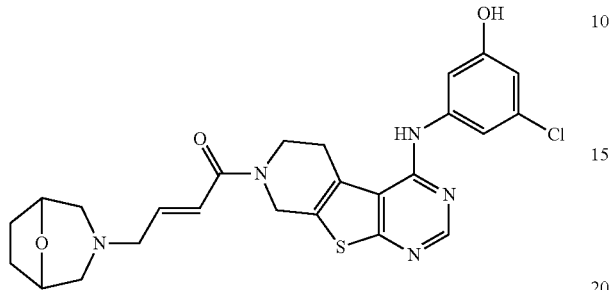

(2E)-4-Bromobut-2-enoic acid (168 mg, 0.81 mmol) and 8-oxa-3-azabicyclo[3.2.1]octane hydrochloride (130 mg, 0.87 mmol) were dissolved in DCM (2.0 mL). DIPEA (210 mg, 1.62 mmol) was added, and the mixture was stirred at rt for 2 h. Subsequently, 3-chloro-5-(5,6,7,8-tetrahydropyrido[4',3':4,5]thieno[2,3-d]pyrimidin-4-ylamino)phenol hydrochloride from Example 65A (200 mg, 0.54 mmol), EDCI (104 mg, 0.54 mmol) and DIPEA (140 mg, 1.08 mmol) were added, and the mixture was stirred at rt overnight. Then, the reaction mixture was diluted with water, and after separation the organic layer was washed with water. The solvent was removed in vacuo, and the crude product was purified by preparative HPLC to yield 106 mg (38%) of the title compound.

$^1$H-NMR (400 MHz, DMSO-$d_6$): δ=1.68-1.76 (m, 2H), 1.81-1.89 (m, 2H), 2.16-2.24 (m, 2H), 2.48-2.58 (2H under DMSO signal), 3.06-3.12 (m, 2H), 3.19-3.31 (m, 2H), 3.83-3.94 (m, 2H), 4.21 (br. s, 2H), 4.83-4.98 (m, 2H), 6.51-6.53 (m, 1H), 6.60-6.81 (m, 2H), 7.15-7.25 (m, 2H), 8.20-8.29 (m, 1H), 8.50 (s, 1H), 9.91 (br. s, 1H).

LC/MS (method 4): $R_t$=1.39 min; MS (ESIpos): m/z=512 [M+H]$^+$.

Example 131

3-({7-[(2E)-4-(3-Azabicyclo[3.2.1]oct-3-yl)but-2-enoyl]-5,6,7,8-tetrahydropyrido[4',3':4,5]thieno[2,3-d]pyrimidin-4-yl}amino)-5-chlorophenol

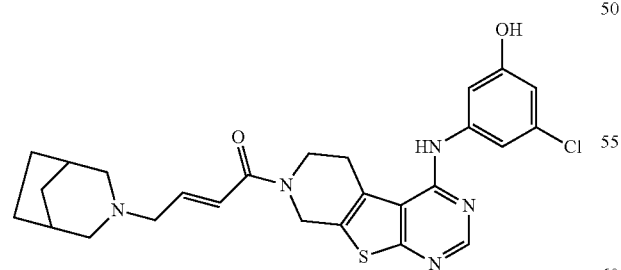

In analogy to Example 130, the title compound was prepared from (2E)-4-bromobut-2-enoic acid (84 mg, 0.41 mmol), 3-chloro-5-(5,6,7,8-tetrahydropyrido[4',3':4,5]thieno[2,3-d]pyrimidin-4-ylamino)phenol hydrochloride from Example 65A (100 mg, 0.27 mmol) and 3-azabicyclo[3.2.1]octane (48 mg, 0.43 mmol) to yield 44 mg (32%).

$^1$H-NMR (400 MHz, DMSO-$d_6$): δ=1.28-1.34 (m, 1H), 1.39-1.46 (m, 1H), 1.49-1.66 (m, 4H), 2.01-2.14 (m, 4H), 2.57-2.66 (m, 2H), 3.20-3.40 (411 under H$_2$O signal), 3.83-3.94 (m, 2H), 4.84-4.98 (m, 2H), 6.51-6.53 (m, 1H), 6.64-6.79 (m, 2H), 7.14-7.24 (m, 2H), 8.25 (br. s, 1H), 8.49 (s, 1H), 10.0 (br. s, 1H).

LC/MS (method 4): $R_t$=1.45 min; MS (ESIpos): m/z=510 [M+H]$^+$.

Example 132

3-({7-[(2E)-4-(7-Azabicyclo[2.2.1]hept-7-yl)but-2-enoyl]-5,6,7,8-tetrahydropyrido[4',3':4,5]thieno[2,3-d]pyrimidin-4-yl}amino)-5-chlorophenol trifluoroacetate

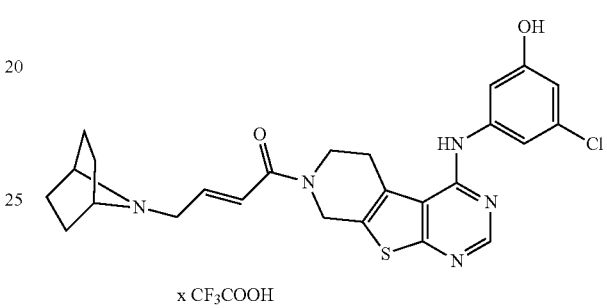

In analogy to Example 130, the title compound was prepared from (2E)-4-bromobut-2-enoic acid (126 mg, 0.61 mmol), 3-chloro-5-(5,6,7,8-tetrahydropyrido[4',3':4,5]thieno[2,3-d]pyrimidin-4-ylamino)phenol hydrochloride from Example 65A (150 mg, 0.41 mmol) and 7-azabicyclo[2.2.1]-heptane hydrochloride (87 mg, 0.65 mmol) to yield 24 mg (11%) as trifluoroacetate salt after purification by preparative HPLC.

$^1$H-NMR (400 MHz, DMSO-$d_6$): δ=1.67-1.76 (m, 4H), 1.89-1.95 (m, 2H), 2.03-2.11 (m, 2H), 3.22-3.33 (m, 2H), 3.60-3.96 (m, 4H), 4.08 (s, 2H), 4.88-4.99 (m, 2H), 6.52-6.54 (m, 1H), 6.67-6.78 (m, 1H), 7.00-7.06 (m, 1H), 7.10-7.25 (m, 2H), 8.22-8.30 (m, 1H), 8.50-8.52 (m, 1H), 9.56-9.67 (m, 1H), 9.93 (br. s, 1H).

LC/MS (method 2): $R_t$=0.85 min; MS (ESIpos): m/z=496 [M+H]$^+$.

Example 133

2,3-Dichloro-5-[(7-{(2E)-4-[methyl(1-methylethyl)amino]but-2-enoyl}-5,6,7,8-tetrahydropyrido[4',3':4,5]thieno[2,3-d]pyrimidin-4-yl)amino]phenol

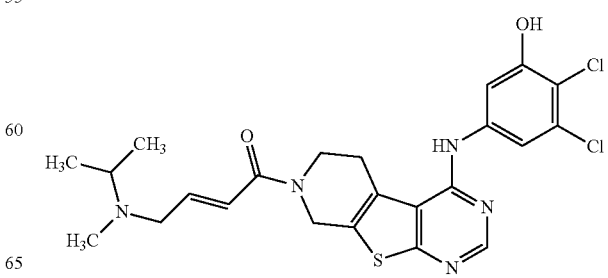

2,3-Dichloro-5-(5,6,7,8-tetrahydropyrido[4',3':4,5]thieno[2,3-d]pyrimidin-4-ylamino)phenol hydrochloride from Example 69A (51 mg, 0.13 mmol) and (2E)-4-[methyl(1-methylethyl)amino]but-2-enoic acid hydrochloride from Example 2A (34 mg, 0.18 mmol) were dissolved in DMF (1.5 mL), and DIPEA (82 mg, 0.63 mmol) and TBTU (61 mg, 0.19 mmol) were added. The mixture was stirred at rt overnight. The product was then directly isolated by preparative HPLC to yield 33 mg (52%) of the title compound.

¹H-NMR (400 MHz, DMSO-d₆): δ=0.97 (d, 6H), 2.12 (s, 3H), 2.74-2.84 (m, 1H), 3.13-3.33 (m, 4H), 3.83-3.94 (m, 2H), 4.84-4.99 (m, 2H), 6.65-6.80 (m, 2H), 7.33-7.43 (m, 1H), 7.44-7.47 (m, 1H), 8.29-8.36 (m, 1H), 8.51 (s, 1H), 10.68 (br. s, 1H).

LC/MS (method 4): R$_t$=1.48 min; MS (ESIpos): m/z=506 [M+H]⁺.

Example 134

5-[(7-{(2E)-4-[tert-Butyl(methyl)amino]but-2-enoyl}-5,6,7,8-tetrahydropyrido[4',3':4,5]thieno[2,3-d]pyrimidin-4-yl)amino]-2,3-dichlorophenol

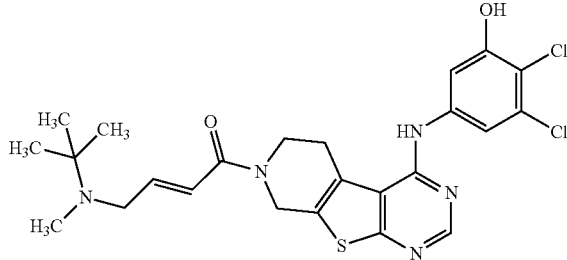 [SMILES: CN(C/C=C/C(=O)N1CCc2c(sc3ncnc(Nc4cc(O)c(Cl)c(Cl)c4)c23)C1)C(C)(C)C]

The compound was synthesized in analogy to Example 147 from 2,3-dichloro-5-(5,6,7,8-tetrahydropyrido[4',3':4,5]thieno[2,3-d]pyrimidin-4-ylamino)phenol hydrochloride from Example 69A (85 mg, 0.21 mmol), (2E)-4-bromobut-2-enoic acid (52 mg, 0.32 mmol) and tert-butyl methylamine (29 mg, 0.34 mmol) to yield 18 mg (16%).

¹H-NMR (400 MHz, DMSO-d₆): δ=1.04 (s, 9H), 2.07-2.14 (m, 3H), 3.13-3.33 (m, 4H), 3.83-3.95 (m, 2H), 4.84-4.99 (m, 2H), 6.64-6.75 (m, 2H), 7.32-7.42 (m, 1H), 7.45 (d, 1H), 8.28-8.36 (m, 1H), 8.50 (s, 1H), 10.69 (br. s, 1H).

LC/MS (method 2): R$_t$=0.95 min; MS (ESIpos): m/z=520 [M+H]⁺.

Example 135

5-({7-[(2E)-4-(3-Azabicyclo[3.2.1]oct-3-yl)but-2-enoyl]-5,6,7,8-tetrahydropyrido[4',3':4,5]thieno[2,3-d]pyrimidin-4-yl}amino)-2,3-dichlorophenol

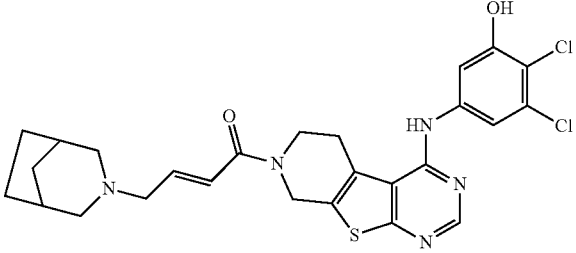 [SMILES: O=C(/C=C/CN1CC2CCC(C2)C1)N1CCc2c(sc3ncnc(Nc4cc(O)c(Cl)c(Cl)c4)c23)C1]

The compound was synthesized in analogy to Example 147 from 2,3-dichloro-5-(5,6,7,8-tetrahydropyrido[4',3':4,5]thieno[2,3-d]pyrimidin-4-ylamino)phenol hydrochloride from Example 69A (100 mg, 0.25 mmol), (2E)-4-bromobut-2-enoic acid (61 mg, 0.37 mmol) and 3-azabicyclo[3.2.1]octane (44 mg, 0.40 mmol) to yield 25 mg (19%).

¹H-NMR (400 MHz, DMSO-d₆): δ=1.27-1.33 (m, 1H), 1.39-1.46 (m, 1H), 1.49-1.65 (m, 4H), 2.01-2.13 (m, 4H), 2.56-2.65 (m, 2H), 3.08-3.13 (m, 2H), 3.20-3.30 (m, 2H), 3.83-3.94 (m, 2H), 4.84-4.97 (m, 2H), 6.66-6.78 (m, 2H), 7.31-7.41 (m, 1H), 7.44 (d, 1H), 8.27-8.34 (m, 1H), 8.50 (s, 1H), 10.80 (br. s, 1H).

LC/MS (method 2): R$_t$=0.97 min; MS (ESIpos): m/z=544 [M+H]⁺.

Example 136

4-Chloro-3-({7-[(2E)-4-(dimethylamino)but-2-enoyl]-5,6,7,8-tetrahydropyrido[4',3':4,5]thieno[2,3-d]pyrimidin-4-yl}amino)phenol

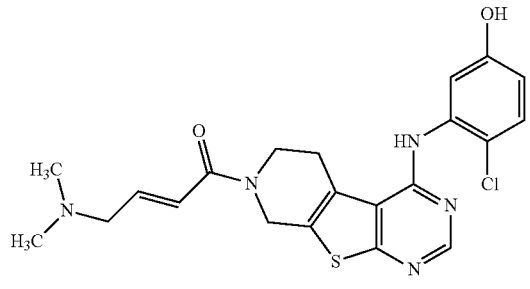 [SMILES: CN(C)C/C=C/C(=O)N1CCc2c(sc3ncnc(Nc4cc(O)ccc4Cl)c23)C1]

The compound was synthesized in analogy to Example 122 from 4-chloro-3-(5,6,7,8-tetrahydropyrido[4',3':4,5]thieno[2,3-d]pyrimidin-4-ylamino)phenol hydrochloride from Example 70A (100 mg, 0.27 mmol) and (2E)-4-(dimethylamino)but-2-enoic acid hydrochloride from Example 1A (63 mg, 0.38 mmol) to yield 17 mg (13%).

LC/MS (method 2): R$_t$=0.72 min; MS (ESIpos): m/z=444 [M+H]⁺.

Example 137

5-({7-[(2E)-4-(Dimethylamino)but-2-enoyl]-5,6,7,8-tetrahydropyrido[4',3':4,5]thieno[2,3-d]-pyrimidin-4-yl}amino)-2,4-difluorophenol

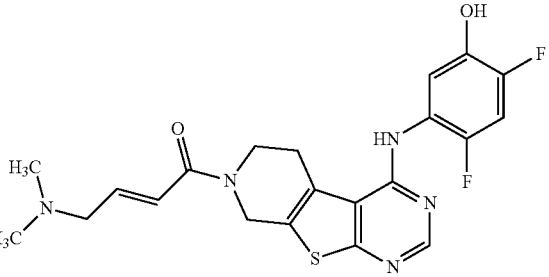

The compound was synthesized in analogy to Example 122 from 2,4-difluoro-5-(5,6,7,8-tetrahydropyrido[4',3':4,5]thieno[2,3-d]pyrimidin-4-ylamino)phenol hydrochloride from Example 71A (100 mg, 0.27 mmol) and (2E)-4-(dimethylamino)but-2-enoic acid hydrochloride from Example 1A (63 mg, 0.38 mmol) to yield 40 mg (32%).

¹H-NMR (400 MHz, DMSO-d₆): δ=2.21 (s, 6H), 3.08-3.27 (m, 4H), 3.85-3.98 (m, 2H), 4.82-4.98 (m, 2H), 6.64-6.81 (m, 2H), 7.24-7.35 (m, 2H), 8.10-8.15 (m, 1H), 8.36 (s, 1H), 9.90 (s, 1H).

LC/MS (method 2): $R_t$=0.68 min; MS (ESIpos): m/z=446 [M+H]$^+$.

Example 138

5-({7-[(2E)-4-(Dimethylamino)but-2-enoyl]-5,6,7,8-tetrahydropyrido[4',3':4,5]thieno[2,3-d]-pyrimidin-4-yl}amino)-4-fluoro-2-methylphenol

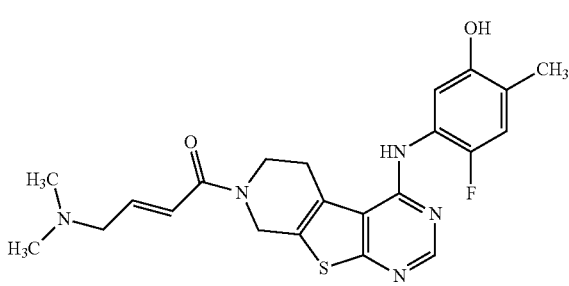

The compound was synthesized in analogy to Example 122 from 4-fluoro-2-methyl-5-(5,6,7,8-tetrahydropyrido[4',3':4,5]thieno[2,3-d]pyrimidin-4-ylamino)phenol hydrochloride from Example 72A (100 mg, 0.27 mmol) and (2E)-4-(dimethylamino)but-2-enoic acid hydrochloride from Example 1A (63 mg, 0.38 mmol) to yield 29 mg (24%).

$^1$H-NMR (400 MHz, DMSO-d$_6$): δ=2.12 (s, 3H), 2.15-2.18 (s, 6H), 3.04-3.09 (m, 2H), 3.14-3.26 (m, 2H), 3.85-3.97 (m, 2H), 4.83-4.97 (m, 2H), 6.64-6.79 (m, 2H), 6.98 (d, 1H), 7.20 (dd, 1H), 8.02-8.08 (m, 1H), 8.35 (s, 1H), 9.34 (s, 1H).

LC/MS (method 4): $R_t$=1.24 min; MS (ESIpos): m/z=442 [M+H]$^+$.

Example 139

N-(3,4-Dichlorophenyl)-6-{(2E)-4-[methyl(1-methylethyl)amino]but-2-enoyl}-5,6,7,8-tetrahydropyrido[3',4':4,5]thieno[2,3-d]pyrimidin-4-amine

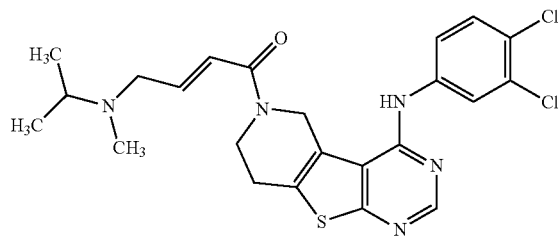 [SMILES: CC(C)N(C)C/C=C/C(=O)N1CCc2sc3ncnc(Nc4ccc(Cl)c(Cl)c4)c3c2C1]

The title compound was synthesized in analogy to Example 89 from N-(3,4-dichlorophenyl)-5,6,7,8-tetrahydropyrido[3',4':4,5]thieno[2,3-d]pyrimidin-4-amine from Example 76A (100 mg, 0.29 mmol) and (2E)-4-[methyl(1-methylethyl)amino]but-2-enoic acid hydrochloride from Example 2A (77 mg, 0.40 mmol) to yield 56 mg (40%).

$^1$H-NMR (400 MHz, DMSO-d$_6$): δ=0.86-1.00 (m, 6H), 2.03-2.13 (m, 3H), 2.70-2.83 (m, 1H), 2.90-3.04 (m, 2H), 3.10-3.20 (m, 2H), 3.87-3.96 (m, 2H), 4.98-5.21 (m, 2H), 6.64 (dt, 1H), 6.77 (d, 1H), 7.59-7.65 (m, 2H), 7.93 (s, 1H), 8.51 (s, 1H), 8.63 (br. s, 1H).

LC/MS (method 6): $R_t$=1.35 min; MS (ESIpos): m/z=490 [M+H]$^+$.

Example 140

N-(3-Chloro-4-fluorophenyl)-8-[(2E)-4-(dimethylamino)but-2-enoyl]-6,7,8,9-tetrahydro-5H-pyrimido[5',4':4,5]thieno[2,3-c]azepin-4-amine

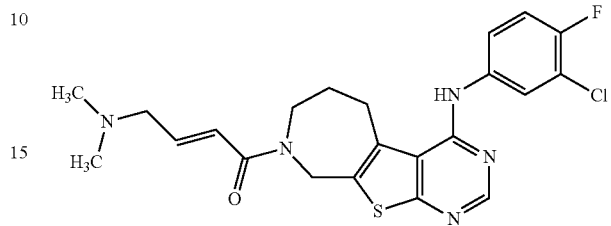 [SMILES: CC(C)N(C)C/C=C/C(=O)N1CCCc2c(sc3ncnc(Nc4ccc(Cl)c(Cl)c4)c23)C1]

The title compound was synthesized in analogy to Example 89 from N-(3-chloro-4-fluorophenyl)-6,7,8,9-tetrahydro-5H-pyrimido[5',4':4,5]thieno[2,3-c]azepin-4-amine from Example 81A (160 mg, 80% purity, 0.37 mmol) and (2E)-4-(dimethylamino)but-2-enoic acid hydrochloride from Example 1A (85 mg, 0.51 mmol) to yield 12 mg (7%).

$^1$H-NMR (400 MHz, DMSO-d$_6$): δ=2.09 (s, 3H), 2.15 (s, 3H), 2.99 (d, 1H), 3.03 (d, 1H), 3.23-3.33 (m, 4H), 3.84 (t, 1H), 3.89 (t, 1H), 4.78 (s, 1H), 4.93 (s, 1H), 6.52-6.66 (m, 2H), 7.40 (t, 1H), 7.53-7.59 (m, 1H), 7.81-7.86 (m, 1H), 8.42 (s, 1H), 8.62 (d, 1H).

LC/MS (method 2): $R_t$=0.93 min; MS (ESIpos): m/z=460 [M+H]$^+$.

Example 141

N-(3,4-Dichlorophenyl)-8-{(2E)-4-[methyl(1-methylethyl)amino]but-2-enoyl}-6,7,8,9-tetrahydro-5H-pyrimido[5',4':4,5]thieno[2,3-c]azepin-4-amine

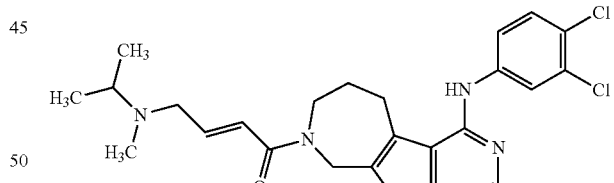

The title compound was synthesized in analogy to Example 89 from N-(3,4-dichlorophenyl)-6,7,8,9-tetrahydro-5H-pyrimido[5',4':4,5]thieno[2,3-c]azepin-4-amine from Example 82A (100 mg, 0.27 mmol) and (2E)-4-[methyl(1-methylethyl)amino]but-2-enoic acid hydrochloride from Example 2A (74 mg, 0.38 mmol) to yield 71 mg (50%).

$^1$H-NMR (400 MHz, DMSO-d$_6$): δ=0.90 and 0.94 (d, Σ6H), 2.01-2.10 (m, 5H), 2.65-2.80 (m, 1H), 3.06-3.15 (m, 2H), 3.22-3.32 (m, 2H), 3.84 (t, 1H), 3.89 (t, 1H), 4.78 (s, 1H), 4.92 (s, 1H), 6.50-6.66 (m, 2H), 7.56-7.64 (m, 2H), 7.93 (dd, 1H), 8.47 (s, 1H), 8.74 (s, 1H).

LC/MS (method 6): $R_t$=1.26 min; MS (ESIpos): m/z=504 [M+H]$^+$.

Example 142

8-{(2E)-4-[Cyclopropyl(methyl)amino]but-2-enoyl}-N-(3,4-dichlorophenyl)-6,7,8,9-tetrahydro-5H-pyrimido[5',4':4,5]thieno[2,3-c]azepin-4-amine

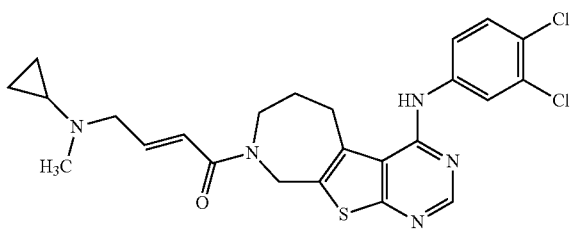 [SMILES: CN(C/C=C/C(=O)N1CCCc2c(sc3ncnc(Nc4ccc(Cl)c(Cl)c4)c23)C1)C1CC1]

In analogy to Example 130, the title compound was prepared from (2E)-4-bromobut-2-enoic acid (127 mg, 0.62 mmol), N-(3,4-dichlorophenyl)-6,7,8,9-tetrahydro-5H-pyrimido[5',4':4,5]thieno[2,3-c]azepin-4-amine from Example 82A (150 mg, 0.41 mmol) and N-methylcyclopropanamine (116 mg, 1.63 mmol) to yield 21 mg (10%).

$^1$H-NMR (400 MHz, DMSO-d$_6$): δ=0.24-0.32 (m, 2H), 0.34-0.45 (m, 2H), 1.63-1.73 (m, 1H), 2.03-2.11 (m, 2H), 2.15 and 2.23 (s, Σ3H), 3.20-3.32 (m, 4H), 3.84 (t, 1H), 3.89 (t, 1H), 4.78 (s, 1H), 4.92 (s, 1H), 6.57-6.69 (m, 2H), 7.56-7.64 (m, 2H), 7.93 (dd, 1H), 8.47 (s, 1H), 8.74 (s, 1H).

LC/MS (method 2): R$_t$=1.04 min; MS (ESIpos): m/z=502 [M+H]$^+$.

Example 143

N-(3,4-Dichlorophenyl)-8-[(2E)-4-(1,4-oxazepan-4-yl)but-2-enoyl]-6,7,8,9-tetrahydro-5H-pyrimido[5',4':4,5]thieno[2,3-c]azepin-4-amine

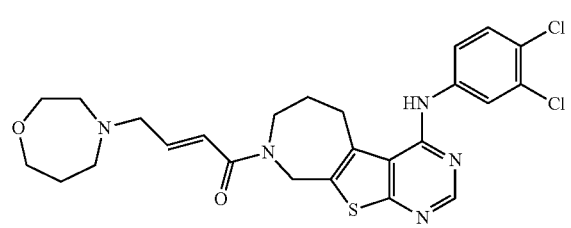 [SMILES: O=C(/C=C/CN1CCCOCC1)N1CCCc2c(sc3ncnc(Nc4ccc(Cl)c(Cl)c4)c23)C1]

In analogy to Example 130, the title compound was prepared from (2E)-4-bromobut-2-enoic acid (85 mg, 0.41 mmol), N-(3,4-dichlorophenyl)-6,7,8,9-tetrahydro-5H-pyrimido[5',4':4,5]thieno[2,3-c]azepin-4-amine from Example 82A (100 mg, 0.27 mmol) and 1,4-oxazepane hydrochloride (60 mg, 0.44 mmol) to yield 41 mg (26%).

$^1$H-NMR (400 MHz, DMSO-d$_6$): δ=1.67-1.82 (m, 2H), 2.02-2.12 (m, 2H), 2.57-2.63 (m, 2H), 3.18-3.30 (m, 4H), 3.49-3.54 (m, 1H), 3.57-3.61 (m, 1H), 3.62-3.69 (m, 2H), 3.81-3.92 (m, 2H), 4.79 (s, 1H), 4.92 (s, 1H), 6.52-6.65 (m, 2H), 7.56-7.64 (m, 2H), 7.93 (dd, 1H), 8.47 (s, 1H), 8.74 (s, 1H).

LC/MS (method 2): R$_t$=1.02 min; MS (ESIpos): m/z=532 [M+H]$^+$.

Example 144

N-[1-(3-Fluorobenzyl)-1H-indazol-5-yl]-8-{(2E)-4-[methyl(1-methylethyl)amino]but-2-enoyl}-6,7,8,9-tetrahydro-5H-pyrimido[5',4':4,5]thieno[2,3-c]azepin-4-amine

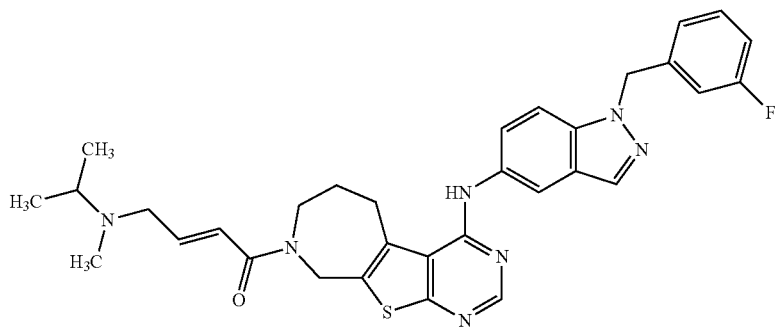 [SMILES: CC(C)N(C)C/C=C/C(=O)N1CCCc2c(sc3ncnc(Nc4ccc5c(cnn5Cc5cccc(F)c5)c4)c23)C1]

The title compound was synthesized in analogy to Example 89 from N-[1-(3-fluorobenzyl)-1H-indazol-5-yl]-6,7,8,9-tetrahydro-5H-pyrimido[5',4':4,5]thieno[2,3-c]azepin-4-amine from Example 83A (100 mg, 0.23 mmol) and (2E)-4-[methyl(1-methylethyl)amino]but-2-enoic acid hydrochloride from Example 2A (61 mg, 0.32 mmol) to yield 39 mg (29%).

LC/MS (method 6): R$_t$=1.27 min; MS (ESIpos): m/z=584 [M+H]$^+$.

Example 145

N-(3-Chloro-4-fluorophenyl)-7-[(2E)-4-(dimethylamino)but-2-enoyl]-6,7,8,9-tetrahydro-5H-pyrimido[5',4':4,5]thieno[2,3-d]azepin-4-amine

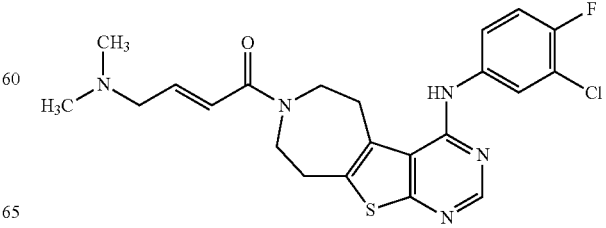

The title compound was prepared in analogy to Example 89 from N-(3-chloro-4-fluorophenyl)-6,7,8,9-tetrahydro-5H-pyrimido[5',4':4,5]thieno[2,3-d]azepin-4-amine from Example 85A (100 mg, 0.29 mmol) and (2E)-4-(dimethylamino)but-2-enoic acid hydrochloride from Example 1A (66 mg, 0.40 mmol) to yield 89 mg (67%).

$^1$H-NMR (400 MHz, DMSO-$d_6$): δ=2.14 (s, 6H), 3.02-3.06 (m, 2H), 3.16-3.24 (m, 2H), 3.36-3.41 (m, 2H), 3.74-3.79 (m, 1H), 3.85-3.95 (m, 3H), 6.58-6.72 (m, 2H), 7.41 (dt, 1H), 7.54-7.60 (m, 1H), 7.83 (ddd, 1H), 8.41 (d, 1H), 8.55 (d, 1H).

LC/MS (method 4): $R_t$=1.41 min; MS (ESIpos): m/z=460 [M+H]$^+$.

Example 146

N-{3-Chloro-4-[(3-fluorobenzyl)oxy]phenyl}-7-[(2E)-4-(dimethylamino)but-2-enoyl]-5,6,7,8-tetrahydropyrido[4',3':4,5]furo[2,3-d]pyrimidin-4-amine

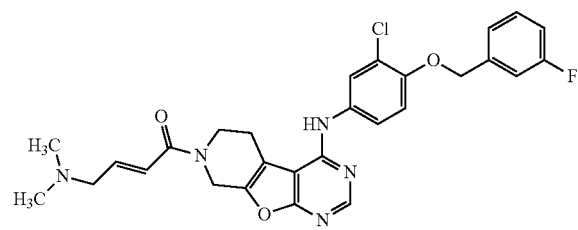 [SMILES: CN(C)C/C=C/C(=O)N1CCc2c(oc3ncnc(Nc4ccc(OCc5cccc(F)c5)c(Cl)c4)c23)C1]

tert-Butyl 4-({3-chloro-4-[(3-fluorobenzyl)oxy]phenyl}amino)-5,8-dihydropyrido[4',3':4,5]furo-[2,3-d]pyrimidine-7(6H)-carboxylate from Example 86A (18 mg, 0.034 mmol) was dissolved in 2-propanol (1.0 mL) and treated with 4 M gaseous hydrogen chloride in dioxane (0.25 mL, 1.0 mmol). The mixture was heated to 80° C. for 2 h. Subsequently, the solvent was removed in vacuo. The residue was reacted in analogy to Example 89 with (2E)-4-(dimethylamino)but-2-enoic acid hydrochloride from Example 1A (8.0 mg, 0.048 mmol) to yield 7.0 mg (38%) of the title compound.

$^1$H-NMR (400 MHz, DMSO-$d_6$): δ=2.17 (s, 6H), 2.88-2.97 (m, 2H), 3.05-3.10 (m, 2H), 3.81-3.90 (m, 2H), 4.73 (s, 1H), 4.84 (s, 1H), 5.24 (s, 2H), 6.63-6.79 (m, 2H), 7.17 (dt, 1H), 7.23 (d, 1H), 7.28-7.34 (m, 2H), 7.47 (dt, 1H), 7.53 (dd, 1H), 7.77 (d, 1H), 8.33 (s, 1H), 8.58 (br. s, 1H). LC/MS (method 4): $R_t$=1.70 min; MS (ESIpos): m/z=536 [M+H]$^+$.

Example 147

7-{(2E)-4-[tert-Butyl(methyl)amino]but-2-enoyl}-4-[(3-chloro-4-fluorophenyl)amino]-5,6,7,8-tetrahydrothieno[2,3-b:5,4-c']dipyridine-3-carbonitrile

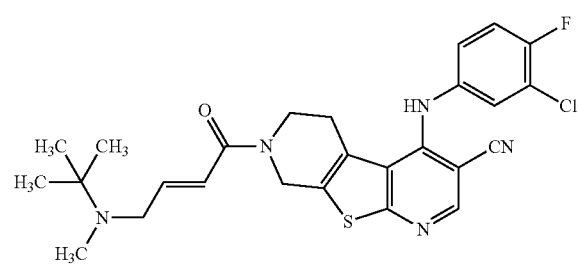 [SMILES: CN(C/C=C/C(=O)N1CCc2c(sc3ncc(C#N)c(Nc4ccc(F)c(Cl)c4)c23)C1)C(C)(C)C]

(2E)-4-Bromobut-2-enoic acid (100 mg, 0.61 mmol) and tert-butyl methylamine (60 mg, 0.67 mmol) were dissolved in DCM (3.0 mL). DIPEA (94 mg, 0.73 mmol) was added, and the mixture was heated overnight to 50° C. After cooling to rt, the compound of Example 55A (75 mg, 0.21 mmol), DCM (1.0 mL), EDCI (48 mg, 0.25 mmol) and DIPEA (32 mg, 0.25 mmol) were added, and the mixture was stirred at rt overnight. Subsequently, it was diluted with water, and the mixture was extracted three times with DCM. The combined organic layers were dried over sodium sulfate, and the solvent was removed in vacuo. The crude product was purified by preparative HPLC to yield 41 mg (37%) of the title compound.

$^1$H-NMR (400 MHz, DMSO-$d_6$): δ=1.03 (s, 9H), 2.09 (s, 3H), 2.98-3.04 (m, 2H), 3.13-3.17 (m, 2H), 3.74-3.87 (m, 2H), 4.84-4.99 (m, 2H), 6.61-6.69 (m, 2H), 6.98-7.07 (m, 1H), 7.22-7.28 (m, 1H), 7.34 (t, 1H), 8.61 (s, 1H), 8.74 (s, 1H).

LC/MS (method 4): $R_t$=1.53 min; MS (ESIpos): m/z=512 [M+H]$^+$.

Example 148

4-[(3,4-Dichlorophenyl)amino]-7-[(2E)-4-(1,4-oxazepan-4-yl)but-2-enoyl]-5,6,7,8-tetrahydrothieno[2,3-b:5,4-c']dipyridine-3-carbonitrile

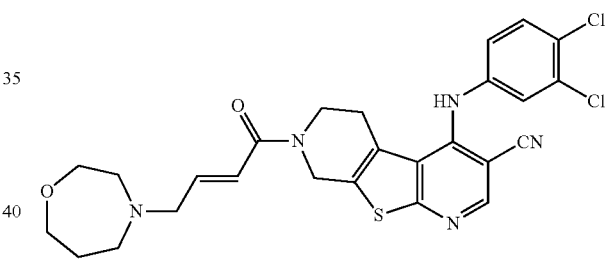

(2E)-4-Bromobut-2-enoic acid (53 mg, 0.32 mmol) and 1,4-oxazepane hydrochloride (48 mg, 0.34 mmol) were dissolved in DCM (2.0 mL), and DIPEA (96 mg, 0.75 mmol) was added. The mixture was stirred at rt for 2 h. Subsequently, 4-[(3,4-dichlorophenyl)amino]-5,6,7,8-tetrahydrothieno[2,3-b:5,4-c']dipyridine-3-carbonitrile from Example 88A (80 mg, 0.21 mmol), DIPEA (28 mg, 0.21 mmol) and EDCI (41 mg, 0.21 mmol) were added. The reaction mixture was stirred at rt overnight. Then, water was added, and the mixture was extracted three times with DCM. The combined organic layers were dried over sodium sulfate. The solvent was removed in vacuo, and the residue was purified by preparative HPLC to yield 19 mg (16%) of the title compound.

$^1$H-NMR (400 MHz, DMSO-$d_6$): δ=1.26 (s, 2H), 1.77-1.86 (m, 2H), 2.60-2.67 (m, 2H), 2.95-3.04 (m, 2H), 3.58-3.67 (m, 4H), 3.70 (t, 2H), 3.75-3.90 (m, 2H), 4.87-5.03 (m, 2H), 6.67-6.79 (m, 2H), 6.90-6.99 (m, 1H), 7.20-7.25 (m, 1H), 7.51 (d, 1H), 8.74 (s, 1H), 8.98 (br. s, 1H).

LC/MS (method 2): $R_t$=0.98 min; MS (ESIpos): m/z=542 [M+H]$^+$.

Example 149

4-({3-Chloro-4-[(3-fluorobenzyl)oxy]phenyl}amino)-7-{(2E)-4-[methyl(1-methylethyl)amino]but-2-enoyl}-5,6,7,8-tetrahydrothieno[2,3-b:5,4-c']dipyridine-3-carbonitrile

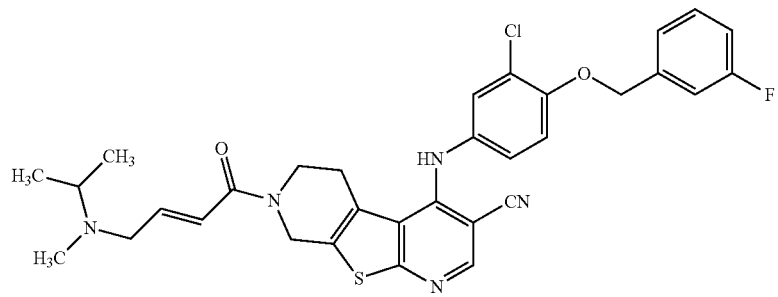 [SMILES: CC(C)N(C)C/C=C/C(=O)N1CCc2c(sc3ncc(C#N)c(Nc4ccc(OCc5cccc(F)c5)c(Cl)c4)c23)C1]

A solution of 4-({3-chloro-4-[(3-fluorobenzyl)oxy]phenyl}amino)-5,6,7,8-tetrahydrothieno[2,3-b:5,4-c']dipyridine-3-carbonitrile from Example 90A (80 mg, 0.17 mmol) and (2E)-4-[methyl(1-methylethyl)amino]but-2-enoic acid hydrochloride from Example 2A (47 mg, 0.24 mmol) in DMF (2 mL) was treated with DIPEA (89 mg, 0.69 mmol) and TBTU (83 mg, 0.26 mmol). The mixture was stirred at rt overnight and then directly purified by preparative HPLC to yield 63 mg (61%) of the title compound.

$^1$H-NMR (400 MHz, DMSO-$d_6$): δ=0.95 (d, 6H), 2.09 (s, 3H), 2.72-2.81 (m, 1H), 3.00-3.08 (m, 2H), 3.13-3.16 (m, 2H), 3.75-3.86 (m, 2H), 4.83-4.87 (m, 2H), 5.21 (s, 2H), 6.62-6.72 (m, 2H), 7.00-7.07 (m, 1H), 7.14-7.19 (m, 2H), 7.24-7.32 (m, 3H), 7.43-7.48 (m, 1H), 8.40-8.52 (m, 2H).

LC/MS (method 2): $R_t$=1.13 min; MS (ESIpos): m/z=604 [M+H]$^+$.

Example 150

7-{(2E)-4-[Methyl(1-methylethyl)amino]but-2-enoyl}-4-{[1-(pyridin-2-ylmethyl)-1H-indazol-5-yl]amino}-5,6,7,8-tetrahydrothieno[2,3-b:5,4-c']dipyridine-3-carbonitrile

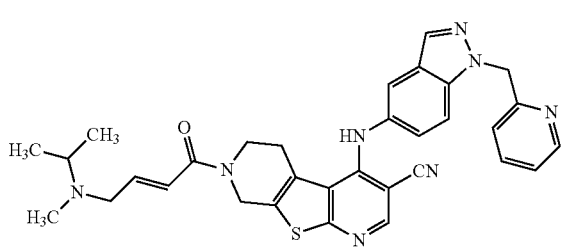 [SMILES: CC(C)N(C)C/C=C/C(=O)N1CCc2c(sc3ncc(C#N)c(Nc4ccc5c(cnn5Cc5ccccn5)c4)c23)C1]

4-{[1-Pyridin-2-ylmethyl)-1H-indazol-5-yl]amino}-5,6,7,8-tetrahydrothieno[2,3-b:5,4-c']dipyridine-3-carbonitrile from Example 92A (70 mg, 0.16 mmol) and (2E)-4-[methyl(1-methylethyl)amino]but-2-enoic acid hydrochloride from Example 2A (43 mg, 0.22 mmol) were dissolved in DMF (2.0 mL), and DIPEA (83 mg, 0.64 mmol) and TBTU (77 mg, 0.24 mmol) were added. The mixture was stirred at rt overnight and then directly purified by preparative HPLC to yield 50 mg (54%) of the title compound.

$^1$H-NMR (400 MHz, DMSO-$d_6$): δ=0.96 (d, 6H), 2.12 (br. s, 3H), 3.00-3.06 (m, 1H), 3.09-3.24 (m, 4H), 3.74-3.87 (m, 2H), 4.83-4.98 (m, 2H), 5.75 (s, 2H), 6.62-6.75 (m, 2H), 6.83-6.90 (m, 1H), 7.25-7.30 (m, 2H), 7.48 (br. s, 1H), 7.66 (d, 1H), 7.69 (dt, 1H), 8.06 (s, 1H), 8.45 (s, 1H), 8.50-8.55 (m, 2H).

LC/MS (method 2): $R_t$=0.81 min; MS (ESIpos): m/z=577 [M+H]$^+$.

Example 151

4-{[1-(3-Fluorobenzyl)-1H-indazol-5-yl]amino}-7-{(2E)-4-[methyl(1-methylethyl)amino]but-2-enoyl}-5,6,7,8-tetrahydrothieno[2,3-b:5,4-c']dipyridine-3-carbonitrile

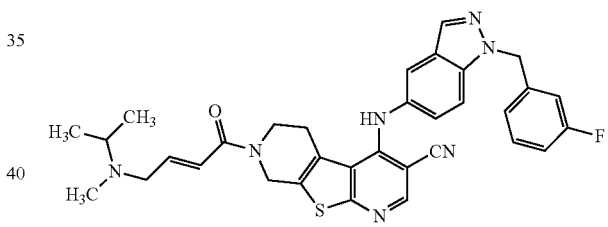

The compound was synthesized in analogy to Example 149 from 4-{[1-(3-fluorobenzyl)-1H-indazol-5-yl]amino}-5,6,7,8-tetrahydrothieno[2,3-b:5,4-c']dipyridine-3-carbonitrile from Example 94A (90 mg, 0.20 mmol) and (2E)-4-[methyl(1-methylethyl)amino]but-2-enoic acid hydrochloride from Example 2A (54 mg, 0.28 mmol) to yield 52 mg (44%).

$^1$H-NMR (400 MHz, DMSO-$d_6$): δ=0.95 (d, 6H), 2.10 (s, 3H), 2.73-2.85 (m, 1H), 3.01-3.19 (m, 4H), 3.75-3.88 (m, 2H), 4.82-4.98 (m, 2H), 5.69 (s, 2H), 6.62-6.72 (m, 2H), 6.94-7.03 (m, 2H), 7.06-7.11 (m, 1H), 7.28 (d, 1H), 7.35 (q, 1H), 7.49 (s, 1H), 7.70 (d, 1H), 8.07 (s, 1H), 8.42-8.53 (m, 2H).

LC/MS (method 2): $R_t$=0.99 min; MS (ESIpos): m/z=594 [M+H]$^+$.

B. EVALUATION OF BIOLOGICAL ACTIVITY

The utility of the compounds of the present invention can be illustrated, for example, by their activity in vitro in the in vitro tumor cell proliferation assays described below. The link between activity in tumor cell proliferation assays in vitro and anti-tumor activity in the clinical setting has been very well established in the art. For example, the therapeutic utility of Taxol (Silvestrini et al., Stem Cells 1993, 11(6), 528-35), Taxotere (Bissery et al., *Anti Cancer Drugs* 1995, 6(3), 339), and Topoisomerase inhibitors (Edelman et al., *Cancer Chemother. Pharmacol.* 1996, 37(5), 385-93) were demonstrated with the use of in vitro tumor proliferation assays.

Demonstration of the activity of the compounds of the present invention may be accomplished through in vitro, ex vivo, and in vivo assays that are well known in the art. For example, to demonstrate the activity of the compounds of the present invention, the following assays may be used.

Kinase Assay:

EGFR inhibitory activity of compounds of the present invention is quantified employing the EGFR HTRF assay as described in the following paragraphs:

Epidermal Growth Factor Receptor (EGFR), affinity-purified from human carcinoma A431 cells (Sigma-Aldrich, # E3641), is used as kinase. As substrate for the kinase reaction, the biotinylated peptide biotin-Ahx-AEEEEYFELVAKKK (C-terminus in amide form) is used (available from, e.g., Biosynthan GmbH, Berlin-Buch, Germany).

EGFR is incubated for 30 min at 22° C. in the presence of different concentrations of test compounds in 5 µl assay buffer [50 mM Hepes/NaOH pH 7.0, 1 mM $MgCl_2$, 5 mM $MnCl_2$, 1.0 mM dithiothreitol, 0.5 mM sodium orthovanadate, 10 µM adenosine triphosphate (ATP), 1 µM substrate, 0.005% (v/v) Tween-20, 1% (v/v) dimethylsulfoxide]. The concentration of EGFR is adjusted depending on the activity of the enzyme lot and is chosen appropriate to have the assay in the linear range; typical concentrations are in the range of 20 U/ml. The reaction is stopped by the addition of 5 µl of a solution of HTRF detection reagents [0.1 µM streptavidine-XLent and 1 nM PT66-Eu-Chelate, an Europium-chelate labelled anti-phosphotyrosine antibody (Perkin Elmer)] in an aqueous EDTA solution [80 mM EDTA, 0.2% (w/v) bovine serum albumin in 50 mM HEPES/NaOH pH 7.0].

The resulting mixture is incubated for 1 h at 22° C. to allow the binding of the biotinylated phosphorylated peptide to the streptavidine-XLent and the PT66-Eu-Chelate. Subsequently, the amount of phosphorylated substrate is evaluated by measurement of the resonance energy transfer from the PT66-Eu-Chelate to the streptavidine-XLent. Therefore, the fluorescence emissions at 620 nm and 665 nm after excitation at 350 nm are measured in an HTRF reader, e.g. a Rubystar (BMG Labtechnologies, Offenburg, Germany) or a Viewlux (Perkin-Elmer). The ratio of the emissions at 665 nm and at 622 nm is taken as the measure for the amount of phosphorylated substrate. The data are normalized (enzyme reaction without inhibitor=0% inhibition, all other assay components but no enzyme=100% inhibition), and $IC_{50}$ values are calculated by a 4-parameter fit using an inhouse software.

Representative data for the compounds of the present invention are given in Table 1:

TABLE 1

| Example No. | EGFR $IC_{50}$ [nM] |
| --- | --- |
| 5 | 1.0 |
| 10 | 1.1 |
| 12 | 1.0 |
| 13 | 2.0 |
| 14 | 1.0 |
| 23 | 4.6 |
| 31 | 1.0 |
| 70 | 1.0 |
| 81 | 12 |
| 84 | 1.4 |
| 86 | 5.0 |
| 87 | 19 |
| 90 | 1.0 |

TABLE 1-continued

| Example No. | EGFR $IC_{50}$ [nM] |
| --- | --- |
| 95 | 10 |
| 119 | 1.0 |
| 123 | 1.0 |
| 134 | 1.0 |
| 139 | 9.2 |
| 143 | 1.0 |
| 148 | 4.3 |
| 151 | 6.4 |

Many of the compounds and compositions described herein exhibit anti-proliferative activity with $IC_{50}$ values ≦50 µM in either of the following specified cell lines and are thus useful to prevent or treat the disorders associated with hyperproliferation. The following assay is one of the methods by which compound activity relating to treatment of the disorders identified herein can be determined.

The tumor cell proliferation assay used to test the compounds of the present invention involves a readout called Cell Titer-Glow® Luminescent Cell Viability Assay developed by Promega® (B. A. Cunningham, "A Growing Issue: Cell Proliferation Assays, Modern kits ease quantification of cell growth", *The Scientist* 2001, 15(13), 26; S. P. Crouch et al., "The use of ATP bioluminescence as a measure of cell proliferation and cytotoxicity", *Journal of Immunological Methods* 1993, 160, 81-88), that measures inhibition of cell proliferation. Generation of a luminescent signal corresponds to the amount of ATP present, which is directly proportional to the number of metabolically active (proliferating) cells.

An alternative cell proliferation assay used to test the compounds is the crystal violet assay which stains DNA and proteins and thereby quantifies cell number.

In Vitro Tumor Cell Proliferation Assay in A431 Cell Line:

A431 cells [human epidermoid carcinoma, ATCC #HTB-20, overexpressing HER1 (EGFR, ErbB1)] were plated at a density of 3000 cells/well in 96-well black-clear bottom tissue culture plates in RPMI media with 10% Fetal Bovine Serum and incubated at 37° C. Twenty-four hours later, test compounds were added at a final concentration range from as high as 30 µM to as low as 300 pM, depending on the activities of the tested compounds, in serial dilutions at a final DMSO concentration of 0.4-0.5%. Cells were incubated for 72 hours at 37° C. in complete growth media after addition of the test compound. Then, using a Promega Cell Titer Glo Luminescent® assay kit, lysis buffer containing 100 microliters of the enzyme luciferase and its substrate, luciferin mixture, was added to each well. The plates were mixed for 2 min on orbital shaker to ensure cell lysis and incubated for 10 min at room temperature in the dark to stabilize luminescence signal. The samples were read on VICTOR 3 using Luminescence protocol. The $IC_{50}$ values were determined by means of a 4-parameter fit using the company's own software.

Alternatively, the cell proliferation was measured by crystal violet staining:

Cultivated human A431 human epidermoid carcinoma cells (ATCC # HTB-20) were plated out in a density of 1500 cells/measurement point in 200 µl of growth medium (RPMI1640, 10% foetal calf serum) in a 96-well multititre plate. After 24 hours, the cells from a plate (zero plate) were stained with crystal violet (see below), while the medium in the other plates was replaced by fresh culture medium (200 µl) to which the test compounds had been added in various concentrations (0 µM, and in the range 0.3 nM-30 µM; the final concentration of the solvent dimethyl sulfoxide was 0.5%). The cells were incubated in the presence of the test substances for 4 days. The cell proliferation was determined by staining the cells with crystal violet: the cells were fixed by adding 20 µl/measurement point of an 11% strength glutaraldehyde solution at room temperature for 15 min. After the fixed cells had been washed three times with water, the plates were dried at room temperature. The cells were stained by adding 100 µl/measurement point of a 0.1% strength crystal violet solution (pH adjusted to pH 3 by adding acetic acid). After the stained cells had been washed three times with water, the plates were dried at room temperature. The dye was dissolved by adding 100 µl/measurement point of a 10% strength acetic acid solution, and the extinction was determined by photometry at a wavelength of 595 nm. The percentage change in cell growth was calculated by normalizing the measurements to the extinctions of the zero point plate (=0%) and the extinction of the untreated (0 µM) cells (=100%). The $IC_{50}$ values were determined by means of a 4-parameter fit using the company's own software.

Representative compounds of this invention showed inhibition of tumor cell proliferation in these assays.

In Vitro Tumor Cell Proliferation Assay in SK-BR-3 Cell Line:

SK-BR-3 cells [human breast cancer, ATCC #HTB-30, overexpressing HER2 (ErbB2)] were plated at a density of 4000 cells/well in 96-well black-clear bottom tissue culture plates in RPMI media with 10% Fetal Bovine Serum and incubated at 37° C. Twenty-four hours later, test compounds were added at a final concentration range from as high as 30 µM to as low as 300 pM, depending on the activities of the tested compounds, in serial dilutions at a final DMSO concentration of 0.4-0.5%. Cells were incubated for 72 hours at 37° C. in complete growth media after addition of the test compound. Then, using a Promega Cell Titer Glo Luminescent® assay kit, lysis buffer containing 100 microliters of the enzyme luciferase and its substrate, luciferin mixture, was added to each well. The plates were mixed for 2 min on orbital shaker to ensure cell lysis and incubated for 10 min at room temperature in the dark to stabilize luminescence signal. The samples were read on VICTOR 3 using Luminescence protocol. The $IC_{50}$ values were determined by means of a 4-parameter fit using the company's own software.

Alternatively, the cell proliferation was measured by crystal violet staining:

Cultivated human SK-BR-3 human breast cancer cells (ATCC #HTB-30) were plated out in a density of 5000 cells/measurement point in 200 µl of growth medium (RPMI1640, 10% foetal calf serum) in a 96-well multititre plate. After 24 hours, the cells from a plate (zero plate) were stained with crystal violet (see below), while the medium in the other plates was replaced by fresh culture medium (200 µl) to which the test compounds had been added in various concentrations (0 µM, and in the range 0.3 nM-30 µM; the final concentration of the solvent dimethyl sulfoxide was 0.5%). The cells were incubated in the presence of the test substances for 4 days. The cell proliferation was determined by staining the cells with crystal violet: the cells were fixed by adding 20 µl/measurement point of an 11% strength glutaraldehyde solution at room temperature for 15 min. After the fixed cells had been washed three times with water, the plates were dried at room temperature. The cells were stained by adding 100 µl/measurement point of a 0.1% strength crystal violet solution (pH adjusted to pH 3 by adding acetic acid). After the stained cells had been washed three times with water, the plates were dried at room temperature. The dye was dissolved by adding 100 µl/measurement point of a 10% strength acetic acid solution, and the extinction was determined by photometry at a wavelength of 595 nm. The percentage change in cell growth was calculated by normalizing the measurements to the extinctions of the zero point plate (=0%) and the extinction of the untreated (0 µM) cells (=100%). The $IC_{50}$ values were determined by means of a 4-parameter fit using the company's own software.

Representative compounds of this invention showed inhibition of tumor cell proliferation in these assays.

In Vitro Tumor Cell Proliferation Assay in H1975 Cells:

H1975 cells [human non small cell lung carcinoma, ATCC #CRL-5908, expressing mutant HER1 (EGFR, ErbB1) (L858R, T790M)] were plated at a density of 3000 cells/well in 96-well black-clear bottom tissue culture plates in RPMI media with 10% Fetal Bovine Serum and incubated at 37° C. Twenty-four hours later, test compounds were added at a final concentration range from as high as 30 µM to as low as 300 pM, depending on the activities of the tested compounds, in serial dilutions at a final DMSO concentration of 0.4-0.5%. Cells were incubated for 72 hours at 37° C. in complete growth media after addition of the test compound. Then, using a Promega Cell Titer Glo Luminescent® assay kit, lysis buffer containing 100 microliters of the enzyme luciferase and its substrate, luciferin mixture, was added to each well. The plates were mixed for 2 min on orbital shaker to ensure cell lysis and incubated for 10 min at room temperature in the dark to stabilize luminescence signal. The samples were read on VICTOR 3 using Luminescence protocol. The $IC_{50}$ values were determined by means of a 4-parameter fit using the company's own software.

Alternatively, the cell proliferation was measured by crystal violet staining:

Cultivated human H1975 cells were plated out in a density of 3000 cells/measurement point in 200 µl of growth medium (RPMI1640, 10% foetal calf serum) in a 96-well multititre plate. After 24 hours, the cells from a plate (zero plate) were stained with crystal violet (see below), while the medium in the other plates was replaced by fresh culture medium (200 µl) to which the test compounds had been added in various concentrations (0 µM, and in the range 0.3 nM-30 µM; the final concentration of the solvent dimethyl sulfoxide was 0.5%). The cells were incubated in the presence of the test substances for 4 days. The cell proliferation was determined by staining the cells with crystal violet: the cells were fixed by adding 20 µl/measurement point of an 11% strength glutaraldehyde solution at room temperature for 15 min. After the fixed cells had been washed three times with water, the plates were dried at room temperature. The cells were stained by adding 100 µl/measurement point of a 0.1% strength crystal violet solution (pH adjusted to pH 3 by adding acetic acid). After the stained cells had been washed three times with water, the plates were dried at room temperature. The dye was dissolved by adding 100 µl/measurement point of a 10% strength acetic acid solution, and the extinction was determined by photometry at a wavelength of 595 nm. The percentage change in cell growth was calculated by normalizing the measurements to the extinctions of the zero point plate (=0%) and the extinction of the untreated (0 µM) cells (=100%). The $IC_{50}$ values were determined by means of a 4-parameter fit using the company's own software.

Representative compounds of this invention showed inhibition of tumor cell proliferation in these assays.

Although the invention has been disclosed with reference to specific embodiments, it is apparent that other embodiments and variations of the invention may be devised by others skilled in the art without departing from the true spirit and scope of the invention. The claims are intended to be construed to include all such embodiments and equivalent variations.

C. EXAMPLES RELATING TO PHARMACEUTICAL COMPOSITIONS

Pharmaceutical compositions according to the present invention can be illustrated as follows:

Sterile I.V. Solution:

A 5 mg/ml solution of the desired compound of this invention can be made using sterile, injectable water, and the pH is adjusted if necessary. The solution is diluted for administration to 1-2 mg/ml with sterile 5% dextrose and is administered as an i.v. infusion over about 60 minutes.

Lyophilized Powder for I.V. Administration:

A sterile preparation can be prepared with (i) 100-1000 mg of the desired compound of this invention as a lyophilized powder, (ii) 32-327 mg/ml sodium citrate, and (iii) 300-3000 mg Dextran 40. The formulation is reconstituted with sterile, injectable saline or 5% dextrose to a concentration of 10 to 20 mg/ml, which is further diluted with saline or 5% dextrose to 0.2 to 0.4 mg/ml, and is administered either as i.v. bolus or by i.v. infusion over 15-60 minutes.

Intramuscular Suspension:

The following solution or suspension can be prepared for intramuscular injection:

50 mg/ml of the desired, water-insoluble compound of this invention; 5 mg/ml sodium carboxymethylcellulose; 4 mg/mL TWEEN 80; 9 mg/ml sodium chloride; 9 mg/ml benzyl alcohol.

Hard Shell Capsules:

A large number of unit capsules are prepared by filling standard two-piece hard galantine capsules each with 100 mg of powdered active ingredient, 150 mg of lactose, 50 mg of cellulose and 6 mg of magnesium stearate.

Soft Gelatin Capsules:

A mixture of active ingredient in a digestible oil such as soybean oil, cottonseed oil or olive oil is prepared and injected by means of a positive displacement pump into molten gelatin to form soft gelatin capsules containing 100 mg of the active ingredient. The capsules are washed and dried. The active ingredient can be dissolved in a mixture of polyethylene glycol, glycerin and sorbitol to prepare a water-miscible medicine mix.

Tablets:

A large number of tablets are prepared by conventional procedures so that the dosage unit is 100 mg of active ingredient, 0.2 mg of colloidal silicon dioxide, 5 mg of magnesium stearate, 275 mg of microcrystalline cellulose, 11 mg of starch, and 98.8 mg of lactose. Appropriate aqueous and non-aqueous coatings may be applied to increase palatability, improve elegance and stability, or delay absorption.

We claim:

1. A compound of formula (I)

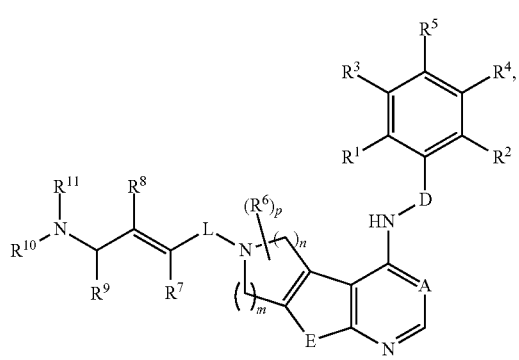

(I)

wherein

A is N or C—CN,

D is absent or is —$CH_2$— or —$CH(CH_3)$—,

E is O, S or N—$R^{12}$, wherein $R^{12}$ is hydrogen or ($C_1$-$C_4$)-alkyl,

L represents —C(=O)—, —S(=O)$_q$— or —S(=O)(=N—$R^{13}$)—, wherein q is 1 or 2, and $R^{13}$ is hydrogen or ($C_1$-$C_4$)-alkyl, m is 1 or 2, n is 1, 2 or 3, p is 0, 1 or 2, $R^1$ represents hydrogen or halogen, $R^2$ represents hydrogen, halogen or ($C_1$-$C_4$)-alkyl, $R^3$ is selected from the group consisting of hydrogen, halogen, cyano, ($C_1$-$C_4$)-alkyl, ($C_1$-$C_4$)-alkoxy, ($C_2$-$C_4$)-alkenyl and ($C_2$-$C_4$)-alkinyl, $R^4$ is selected from the group consisting of hydrogen, halogen, cyano, ($C_1$-$C_4$)-alkyl, hydroxy, ($C_1$-$C_4$)-alkoxy, ($C_2$-$C_4$)-alkenyl and ($C_2$-$C_4$)-alkinyl, $R^5$ is selected from the group consisting of hydrogen, halogen, cyano, ($C_1$-$C_4$)-alkyl, ($C_2$-$C_4$)-alkenyl and ($C_2$-$C_4$)-alkinyl, or $R^5$ is a group of the formula ♦-O—$(CH_2)_r$—$R^{14}$, wherein ♦ denotes the point of attachment, r is 0, 1 or 2, and $R^{14}$ represents phenyl or 5- or 6-membered heteroaryl which are optionally substituted with one to three substituents independently selected from the group consisting of halogen, ($C_1$-$C_4$)-alkyl and ($C_1$-$C_4$)-alkoxy, or $R^4$ and $R^5$ are linked together and form a fused heterocyclic moiety of the formula

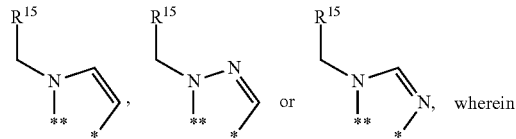

* indicates the point of attachment to the phenyl ring in $R^4$ position,
** indicates the point of attachment to the phenyl ring in $R^5$ position, and $R^{15}$ represents phenyl or 5- or 6-membered heteroaryl which are optionally substituted with one to three substituents independently selected from the group consisting of halogen, ($C_1$-$C_4$)-alkyl and ($C_1$-$C_4$)-alkoxy, $R^6$ represents a substituent independently selected from the group consisting of ($C_1$-$C_4$)-alkyl, hydroxy and ($C_1$-$C_4$)-alkoxy, $R^7$ and $R^8$ both represent hydrogen or are taken together to form a bond, resulting in an acetylenic linkage, and either $R^9$ and $R^{10}$ are joined, and taken together with the atoms to which they are attached, form a 5- to 7-membered heterocycloalkyl ring which is optionally substituted with one or two substituents independently selected from the group consisting of ($C_1$-$C_4$)-alkyl, hydroxy and ($C_1$-$C_4$)-alkoxy, and $R^{11}$ represents hydrogen or ($C_1$-$C_4$)-alkyl, or $R^9$ is hydrogen, and then $R^{10}$ and $R^{11}$ are independently selected from the group consisting of hydrogen, $(C_1-C_6)$-alkyl, $(C_3-C_{10})$-cycloalkyl and 4- to 7-membered heterocycloalkyl, wherein (i) said $(C_1-C_6)$-alkyl is optionally substituted with one to three substituents independently selected from the group consisting of fluoro, cyano, hydroxy, $(C_1-C_4)$-alkoxy, oxo, amino, mono-$(C_1-C_4)$-alkylamino, di-$(C_1-C_4)$-alkylamino, $(C_1-C_4)$-alkylcarbonylamino, $(C_1-C_4)$-alkoxycarbonylamino, hydroxycarbonyl, $(C_1-C_4)$-alkoxycarbonyl, aminocarbonyl, mono-$(C_1-C_4)$-alkylaminocarbonyl, di-$(C_1-C_4)$-alkylaminocarbonyl, $(C_1-C_4)$-alkylsulfonyl, S—$(C_1-C_4)$-alkylsulfonimidoyl, $(C_3-C_7)$-cycloalkyl, phenyl, 5- or 6-membered heteroaryl and 4- to 7-membered heterocycloalkyl, wherein said $(C_3-C_7)$-cycloalkyl, phenyl, 5- or 6-membered heteroaryl and 4- to 7-membered heterocycloalkyl substituents in turn are optionally substituted with one or two residues independently selected from the group consisting of fluoro, chloro, trifluoromethyl, $(C_1-C_4)$-alkyl, hydroxy, $(C_1-C_4)$-alkoxy, amino, mono-$(C_1-C_4)$-alkylamino and di-$(C_1-C_4)$-alkylamino, and (ii) said $(C_3-C_{10})$-cycloalkyl and 4- to 7-membered heterocycloalkyl are optionally substituted with one to three substituents independently selected from the group consisting of $(C_1-C_4)$-alkyl, oxo, hydroxy, $(C_1-C_4)$-alkoxy, amino, mono-$(C_1-C_4)$-alkylamino and di-$(C_1-C_4)$-alkylamino, or $R^{10}$ and $R^{11}$ are joined, and taken together with the nitrogen atom to which they are attached, form a 3- to 10-membered heterocycloalkyl ring which is optionally substituted with one or two substituents independently selected from the group consisting of $(C_1-C_6)$-alkyl, hydroxy, $(C_1-C_4)$-alkoxy, amino, mono-$(C_1-C_4)$-alkylamino, di-$(C_1-C_4)$-alkylamino, $(C_1-C_4)$-alkylcarbonylamino, $(C_1-C_4)$-alkylcarbonyl, $(C_1-C_4)$-alkylsulfonyl, hydroxycarbonyl, $(C_1-C_4)$-alkoxycarbonyl, aminocarbonyl, mono-$(C_1-C_4)$-alkylaminocarbonyl, di-$(C_1-C_4)$-alkylaminocarbonyl, $(C_3-C_7)$-cycloalkyl, phenyl, phenoxy, 5- or 6-membered heteroaryl and 4- to 7-membered heterocycloalkyl, wherein (i) said $(C_1-C_6)$-alkyl substituent in turn is optionally substituted with one or two residues independently selected from the group consisting of hydroxy, $(C_1-C_4)$-alkoxy, oxo, amino, mono-$(C_1-C_4)$-alkylamino, di-$(C_1-C_4)$-alkylamino, $(C_1-C_4)$-alkylcarbonyl-amino, $(C_1-C_4)$-alkoxycarbonylamino, hydroxycarbonyl, $(C_1-C_4)$-alkoxycarbonyl, amino-carbonyl, mono-$(C_1-C_4)$-alkylaminocarbonyl, di-$(C_1-C_4)$-alkylaminocarbonyl and 4- to 7-membered heterocycloalkyl, wherein said $(C_1-C_4)$-alkoxy residue is optionally substituted with hydroxy or $(C_1-C_4)$-alkoxy, and (ii) said $(C_3-C_7)$-cycloalkyl, phenyl, phenoxy, 5- or 6-membered heteroaryl and 4- to 7-membered heterocycloalkyl substituents in turn are optionally substituted with one or two residues independently selected from the group consisting of fluoro, chloro, tri-fluoromethyl, $(C_1-C_4)$-alkyl, hydroxy, $(C_1-C_4)$-alkoxy, amino, mono-$(C_1-C_4)$-alkylamino and di-$(C_1-C_4)$-alkylamino, or $R^{10}$ and $R^{11}$ are joined, and taken together with the nitrogen atom to which they are attached, form a heterocyclic group of the formula

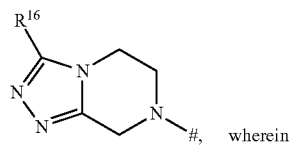

# denotes the point of attachment to the $CHR^9$ group, and $R^{16}$ represents hydrogen, trifluoromethyl or $(C_1-C_4)$-alkyl, or a pharmaceutically acceptable salt thereof.

2. The compound of claim 1, wherein L is —C(=O)—, p is 0, and $R^7$ and $R^8$ both are hydrogen, or a pharmaceutically acceptable salt thereof.

3. The compound of claim 1, wherein A is C—CN, or a pharmaceutically acceptable salt thereof.

4. The compound of claim 1, wherein D is —CH(CH_3)—, or a pharmaceutically acceptable salt thereof.

5. The compound of claim 1, wherein E is O, or a pharmaceutically acceptable salt thereof.

6. The compound of claim 1, wherein m and n both are 1, or a pharmaceutically acceptable salt thereof.

7. The compound of claim 1, wherein $R^4$ is hydroxy, or a pharmaceutically acceptable salt thereof.

8. The compound of claim 1, wherein

A is N,

D is absent or is —CH(CH_3)—,

E is S,

L is —C(=O)—, m is 1, n is 2, p is 0, $R^1$ represents hydrogen, fluoro or chloro, $R^2$ represents hydrogen, fluoro, chloro or methyl, $R^3$ represents hydrogen, fluoro, chloro, cyano, methyl, ethyl, methoxy or ethinyl, $R^4$ represents hydrogen, fluoro, chloro, cyano, methyl, ethyl, hydroxy, methoxy or ethinyl, $R^5$ represents hydrogen, fluoro, chloro, cyano or methyl, or $R^5$ is a group of the formula ♦-O—CH_2—$R^{14}$, wherein ♦ denotes the point of attachment, and $R^{14}$ represents phenyl or pyridyl which are optionally substituted with one or two substituents independently selected from the group consisting of fluoro, chloro, methyl and methoxy, or $R^4$ and $R^5$ are linked together and form a fused heterocyclic moiety of the formula

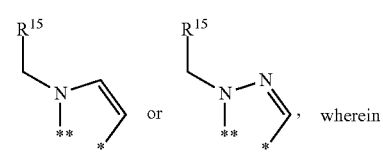

* indicates the point of attachment to the phenyl ring in $R^4$ position,

** indicates the point of attachment to the phenyl ring in $R^5$ position, and $R^{15}$ represents phenyl or pyridyl which are optionally substituted with one or two substituents independently selected from the group consisting of fluoro, chloro, methyl and methoxy, $R^7$ and $R^8$ both are hydrogen, $R^9$ is hydrogen, $R^{10}$ represents hydrogen, $(C_1-C_6)$-alkyl or $(C_3-C_7)$-cycloalkyl, wherein said $(C_1-C_6)$-alkyl and $(C_3-C_7)$-cycloalkyl are optionally substituted with one or two substituents independently selected from the group consisting of hydroxy, $(C_1-C_4)$-alkoxy, amino, mono-$(C_1-C_4)$-alkylamino and di-$(C_1-C_4)$-alkylamino, and $R^{11}$ represents $(C_1-C_6)$-alkyl which is substituted with one or two substituents independently selected from the group consisting of fluoro, cyano, $(C_1-C_4)$-alkoxy, amino, $(C_1-C_4)$-alkylcarbonylamino, $(C_1-C_4)$-alkoxycarbonylamino, hydroxycarbonyl, $(C_1-C_4)$-alkoxycarbonyl, aminocarbonyl, mono-$(C_1-C_4)$-alkylaminocarbonyl, di-$(C_1-C_4)$-alkylaminocarbonyl, $(C_1-C_4)$-alkylsulfonyl, S—$(C_1-C_4)$-alkylsulfonimidoyl, $(C_3-C_7)$-cycloalkyl, phenyl, 5- or 6-membered heteroaryl and 4- to 7-membered hetero-cycloalkyl, and which may be further substituted with hydroxy, mono-$(C_1-C_4)$-alkylamino or di-$(C_1-C_4)$-alkylamino, wherein said $(C_3-C_7)$-cycloalkyl, phenyl, 5- or 6-membered heteroaryl and 4- to 7-membered heterocycloalkyl substituents in turn are optionally substituted with one or two residues independently selected from the group consisting of fluoro, chloro, tri-fluoromethyl, $(C_1-C_4)$-alkyl, hydroxy, $(C_1-C_4)$-alkoxy, amino, mono-$(C_1-C_4)$-alkylamino and di-$(C_1-C_4)$-alkylamino, or $R^{11}$ represents $(C_3-C_7)$-cycloalkyl which is substituted with one or two substituents independently selected from the group consisting of $(C_1-C_4)$-alkyl, oxo, $(C_1-C_4)$-alkoxy and amino, and which may be further substituted with hydroxy, mono-$(C_1-C_4)$-alkylamino or di-$(C_1-C_4)$-alkylamino, or represents adamantyl, or $R^{11}$ represents 4- to 7-membered heterocycloalkyl which is optionally substituted with one or two substituents independently selected from the group consisting of $(C_1-C_4)$-alkyl, oxo, hydroxy, $(C_1-C_4)$-alkoxy, amino, mono-$(C_1-C_4)$-alkylamino and di-$(C_1-C_4)$-alkylamino, or a pharmaceutically acceptable salt thereof.

9. The compound of claim 1, wherein

A is N,

D is absent or is —CH(CH$_3$)—,

E is S,

L is —C(=O)—, m is 1, n is 2, p is 0, $R^1$ represents hydrogen, fluoro or chloro, $R^2$ represents hydrogen, fluoro, chloro or methyl, $R^3$ represents hydrogen, fluoro, chloro, cyano, methyl, ethyl, methoxy or ethinyl, $R^4$ represents hydrogen, fluoro, chloro, cyano, methyl, ethyl, hydroxy, methoxy or ethinyl, $R^5$ represents hydrogen, fluoro, chloro, cyano or methyl, or $R^5$ is a group of the formula ♦-O—CH$_2$—$R^{14}$, wherein ♦ denotes the point of attachment, and $R^{14}$ represents phenyl or pyridyl which are optionally substituted with one or two substituents independently selected from the group consisting of fluoro, chloro, methyl and methoxy, or $R^4$ and $R^5$ are linked together and form a fused heterocyclic moiety of the formula

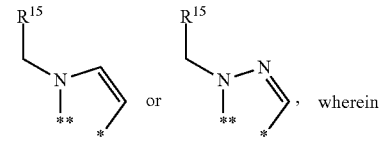

wherein

\* indicates the point of attachment to the phenyl ring in $R^4$ position,

\*\* indicates the point of attachment to the phenyl ring in $R^5$ position, and $R^{15}$ represents phenyl or pyridyl which are optionally substituted with one or two substituents independently selected from the group consisting of fluoro, chloro, methyl and methoxy, $R^7$ and $R^8$ both are hydrogen, $R^9$ is hydrogen, and $R^{10}$ and $R^{11}$ are joined, and taken together with the nitrogen atom to which they are attached, form a heterocycloalkyl group of the formula

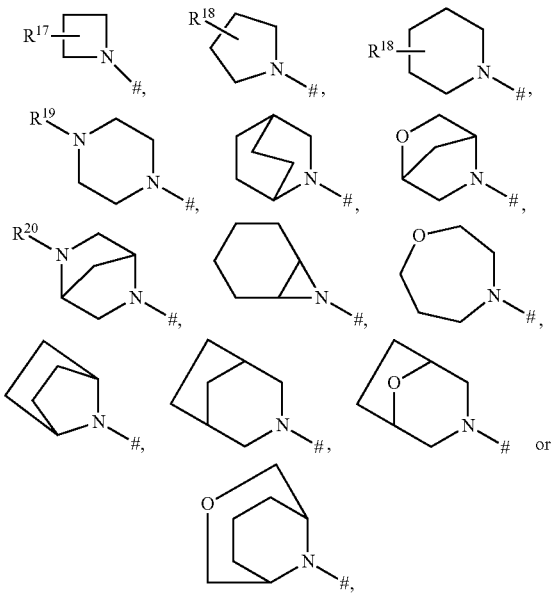

wherein

\# denotes the point of attachment to the CHR$^9$ group, $R^{17}$ represents hydrogen, $(C_1-C_4)$-alkoxy, $(C_1-C_4)$-alkylcarbonyl, $(C_1-C_4)$-alkoxycarbonyl, aminocarbonyl, mono-$(C_1-C_4)$-alkylaminocarbonyl, di-$(C_1-C_4)$-alkylaminocarbonyl, $(C_3-C_6)$-cycloalkyl, phenyl or phenoxy, wherein said phenyl and phenoxy are optionally substituted with one or two residues independently selected from the group consisting of fluoro, chloro, $(C_1-C_4)$-alkyl and $(C_1-C_4)$-alkoxy, or
represents $(C_1-C_4)$-alkyl which is optionally substituted with hydroxy, $(C_1-C_4)$-alkoxy, amino, mono-$(C_1-C_4)$-alkylamino or di-$(C_1-C_4)$-alkylamino, $R^{18}$ represents $(C_1-C_4)$-alkylcarbonyl, $(C_1-C_4)$-alkoxycarbonyl, aminocarbonyl, mono-$(C_1-C_4)$-alkylaminocarbonyl, di-$(C_1-C_4)$-alkylaminocarbonyl, $(C_3-C_6)$-cycloalkyl or phenyl, or represents $(C_1-C_4)$-alkyl which is substituted with $(C_1-C_4)$-alkoxy, amino, mono-$(C_1-C_4)$-alkylamino, di-$(C_1-C_4)$-alkylamino, $(C_1-C_4)$-alkylcarbonylamino, $(C_1-C_4)$-alkoxycarbonyl, aminocarbonyl, mono-$(C_1-C_4)$-alkylaminocarbonyl or di-$(C_1-C_4)$-alkylaminocarbonyl, $R^{19}$ represents hydrogen, $(C_1-C_4)$-alkylcarbonyl, $(C_1-C_4)$-alkylsulfonyl, $(C_1-C_4)$-alkoxy-carbonyl, aminocarbonyl, mono-$(C_1-C_4)$-alkylaminocarbonyl, di-$(C_1-C_4)$-alkylamino-carbonyl, $(C_3-C_6)$-cycloalkyl, phenyl or 5- or 6-membered heteroaryl, wherein said $(C_3-C_6)$-cycloalkyl, phenyl and 5- or 6-membered heteroaryl are optionally substituted with one or two residues independently selected from the group consisting of fluoro, chloro, $(C_1-C_4)$-alkyl, hydroxy and $(C_1-C_4)$-alkoxy, or
represents $(C_1-C_4)$-alkyl which is substituted with one or two residues independently selected from the group consisting of hydroxy, $(C_1-C_4)$-alkoxy, oxo, amino, mono-$(C_1-C_4)$-alkylamino, di-$(C_1-C_4)$-alkylamino, $(C_1-C_4)$-alkoxycarbonyl, aminocarbonyl, mono-$(C_1-C_4)$-alkylaminocarbonyl, di-$(C_1-C_4)$-alkylaminocarbonyl and 5- to 7-membered heterocycloalkyl, wherein said $(C_1-C_4)$-alkoxy residue in turn is optionally substituted with hydroxy, methoxy or ethoxy, and
$R^{20}$ represents hydrogen, $(C_1-C_4)$-alkylcarbonyl, $(C_1-C_4)$-alkylsulfonyl, $(C_1-C_4)$-alkoxy-carbonyl or di-$(C_1-C_4)$-alkylaminocarbonyl, or
represents $(C_1-C_4)$-alkyl which is optionally substituted with hydroxy or $(C_1-C_4)$-alkoxy, or a pharmaceutically acceptable salt thereof.

10. The compound of claim 1, wherein
A is N,
D is absent or is —CH(CH$_3$)—,
E is S,
L is —C(=O)—,
m is 1,
n is 2,
p is 0,
$R^1$ represents hydrogen, fluoro or chloro,
$R^2$ represents hydrogen, fluoro, chloro or methyl,
$R^3$ represents hydrogen, fluoro, chloro, cyano, methyl, ethyl, methoxy or ethynyl,
$R^4$ represents hydrogen, fluoro, chloro, cyano, methyl, ethyl, hydroxy, methoxy or ethynyl,
$R^5$ represents hydrogen, fluoro, chloro, cyano or methyl, or
$R^5$ is a group of the formula ◆-O—CH$_2$—$R^{14}$, wherein
◆ denotes the point of attachment,
and
$R^{14}$ represents phenyl or pyridyl which are optionally substituted with one or two substituents independently selected from the group consisting of fluoro, chloro, methyl and methoxy,
or
$R^4$ and $R^5$ are linked together and form a fused heterocyclic moiety of the formula

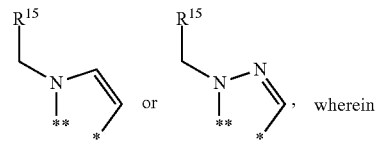

* indicates the point of attachment to the phenyl ring in $R^4$ position,
** indicates the point of attachment to the phenyl ring in $R^5$ position,
and
$R^{15}$ represents phenyl or pyridyl which are optionally substituted with one or two substituents independently selected from the group consisting of fluoro, chloro, methyl and methoxy,
$R^7$ and $R^8$ both are hydrogen,
$R^9$ and $R^{10}$ are joined, and taken together with the atoms to which they are attached, form a pyrrolidine or piperidine ring which is optionally substituted with one or two substituents independently selected from the group consisting of $(C_1-C_4)$-alkyl, hydroxy and $(C_1-C_4)$-alkoxy,
and
$R^{11}$ represents hydrogen or $(C_1-C_4)$-alkyl,
or a pharmaceutically acceptable salt thereof.

11. The compound of claim 1, wherein
A is N,
D is absent,
E is S,
L is —C(=O)—,
m is 1,
n is 2,
p is 0,
$R^1$ represents hydrogen, fluoro or chloro,
$R^2$ represents hydrogen, fluoro or chloro,
$R^3$ represents hydrogen, fluoro, chloro or ethynyl,
$R^4$ represents hydrogen, fluoro, chloro or hydroxy,
$R^5$ represents hydrogen, fluoro or chloro, or
$R^5$ is a group of the formula ◆-O—CH$_2$—$R^{14}$, wherein
◆ denotes the point of attachment,
and
$R^{14}$ represents phenyl which is optionally substituted with one or two fluoro atoms, or represents pyridyl,
or
$R^4$ and $R^5$ are linked together and form a fused heterocyclic moiety of the formula

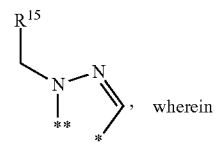

* indicates the point of attachment to the phenyl ring in $R^4$ position,
** indicates the point of attachment to the phenyl ring in $R^5$ position,
and
$R^{15}$ represents phenyl which is optionally substituted with one or two fluoro atoms, or represents pyridyl,
$R^7$ and $R^8$ both are hydrogen,
$R^9$ is hydrogen,
$R^{10}$ represents hydrogen, $(C_1-C_4)$-alkyl or cyclopropyl, wherein said $(C_1-C_4)$-alkyl is optionally substituted with hydroxy or $(C_1-C_4)$-alkoxy, and
- $R^{11}$ represents $(C_1-C_4)$-alkyl which is substituted with a group selected from $(C_1-C_4)$-alkoxy, hydroxycarbonyl, $(C_1-C_4)$-alkoxycarbonyl, di-$(C_1-C_4)$-alkylaminocarbonyl, $(C_1-C_4)$-alkylsulfonyl, 5- or 6-membered heteroaryl and 4- to 7-membered heterocycloalkyl, wherein said 5- or 6-membered heteroaryl and 4- to 7-membered heterocycloalkyl groups in turn are optionally substituted with one or two $(C_1-C_4)$-alkyl residues, or

- $R^{10}$ and $R^{11}$ are joined, and taken together with the nitrogen atom to which they are attached, form a heterocycloalkyl group of the formula wherein
- # denotes the point of attachment to the $CHR^9$ group,
- $R^{17}$ represents hydrogen or phenoxy which is optionally substituted with one or two residues independently selected from the group consisting of fluoro, chloro, methyl and methoxy,
- $R^{18}$ represents $(C_1-C_4)$-alkoxycarbonyl, aminocarbonyl, mono-$(C_1-C_4)$-alkylamino-carbonyl or di-$(C_1-C_4)$-alkylaminocarbonyl, or represents $(C_1-C_4)$-alkyl which is substituted with $(C_1-C_4)$-alkoxy, $(C_1-C_4)$-alkyl-carbonylamino or $(C_1-C_4)$-alkoxycarbonyl,

- $R^{19}$ represents $(C_1-C_4)$-alkylcarbonyl, $(C_1-C_4)$-alkylsulfonyl, $(C_1-C_4)$-alkoxycarbonyl, aminocarbonyl, mono-$(C_1-C_4)$-alkylaminocarbonyl, di-$(C_1-C_4)$-alkylaminocarbonyl, phenyl, pyridyl or pyrimidinyl,
- wherein said phenyl is optionally substituted with hydroxy or methoxy, or represents $(C_1-C_4)$-alkyl which is substituted with a group selected from hydroxy, $(C_1-C_4)$-alkoxy, di-$(C_1-C_4)$-alkylamino, $(C_1-C_4)$-alkoxycarbonyl, aminocarbonyl, mono-$(C_1-C_4)$-alkylaminocarbonyl and di-$(C_1-C_4)$-alkylaminocarbonyl, and

- $R^{20}$ represents di-$(C_1-C_4)$-alkylaminocarbonyl, or $(C_1-C_4)$-alkyl which is optionally substituted with hydroxy or $(C_1-C_4)$-alkoxy, or a pharmaceutically acceptable salt thereof.

12. The compound of claim 1, wherein
A is N,
D is absent,
E is S,
L is —C(=O)—,
m is 1,
n is 2,
p is 0,
$R^1$ represents hydrogen, fluoro or chloro,
$R^2$ represents hydrogen, fluoro or chloro,
$R^3$ represents hydrogen, fluoro, chloro or ethinyl,
$R^4$ represents hydroxy,
$R^5$ represents hydrogen, fluoro, chloro or methyl,
$R^7$ and $R^8$ both are hydrogen,
$R^9$ is hydrogen,
$R^{10}$ represents hydrogen, $(C_1-C_4)$-alkyl or cyclopropyl, wherein said $(C_1-C_4)$-alkyl is optionally substituted with hydroxy, mono-$(C_1-C_4)$-alkylamino or di-$(C_1-C_4)$-alkylamino, and
$R^{11}$ represents $(C_1-C_6)$-alkyl or $(C_3-C_6)$-cycloalkyl which are optionally substituted with one or two substituents independently selected from the group consisting of hydroxy, mono-$(C_1-C_4)$-alkylamino and di-$(C_1-C_4)$-alkylamino, or $R^{10}$ and $R^{11}$ are joined, and taken together with the nitrogen atom to which they are attached, form a heterocycloalkyl group of the formula wherein
# denotes the point of attachment to the $CHR^9$ group,
s is 0, 1 or 2,
$R^{18}$ represents hydrogen, $(C_1-C_4)$-alkyl, hydroxy, $(C_1-C_4)$-alkoxy, amino, mono-$(C_1-C_4)$-alkylamino or di-$(C_1-C_4)$-alkylamino,
and
$R^{19}$ represents $(C_1-C_4)$-alkyl,
or a pharmaceutically acceptable salt thereof.

13. The compound of claim 1, wherein
A is C—CN,
D is absent,
E is S,
L is —C(=O)—,
m is 1,
n is 1 or 2,
p is 0,
$R^1$ represents hydrogen, fluoro or chloro,
$R^2$ represents hydrogen, fluoro or chloro,
$R^3$ represents hydrogen, fluoro, chloro or ethinyl,
$R^4$ represents hydrogen, fluoro, chloro or hydroxy,
$R^5$ represents hydrogen, fluoro or chloro, or $R^5$ is a group of the formula ♦-O—$CH_2$—$R^{14}$, wherein
♦ denotes the point of attachment,
and $R^{14}$ represents phenyl which is optionally substituted with one or two fluoro atoms, or represents pyridyl, or $R^4$ and $R^5$ are linked together and form a fused heterocyclic moiety of the formula

[structure of fused heterocyclic moiety with $R^{15}$], wherein

* indicates the point of attachment to the phenyl ring in $R^4$ position,
** indicates the point of attachment to the phenyl ring in $R^5$ position, and $R^{15}$ represents phenyl which is optionally substituted with one or two fluoro atoms, or represents pyridyl, $R^7$ and $R^8$ both are hydrogen, $R^9$ is hydrogen, $R^{10}$ represents hydrogen, $(C_1-C_4)$-alkyl or cyclopropyl, wherein said $(C_1-C_4)$-alkyl is optionally substituted with hydroxy or $(C_1-C_4)$-alkoxy, and $R^{11}$ represents $(C_1-C_4)$-alkyl or $(C_3-C_6)$-cycloalkyl, wherein (i) said $(C_1-C_4)$-alkyl is optionally substituted with a group selected from hydroxy, $(C_1-C_4)$-alkoxy, amino, mono-$(C_1-C_4)$-alkylamino, di-$(C_1-C_4)$-alkylamino, hydroxycarbonyl, $(C_1-C_4)$-alkoxycarbonyl, di-$(C_1-C_4)$-alkylaminocarbonyl, $(C_1-C_4)$-alkylsulfonyl, 5- or 6-membered heteroaryl and 4- to 7-membered heterocycloalkyl, wherein said 5- or 6-membered heteroaryl and 4- to 7-membered heterocycloalkyl groups in turn are optionally substituted with one or two $(C_1-C_4)$-alkyl residues, and (ii) said $(C_3-C_6)$-cycloalkyl is optionally substituted with one or two substituents independently selected from the group consisting of $(C_1-C_4)$-alkyl, hydroxy and $(C_1-C_4)$-alkoxy, or $R^{10}$ and $R^{11}$ are joined, and taken together with the nitrogen atom to which they are attached, form a heterocycloalkyl group of the formula

[structures of heterocycloalkyl groups with $R^{17}$, $R^{18}$, $R^{19}$]

-continued

[additional structure]

wherein

\# denotes the point of attachment to the $CHR^9$ group, $R^{17}$ represents hydrogen or phenoxy which is optionally substituted with one or two residues independently selected from the group consisting of fluoro, chloro, methyl and methoxy, $R^{18}$ represents hydrogen, hydroxy, $(C_1-C_4)$-alkoxy, amino, mono-$(C_1-C_4)$-alkylamino, di-$(C_1-C_4)$-alkylamino, $(C_1-C_4)$-alkoxycarbonyl, aminocarbonyl, mono-$(C_1-C_4)$-alkyl-aminocarbonyl or di-$(C_1-C_4)$-alkylaminocarbonyl, or represents $(C_1-C_4)$-alkyl which is optionally substituted with hydroxy, $(C_1-C_4)$-alkoxy, amino, mono-$(C_1-C_4)$-alkylamino, di-$(C_1-C_4)$-alkylamino, $(C_1-C_4)$-alkylcarbonylamino or $(C_1-C_4)$-alkoxycarbonyl, and $R^{19}$ represents hydrogen, $(C_1-C_4)$-alkylcarbonyl, $(C_1-C_4)$-alkylsulfonyl, $(C_1-C_4)$-alkoxy-carbonyl, aminocarbonyl, mono-$(C_1-C_4)$-alkylaminocarbonyl, di-$(C_1-C_4)$-alkylamino-carbonyl, phenyl, pyridyl or pyrimidinyl, wherein said phenyl is optionally substituted with hydroxy or methoxy, or represents $(C_1-C_4)$-alkyl which is optionally substituted with hydroxy, $(C_1-C_4)$-alkoxy, amino, mono-$(C_1-C_4)$-alkylamino, di-$(C_1-C_4)$-alkylamino, $(C_1-C_4)$-alkoxycarbonyl, amino-carbonyl, mono-$(C_1-C_4)$-alkylaminocarbonyl or di-$(C_1-C_4)$-alkylaminocarbonyl, or a pharmaceutically acceptable salt thereof.

14. The compound of claim 1, wherein

A is N or C—CN,

D is absent,

E is O,

L is —C(=O)—, m is 1, n is 2, p is 0, $R^1$ represents hydrogen, fluoro or chloro, $R^2$ represents hydrogen, fluoro or chloro, $R^3$ represents hydrogen, fluoro, chloro or ethinyl, $R^4$ represents hydrogen, fluoro, chloro or hydroxy, $R^5$ represents hydrogen, fluoro or chloro, or $R^5$ is a group of the formula ♦-O—$CH_2$—$R^{14}$, wherein ♦ denotes the point of attachment, and $R^{14}$ represents phenyl which is optionally substituted with one or two fluoro atoms, or represents pyridyl, or $R^4$ and $R^5$ are linked together and form a fused heterocyclic moiety of the formula

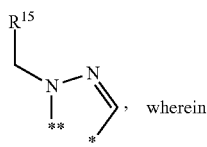, wherein

* indicates the point of attachment to the phenyl ring in $R^4$ position,
** indicates the point of attachment to the phenyl ring in $R^5$ position, and
$R^{15}$ represents phenyl which is optionally substituted with one or two fluoro atoms, or represents pyridyl,
$R^7$ and $R^8$ both are hydrogen,
$R^9$ is hydrogen,
$R^{10}$ represents hydrogen, $(C_1$-$C_4)$-alkyl or cyclopropyl, wherein said $(C_1$-$C_4)$-alkyl is optionally substituted with hydroxy or $(C_1$-$C_4)$-alkoxy, and
$R^{11}$ represents $(C_1$-$C_4)$-alkyl or $(C_3$-$C_6)$-cycloalkyl, wherein
(i) said $(C_1$-$C_4)$-alkyl is optionally substituted with a group selected from hydroxy, $(C_1$-$C_4)$-alkoxy, amino, mono-$(C_1$-$C_4)$-alkylamino, di-$(C_1$-$C_4)$-alkylamino, hydroxycarbonyl, $(C_1$-$C_4)$-alkoxycarbonyl, di-$(C_1$-$C_4)$-alkylaminocarbonyl, $(C_1$-$C_4)$-alkylsulfonyl, 5- or 6-membered heteroaryl and 4- to 7-membered heterocycloalkyl,
wherein said 5- or 6-membered heteroaryl and 4- to 7-membered heterocycloalkyl groups in turn are optionally substituted with one or two $(C_1$-$C_4)$-alkyl residues, and
(ii) said $(C_3$-$C_6)$-cycloalkyl is optionally substituted with one or two substituents independently selected from the group consisting of $(C_1$-$C_4)$-alkyl, hydroxy and $(C_1$-$C_4)$-alkoxy,
or a pharmaceutically acceptable salt thereof.

15. The compound of claim 1, wherein
A is N,
D is absent,
E is S,
L is —C(=O)—,
m is 1,
n is 1,
p is 0,
$R^1$ represents hydrogen, fluoro or chloro,
$R^2$ represents hydrogen, fluoro or chloro,
$R^3$ represents hydrogen, fluoro, chloro or ethinyl,
$R^4$ represents hydrogen, fluoro, chloro or hydroxy,
$R^5$ represents hydrogen, fluoro or chloro,
or
$R^5$ is a group of the formula ♦-O—CH$_2$—$R^{14}$, wherein
♦ denotes the point of attachment,
and
$R^{14}$ represents phenyl which is optionally substituted with one or two fluoro atoms, or represents pyridyl,
or
$R^4$ and $R^5$ are linked together and form a fused heterocyclic moiety of the formula

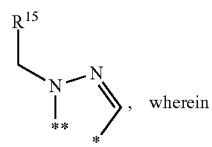, wherein

* indicates the point of attachment to the phenyl ring in $R^4$ position,
** indicates the point of attachment to the phenyl ring in $R^5$ position,
and
$R^{15}$ represents phenyl which is optionally substituted with one or two fluoro atoms, or represents pyridyl,
$R^7$ and $R^8$ both are hydrogen,
$R^9$ is hydrogen,
$R^{10}$ represents hydrogen, $(C_1$-$C_4)$-alkyl or cyclopropyl, wherein said $(C_1$-$C_4)$-alkyl is optionally substituted with hydroxy or $(C_1$-$C_4)$-alkoxy, and
$R^{11}$ represents $(C_1$-$C_4)$-alkyl or $(C_3$-$C_6)$-cycloalkyl, wherein
(i) said $(C_1$-$C_4)$-alkyl is optionally substituted with a group selected from hydroxy, $(C_1$-$C_4)$-alkoxy, amino, mono-$(C_1$-$C_4)$-alkylamino, di-$(C_1$-$C_4)$-alkylamino, hydroxycarbonyl, $(C_1$-$C_4)$-alkoxycarbonyl, di-$(C_1$-$C_4)$-alkylaminocarbonyl, $(C_1$-$C_4)$-alkylsulfonyl, 5- or 6-membered heteroaryl and 4- to 7-membered heterocycloalkyl,
wherein said 5- or 6-membered heteroaryl and 4- to 7-membered heterocycloalkyl groups in turn are optionally substituted with one or two $(C_1$-$C_4)$-alkyl residues, and
(ii) said $(C_3$-$C_6)$-cycloalkyl is optionally substituted with one or two substituents independently selected from the group consisting of $(C_1$-$C_4)$-alkyl, hydroxy and $(C_1$-$C_4)$-alkoxy,
or a pharmaceutically acceptable salt thereof.

16. A process for preparing a compound as defined in claim 1, comprising
[A] reacting a compound of formula (II)

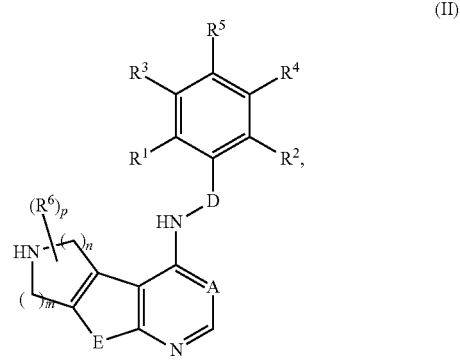

wherein A, D, E, $R^1$ to $R^6$, m, n and p have the meanings indicated in claim 1, in the presence of an amide coupling reagent and/or a base, with a compound of formula (III)

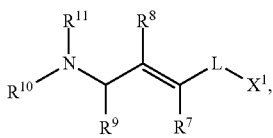
(III)

wherein L and $R^7$ to $R^{11}$ have the meanings indicated in claim 1,
and
$X^1$ represents hydroxy or a leaving group such as chloro or bromo,
or
[B] reacting a compound of formula (IV)

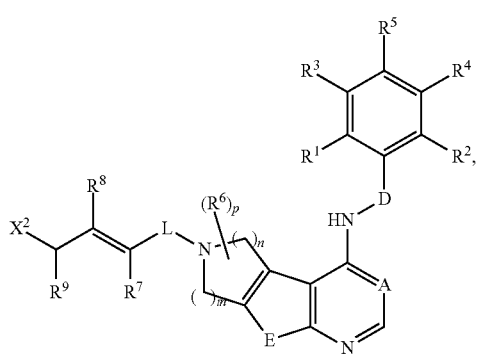
(IV)

wherein A, D, E, L, $R^1$ to $R^9$, m, n and p have the meanings indicated in claim 1, and
$X^2$ represents a leaving group such as chloro, bromo, iodo, mesylate or tosylate, optionally in the presence of an auxiliary base, with a compound of formula (V)

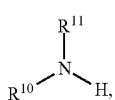
(V)

wherein $R^{10}$ and $R^{11}$ have the meanings indicated in claim 1,
or
[C] reacting a compound of formula (VI)

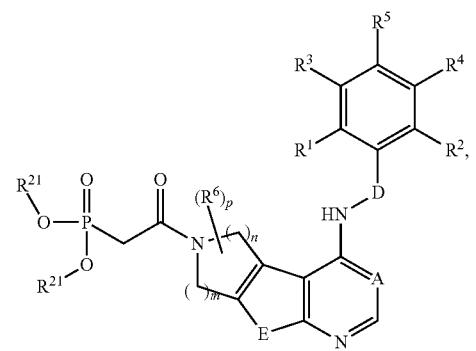
(VI)

wherein A, D, E, $R^1$ to $R^6$, m, n and p have the meanings indicated in claims 1,
and
$R^{21}$ represents $(C_1-C_4)$-alkyl,
in the presence of a base, with a compound of formula (VII)

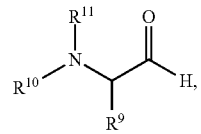
(VII)

wherein $R^9$, $R^{10}$ and $R^{11}$ have the meanings indicated in claim 1,
or
[D] reacting a compound of formula (VIII)

(VIII)

wherein A, E, L, $R^6$ to $R^{11}$, m, n and p have the meanings indicated in claim 1,
and
$X^3$ represents a leaving group such as chloro, bromo or iodo,
in the presence of an acid or base or by means of a palladium catalyst, with a compound of formula (IX)

(IX)

wherein D and $R^1$ to $R^5$ have the meanings indicated in claim 1,
and optionally converting the resulting compound of formula (I) into a salt thereof by treatment with the corresponding acids or bases.

17. A pharmaceutical composition comprising a compound as defined in claim 1, or a pharmaceutically acceptable salt thereof, and a pharmaceutically acceptable diluent or carrier.

18. The pharmaceutical composition of claim 17 further comprising at least one anti-cell proliferative agent.

19. A method of treating a cancer selected from breast, respiratory tract, and skin cancers in a mammal, comprising administering to a mammal in need thereof a therapeutically effective amount of one or more compounds as defined in claim 1.

20. The method of claim 19 wherein the compound as defined in claim 1 is administered in conjunction with surgery or radiation therapy.

* * * * *